(12) United States Patent
Li et al.

(10) Patent No.: US 10,033,003 B2
(45) Date of Patent: Jul. 24, 2018

(54) TETRADENTATE METAL COMPLEXES WITH CARBON GROUP BRIDGING LIGANDS

(71) Applicant: Arizona Board of Regents on behalf of Arizona State University, Scottsdale, AZ (US)

(72) Inventors: Jian Li, Tempe, AZ (US); Guijie Li, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 14/937,318

(22) Filed: Nov. 10, 2015

(65) Prior Publication Data

US 2016/0133862 A1    May 12, 2016

Related U.S. Application Data

(60) Provisional application No. 62/077,431, filed on Nov. 10, 2014.

(51) Int. Cl.
*C07F 15/00* (2006.01)
*H01L 51/50* (2006.01)
(Continued)

(52) U.S. Cl.
CPC ............ *H01L 51/0087* (2013.01); *C07F 1/12* (2013.01); *C07F 7/0816* (2013.01); *C07F 7/30* (2013.01);
(Continued)

(58) Field of Classification Search
CPC ................................ C07F 15/00; H01L 51/50
(Continued)

(56) References Cited

U.S. PATENT DOCUMENTS 4,769,292 A    9/1988  Tang et al.
5,707,745 A    1/1998  Forrest et al.
(Continued)

FOREIGN PATENT DOCUMENTS

CN    1680366 A    10/2005
CN    1777663       5/2006
(Continued)

OTHER PUBLICATIONS

Wong; Challenges in organometallic research—Great opportunity for solar cells and OLEDs, Journal of Organometallic Chemistry, 2009, 694, 2644-2647.
JP2009267244, English Translation from EPO, Nov. 2009, 80 pages.
JP2010135689, English translation from EPO, Jun. 2010, 95 pages.
Chi et al.; Transition-metal phosphors with cyclometalating ligands: fundamentals and applications, Chemical Society Reviews, vol. 39, No. 2, Feb. 2010, pp. 638-655.
(Continued)

*Primary Examiner* — Charanjit Aulakh
(74) *Attorney, Agent, or Firm* — Fish & Richardson P.C.

(57) ABSTRACT

Platinum, palladium, and gold complexes suitable for use as phosphorescent emitters or as delayed fluorescent and phosphorescent emitters having one of the following structures:

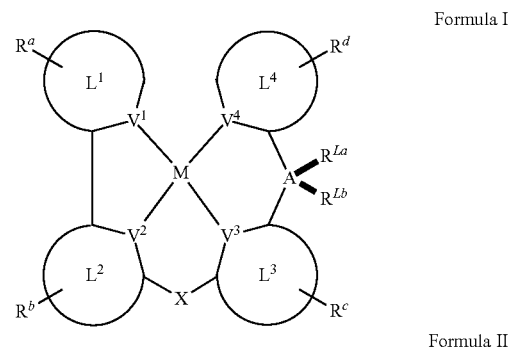

Formula I

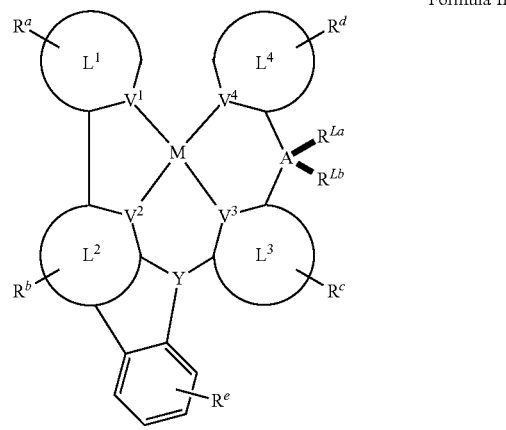

Formula II

Formula III (Continued)

-continued
Formula IV
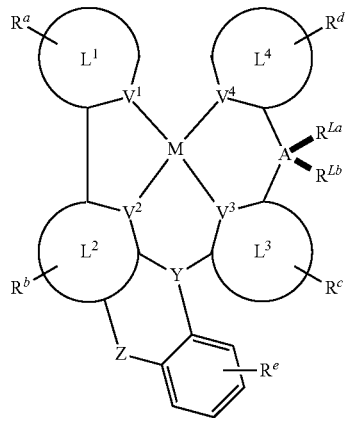
Formula V
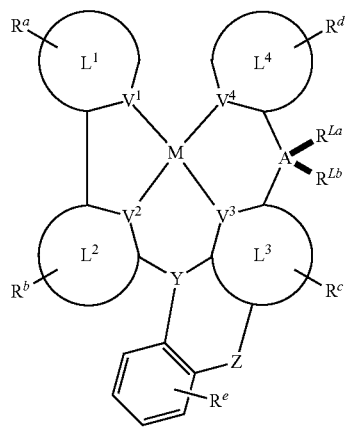
Formula VI
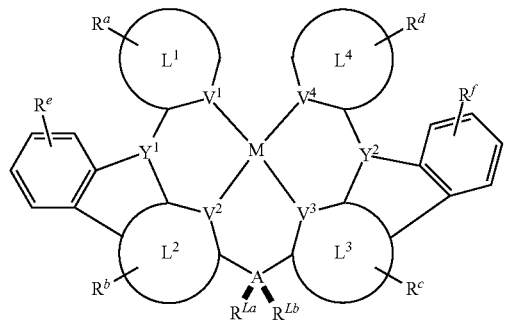
Formula VII
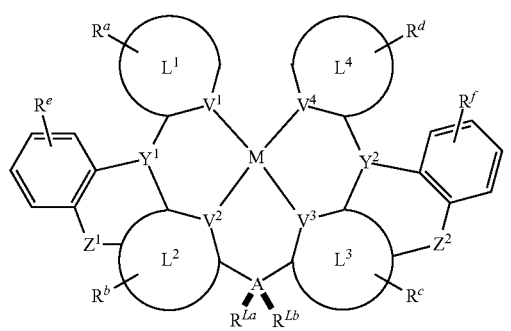
-continued
Formula VIII
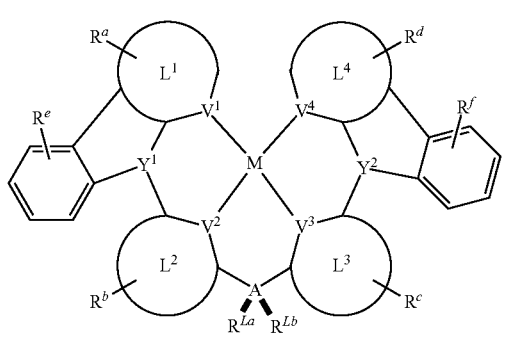
Formula IX
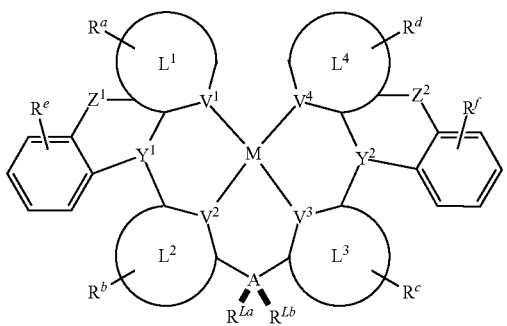
15 Claims, 2 Drawing Sheets
(51) Int. Cl.
H01L 51/00 (2006.01)
C09K 11/06 (2006.01)
C07F 9/70 (2006.01)
C07F 1/12 (2006.01)
C07F 7/08 (2006.01)
C07F 7/30 (2006.01)
C07F 9/6561 (2006.01)
(52) U.S. Cl.
CPC ............ C07F 9/6561 (2013.01); C07F 9/703 (2013.01); C07F 15/006 (2013.01); C07F 15/0086 (2013.01); C09K 11/06 (2013.01); H01L 51/0084 (2013.01); H01L 51/0091 (2013.01); C09K 2211/104 (2013.01); C09K 2211/1007 (2013.01); C09K 2211/1011 (2013.01); C09K 2211/1014 (2013.01); C09K 2211/1029 (2013.01); C09K 2211/1033 (2013.01); C09K 2211/1037 (2013.01); C09K 2211/1044 (2013.01); C09K 2211/1055 (2013.01); C09K 2211/1059 (2013.01); C09K 2211/1092 (2013.01); C09K 2211/1096 (2013.01); C09K 2211/185 (2013.01); C09K 2211/188 (2013.01); H01L 51/5016 (2013.01)
(58) Field of Classification Search
USPC .............................................. 546/2; 313/504
See application file for complete search history.

(56) References Cited

U.S. PATENT DOCUMENTS

| | | | |
|---|---|---|---|
| 5,844,363 A | 12/1998 | Gu et al. |
| 6,200,695 B1 | 3/2001 | Arai et al. |
| 6,303,238 B1 | 10/2001 | Thompson et al. |
| 6,780,528 B2 | 8/2004 | Tsuboyama et al. |
| 7,002,013 B1 | 2/2006 | Chi et al. |
| 7,037,599 B2 | 5/2006 | Culligan et al. |
| 7,064,228 B1 | 6/2006 | Yu et al. |
| 7,268,485 B2 | 9/2007 | Tyan et al. |
| 7,279,704 B2 | 10/2007 | Walters et al. |
| 7,332,232 B2 | 2/2008 | Ma et al. |
| 7,442,797 B2 | 10/2008 | Itoh et al. |
| 7,501,190 B2 | 3/2009 | Ise |
| 7,655,322 B2 | 2/2010 | Forrest et al. |
| 7,854,513 B2 | 12/2010 | Quach |
| 7,947,383 B2 | 5/2011 | Ise et al. |
| 8,133,597 B2 | 3/2012 | Yasukawa et al. |
| 8,389,725 B2 | 3/2013 | Li et al. |
| 8,617,723 B2 | 12/2013 | Stoessel |
| 8,816,080 B2 | 8/2014 | Li et al. |
| 8,871,361 B2 | 10/2014 | Xia et al. |
| 8,927,713 B2 | 1/2015 | Li et al. |
| 8,946,417 B2 | 2/2015 | Li et al. |
| 9,059,412 B2 | 6/2015 | Zeng et al. |
| 9,221,857 B2 | 12/2015 | Li et al. |
| 9,224,963 B2 | 12/2015 | Li et al. |
| 9,238,668 B2 | 1/2016 | Li et al. |
| 9,312,502 B2 | 4/2016 | Li et al. |
| 9,312,505 B2 | 4/2016 | Brooks et al. |
| 9,318,725 B2 | 4/2016 | Li |
| 9,324,957 B2 | 4/2016 | Li et al. |
| 9,382,273 B2 | 7/2016 | Li et al. |
| 9,385,329 B2 | 7/2016 | Li et al. |
| 9,425,415 B2 | 8/2016 | Li et al. |
| 9,461,254 B2 * | 10/2016 | Tsai .................. C07F 15/0086 |
| 9,550,801 B2 | 1/2017 | Li et al. |
| 9,617,291 B2 | 4/2017 | Li |
| 9,673,409 B2 | 6/2017 | Li et al. |
| 9,698,359 B2 | 7/2017 | Li et al. |
| 9,711,739 B2 | 7/2017 | Li |
| 9,711,742 B2 | 7/2017 | Li et al. |
| 9,755,163 B2 | 9/2017 | Li et al. |
| 9,818,959 B2 | 11/2017 | Li |
| 2001/0019782 A1 | 9/2001 | Igarashi et al. |
| 2002/0068190 A1 | 6/2002 | Tsuboyama et al. |
| 2003/0062519 A1 | 4/2003 | Yamazaki et al. |
| 2003/0186077 A1 | 10/2003 | Chen et al. |
| 2004/0230061 A1 | 11/2004 | Seo et al. |
| 2005/0170207 A1 | 8/2005 | Ma et al. |
| 2005/0260446 A1 | 11/2005 | Mackenzie et al. |
| 2006/0024522 A1 | 2/2006 | Thompson |
| 2006/0073359 A1 | 4/2006 | Ise et al. |
| 2006/0094875 A1 | 5/2006 | Itoh et al. |
| 2006/0127696 A1 | 6/2006 | Stossel et al. |
| 2006/0182992 A1 | 8/2006 | Nii et al. |
| 2006/0202197 A1 | 9/2006 | Nakayama et al. |
| 2006/0210831 A1 | 9/2006 | Sano et al. |
| 2006/0263635 A1 | 11/2006 | Ise |
| 2006/0286406 A1 | 12/2006 | Igarashi et al. |
| 2007/0057630 A1 | 3/2007 | Nishita et al. |
| 2007/0059551 A1 | 3/2007 | Yamazaki |
| 2007/0082284 A1 | 4/2007 | Stoessel et al. |
| 2007/0103060 A1 | 5/2007 | Itoh et al. |
| 2008/0001530 A1 | 1/2008 | Ise et al. |
| 2008/0036373 A1 | 2/2008 | Itoh et al. |
| 2008/0054799 A1 | 3/2008 | Satou |
| 2008/0079358 A1 | 4/2008 | Satou |
| 2008/0111476 A1 | 5/2008 | Choi et al. |
| 2008/0241518 A1 | 10/2008 | Satou et al. |
| 2008/0241589 A1 | 10/2008 | Fukunaga et al. |
| 2009/0026936 A1 | 1/2009 | Satou et al. |
| 2009/0026939 A1 | 1/2009 | Kinoshita et al. |
| 2009/0032989 A1 | 2/2009 | Karim et al. |
| 2009/0039768 A1 | 2/2009 | Igarashi et al. |
| 2009/0079340 A1 | 3/2009 | Kinoshita et al. |
| 2009/0128008 A1 | 5/2009 | Ise et al. |
| 2009/0218561 A1 | 9/2009 | Kitamura et al. |
| 2009/0261721 A1 | 10/2009 | Murakami et al. |
| 2009/0267500 A1 | 10/2009 | Kinoshita et al. |
| 2010/0000606 A1 | 1/2010 | Thompson et al. |
| 2010/0013386 A1 | 1/2010 | Thompson et al. |
| 2010/0141127 A1 | 6/2010 | Xia et al. |
| 2010/0171111 A1 | 7/2010 | Takada et al. |
| 2010/0171418 A1 | 7/2010 | Kinoshita et al. |
| 2010/0270540 A1 | 10/2010 | Chung et al. |
| 2010/0297522 A1 | 11/2010 | Creeth et al. |
| 2011/0049496 A1 | 3/2011 | Fukuzaki |
| 2011/0062858 A1 | 3/2011 | Yersin et al. |
| 2012/0095232 A1 | 4/2012 | Li et al. |
| 2012/0181528 A1 | 7/2012 | Takada et al. |
| 2012/0199823 A1 | 8/2012 | Molt et al. |
| 2012/0215001 A1 | 8/2012 | Li et al. |
| 2012/0223634 A1 | 9/2012 | Xia et al. |
| 2012/0264938 A1 | 10/2012 | Li et al. |
| 2012/0273736 A1 | 11/2012 | James et al. |
| 2012/0302753 A1 | 11/2012 | Li |
| 2013/0048963 A1 | 2/2013 | Beers et al. |
| 2013/0168656 A1 | 7/2013 | Tsai et al. |
| 2013/0203996 A1 | 8/2013 | Li et al. |
| 2013/0237706 A1 | 9/2013 | Li |
| 2013/0341600 A1 | 12/2013 | Lin et al. |
| 2014/0014922 A1 | 1/2014 | Lin et al. |
| 2014/0027733 A1 | 1/2014 | Zeng et al. |
| 2014/0084261 A1 | 3/2014 | Brooks et al. |
| 2014/0114072 A1 | 4/2014 | Li et al. |
| 2014/0191206 A1 | 7/2014 | Cho |
| 2014/0203248 A1 | 7/2014 | Zhou et al. |
| 2014/0326960 A1 | 11/2014 | Kim et al. |
| 2014/0330019 A1 | 11/2014 | Li et al. |
| 2014/0364605 A1 | 12/2014 | Li et al. |
| 2015/0008419 A1 | 1/2015 | Li |
| 2015/0028323 A1 | 1/2015 | Xia et al. |
| 2015/0069334 A1 | 3/2015 | Xia et al. |
| 2015/0105556 A1 | 4/2015 | Li et al. |
| 2015/0162552 A1 | 6/2015 | Li et al. |
| 2015/0194616 A1 | 7/2015 | Li et al. |
| 2015/0207086 A1 | 7/2015 | Li et al. |
| 2015/0228914 A1 | 8/2015 | Li et al. |
| 2015/0274762 A1 | 10/2015 | Li et al. |
| 2015/0287938 A1 | 10/2015 | Li et al. |
| 2015/0318500 A1 | 11/2015 | Li |
| 2015/0349279 A1 | 12/2015 | Li et al. |
| 2016/0028028 A1 | 1/2016 | Li et al. |
| 2016/0043331 A1 | 2/2016 | Li et al. |
| 2016/0072082 A1 | 3/2016 | Brooks et al. |
| 2016/0133862 A1 | 5/2016 | Li et al. |
| 2016/0197285 A1 | 7/2016 | Zeng et al. |
| 2016/0197291 A1 | 7/2016 | Li et al. |
| 2016/0285015 A1 | 9/2016 | Li et al. |
| 2016/0359120 A1 | 12/2016 | Li |
| 2016/0359125 A1 | 12/2016 | Li et al. |
| 2017/0005278 A1 | 1/2017 | Li et al. |
| 2017/0012224 A1 | 1/2017 | Li et al. |
| 2017/0040555 A1 | 2/2017 | Li et al. |
| 2017/0047533 A1 | 2/2017 | Li |
| 2017/0066792 A1 | 3/2017 | Li |
| 2017/0069855 A1 | 3/2017 | Li |
| 2017/0267923 A1 | 9/2017 | Li |
| 2017/0271611 A1 | 9/2017 | Li et al. |
| 2017/0301871 A1 | 10/2017 | Li |
| 2017/0305881 A1 | 10/2017 | Li et al. |
| 2017/0331056 A1 | 11/2017 | Li et al. |

FOREIGN PATENT DOCUMENTS

| | | |
|---|---|---|
| CN | 1894269 | 1/2007 |
| CN | 101142223 | 3/2008 |
| CN | 101667626 | 3/2010 |
| CN | 102449108 A | 5/2012 |
| CN | 102892860 | 1/2013 |
| CN | 102971396 | 3/2013 |
| CN | 104232076 | 12/2014 |
| CN | 104377231 | 2/2015 |
| CN | 104693243 | 6/2015 |
| CN | 105367605 A1 | 3/2016 |

(56) References Cited

FOREIGN PATENT DOCUMENTS

| | | |
|---|---|---|
| CN | 105418591 A1 | 3/2016 |
| EP | 1808052 | 7/2007 |
| EP | 1874893 | 1/2008 |
| EP | 1874894 | 1/2008 |
| EP | 1919928 | 5/2008 |
| EP | 2036907 | 3/2009 |
| EP | 2096690 | 9/2009 |
| EP | 2417217 | 2/2012 |
| EP | 2112213 | 7/2012 |
| EP | 2711999 | 3/2014 |
| JP | 200210505 A | 4/2002 |
| JP | 2005267557 | 9/2005 |
| JP | 2005310733 | 11/2005 |
| JP | 2006047240 | 2/2006 |
| JP | 2006232784 | 9/2006 |
| JP | 2006242080 | 9/2006 |
| JP | 2006242081 | 9/2006 |
| JP | 2006256999 | 9/2006 |
| JP | 2006257238 | 9/2006 |
| JP | 2006261623 | 9/2006 |
| JP | 2006290988 | 10/2006 |
| JP | 2006313796 | 11/2006 |
| JP | 2006332622 | 12/2006 |
| JP | 2006351638 | 12/2006 |
| JP | 2007019462 | 1/2007 |
| JP | 2007031678 A | 2/2007 |
| JP | 2007042875 | 2/2007 |
| JP | 2007053132 | 3/2007 |
| JP | 2007066581 | 3/2007 |
| JP | 2007073620 | 3/2007 |
| JP | 2007073845 | 3/2007 |
| JP | 2007073900 | 3/2007 |
| JP | 2007080593 | 3/2007 |
| JP | 2007080677 | 3/2007 |
| JP | 2007088105 | 4/2007 |
| JP | 2007088164 | 4/2007 |
| JP | 2007096259 | 4/2007 |
| JP | 2007099765 A | 4/2007 |
| JP | 2007110067 | 4/2007 |
| JP | 2007110102 | 4/2007 |
| JP | 2007258550 | 10/2007 |
| JP | 2007324309 | 12/2007 |
| JP | 2008010353 | 1/2008 |
| JP | 2008091860 | 4/2008 |
| JP | 2008103535 | 5/2008 |
| JP | 2008108617 | 5/2008 |
| JP | 2008109085 | 5/2008 |
| JP | 2008109103 | 5/2008 |
| JP | 2008160087 | 7/2008 |
| JP | 2008198801 | 8/2008 |
| JP | 2008270729 | 11/2008 |
| JP | 2008270736 | 11/2008 |
| JP | 2009016184 | 1/2009 |
| JP | 2009016579 | 1/2009 |
| JP | 2009032977 | 2/2009 |
| JP | 2009032988 | 2/2009 |
| JP | 2009076509 A | 4/2009 |
| JP | 2009266943 | 11/2009 |
| JP | 2009267171 | 11/2009 |
| JP | 2009267244 | 11/2009 |
| JP | 2009272339 | 11/2009 |
| JP | 2009283891 | 12/2009 |
| JP | 2010135689 | 6/2010 |
| JP | 2012222255 | 11/2012 |
| JP | 2013525436 | 6/2013 |
| JP | 5604505 | 10/2014 |
| JP | 2014221807 | 11/2014 |
| JP | 2015081257 | 4/2015 |
| KR | 1020060115371 | 11/2006 |
| KR | 2007061830 | 6/2007 |
| KR | 2007112465 | 11/2007 |
| KR | 1020130043460 | 4/2013 |
| KR | 101338250 | 12/2013 |
| TW | 200701835 | 1/2007 |
| TW | 201307365 | 2/2013 |
| TW | 201710277 | 3/2017 |
| WO | WO2008054578 | 5/2000 |
| WO | WO2000070655 | 11/2000 |
| WO | WO2004003108 A1 | 1/2004 |
| WO | WO2004085450 | 10/2004 |
| WO | WO2004108857 | 12/2004 |
| WO | WO2005042444 | 5/2005 |
| WO | WO2005042550 | 5/2005 |
| WO | WO2005113704 | 12/2005 |
| WO | WO2006033440 | 3/2006 |
| WO | WO2006067074 | 6/2006 |
| WO | WO2006098505 | 9/2006 |
| WO | WO2006113106 | 10/2006 |
| WO | WO2006115299 | 11/2006 |
| WO | WO2006115301 | 11/2006 |
| WO | WO2007034985 | 3/2007 |
| WO | WO2007069498 | 6/2007 |
| WO | WO2008066195 | 6/2008 |
| WO | WO2008066196 | 6/2008 |
| WO | WO2008101842 | 8/2008 |
| WO | WO2008117889 | 10/2008 |
| WO | WO2008123540 | 10/2008 |
| WO | WO2009017211 | 2/2009 |
| WO | WO2009023667 | 2/2009 |
| WO | WO2010007098 | 1/2010 |
| WO | WO20100056669 | 5/2010 |
| WO | WO2010093176 | 8/2010 |
| WO | WO2010118026 | 10/2010 |
| WO | WO2011064335 | 6/2011 |
| WO | WO2011070989 | 6/2011 |
| WO | WO2011089163 | 7/2011 |
| WO | WO2011137429 | 11/2011 |
| WO | WO2011137431 | 11/2011 |
| WO | WO2012112853 | 8/2012 |
| WO | WO2012142387 | 10/2012 |
| WO | WO2012162488 | 11/2012 |
| WO | WO2012163471 | 12/2012 |
| WO | WO2013130483 | 9/2013 |
| WO | WO2014016611 A1 | 1/2014 |
| WO | WO2014031977 | 2/2014 |
| WO | WO2014047616 | 3/2014 |
| WO | WO2014109814 | 7/2014 |
| WO | WO2014208271 | 12/2014 |
| WO | WO2015027060 | 2/2015 |
| WO | WO2015131158 | 9/2015 |
| WO | WO2016025921 | 2/2016 |
| WO | WO2016029137 | 2/2016 |
| WO | WO2016029186 | 2/2016 |
| WO | WO2016197019 | 12/2016 |

OTHER PUBLICATIONS

Satake et al., "Interconvertible Cationic and Neutral Pyridinylimidazole η3-Allylpalladium Complexes. Structural Assignment by 1H, 13C, and 15N NMR and X-ray Diffraction", Organometallics, vol. 18, No. 24, 1999, pp. 5108-5111.
Baldo et al., "Highly Efficient Phosphorescent Emission from Organic Electroluminescent Devices," Nature, vol. 395, Sep. 10, 1998, pp. 151-154.
Baldo et al., "Very high-efficiency green organic light-emitting devices based on electrophosphorescence," Applied Physics Letters, vol. 75, No. 1, Jul. 5, 1999, pp. 4-6.
Xiao-Chu Hang et al., "Highly Efficient Blue-Emitting Cyclometalated Platinum(II) Complexes by Judicious Molecular Design," Angewandte Chemie, International Edition, vol. 52, Issue 26, Jun. 24, 2013, pp. 6753-6756.
Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013, pp. 2624-2628.
Barry O'Brien et al.: White organic light emitting diodes using Pt-based red, green and blue phosphorescent dopants. Proc. SPIE, vol. 8829, pp. 1-6, Aug. 25, 2013.
Ayan Maity et al., "Room-temperature synthesis of cyclometalated iridium(III) complexes; kinetic isomers and reactive functionalities" Chem. Sci., vol. 4, pp. 1175-1181 (2013).
Shiro Koseki et al., "Spin-orbit coupling analyses of the geometrical effects on phosphorescence in Ir(ppy)$_3$ and its derivatives", J. Phys. Chem. C, vol. 117, pp. 5314-5327 (2013).

(56) References Cited

OTHER PUBLICATIONS

Ji Hyun Seo et al., "Efficient blue-green organic light-emitting diodes based on heteroleptic tris-cyclometalated iridium (III) complexes". Thin Solid Films, vol. 517, pp. 1807-1810 (2009).
Vanessa Wood et al., "Colloidal quantum dot light-emitting devices," Nano Reviews, vol. 1, 2010, 8 pages.
Glauco Ponterini et al., "Comparison of Radiationless Decay Processes in Osmium and Platinum Porphyrins," J. Am. Chem. Soc., vol. 105, No. 14, 1983, pp. 4639-4645.
Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.
Brian W. D'Andrade et al., "Controlling Exciton Diffusion in Multilayer White Phosphorescent Organic Light Emitting Devices," Adv. Mater., vol. 14, No. 2, Jan. 16, 2002, pp. 147-151.
Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.
Evan L. Williams et al., "Excimer-Based White Phosphorescent Organic Light Emitting Diodes with Nearly 100% Internal Quantum Efficiency," Adv. Mater., vol. 19, 2007, pp. 197-202.
Shih-Chun Lo et al., "High-Triplet-Energy Dendrons: Enhancing the Luminescence of Deep Blue Phosphorescent Iridium(III) Complexes," J. Am. Chem. Soc., vol. 131, 2009, pp. 16681-16688.
Jan Kalinowski et al., "Light-emitting devices based on organometallic platinum complexes as emitters," Coordination Chemistry Reviews, vol. 255, 2011, pp. 2401-2425.
Ke Feng et al., "Norbornene-Based Copolymers Containing Platinum Complexes and Bis(carbazolyl)benzene Groups in Their Side-Chains," Macromolecules, vol. 42, 2009, pp. 6855-6864.
Chi-Ming Che et al., "Photophysical Properties and OLED Applications of Phosphorescent Platinum(II) Schiff Base Complexes," Chem. Eur. J., vol. 16, 2010, pp. 233-247.
Stephen R. Forrest, "The path to ubiquitous and low-cost organic electronic appliances on plastic," Nature, vol. 428, Apr. 29, 2004, pp. 911-918.
Xiaofan Ren et al., "Ultrahigh Energy Gap Hosts in Deep Blue Organic Electrophosphorescent Devices," Chem. Mater., vol. 16, 2004, pp. 4743-4747.
Jeonghun Kwak et al., "Bright and Efficient Full-Color Colloidal Quantum Dot Light-Emitting Diodes Using an Inverted Device Structure," Nano Lett., 2012, Vo. 12, pp. 2362-2366.
Hirohiko Fukagawa et al., "Highly Efficient and Stable Red Phosphorescent Organic Light-Emitting Diodes Using Platinum Complexes," Adv. Mater., 2012, vol. 24, pp. 5099-5103.
Eric Turner et al., "Cyclometalated Platinum Complexes with Luminescent Quantum Yields Approaching 100%," Inorg. Chem., 2013, vol. 52, pp. 7344-7351.
Steven C. F. Kui et al., "Robust Phosphorescent Platinum(II) Complexes Containing Tetradentate O^N^C^N Ligands: Excimeric Excited State and Application in Organic White-Light-Emitting Diodes," Chem. Eur. J., 2013, vol. 19, pp. 69-73.
Steven C. F. Kui et al., "Robust phosphorescent platinum(II) complexes with tetradentate O^N^C^N ligands: high efficiency OLEDs with excellent efficiency stability," Chem. Commun., 2013, vol. 49, pp. 1497-1499.
Guijie Li et al., "Efficient and stable red organic light emitting devices from a tetradentate cyclometalated platinum complex," Organic Electronics, 2014, vol. 15 pp. 1862-1867.
Guijie Li et al., Efficient and Stable White Organic Light-Emitting Diodes Employing a Single Emitter, Adv. Mater., 2014, vol. 26, pp. 2931-2936.
Barry O'Brien et al., "High efficiency white organic light emitting diodes employing blue and red platinum emitters," Journal of Photonics for Energy, vol. 4, 2014, pp. 043597-1-8.
Kai Li et al., "Light-emitting platinum(II) complexes supported by tetradentate dianionic bis(N-heterocyclic carbene) ligands: towards robust blue electrophosphors," Chem. Sci., 2013, vol. 4, pp. 2630-2644.
Tyler Fleetham et al., "Efficient "pure" blue OLEDs employing tetradentate Pt complexes with a narrow spectral bandwidth," Advanced Materials (Weinheim, Germany), Vo. 26, No. 41, 2014, pp. 7116-7121.
Murakami; JP 2007258550, English machine translation from EPO, Oct. 4, 2007. 80 pages.
Murakami; JP 2007324309, English machine translation from EPO, Dec. 13, 2007, 89 pages.
Dorwald; "Side Reactions in Organic Synthesis: A Guide to Successful Synthesis Design," Chapter 1, 2005 Wiley-VCH Verlag GmbH & Co. KGaA, Wienheim, 32 pages.
Marc Lepeltier et al., "Efficient blue green organic light-emitting devices based on a monofluorinated heteroleptic Iridium(III) complex," Synthetic Metals, vol. 199, 2015, pp. 139-146.
Stefan Bernhard, "The First Six Years: A Report," Department of Chemistry, Princeton University, May 2008, 11 pages.
Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.
Ivaylo Ivanov et at, "Comparison of the INDO band structures of polyacetylene, polythiophene, polyfuran, and polypyrrole," Synthetic Metals, vol. 116, Issues 1-3, Jan. 1, 2001, pp. 111-114.
Zhi-Qiang Zhu et.al., "Harvesting All Electrogenerated Excitons through Metal Assisted Delayed Fluorescent Materials," Adv. Mater. 27 (2015) 2533-2537.
Zhi-Qiang Zhu et. al.. "Efficient Cyclometalated Platinum(II) Complex with Superior Operational Stability," Adv. Mater. 29 (2017) 1605002.
Chew, S. et al.: Photoluminescence and electroluminescence of a new blue-emitting homoleptic iridium complex. Applied Phys. Letters; 2006, vol. 88, pp. 093510-1-093510-3.
Xin Li et al., "Density functional theory study of photophysical properties of iridium (III) complexes with phenylisoquinoline and phenylpyridine ligands", The Journal of Physical Chemistry C, 2011, vol. 115, No. 42, pp. 20722-20731.
Sylvia Bettington et al. "Tris-Cyclometalated Iridium(III) Complexes of Carbazole(fluorenyl)pyridine Ligands: Synthesis, Redox and Photophysical Properties, and Electrophosphorescent Light-Emitting Diodes" Chemistry: A European Journal, 2007, vol. 13, pp. 1423-1431.
Christoph Ulbricht et al., "Synthesis and Characterization of Oxetane-Functionalized Phosphorescent Ir(III)—Complexes", Macromol. Chem. Phys. 2009, 210, pp. 531-541.
Dan Wang et al., "Carbazole and arylamine functionalized iridium complexes for efficient electro-phosphorescent light-emitting diodes", Inorganica Chimica Acta 370 (2011) pp. 340-345.
Huaijun Tang et al., "Novel yellow phosphorescent iridium complexes containing a carbazoleeoxadiazole unit used in polymeric light-emitting diodes", Dyes and Pigments 91 (2011) pp. 413-421.
Hoe-Joo Seo et al., "Blue phosphorescent iridium(III) complexes containing carbazole-functionalized phenyl pyridine for organic light-emitting diodes: energy transfer from carbazolyl moieties to iridium(III) cores", RSC Advances, 2011, 1, pp. 755-757.
Jack W. Levell et al., "Carbazole/iridium dendrimer side-chain phosphorescent copolymers for efficient light emitting devices", New J. Chem., 2012, 36, pp. 407-413.
Z Liu et al., "Green and blue-green phosphorescent heteroleptic iridium complexes containing carbazole-functionalized beta-diketonate for non-doped organic light-emitting diodes", Organic Electronics 9 (2008) pp. 171-182.
Zhaowu Xu et al., "Synthesis and properties of iridium complexes based 1,3,4-oxadiazoles derivatives", Tetrahedron 64 (2008) pp. 1860-1867.
D.F. O'Brien et al., "Improved energy transfer in electrophosphorescent devices," Appl. Phys. Lett., vol. 74, No. 3, Jan. 18, 1999, pp. 442-444.
Vadim Adamovich et al., "High efficiency single dopant white electrophosphorescent light emitting diodes," New J. Chem., 2002, 26, pp. 1171-1178.

(56) References Cited

OTHER PUBLICATIONS

Kwon-Hyeon Kim et al., "Controlling Emitting Dipole Orientation with Methyl Substituents on Main Ligand of Iridium Complexes for Highly Efficient Phosphorescent Organic Light-Emitting Diodes", Adv. Optical Mater. 2015, 3, pp. 1191-1196.

Matthew J. Jurow et al., "Understanding and predicting the orientation of heteroleptic phosphors in organic light-emitting materials", Nature Materials, vol. 15, Jan. 2016, pp. 85-93.

Kwon-Hyeon Kim et al., "Crystal Organic Light-Emitting Diodes with Perfectly Oriented Non-Doped Pt-Based Emitting Layer", Adv. Mater. 2016, 28, pp. 2526-2532.

* cited by examiner

TETRADENTATE METAL COMPLEXES WITH CARBON GROUP BRIDGING LIGANDS

CROSS-REFERENCE TO RELATED APPLICATION

This application claims priority to U.S. Provisional Patent Application No. 62/077,431 entitled "TETRADENTATE METAL COMPLEXES WITH CARBON GROUP BRIDGING LIGANDS" filed on Nov. 10, 2014, which is hereby incorporated by reference in its entirety.

TECHNICAL FIELD

The present disclosure relates to multidentate metal complexes suitable for use as phosphorescent or delayed fluorescent and phosphorescent emitters in display and lighting applications.

BACKGROUND

Compounds capable of absorbing and/or emitting light can be ideally suited for use in a wide variety of optical and electroluminescent devices, including, for example, photo-absorbing devices such as solar- and photo-sensitive devices, organic light emitting diodes (OLEDs), photo-emitting devices, and devices capable of both photo-absorption and emission and as markers for bio-applications. Much research has been devoted to the discovery and optimization of organic and organometallic materials for using in optical and electroluminescent devices. Generally, research in this area aims to accomplish a number of goals, including improvements in absorption and emission efficiency and improvements in the stability of devices, as well as improvements in processing ability.

Despite significant advances in research devoted to optical and electro-optical materials (e.g., red and green phosphorescent organometallic materials are commercially available and have been used as phosphors in organic light emitting diodes (OLEDs), lighting and advanced displays), many currently available materials exhibit a number of disadvantages, including poor processing ability, inefficient emission or absorption, and less than ideal stability, among others.

Good blue emitters are particularly scarce, with one challenge being the stability of the blue devices. The choice of the host materials has an impact on the stability and the efficiency of the devices. The lowest triplet excited state energy of the blue phosphors is very high compared with that of the red and green phosphors, which means that the lowest triplet excited state energy of host materials for the blue devices should be even higher. Thus, one of the problems is that there are limited host materials to be used for the blue devices. Accordingly, a need exists for new materials which exhibit improved performance in optical emitting and absorbing applications.

SUMMARY

The present disclosure relates to metal complexes suitable for use as emitters in organic light emitting diodes (OLEDs), display and lighting applications.

Disclosed herein are complexes of Formula I:

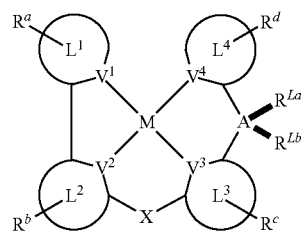

Formula I wherein:

M is Pt, Pd, or Au,

A is C, Si, or Ge, each of $L^1$, $L^2$, $L^3$, and $L^4$ is independently a substituted or an unsubstituted aryl, cycloalkyl, cycloalkenyl, heteroaryl, heterocyclyl, carbene, or N-heterocyclic carbene, each of $V^1$, $V^2$, $V^3$, and $V^4$ is coordinated with M and is independently N, C, P, B, or Si, X is $CH_2$, $CR^1R^2$, C=O, $SiH_2$, $SiR^1R^2$, $GeH_2$, $GeR^1R^2$, NH, $NR^3$, PH, $PR^3$, $R^3P$=O, $AsR^3$, $R^3As$=O, O, S, S=O, $SO_2$, Se, Se=O, $SeO_2$, BH, $BR^3$, $R^3Bi$=O, BiH, or $BiR^3$, each of $R^{La}$ and $R^{Lb}$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and $R^{La}$ and $R^{Lb}$ are optionally joined to form a fused ring, each of $R^a$, $R^b$, $R^c$, and $R^d$ is independently present or absent, and if present each of $R^b$ and $R^c$ independently represents mono-, di-, or tri-substitutions, and each of $R^a$ and $R^d$ independently represents mono-, di-, tri-, or tetra-substitutions, and each $R^a$, $R^b$, $R^c$, and $R^d$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and each of $R^1$, $R^2$, and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, the complex has the structure of Formula II, Formula III, Formula IV or Formula V:

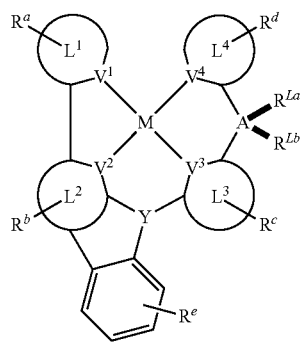

Formula II

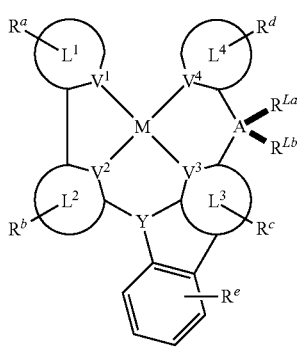

Formula III

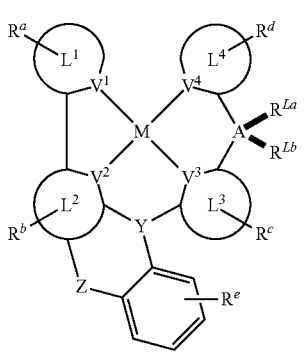

Formula IV

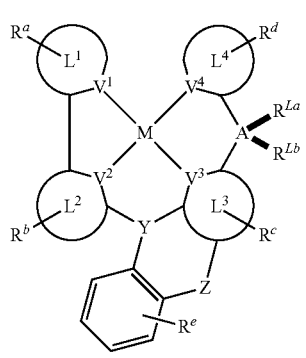

Formula V wherein:

M is Pt, Pd, or Au,

A is C, Si, or Ge, each of $L^1$, $L^2$, $L^3$, and $L^4$ is independently substituted or unsubstituted aryl, cycloalkyl, cycloalkenyl, heteroaryl, heterocyclyl, carbene, or N-heterocyclic carbene, each of $V^1$, $V^2$, $V^3$, and $V^4$ is coordinated with M and is independently N, C, P, B, or Si, Y is CH, $CR^1$, SiH, $SiR^1$, GeH, $GeR^1$, N, P, P=O, As, As=O, B, Bi, Bi=O, Z is $CH_2$, $CR^1R^2$, C=O, $SiR^1R^2$, $GeH_2$, $GeR^1R^2$, NH, $NR^3$, PH, $PR^3$, $R^3P$=O, $AsR^3$, $R^3As$=O, O, S, S=O, $SO_2$, Se, Se=O, $SeO_2$, BH, $BR^3$, $R^3Bi$=O, BiH, or $BiR^3$, each of $R^{La}$ and $R^{Lb}$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and $R^{La}$ and $R^{Lb}$ are optionally joined to form a fused ring, each of $R^a$, $R^b$, $R^c$, $R^d$, and $R^e$ is independently present or absent, and if present each of $R^a$, $R^b$, $R^c$, $R^d$, and $R^e$ independently represents mono-, di-, or tri-substitutions, and wherein each of $R^a$, $R^b$, $R^c$, $R^d$ and $R^e$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and each of $R^1$, $R^2$, and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, the complex has the structure of Formula VI, Formula VII, Formula VIII and Formula IX:

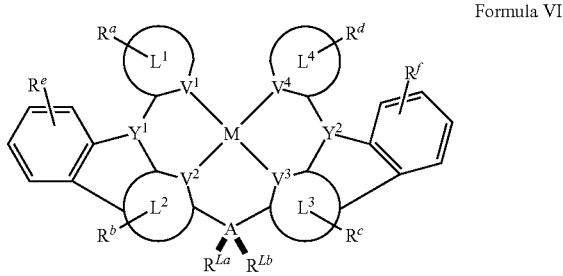

Formula VI

-continued

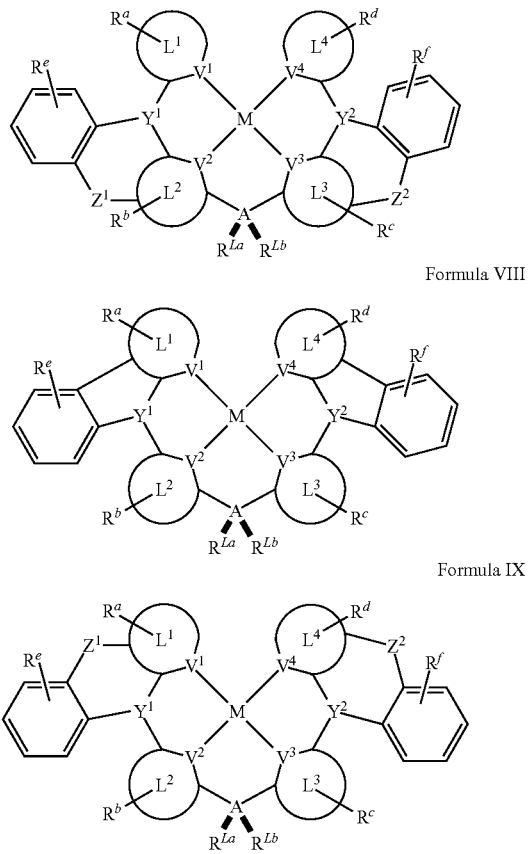

Formula VII

Formula VIII

Formula IX wherein:

M is Pt, Pd, or Au,

A is C, Si, or Ge, each of $L^1$, $L^2$, $L^3$, and $L^4$ is independently a substituted or an unsubstituted aryl, cycloalkyl, cycloalkenyl, heteroaryl, heterocyclyl, carbene, or N-heterocyclic carbene, each of $V^1$, $V^2$, $V^3$, and $V^4$ is coordinated with M and is independently N, C, P, B, or Si, each of $Y^1$ and $Y^2$ is independently CH, $CR^1$, SiH, $SiR^1$, GeH, $GeR^1$, N, P, P=O, As, As=O, B, Bi, or Bi=O, each of $Z^1$ and $Z^2$ is independently $CH_2$, $CR^1R^2$, C=O, $SiR^1R^2$, $GeH_2$, $GeR^1R^2$, NH, $NR^3$, PH, $PR^3$, $R^3P$=O, $AsR^3$, $R^3As$=O, O, S, S=O, $SO_2$, Se, Se=O, $SeO_2$, BH, $BR^3$, $R^3Bi$=O, BiH, or $BiR^3$, each of $R^{La}$ and $R^{Lb}$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and $R^{La}$ and $R^{Lb}$ are optionally joined to form a fused ring, each of $R^a$, $R^b$, $R^c$, $R^d$, $R^e$, and $R^f$ is independently present or absent, and if present each of $R^b$, $R^c$, $R^e$ and $R^f$ independently represents mono-, di-, or tri-substitutions, each of $R^a$ and $R^d$ independently represents mono-, di-, tri-, or tetra-substitutions, and each of $R^a$, $R^b$, $R^c$, $R^d$, $R^e$ and $R^f$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and $R^1$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

Also disclosed herein are compositions including one or more compounds disclosed herein.

Also disclosed herein are devices, such as OLEDs, including one or more compounds or compositions disclosed herein.

Figure 1:
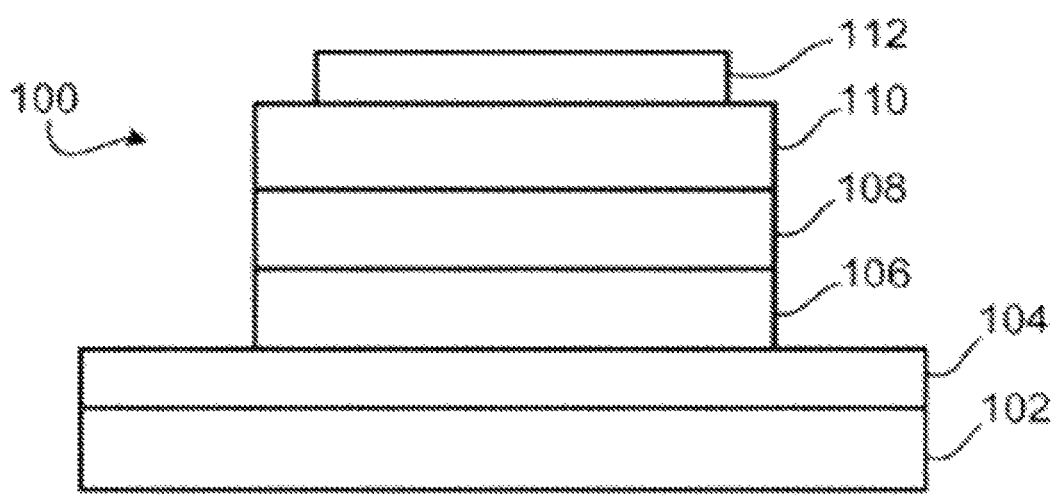
FIG. 1 depicts a device including a metal complex as disclosed herein.

Additional aspects will be set forth in the description which follows. Advantages will be realized and attained by means of the elements and combinations particularly pointed out in the claims. It is to be understood that both the foregoing general description and the following detailed description are exemplary and explanatory only and are not restrictive.

DETAILED DESCRIPTION

The present disclosure can be understood more readily by reference to the following detailed description and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing, example methods and materials are now described.

As used in the specification and the appended claims, the singular forms "a", "an", and "the" include plural referents unless the context clearly dictates otherwise. Thus, for example, reference to "a component" includes mixtures of two or more components.

As used herein, the terms "optional" or "optionally" means that the subsequently described event or circumstance may or may not occur, and that the description includes instances where said event or circumstance occurs and instances where it does not.

Disclosed are the components to be used to prepare the compositions described herein as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions. Thus, if there are a variety of additional steps that can be performed it is understood that each of these additional steps can be performed with any specific embodiment or combination of embodiments of the methods.

As referred to herein, a linking atom or group can connect two atoms such as, for example, a N atom and a C atom. A linking atome or group is in one aspect disclosed as X, Y, $Y^1$, $Y^2$, and/or Z herein. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties include amine, amide, thiol, aryl, heteroaryl, cycloalkyl, and heterocyclyl moieties.

The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "A", "$A^1$", "$A^2$", "$A^3$", and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $-NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula $-OC(O)A^1$ or $-C(O)OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula $-(A^1O(O)C-A^2-C(O)O)_a-$, or $-(A^1O(O)C-A^2-OC(O))_a-$, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula $-(A^1O-A^2O)_a-$, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "polymeric" includes polyalkylene, polyether, polyester, and other groups with repeating units, such as, but not limited to $-(CH_2O)_n-CH_3$, $-(CH_2CH_2O)_n-CH_3$, $-[CH_2CH(CH_3)]_n-CH_3$, $-[CH_2CH(COOCH_3)]_n-CH_3$, $-[CH_2CH(COOCH_2CH_3)]_n-CH_3$, and $-[CH_2CH(COO^tBu)]_n-CH_3$, where n is an integer (e.g., n>1 or n>2).

The term "halide" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula $-N_3$.

The term "nitro" as used herein is represented by the formula $-NO_2$.

The term "nitrile" as used herein is represented by the formula —CN.

The term "silyl" as used herein is represented by the formula $-SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas $-S(O)A^1$, $-S(O)_2A^1$, $-OS(O)_2A^1$, or $-OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula $-S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

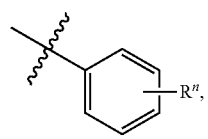

which is understood to be equivalent to a formula:

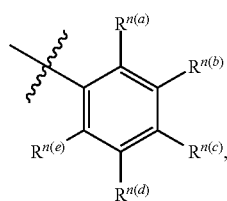

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Several references to R, $R^1$, $R^2$, $R^3$, $R^4$, $R^5$, $R^6$, etc. are made in chemical structures and moieties disclosed and described herein. Any description of R, $R^1$, $R^2$, $R^3$, $R^4$, $R^5$, $R^6$, etc. in the specification is applicable to any structure or moiety reciting R, $R^1$, $R^2$, $R^3$, $R^4$, $R^5$, $R^6$, etc. respectively.

1. Compounds

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

Excitons decay from singlet excited states to ground state to yield prompt luminescence, which is fluorescence. Excitons decay from triplet excited states to ground state to generate luminescence, which is phosphorescence. Because the strong spin-orbit coupling of the heavy metal atom enhances intersystem crossing (ISC) very efficiently between singlet and triplet excited state, phosphorescent metal complexes, such as platinum complexes, have demonstrated their potential to harvest both the singlet and triplet excitons to achieve 100% internal quantum efficiency. Thus phosphorescent metal complexes are good candidates as dopants in the emissive layer of organic light emitting devices (OLEDs) and a great deal of attention has been received both in the academic and industrial fields. And much achievement has been made in the past decade to lead to the lucrative commercialization of the technology, for example, OLEDs have been used in advanced displays in smart phones, televisions and digital cameras.

However, to date, blue electroluminescent devices remain the most challenging area of this technology, due at least in part to instability of the blue devices. It is generally understood that the choice of host materials is a factor in the stability of the blue devices. But the lowest triplet excited state ($T_1$) energy of the blue phosphors is high, which generally means that the lowest triplet excited state ($T_1$) energy of host materials for the blue devices should be even higher. This leads to difficulty in the development of the host materials for the blue devices.

This disclosure provides a materials design route by introducing a carbon group (C, Si, Ge) bridging to the ligand of the metal complexes. As described herein, it was found that the photoluminescence spectrum of the carbon bridging Pt complex had a significant blue shift comparing to the nitrogen bridging one with the same emissive group. It was also found that chemical structures of the emissive luminophores and the ligands could be modified, and also the metal could be changed to adjust the singlet states energy and the triplet states energy of the metal complexes, which all could affect the optical properties of the complexes.

The metal complexes described herein can be tailored or tuned to a specific application that requires a particular emission or absorption characteristic. The optical properties of the metal complexes in this disclosure can be tuned by varying the structure of the ligand surrounding the metal center or varying the structure of fluorescent luminophore(s) on the ligands. For example, the metal complexes having a ligand with electron donating substituents or electron withdrawing substituents can generally exhibit different optical properties, including emission and absorption spectra. The color of the metal complexes can be tuned by modifying the conjugated groups on the fluorescent luminophores and ligands.

The emission of such complexes can be tuned (e.g., from the ultraviolet to near-infrared) by, for example, modifying the ligand or fluorescent luminophore structure. A fluorescent luminophore is a group of atoms in an organic molecule that can absorb energy to generate singlet excited state(s). The singlet exciton(s) produce(s) decay rapidly to yield prompt luminescence. In one aspect, the complexes can provide emission over a majority of the visible spectrum. In a specific example, the complexes described herein can emit light over a range of from about 400 nm to about 700 nm. In another aspect, the complexes have improved stability and efficiency over traditional emission complexes. In yet another aspect, the complexes can be useful as luminescent labels in, for example, bio-applications, anti-cancer agents, emitters in organic light emitting diodes (OLEDs), or a combination thereof. In another aspect, the complexes can be useful in light emitting devices, such as, for example, compact fluorescent lamps (CFL), light emitting diodes (LEDs), incandescent lamps, and the like.

Disclosed herein are compounds or compound complexes comprising platinum, palladium or gold. The terms compound, compound complex, and complex are used interchangeably herein. In one aspect, the compounds disclosed herein have a neutral charge.

The compounds disclosed herein can exhibit desirable properties and have emission and/or absorption spectra that can be tuned via the selection of appropriate ligands. In another aspect, any one or more of the compounds, structures, or portions thereof, specifically recited herein may be excluded.

The compounds disclosed herein are suited for use in a wide variety of optical and electro-optical devices, including, but not limited to, photo-absorbing devices such as solar- and photo-sensitive devices, organic light emitting diodes (OLEDs), photo-emitting devices, or devices capable of both photo-absorption and emission and as markers for bio-applications.

As briefly described above, the disclosed compounds are platinum complexes. In one aspect, the compounds disclosed herein can be used as host materials for OLED applications, such as full color displays.

The compounds disclosed herein are useful in a variety of applications. As light emitting materials, the compounds can be useful in organic light emitting diodes (OLEDs), luminescent devices and displays, and other light emitting devices.

In another aspect, the compounds can provide improved efficiency and/or operational lifetimes in lighting devices, such as, for example, organic light emitting devices, as compared to conventional materials.

Compounds described herein can be made using a variety of methods, including, but not limited to those recited in the examples.

The compounds disclosed herein include delayed fluorescent emitters, phosphorescent emitters, or a combination thereof. In one aspect, the compounds disclosed herein are delayed fluorescent emitters. In another aspect, the compounds disclosed herein are phosphorescent emitters. In yet another aspect, a compound disclosed herein is both a delayed fluorescent emitter and a phosphorescent emitter.

Disclosed herein are complexes of Formula I:

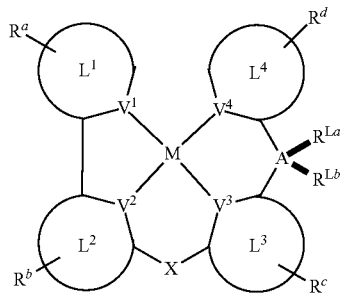

Formula I wherein:
M is Pt, Pd, or Au,
A is C, Si, or Ge,
each of $L^1$, $L^2$, $L^3$, and $L^4$ is independently a substituted or an unsubstituted aryl, cycloalkyl, cycloalkenyl, heteroaryl, heterocyclyl, carbene, or N-heterocyclic carbene,
each of $V^1$, $V^2$, $V^3$, and $V^4$ is coordinated with M and is independently N, C, P, B, or Si,
X is $CH_2$, $CR^1R^2$, C=O, $SiH_2$, $SiR^1R^2$, $GeH_2$, $GeR^1R^2$, NH, $NR^3$, PH, $PR^3$, $R^3P$=O, $AsR^3$, $R^3As$=O, O, S, S=O, $SO_2$, Se, Se=O, $SeO_2$, BH, $BR^3$, $R^3Bi$=O, BiH, or $BiR^3$,
each of $R^{La}$ and $R^{Lb}$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and $R^{La}$ and $R^{Lb}$ are optionally joined to form a fused ring,
each of $R^a$, $R^b$, $R^c$, and $R^d$ is independently present or absent, and if present each of $R^b$ and $R^c$ independently represents mono-, di-, or tri-substitutions, each of $R^a$ and $R^d$ independently represents mono-, di-, tri-, or tetra-substitutions, and each of $R^a$, $R^b$, $R^c$, and $R^d$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and
each of $R^1$, $R^2$, and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, the complex has the structure of Formula II, Formula III, Formula IV or Formula V:

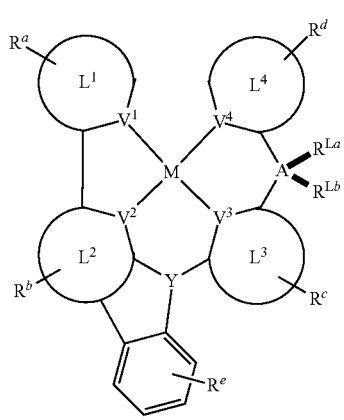

Formula II

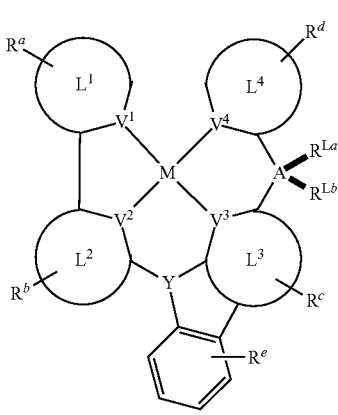

Formula III

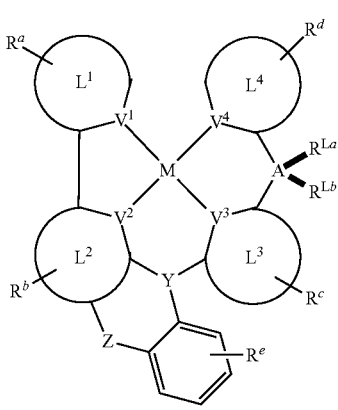

Formula IV

Formula V

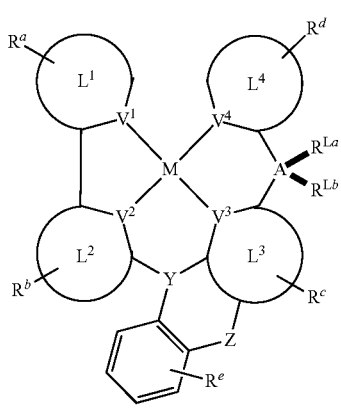

wherein:
M is Pt, Pd, or Au,
A is C, Si, or Ge,
each of $L^1$, $L^2$, $L^3$, and $L^4$ is independently a substituted or an unsubstituted aryl, cycloalkyl, cycloalkenyl, heteroaryl, heterocyclyl, carbene, or N-heterocyclic carbene,
each of $V^1$, $V^2$, $V^3$, and $V^4$ is coordinated with M and is independently N, C, P, B, or Si,
Y is CH, $CR^1$, SiH, $SiR^1$, GeH, $GeR^1$, N, P, P=O, As, As=O, B, Bi, or Bi=O,
Z is $CH_2$, $CR^1R^2$, C=O, $SiR^1R^2$, $GeH_2$, $GeR^1R^2$, NH, $NR^3$, PH, $PR^3$, $R^3P$=O, $AsR^3$, $R^3As$=O, O, S, S=O, $SO_2$, Se, Se=O, $SeO_2$, BH, $BR^3$, $R^3Bi$=O, BiH, or $BiR^3$,
each of $R^{La}$ and $R^{Lb}$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and $R^{La}$ and $R^{Lb}$ are optionally joined to form a fused ring,
each of $R^a$, $R^b$, $R^c$, $R^d$, and $R^e$ is independently present or absent, and if present each of $R^a$, $R^b$, $R^c$, $R^d$, $R^e$ independently represents mono-, di-, or tri-substitutions, and wherein each of $R^a$, $R^b$, $R^c$, $R^d$ and $R^e$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and
each of $R^1$, $R^2$, and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, the complex has the structure of Formula VI, Formula VII, Formula VIII and Formula IX:

Formula VI

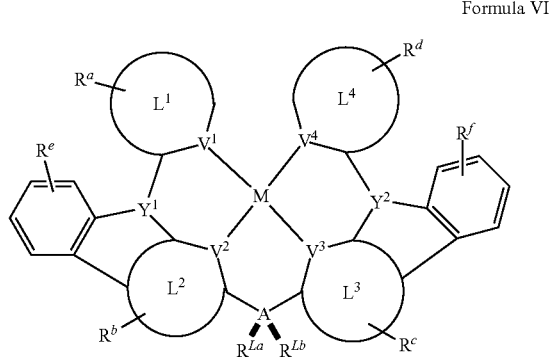

Formula VII

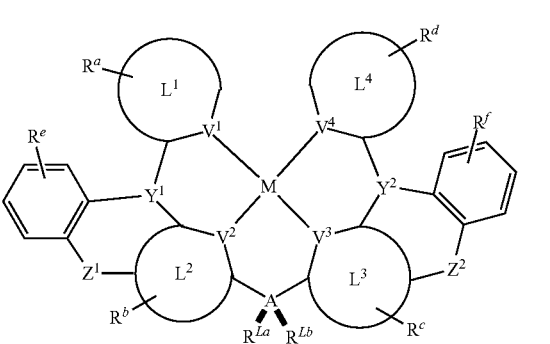

Formula VIII

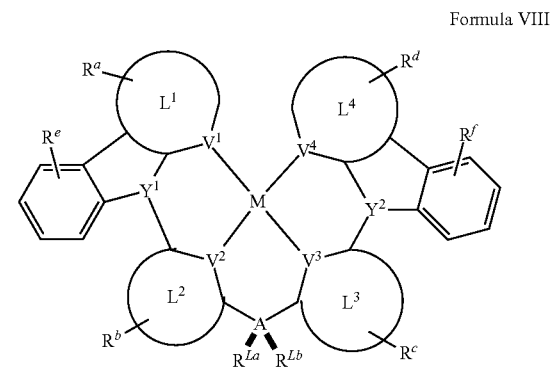

-continued

Formula IX

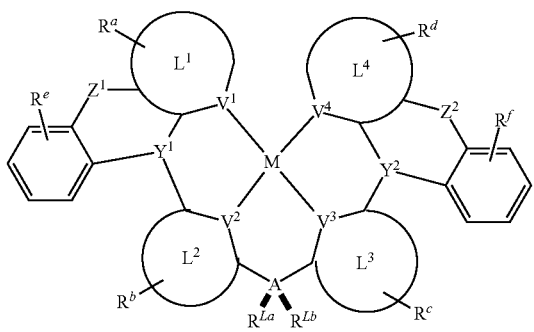

wherein:

M is Pt, Pd, or Au,

A is C, Si, or Ge, each of L¹, L², L³, and L⁴ is independently a substituted or an unsubstituted aryl, cycloalkyl, cycloalkenyl, heteroaryl, heterocyclyl, carbene, or N-heterocyclic carbene, each of V¹, V², V³, and V⁴ is coordinated with M and is independently N, C, P, B, or Si, each of Y¹ and Y² is independently CH, CR¹, SiH, SiR¹, GeH, GeR¹, N, P, P=O, As, As=O, B, Bi, or Bi=O, Z¹ and Z² is independently CH₂, CR¹R², C=O, SiR¹R², GeH₂, GeR¹R², NH, NR³, PH, PR³, R³P=O, AsR³, R³As=O, O, S, S=O, SO₂, Se, Se=O, SeO₂, BH, BR³, R³Bi=O, BiH, or BiR³, each of $R^{La}$ and $R^{Lb}$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and $R^{La}$ and $R^{Lb}$ are optionally joined to form a fused ring, each of $R^a$, $R^b$, $R^c$, $R^d$, $R^e$, and $R^f$ is present or absent, and if present each of $R^b$, $R^c$, $R^e$, and $R^f$ independently represents mono-, di-, or tri-substitutions, $R^a$ and $R^d$ independently represents mono-, di-, tri-, or tetra-substitutions, and each of $R^a$, $R^b$, $R^e$, $R^d$, $R^e$, and $R^f$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and each of R¹, R², and R³ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

For Formulas I-VI as described herein, groups may be defined as described below.

A. M Groups

In one aspect, M is Pt.

In another aspect, M is Pd.

In yet another aspect, M is Au.

B. A Groups

In one aspect, A is C.

In another aspect, A is Si.

In yet another aspect, A is Ge.

C. $R^{La}$ and $R^{Lb}$ Groups

In one aspect, each of $R^{La}$ and $R^{Lb}$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In another aspect, $R^{La}$ and $R^{Lb}$ are optionally joined to form a fused ring.

In one aspect, for any of the formulas illustrated in this disclosure,

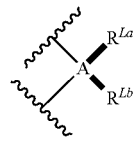

is one of following structures:

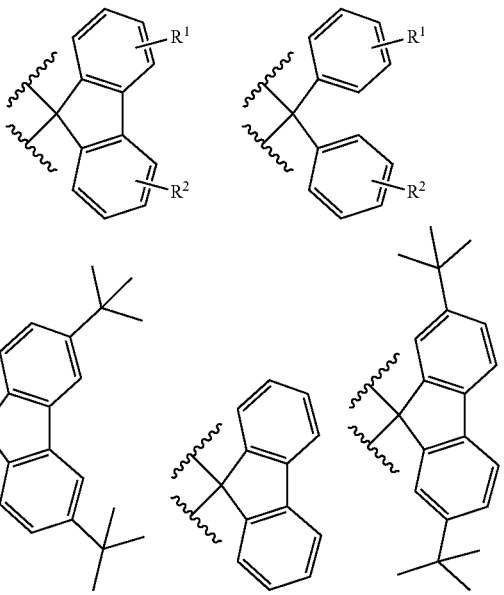

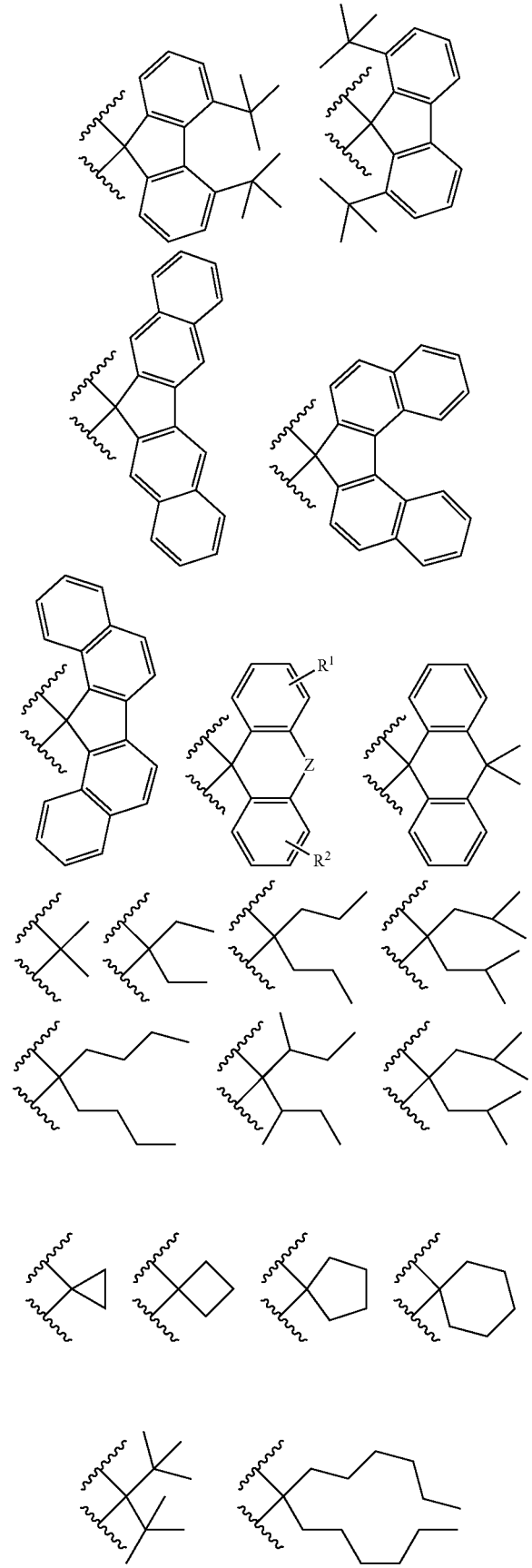
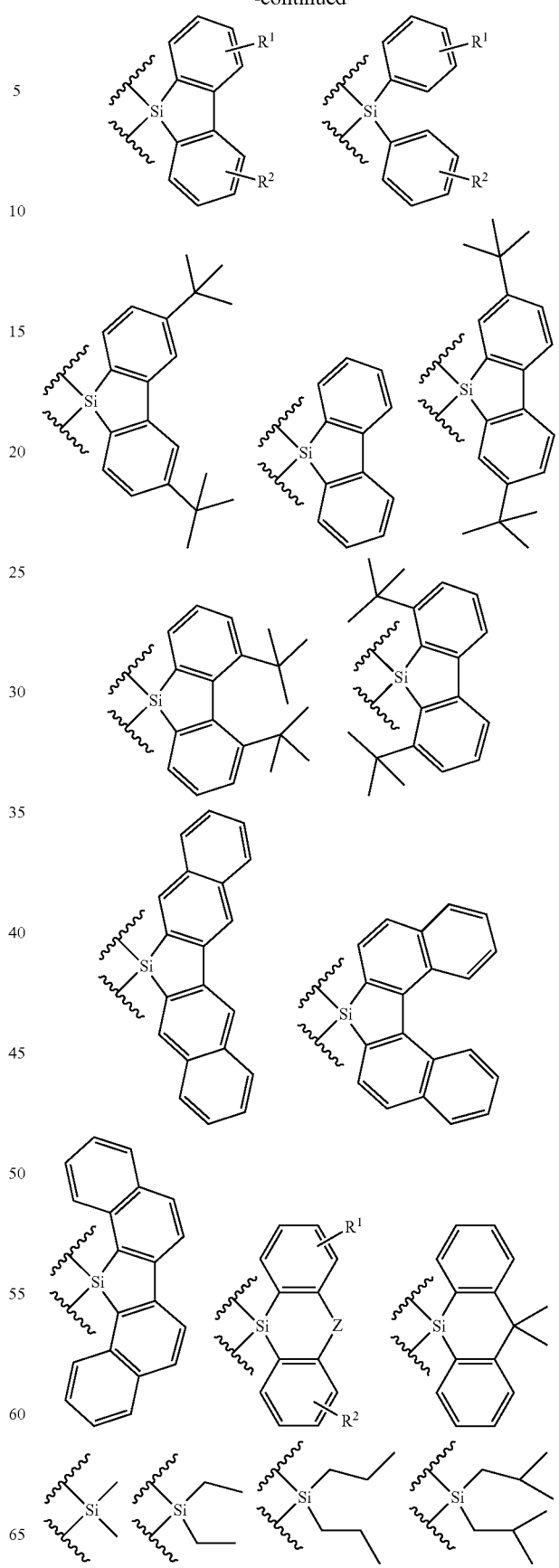

-continued

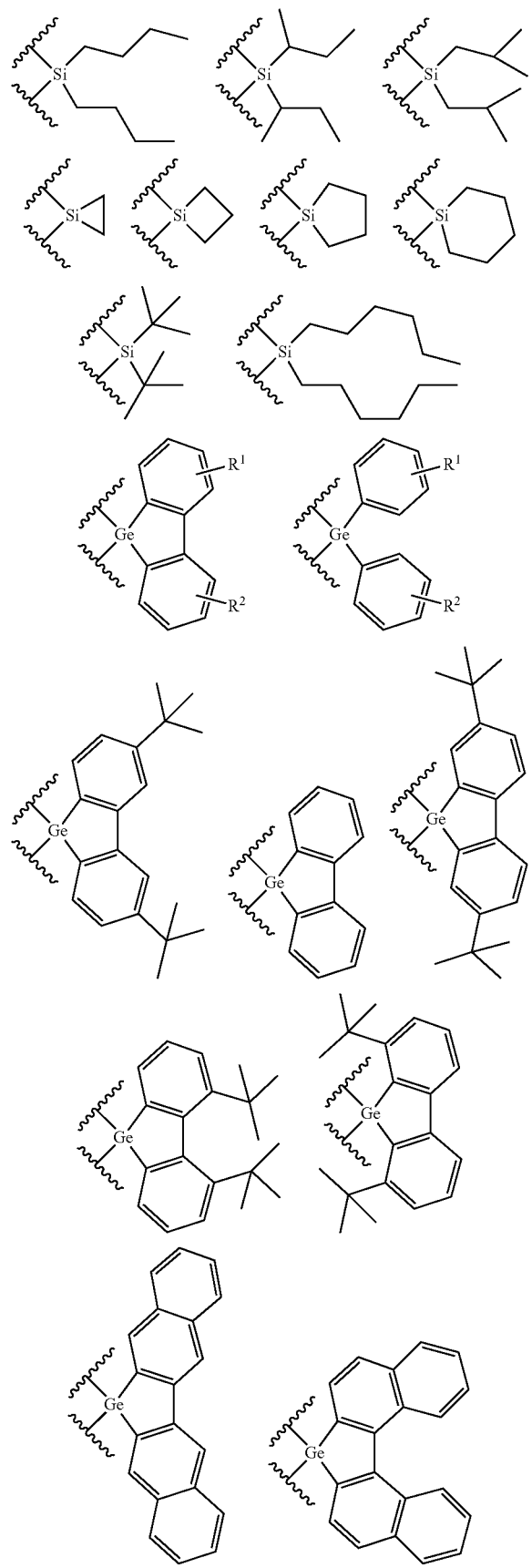

-continued

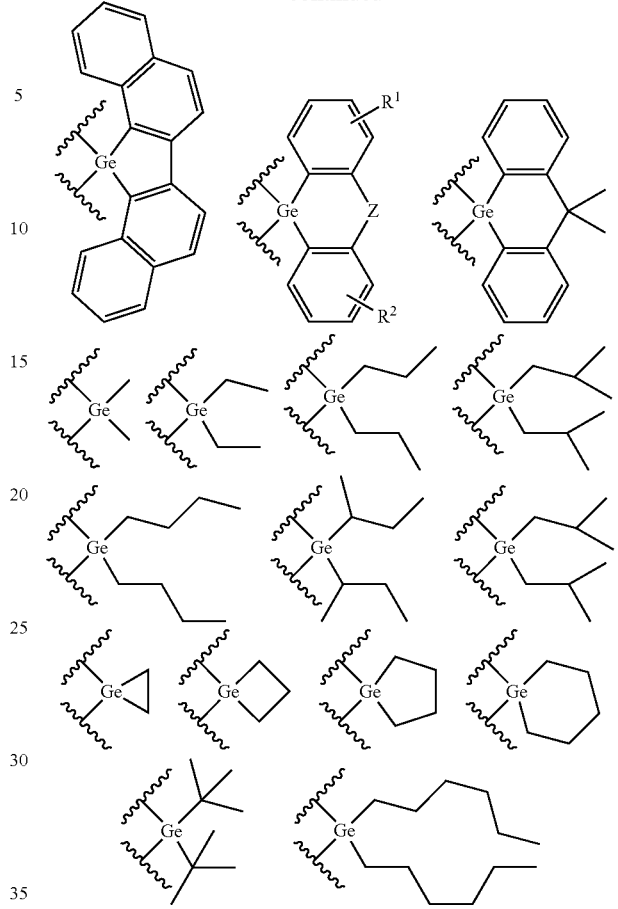

wherein:
Z is $CH_2$, $CR^1R^2$, $C=O$, $SiR^1R^2$, $GeH_2$, $GeR^1R^2$, NH, $NR^3$, PH, $PR^3$, $R^3P=O$, $AsR^3$, $R^3As=O$, O, S, $S=O$, $SO_2$, Se, $Se=O$, $SeO_2$, BH, $BR^3$, $R^3Bi=O$, BiH, or $BiR^3$, and each of $R^1$ and $R^2$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

D. V Groups

In one aspect, each of $V^1$, $V^2$, $V^3$, and $V^4$ is coordinated with M and is independently N, C, P, B, or Si.

In another aspect, each of $V^1$, $V^2$, $V^3$, and $V^4$ is independently N or C.

In yet another aspect, each of $V^1$, $V^2$, $V^3$, and $V^4$ is independently P or B.

In yet another aspect, each of $V^1$, $V^2$, $V^3$, and $V^4$ is Si.

E. X Groups

In one aspect, X is $CH_2$, $CR^1R^2$, $C=O$, $SiH_2$, $SiR^1R^2$, $GeH_2$, $GeR^1R^2$, NH, $NR^3$, PH, $PR^3$, $R^3P=O$, $AsR^3$, $R^3As=O$, O, S, $S=O$, $SO_2$, Se, $Se=O$, $SeO_2$, BH, $BR^3$, $R^3Bi=O$, BiH, or $BiR^3$.

In another aspect, X is O, S, or $CH_2$.

In yet another aspect, X is $CR^1R^2$, C=O, $SiH_2$, $SiR^1R^2$, $GeH_2$, or $GeR^1R^2$.

In yet another aspect, X is NR, $PR^3$, $R^3P$=O, $AsR^3$, or $R^3As$=O.

In yet another aspect, X is S=O, $SO_2$, Se, Se=O, or $SeO_2$.

In yet another aspect, X is $BR^3$, $R^3Bi$=O, or $BiR^3$.

F. Y Groups

In one aspect, Y is CH, $CR^1$, SiH, or $SiR^1$.

In another aspect, Y is GeH or $GeR^1$.

In yet another aspect, Y is N, P, P=O, As, or As=O.

In yet another aspect, Y is B, Bi, or Bi=O.

G. Z Groups

In one aspect, Z is $CH_2$, $CR^1R^2$, C=O, $SiR^1R^2$, $GeH_2$, $GeR^1R^2$, NH, $NR^3$, PH, $PR^3$, $R^3P$=O, $AsR^3$, $R^3As$=O, O, S, S=O, $SO_2$, Se, Se=O, $SeO_2$, BH, $BR^3$, $R^3Bi$=O, BiH, or $BiR^3$.

In another aspect, Z is O, S, or $CR^1R^2$.

H. L Groups

In one aspect, $L^1$ is aryl, cycloalkyl, cycloalkenyl, heteroaryl, heterocyclyl, carbene, or N-heterocyclic carbene. In one example, $L^1$ is aryl, cycloalkyl, cycloalkenyl, heteroaryl, or N-heterocyclyl. In another example, $L^1$ is aryl or heteroaryl. In yet another example, $L^1$ is aryl.

In one aspect, $L^2$ is aryl, cycloalkyl, cycloalkenyl, heteroaryl, heterocyclyl, carbene, or N-heterocyclic carbene. In one example, $L^2$ is aryl, cycloalkyl, cycloalkenyl, heteroaryl, or N-heterocyclyl. In another example, $L^2$ is aryl or heteroaryl. In yet another example, $L^2$ is aryl.

In one aspect, $L^3$ is aryl, cycloalkyl, cycloalkenyl, heteroaryl, heterocyclyl, carbene, or N-heterocyclic carbene. In one example, $L^3$ is aryl, cycloalkyl, cycloalkenyl, heteroaryl, or heterocyclyl. In another example, $L^3$ is aryl or heteroaryl. In yet another example, $L^3$ is aryl.

In one aspect, $L^4$ is aryl, cycloalkyl, cycloalkenyl, heteroaryl, heterocyclyl, carbene, or N-heterocyclic carbene. In one example, $L^4$ is aryl, cycloalkyl, cycloalkenyl, heteroaryl, or heterocyclyl. In another example, $L^4$ is aryl or heteroaryl. In yet another example, $L^4$ is heteroaryl. In yet another example, $L^4$ is heterocyclyl. It is understood that $V^4$ can be a part of $L^4$ and is intended to be included the description of $L^4$ above.

In one aspect, for any of the formulas disclosed herein, each of

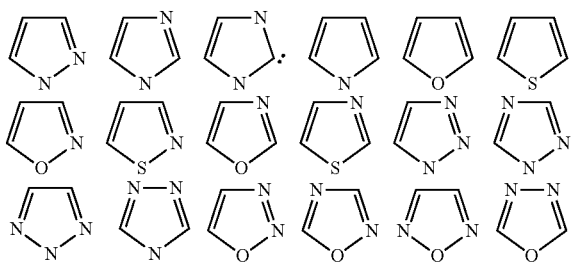

is independently one following structures:

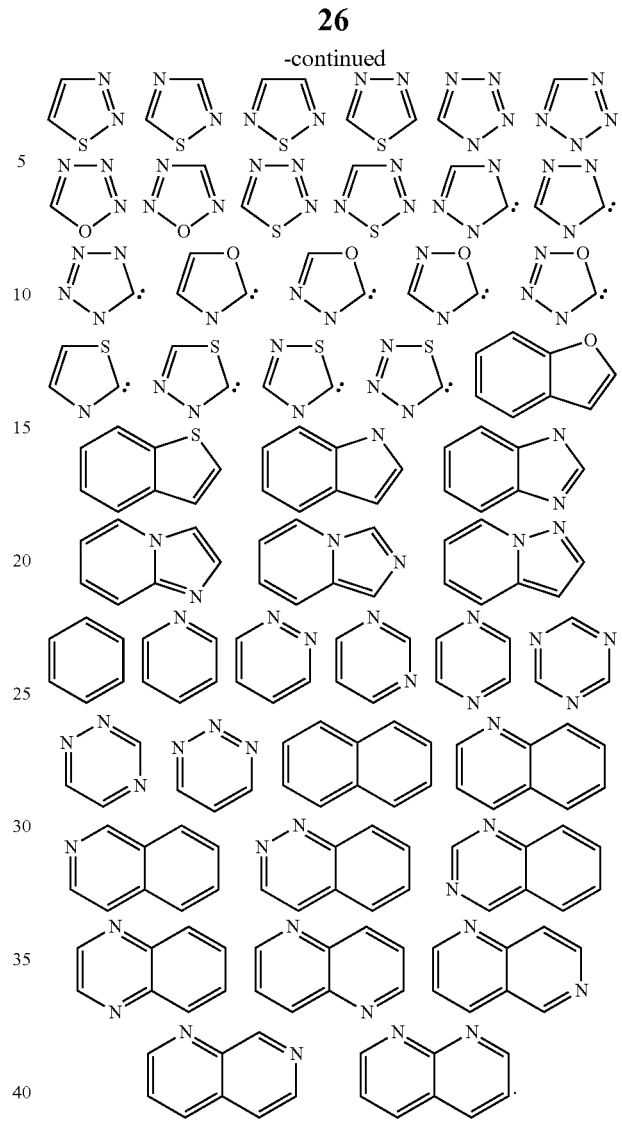

It is understood that one or more of $R^a$, $R^b$, $R^c$, $R^d$, $R^e$, and $R^f$ as described herein can be bonded to one of the above structures as permitted by valency.

In one aspect,

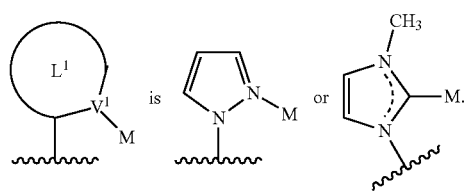

In one aspect,

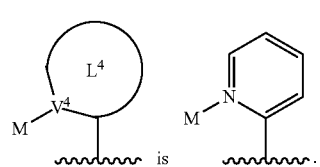

In one aspect, for any of the formulas illustrated in this disclosure, each of
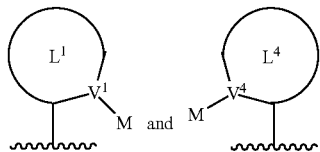
is independently one of following structures:
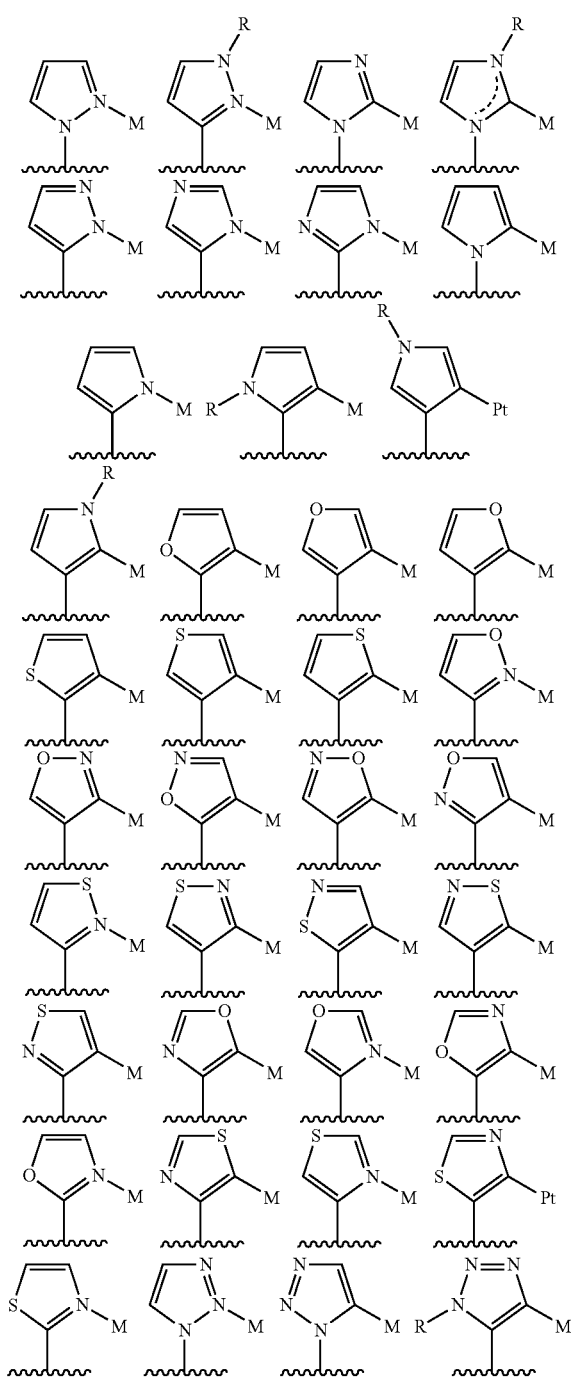
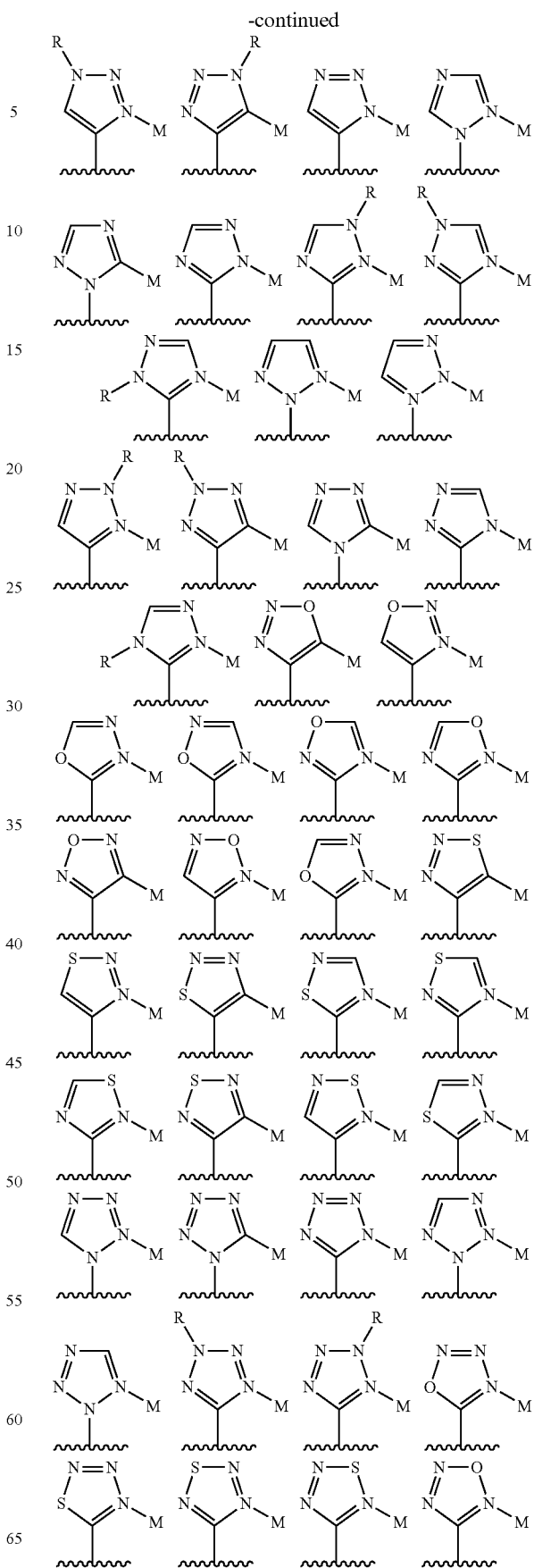

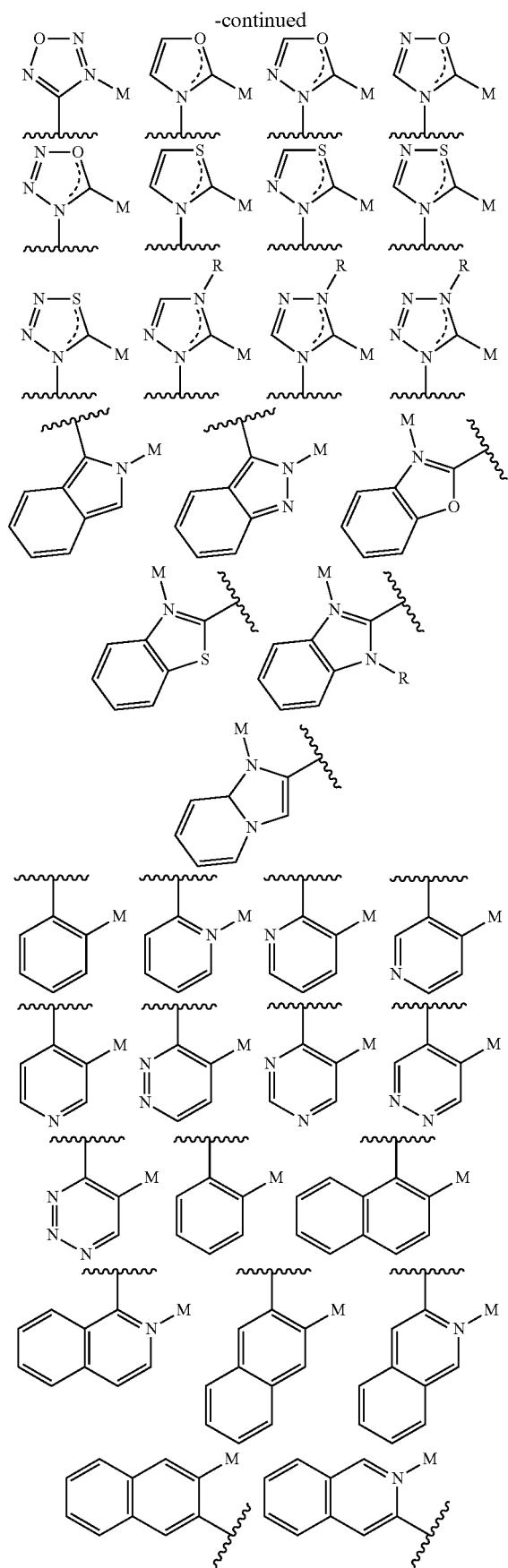
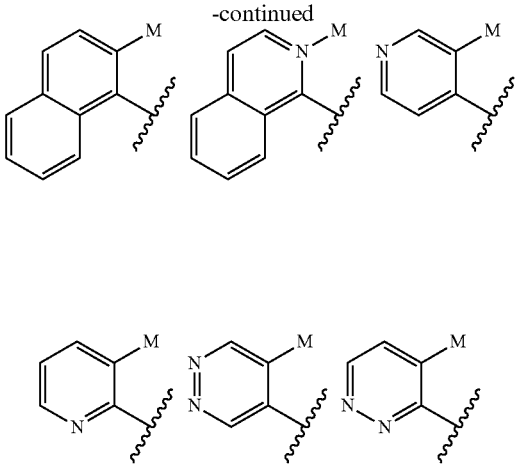

wherein R is hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect,

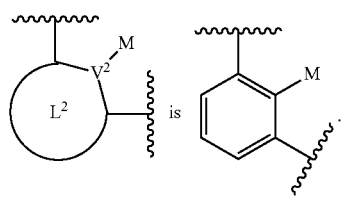

In one aspect,

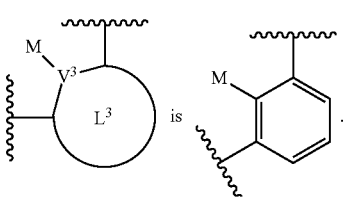

In one aspect, for any of the formulas disclosed herein, each of

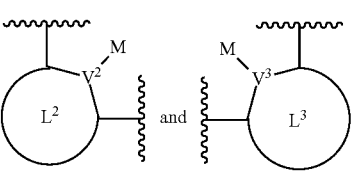

is independently one of the following structures:

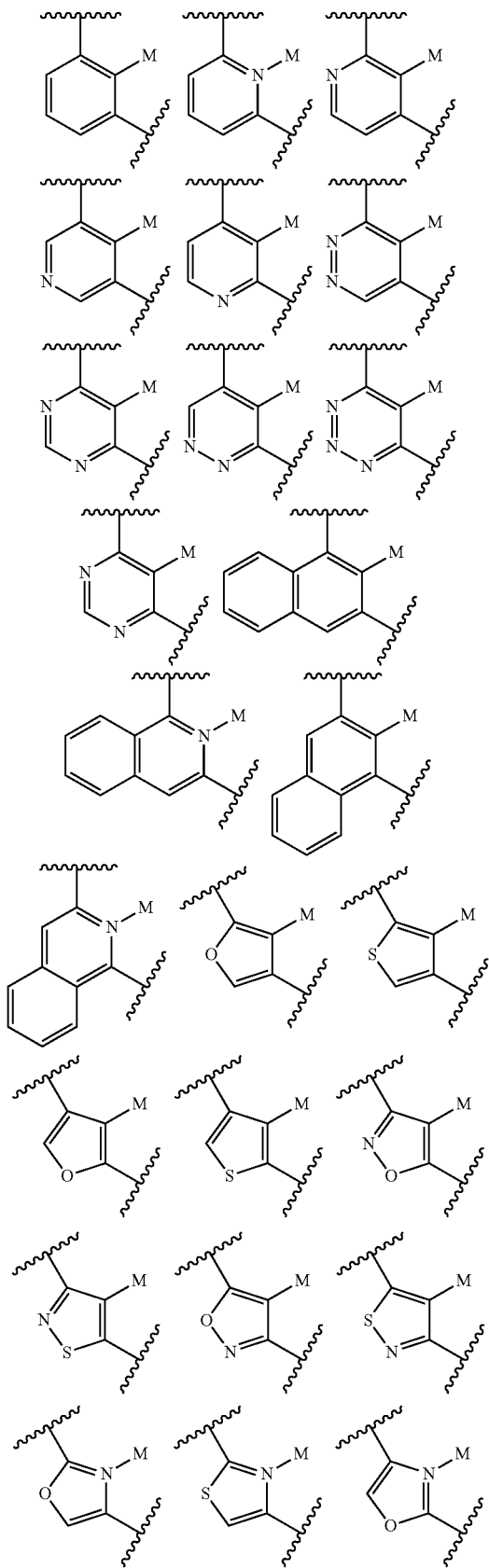
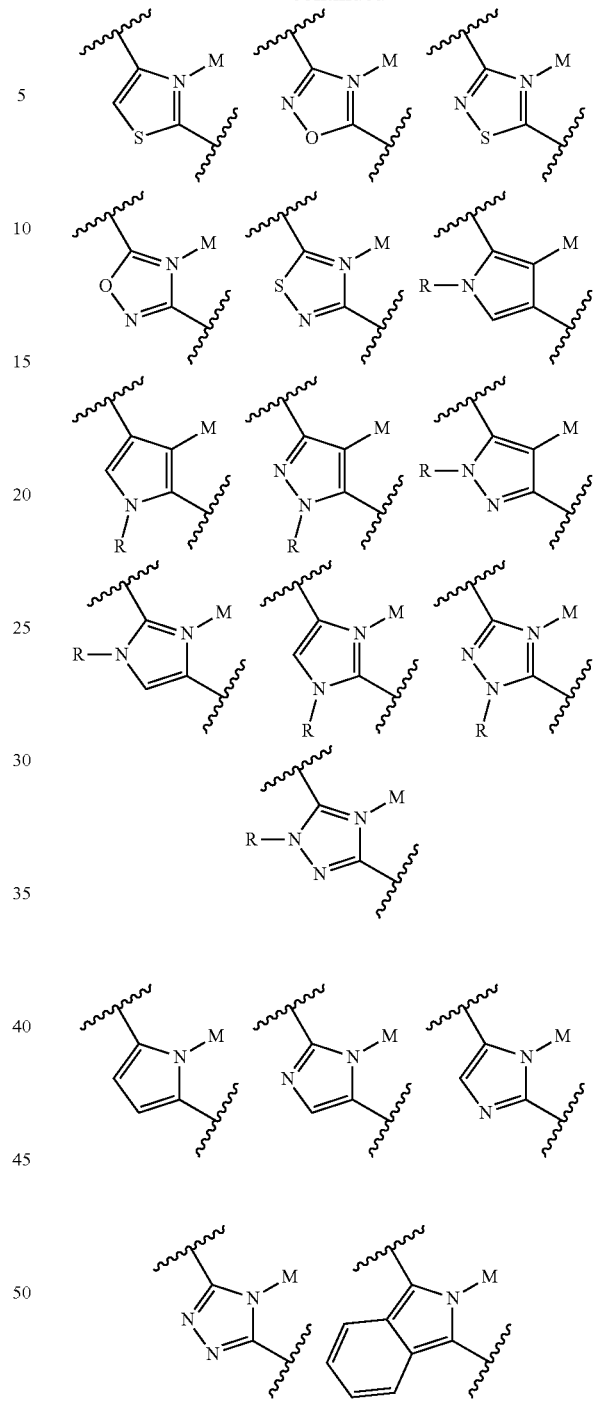

wherein R is hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, for any of the formulas disclosed herein, each of
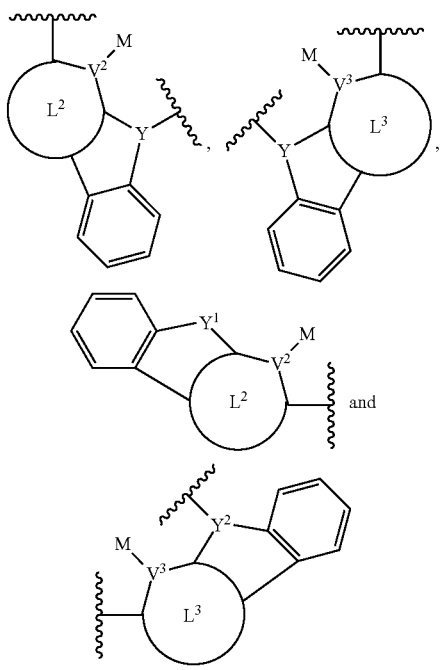
is independently one of the following structures:
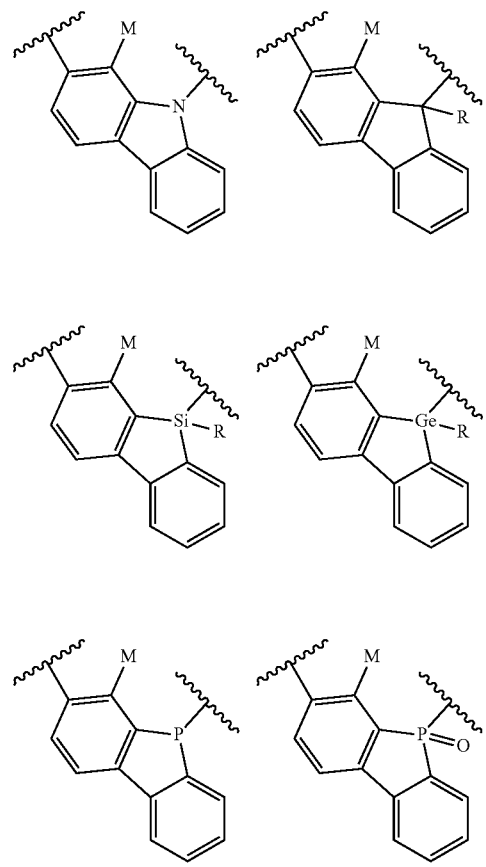
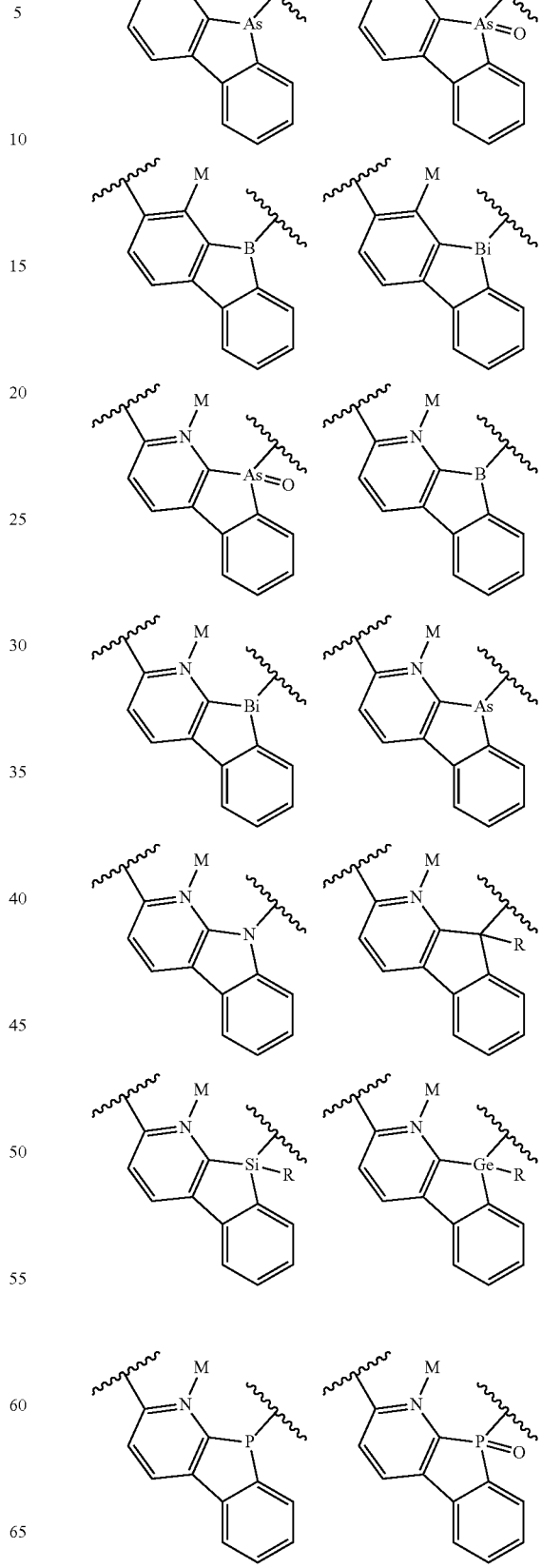

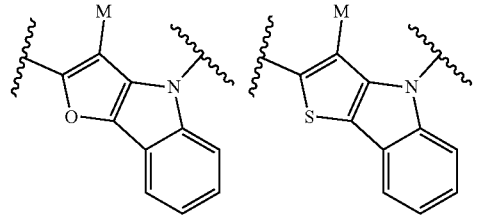
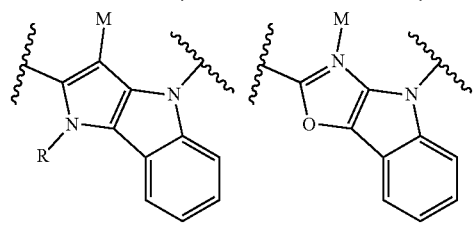
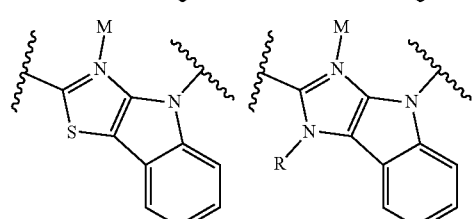
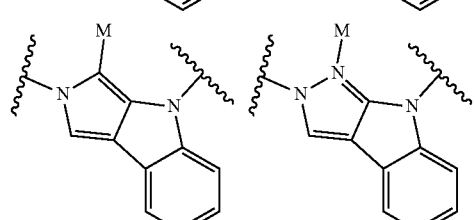
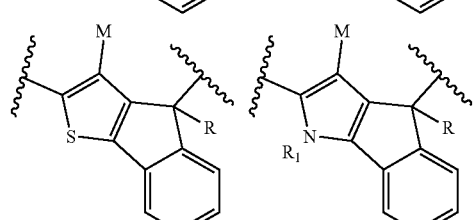
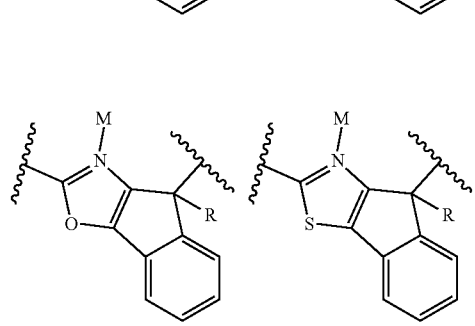
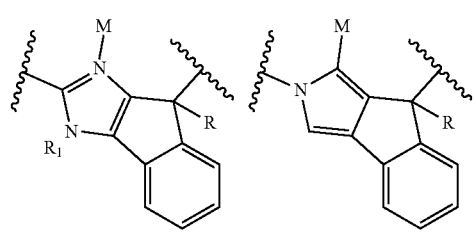

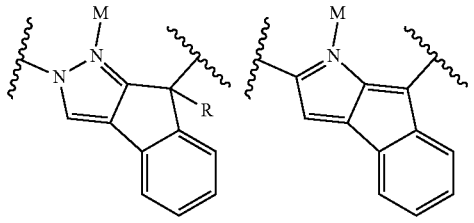
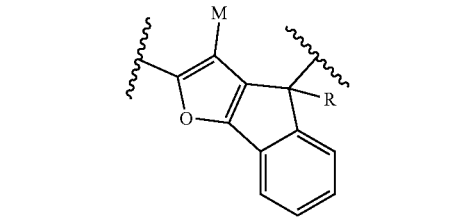

wherein R is hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, for any of the formulas disclosed herein, each of

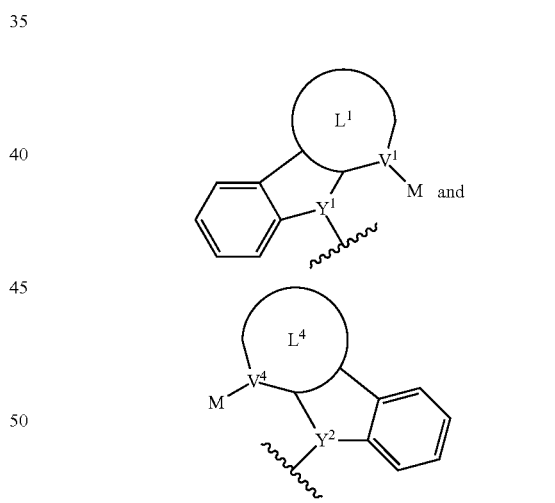

is independently one of the following structures:

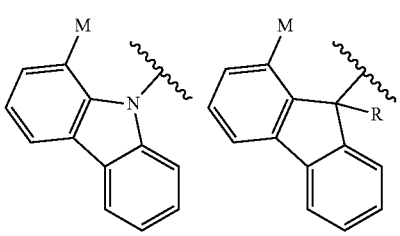

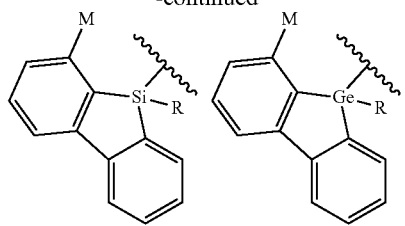
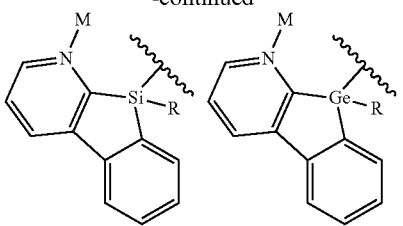
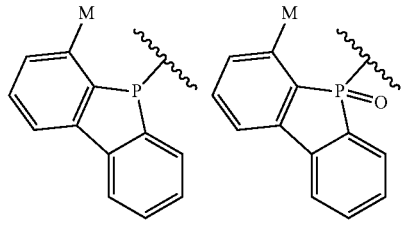
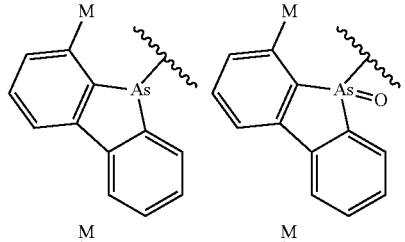
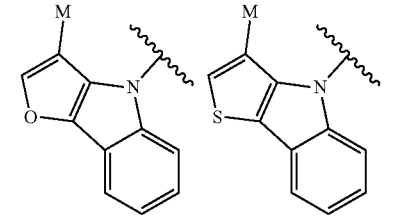
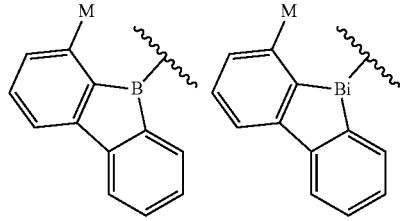
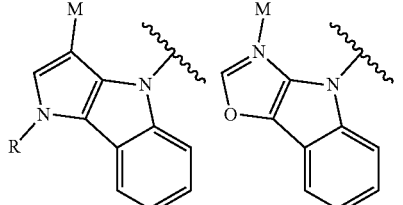
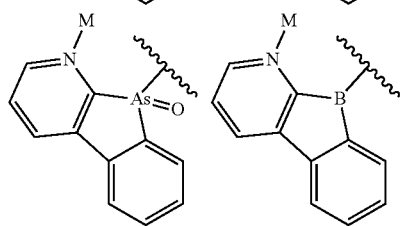
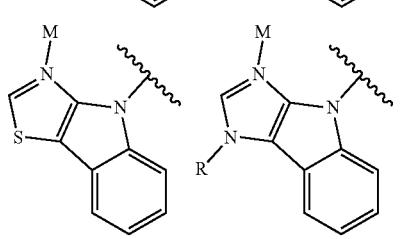
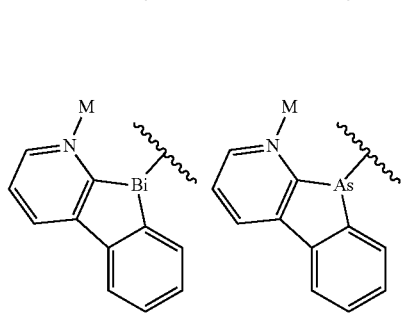
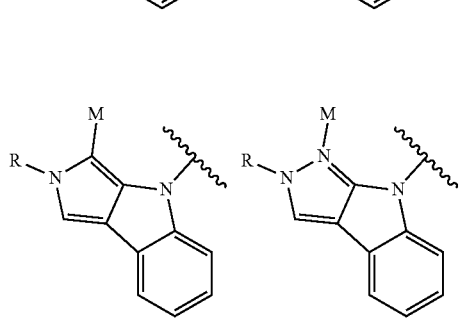
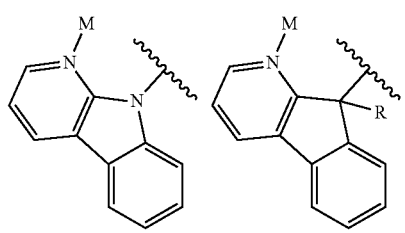
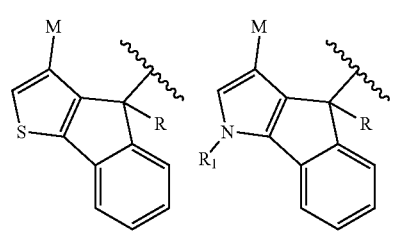

-continued

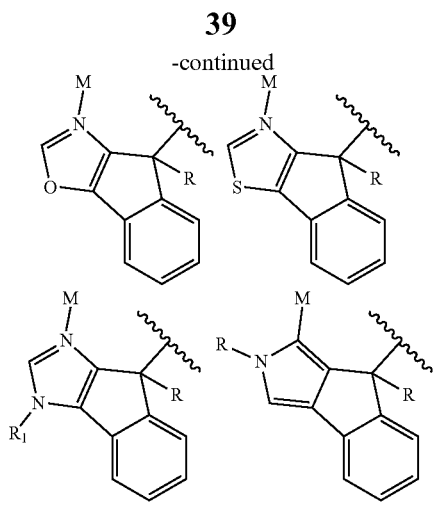

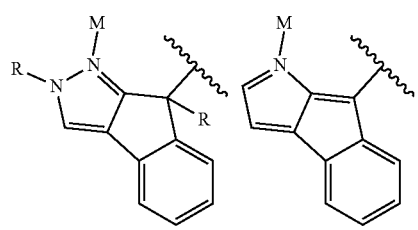

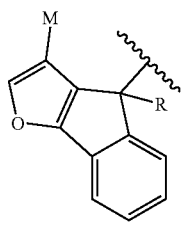

wherein R is hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, for any of the formulas disclosed herein, each of

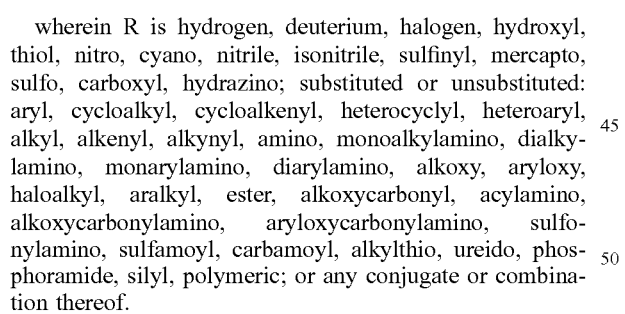

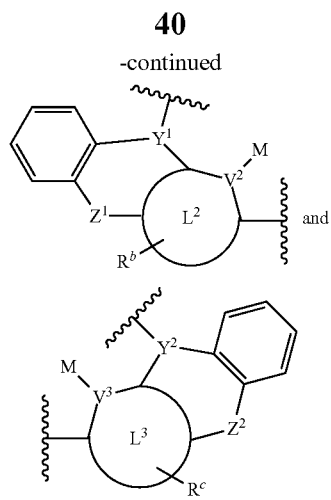

is independently one of the following structures:

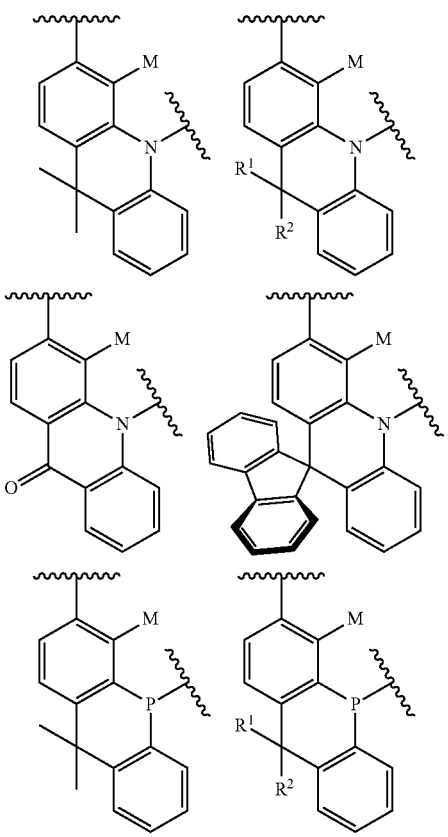

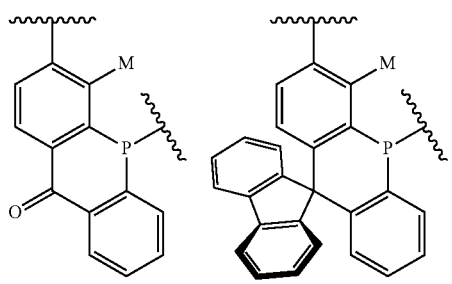

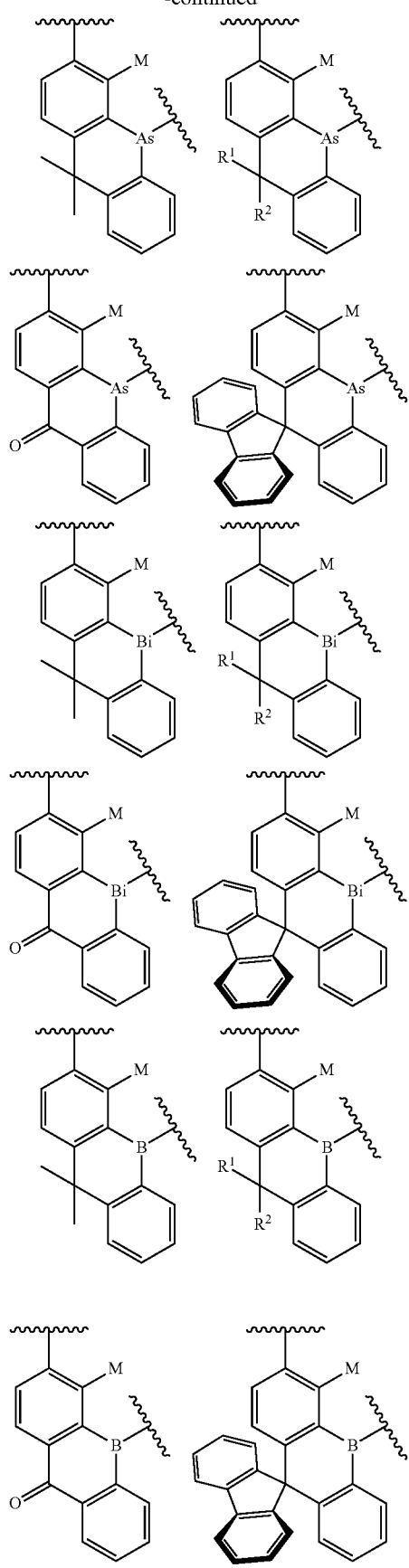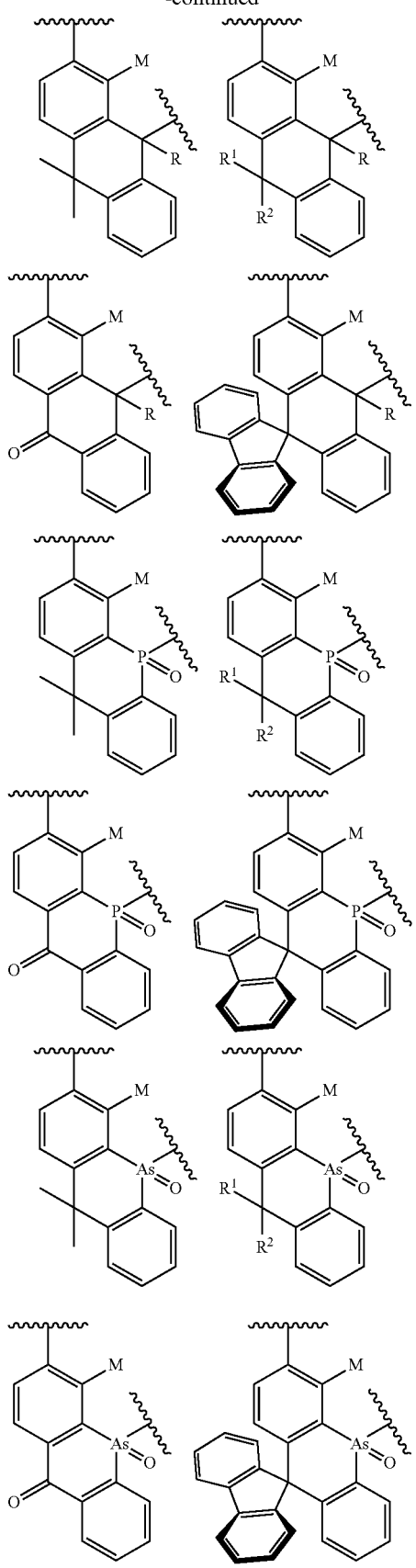

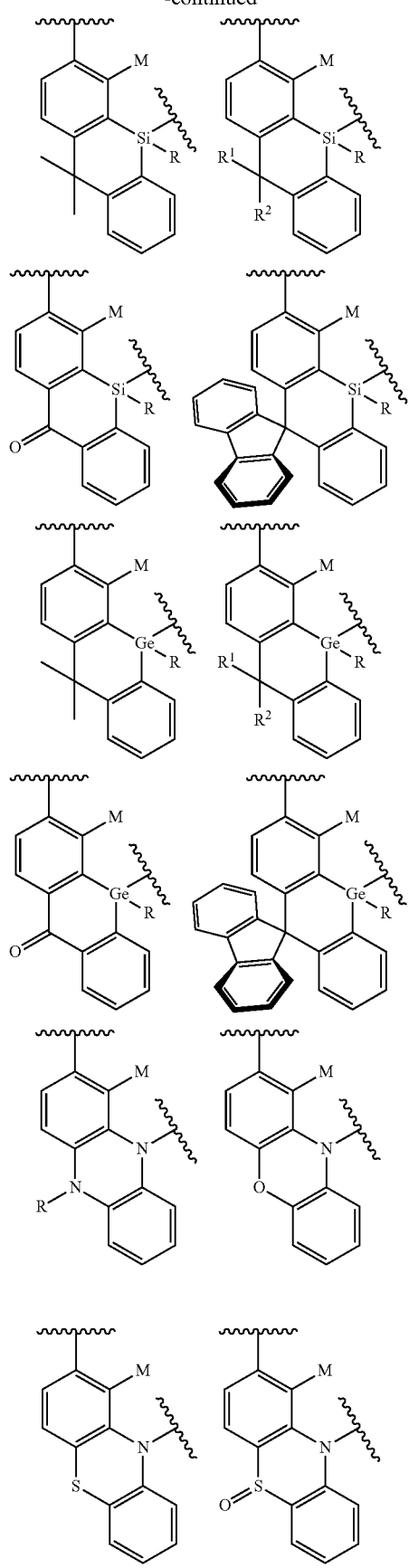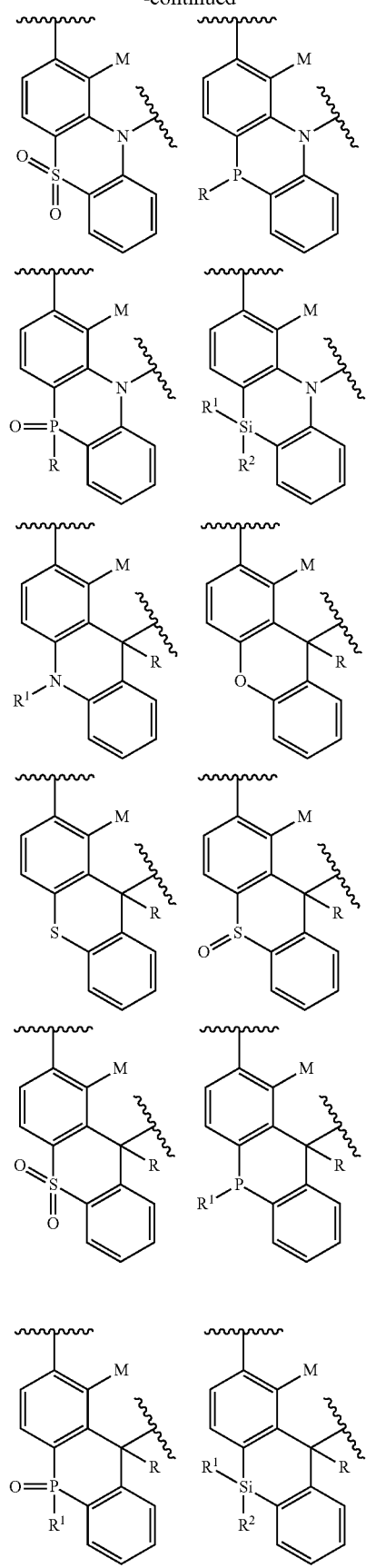

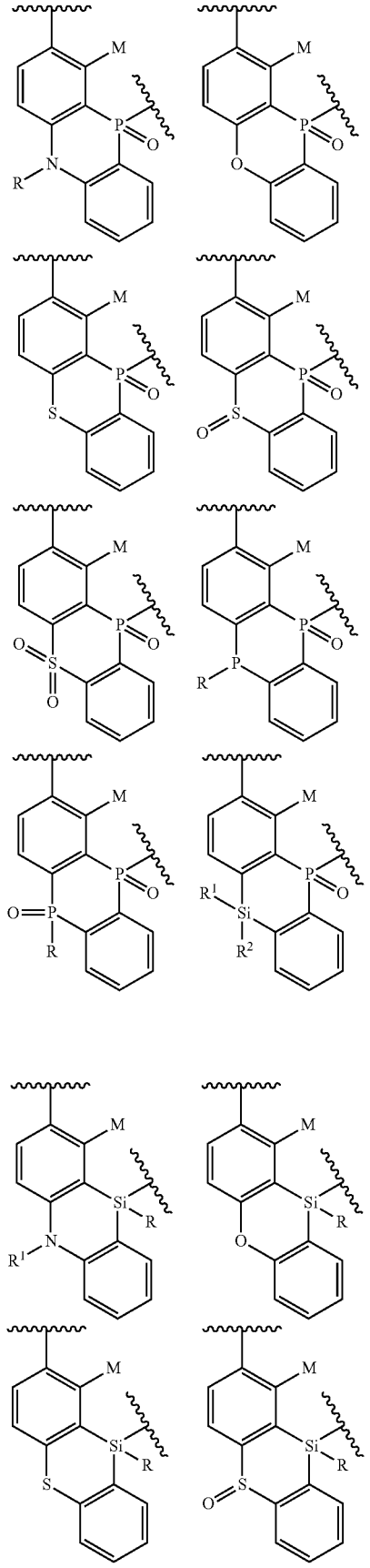
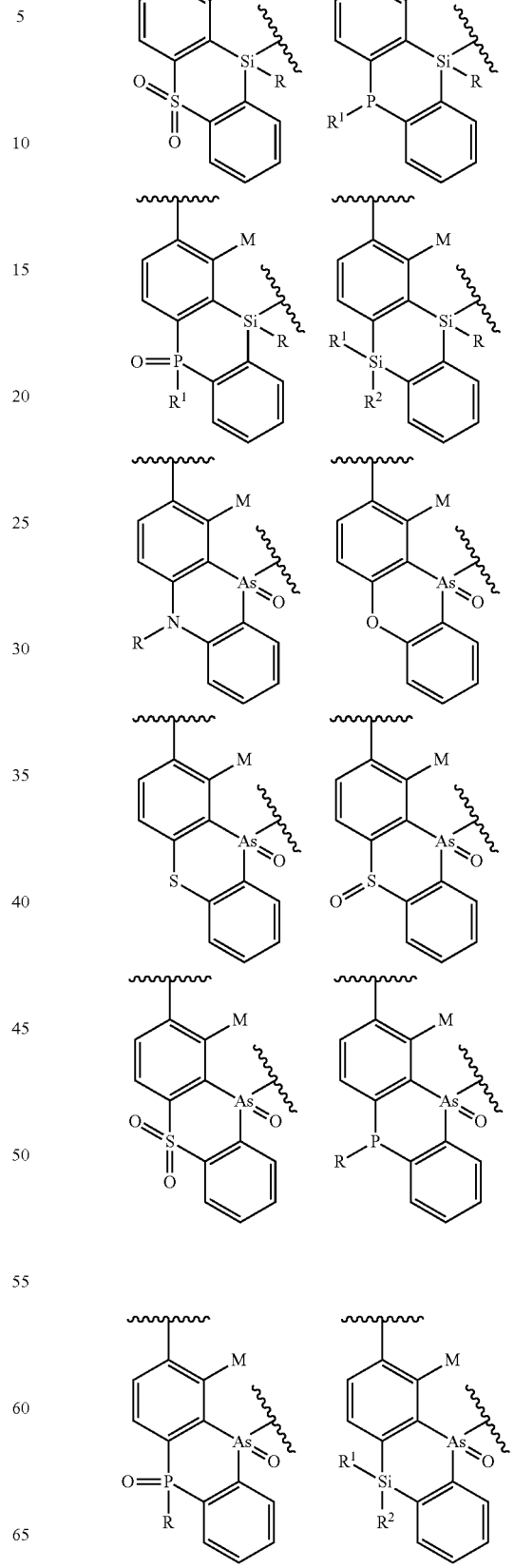

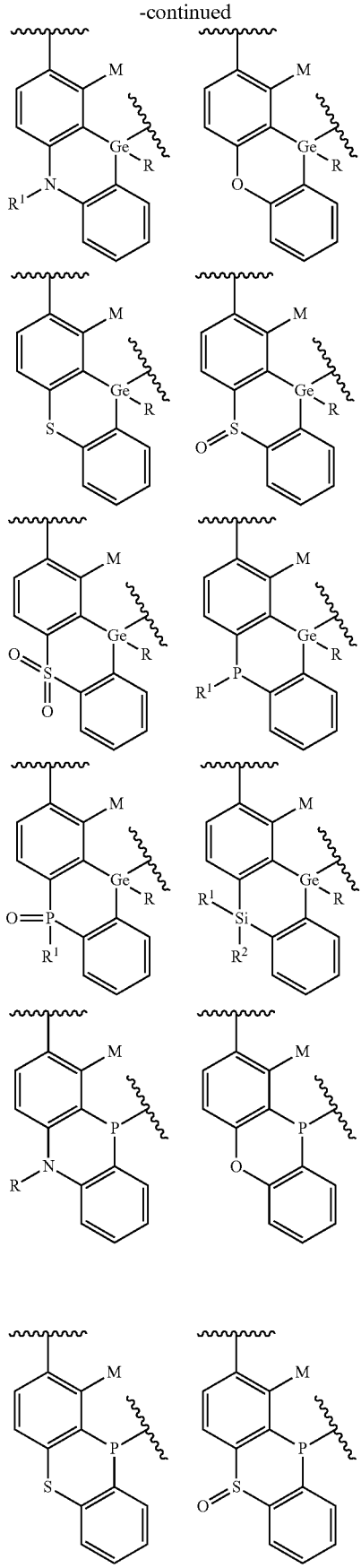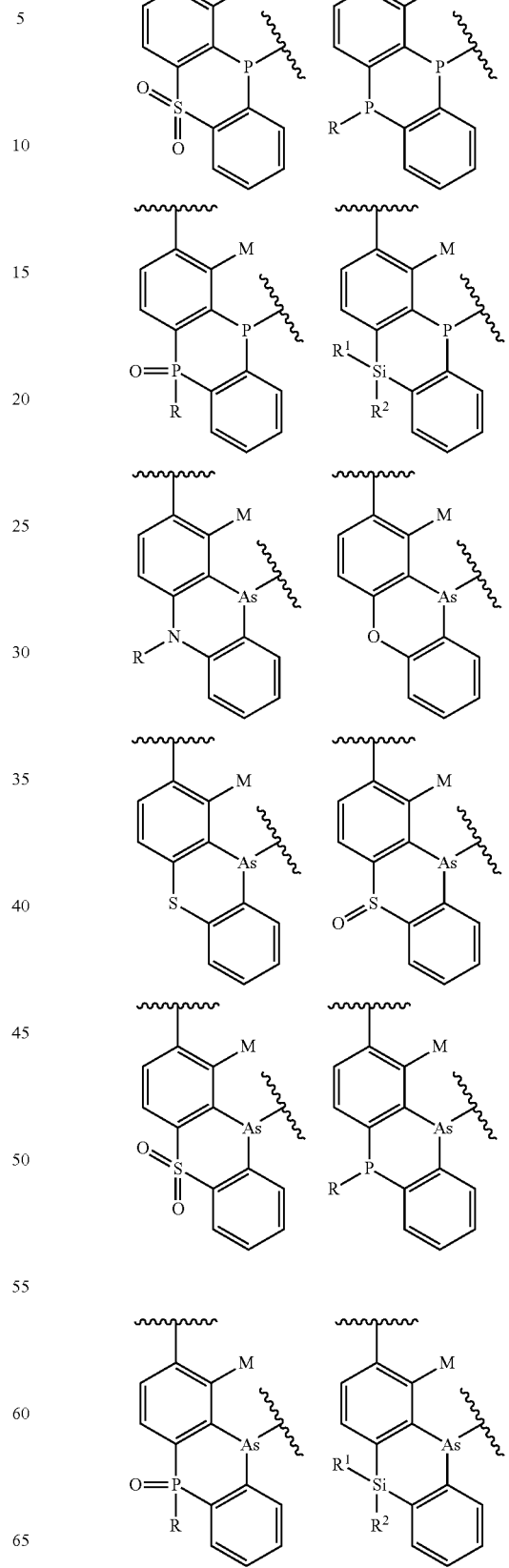

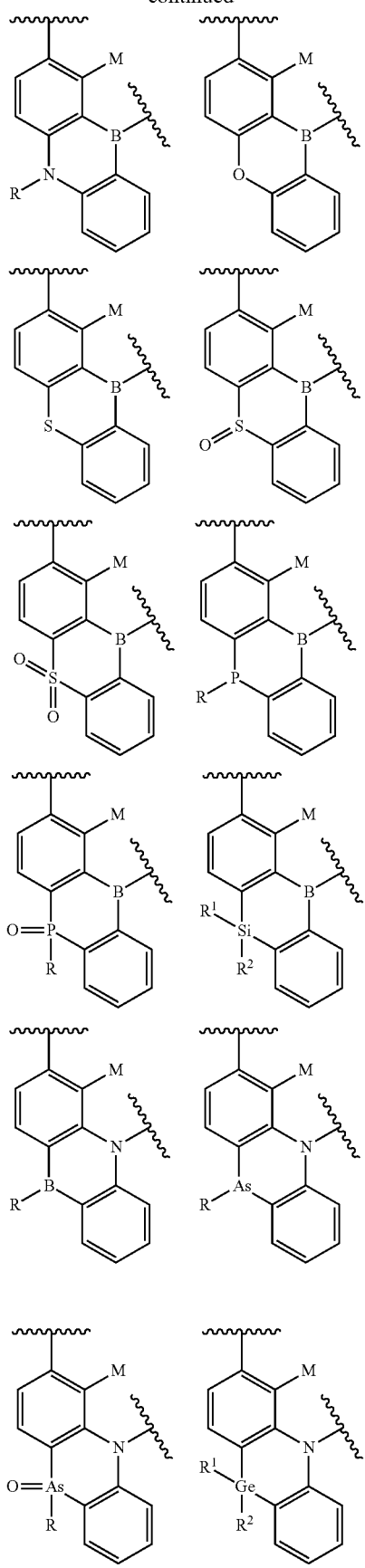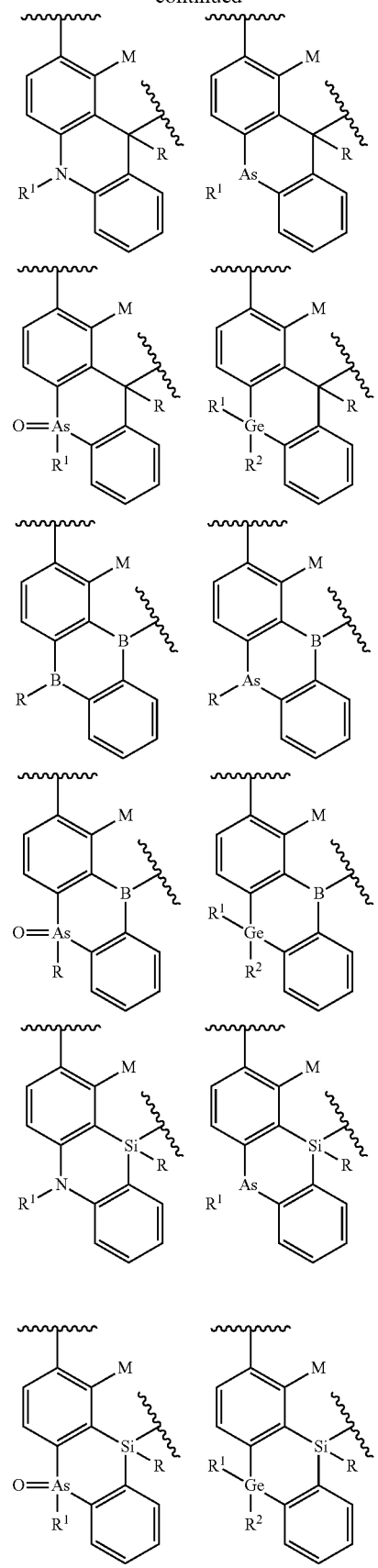

-continued
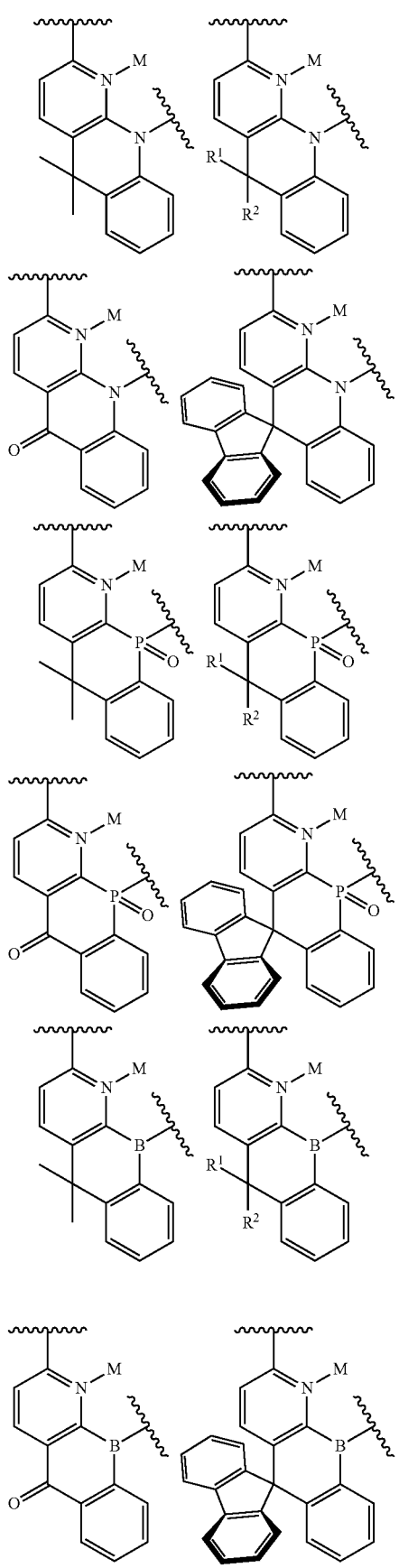
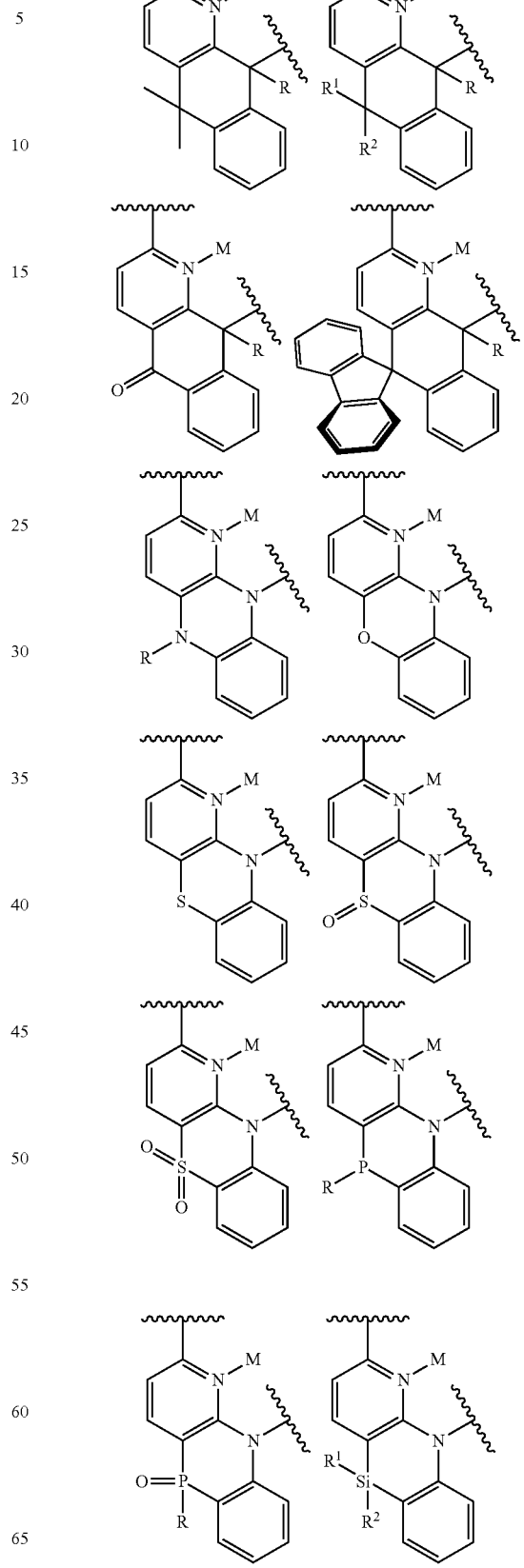

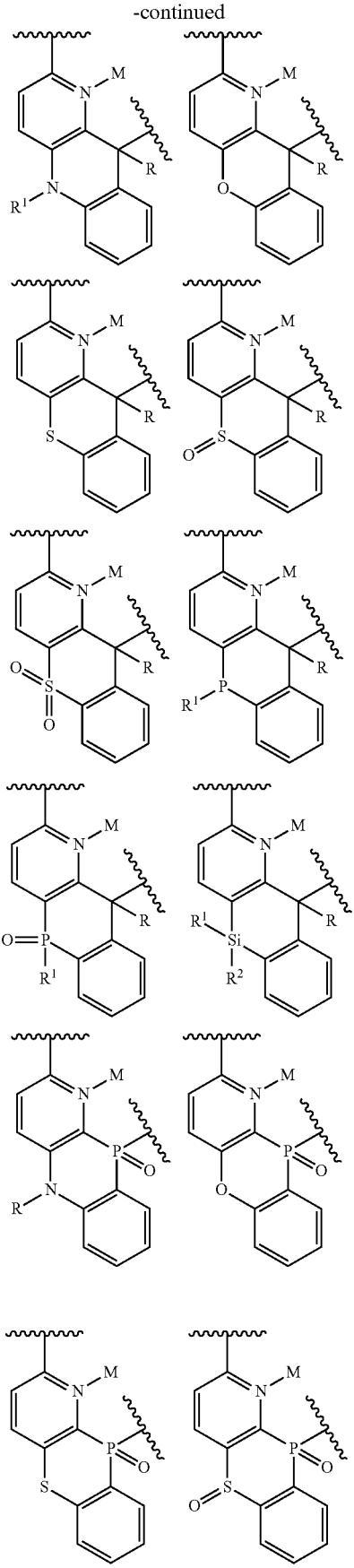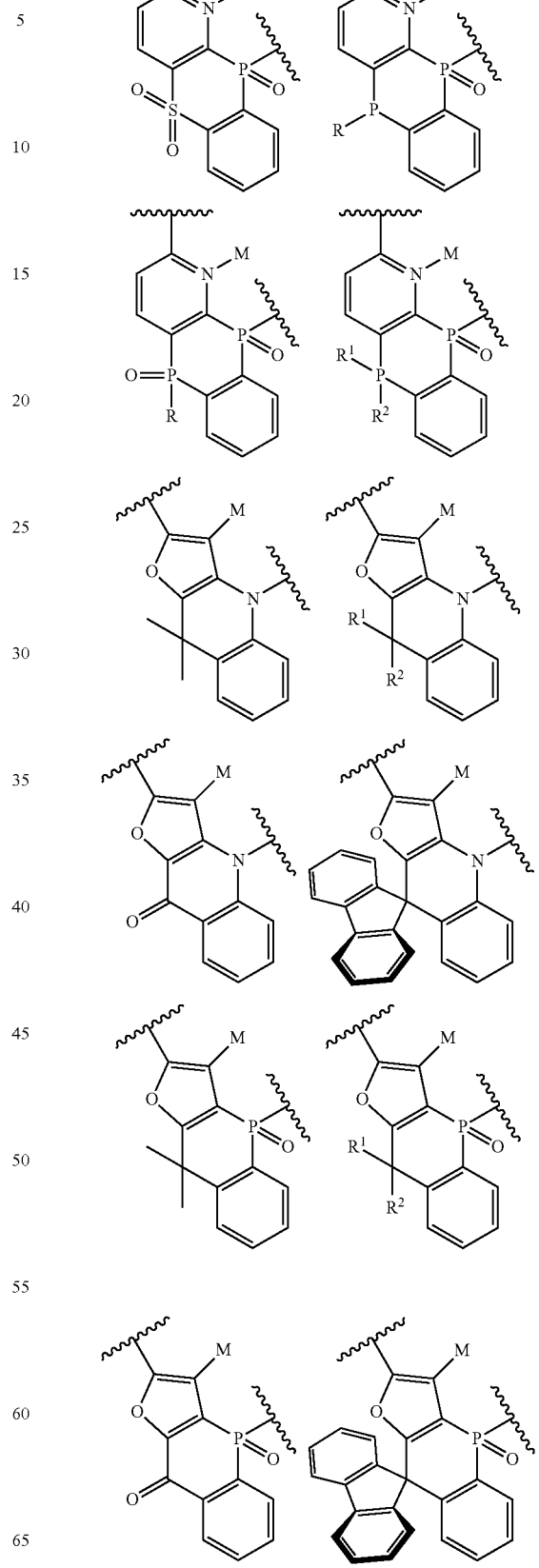

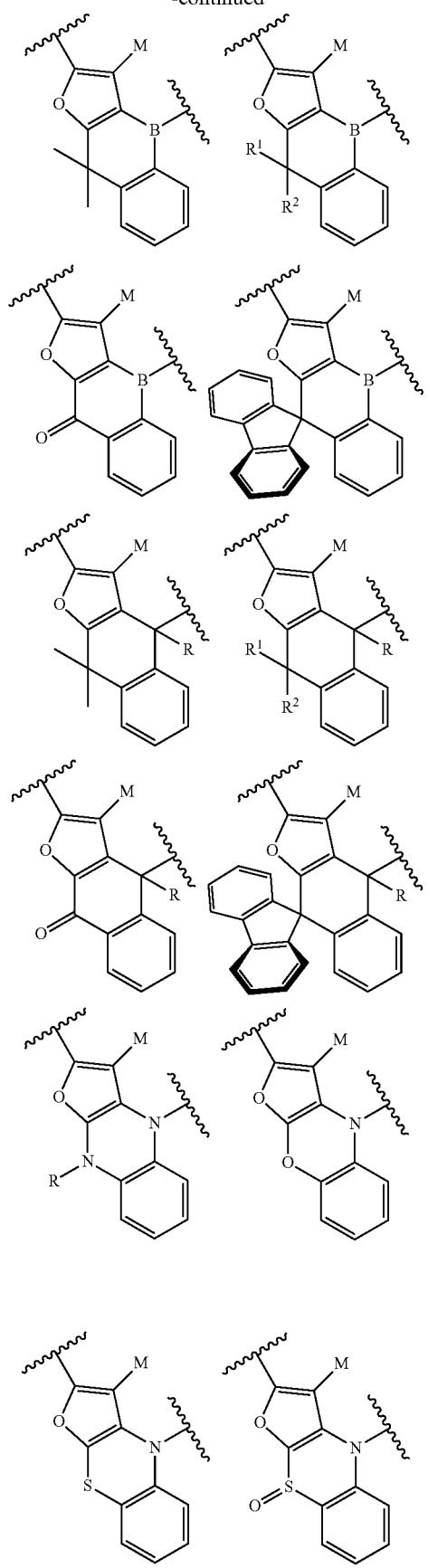
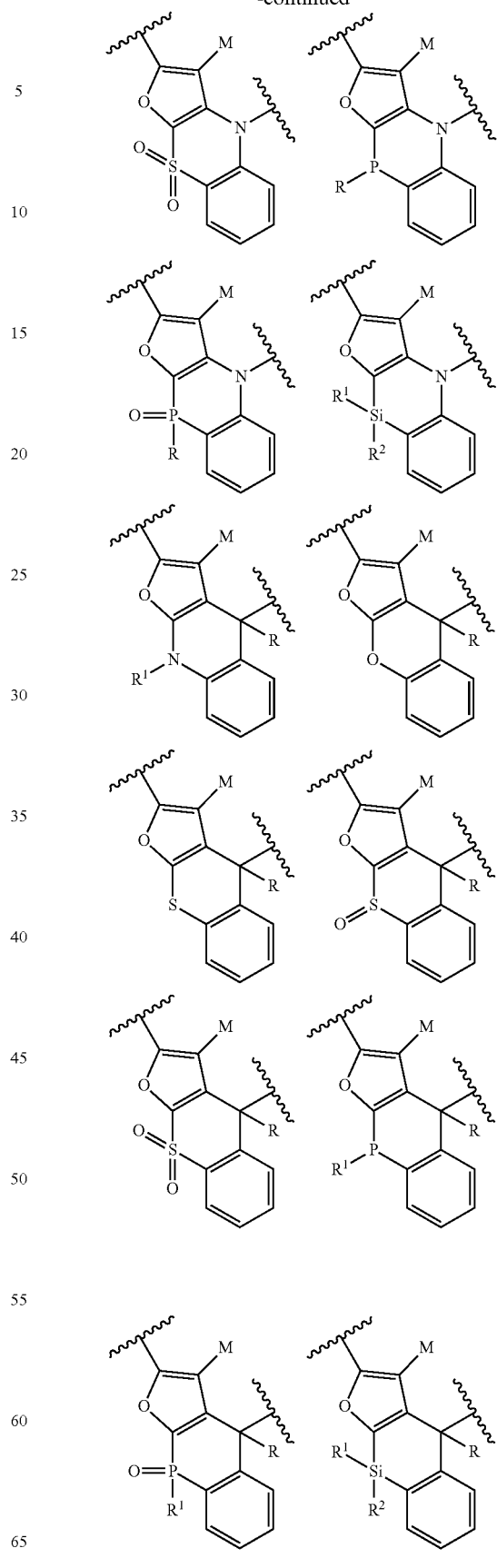

-continued
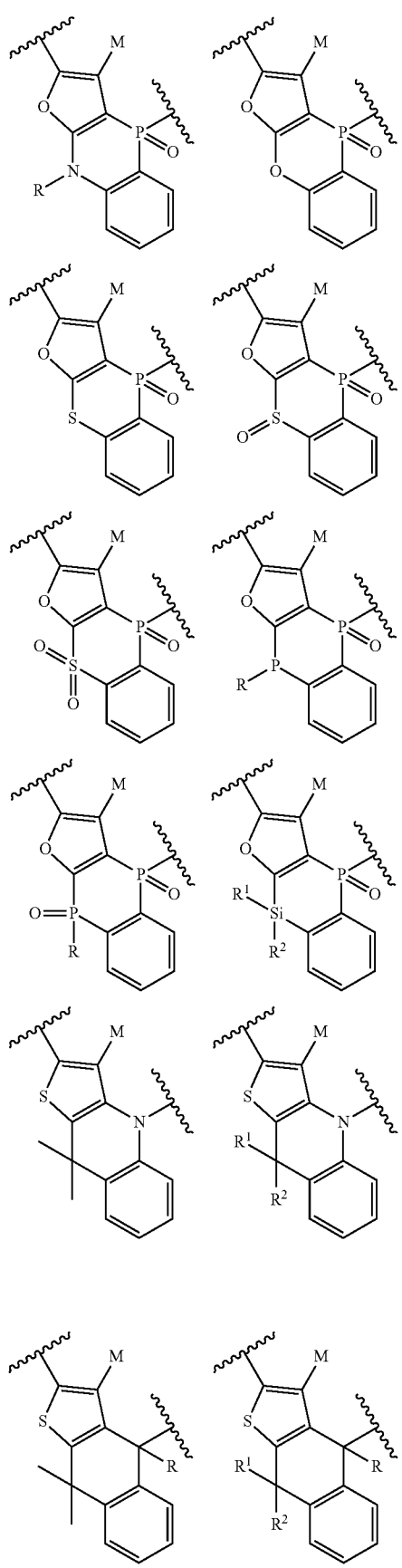
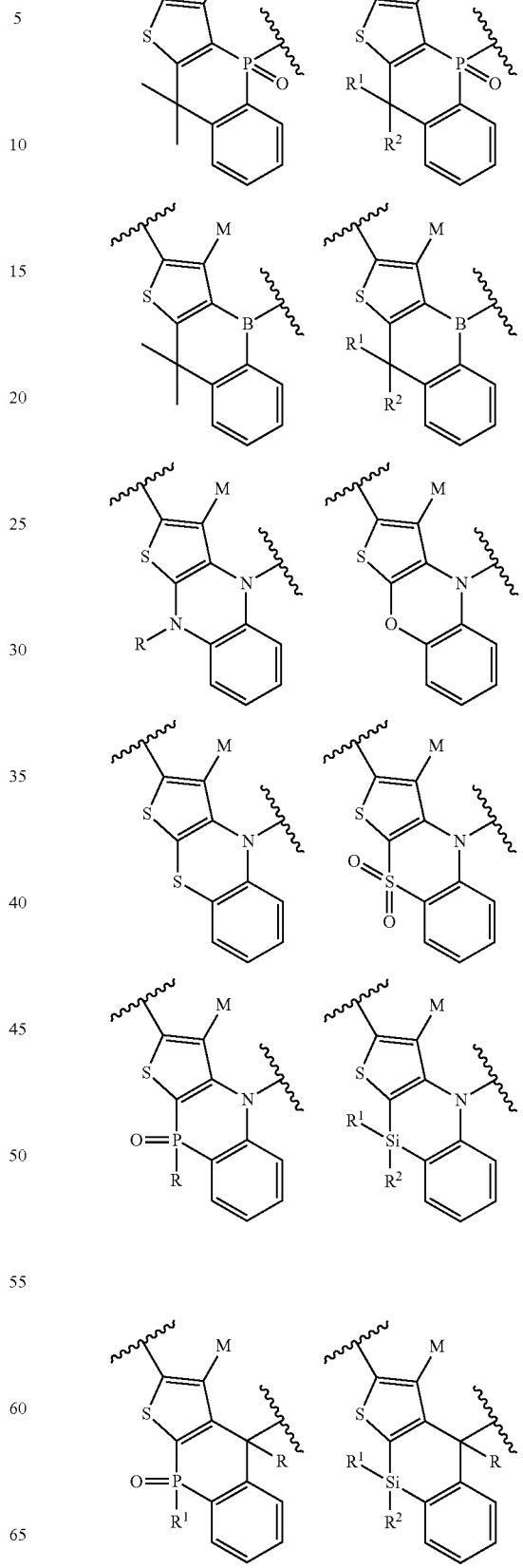

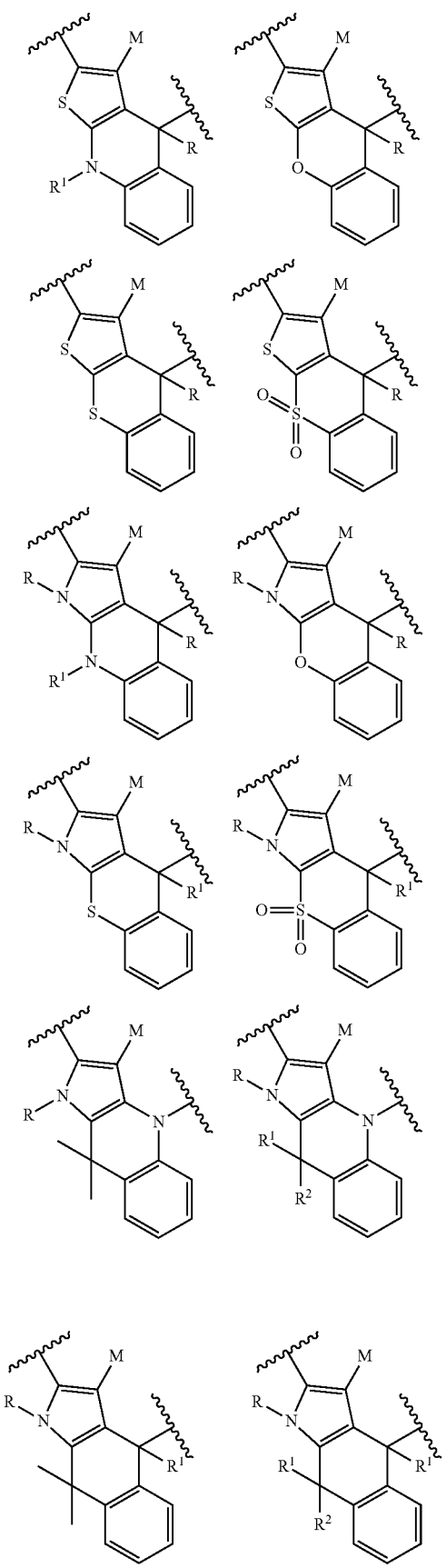
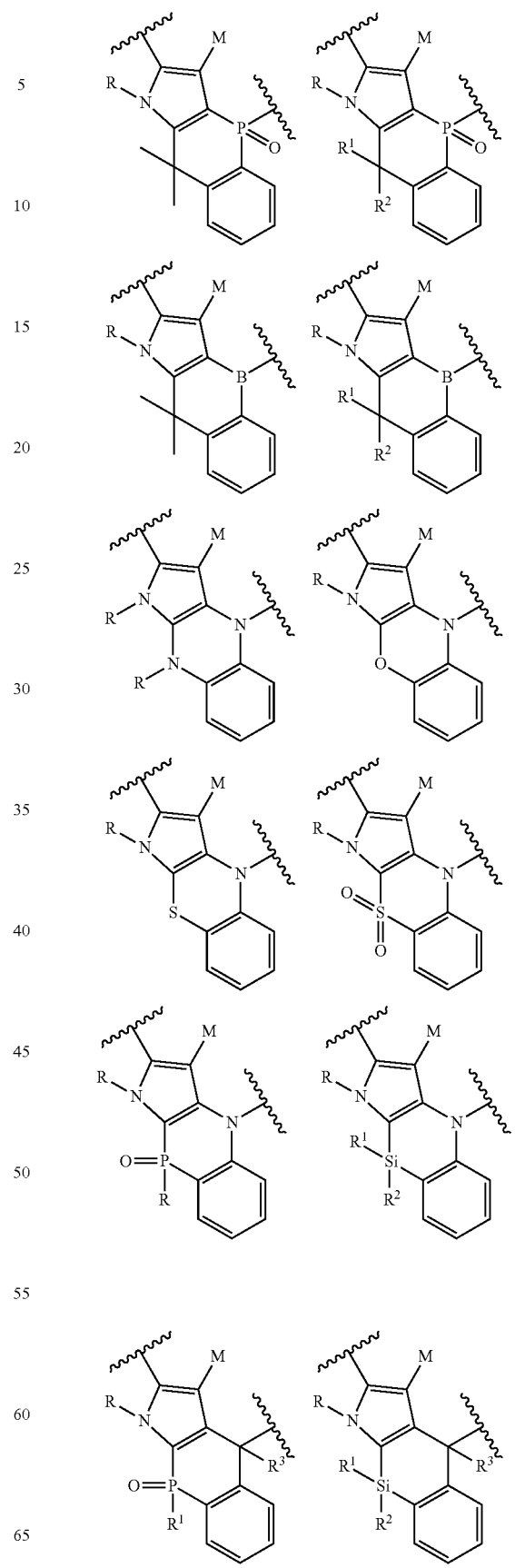

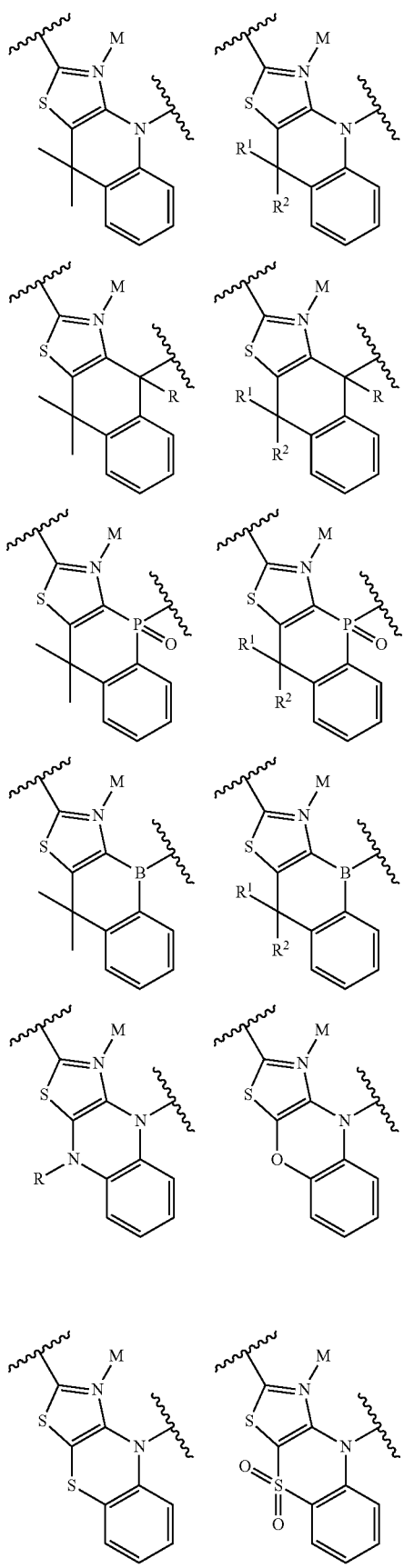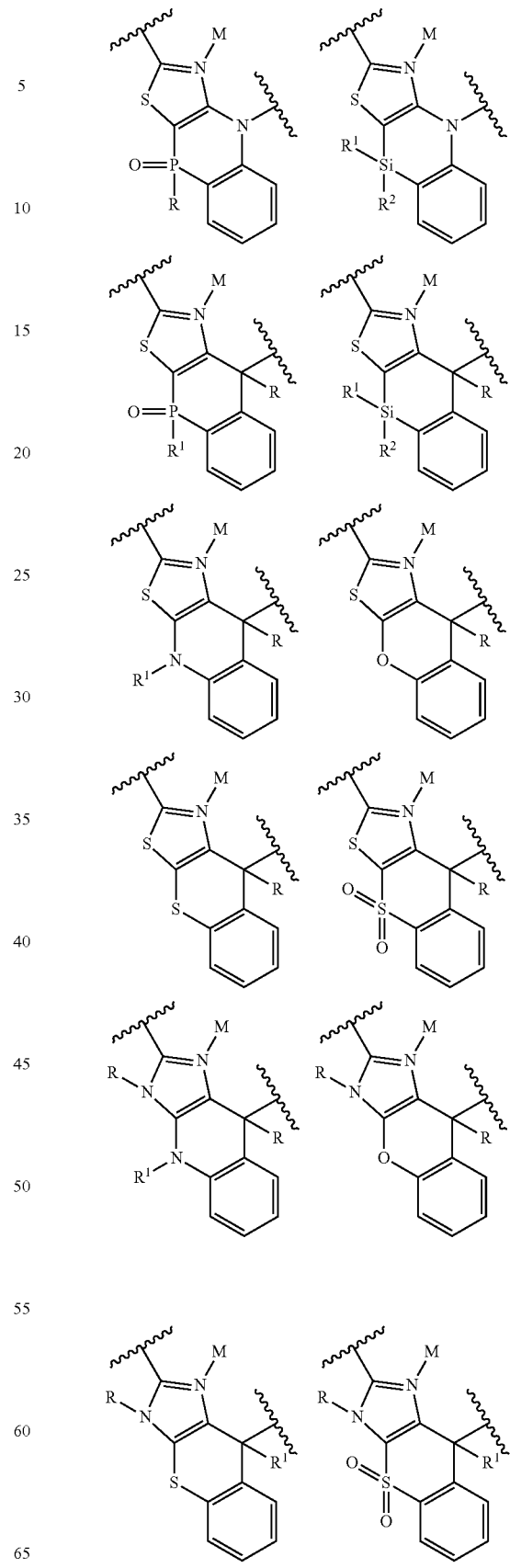

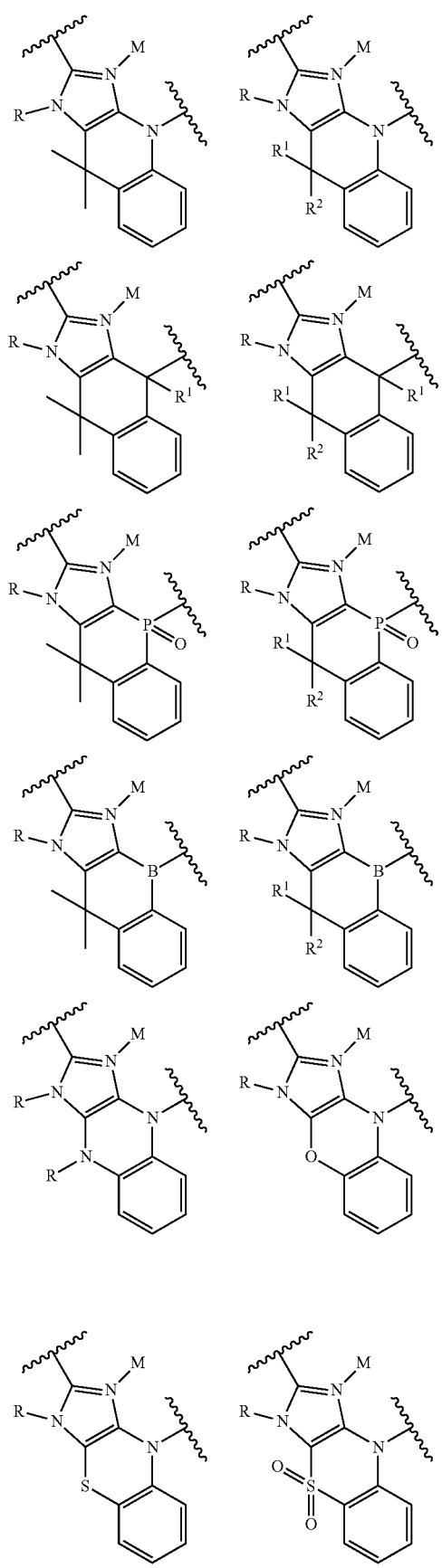
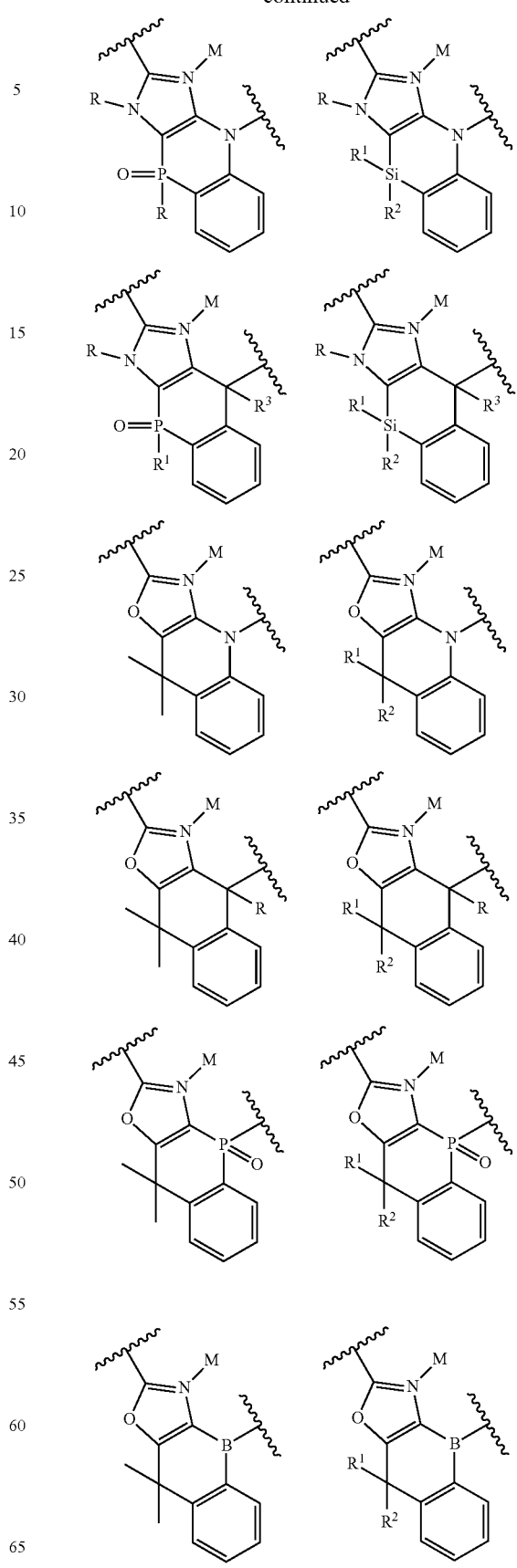

-continued
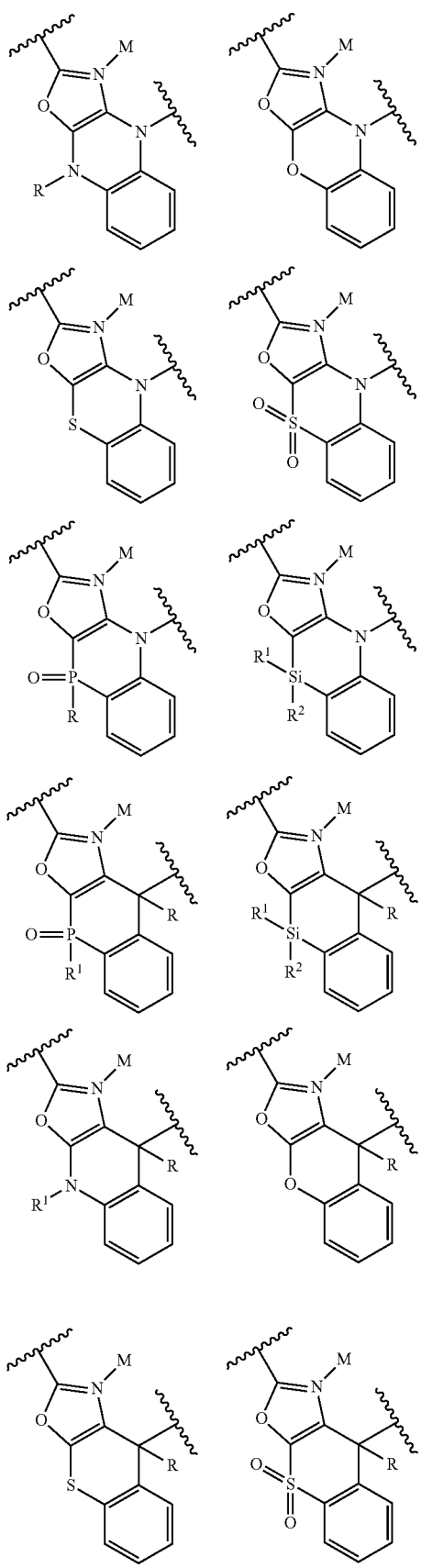
-continued
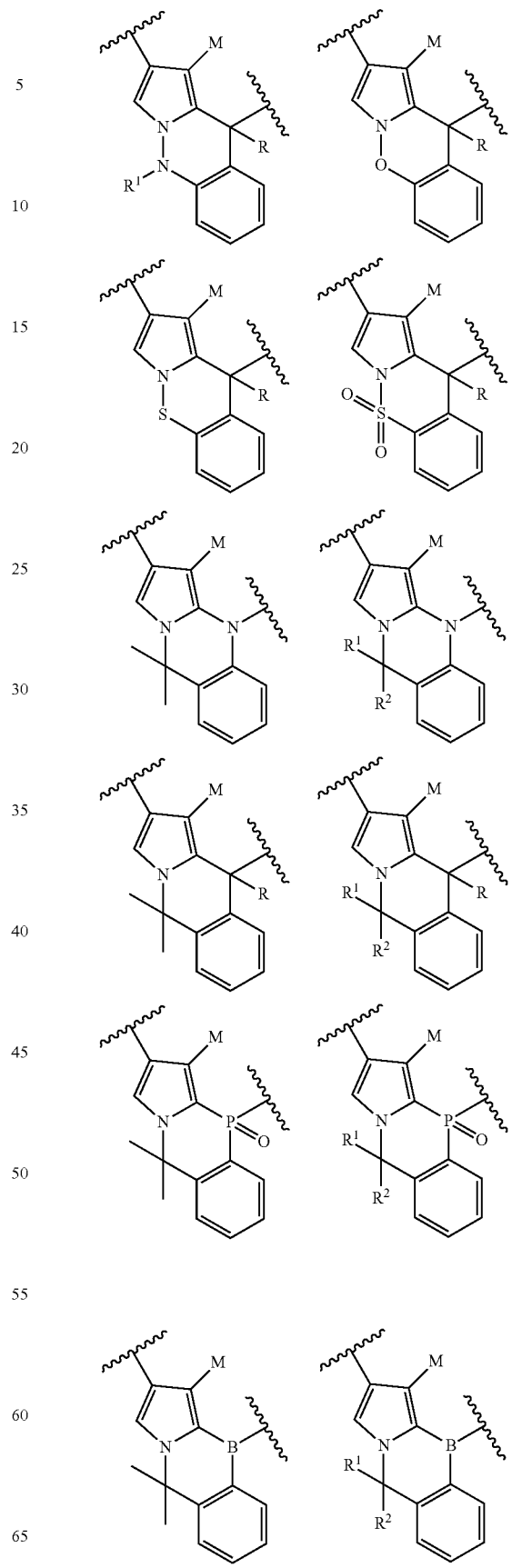

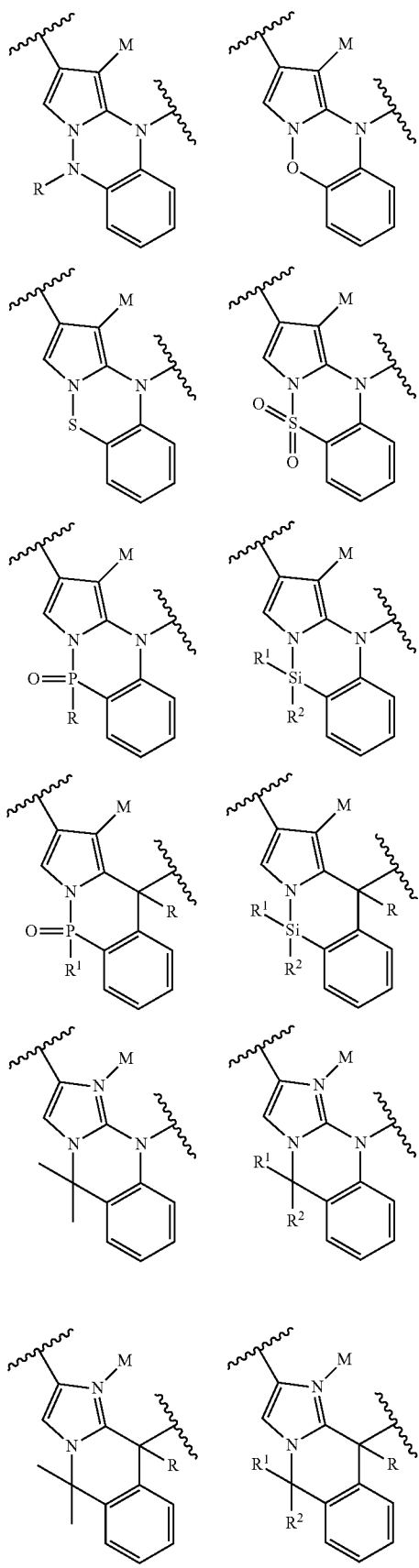
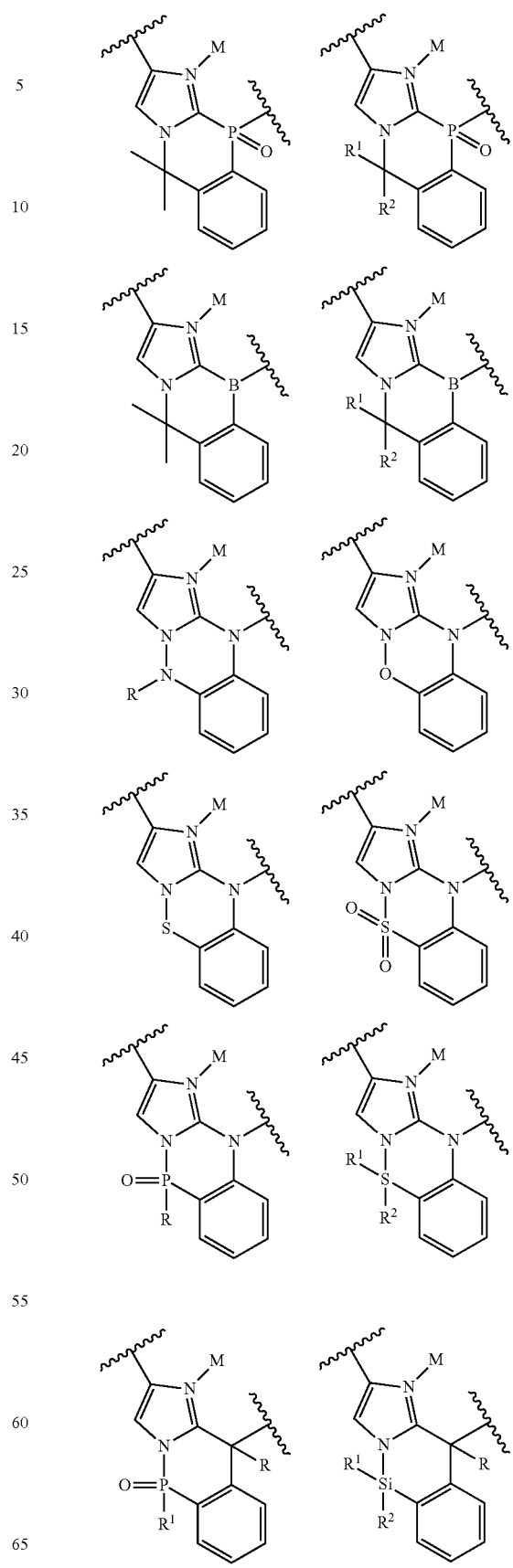

-continued

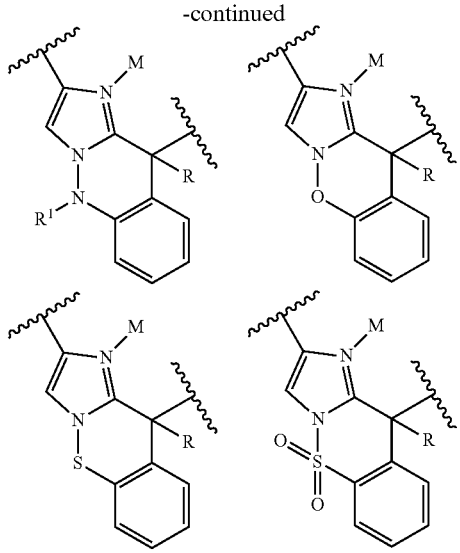

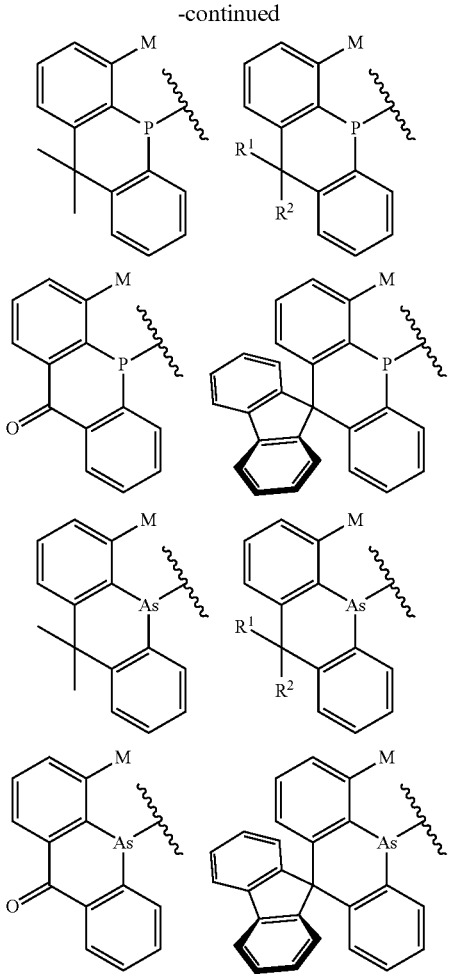

wherein each of R, $R^1$, $R^2$, and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, for any of the formulas disclosed herein, each of

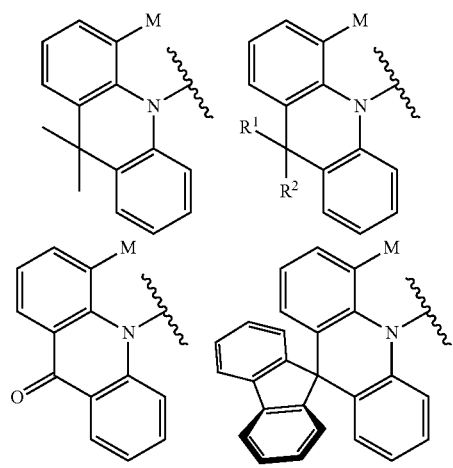

and is independently one of the following structures:

-continued
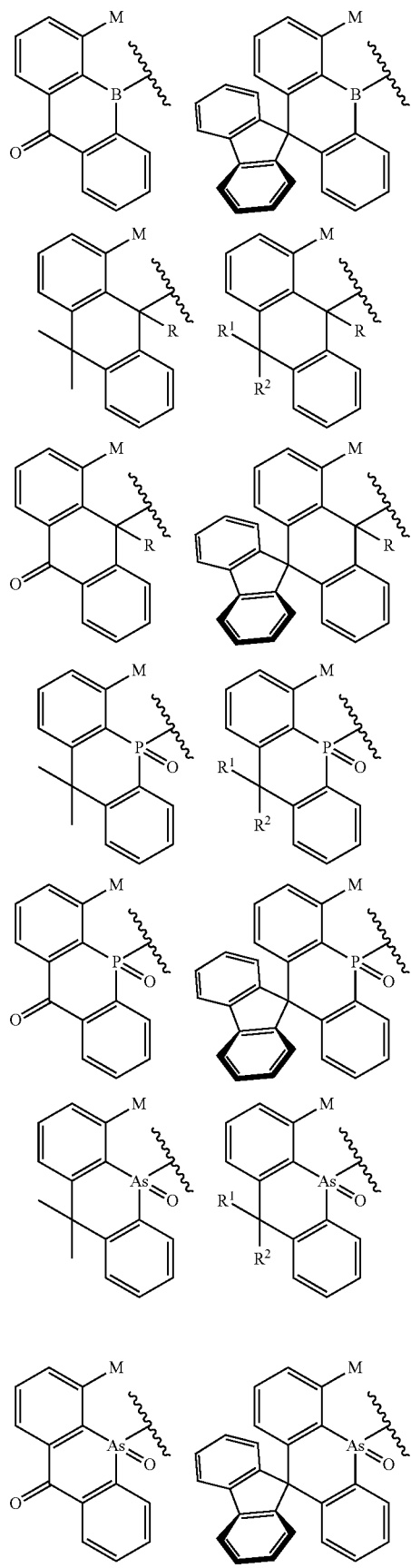
-continued
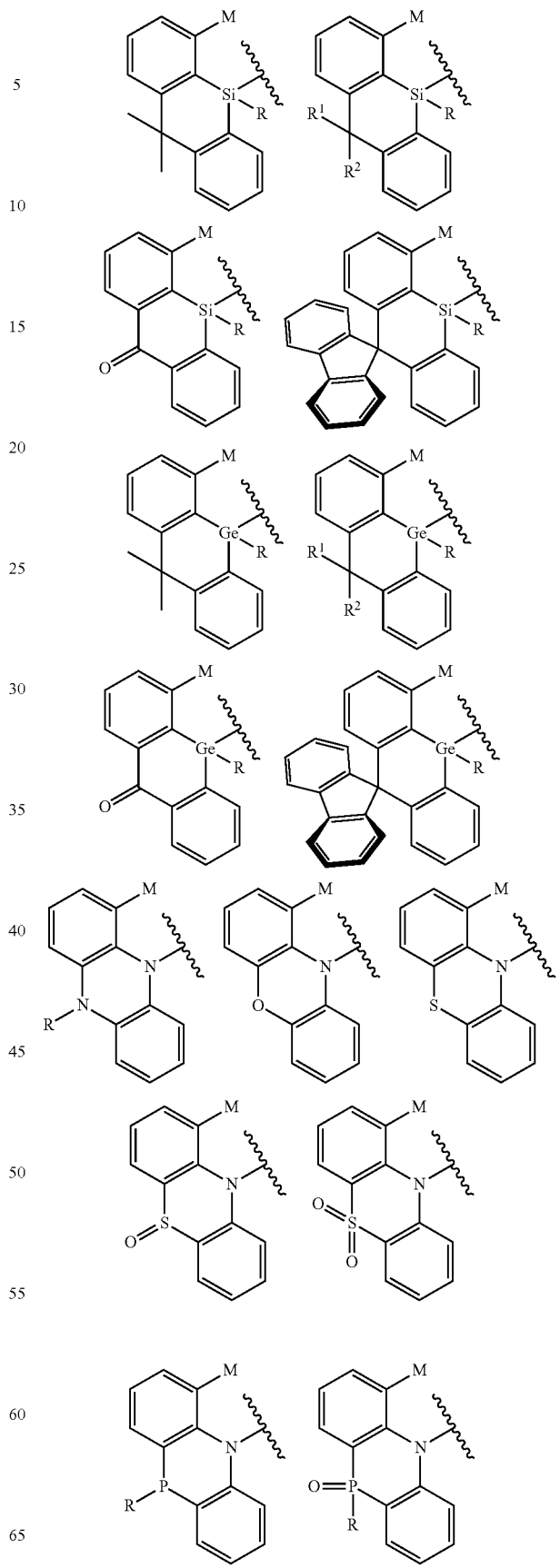

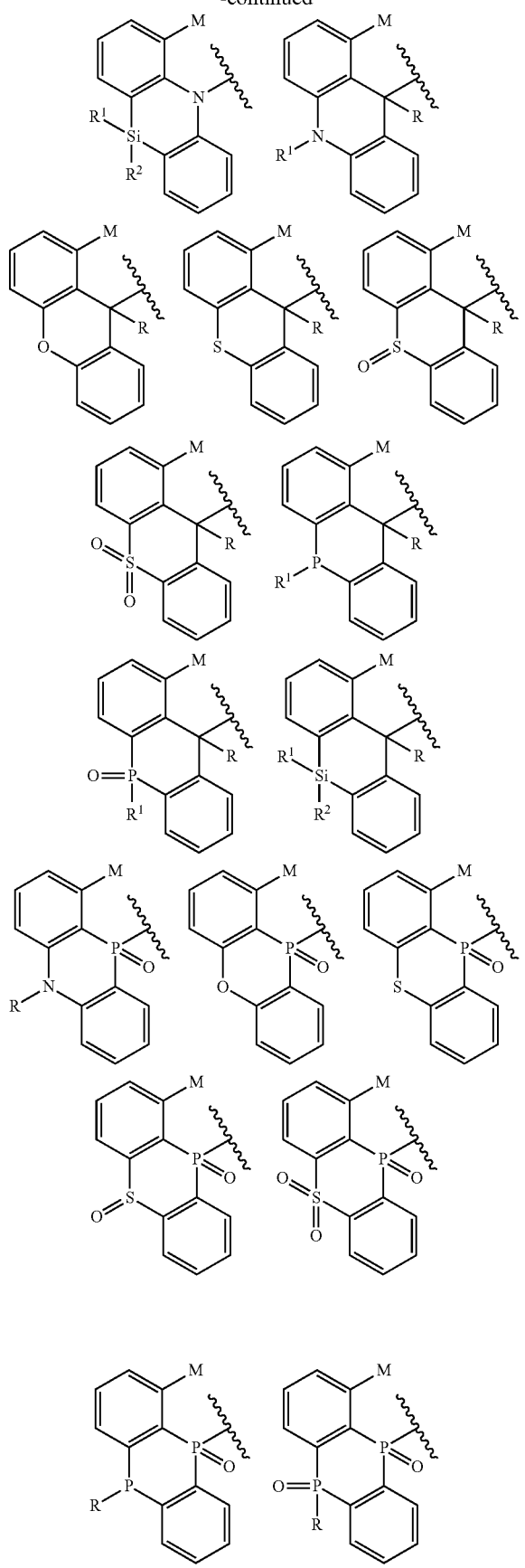
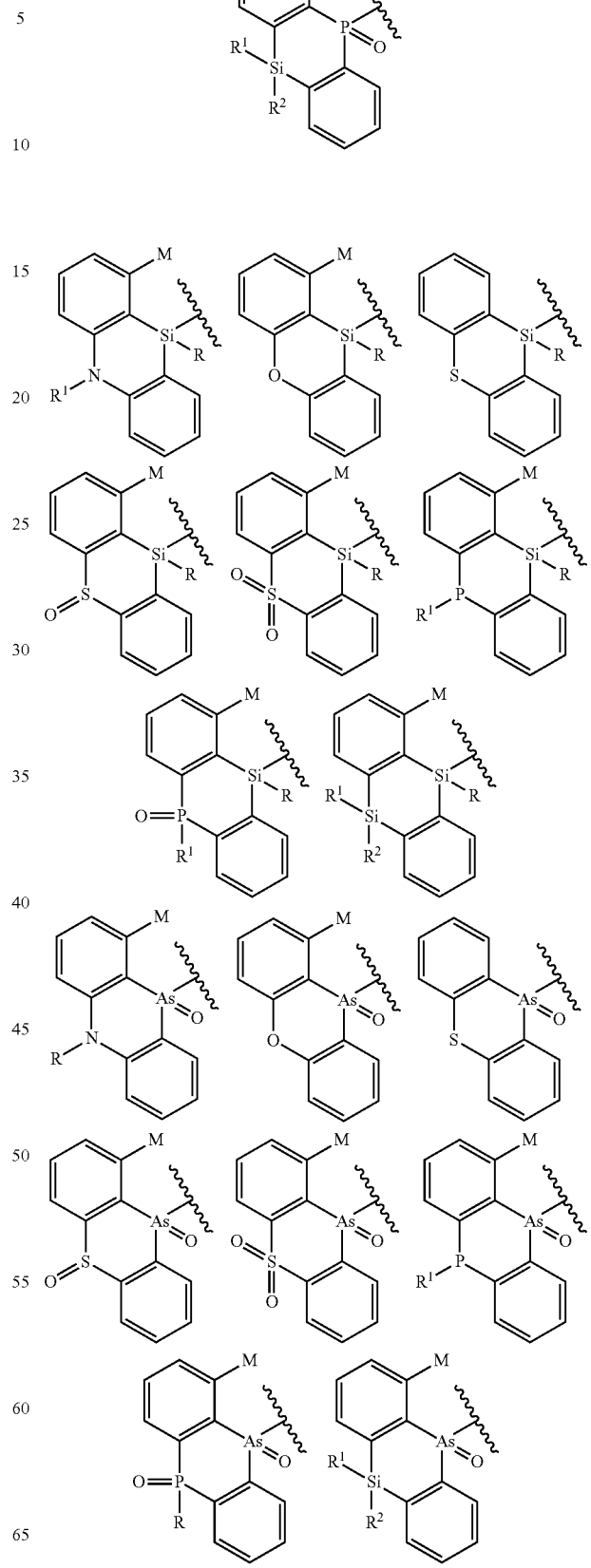

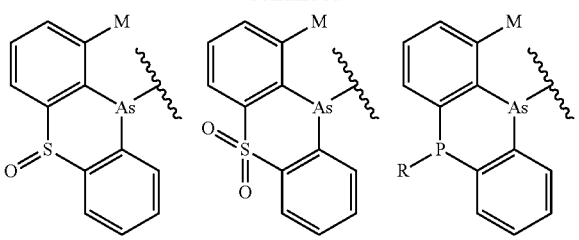
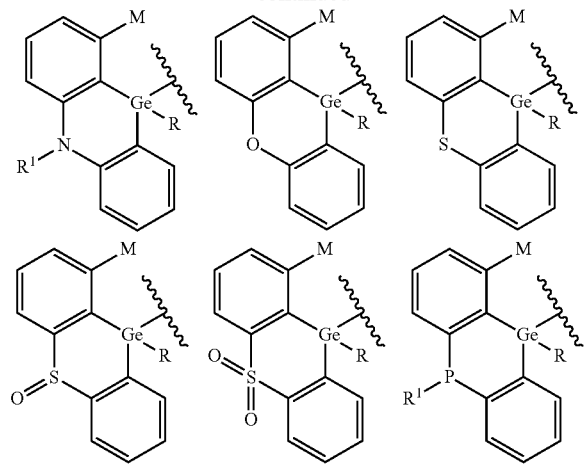
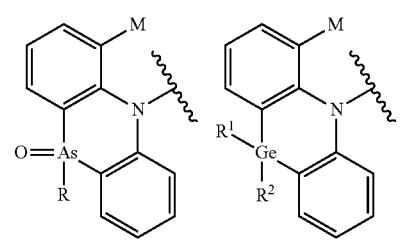
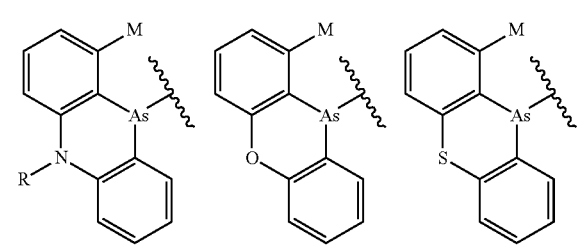

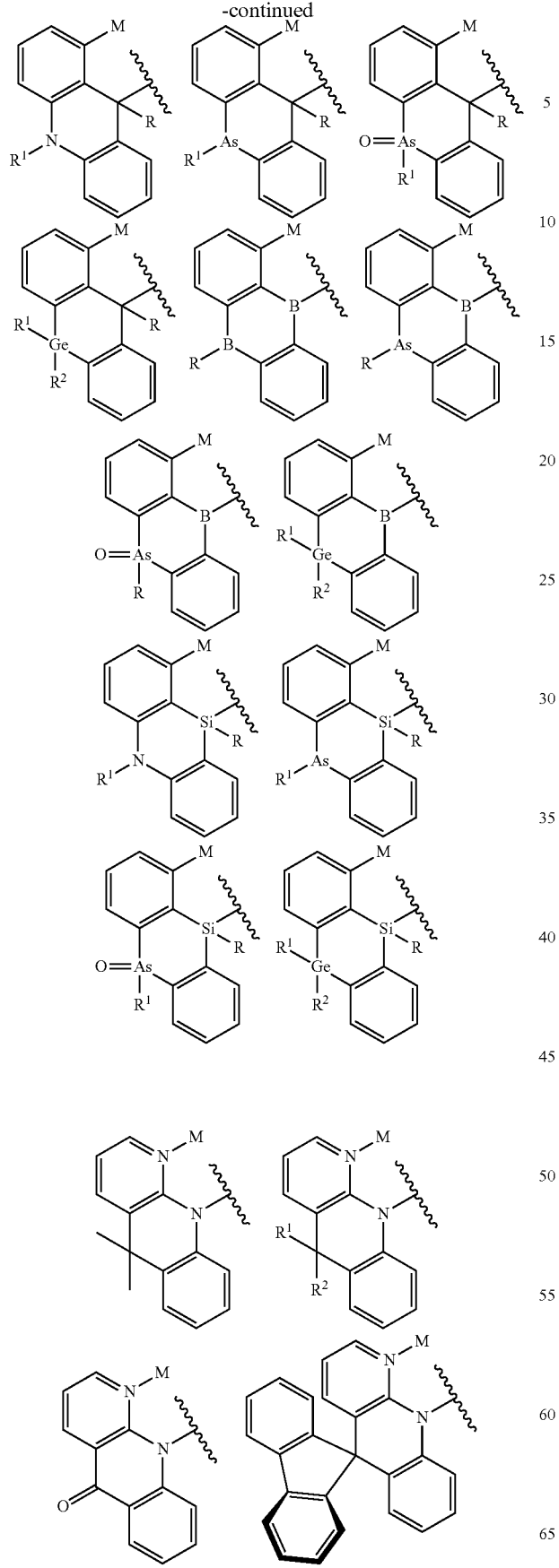
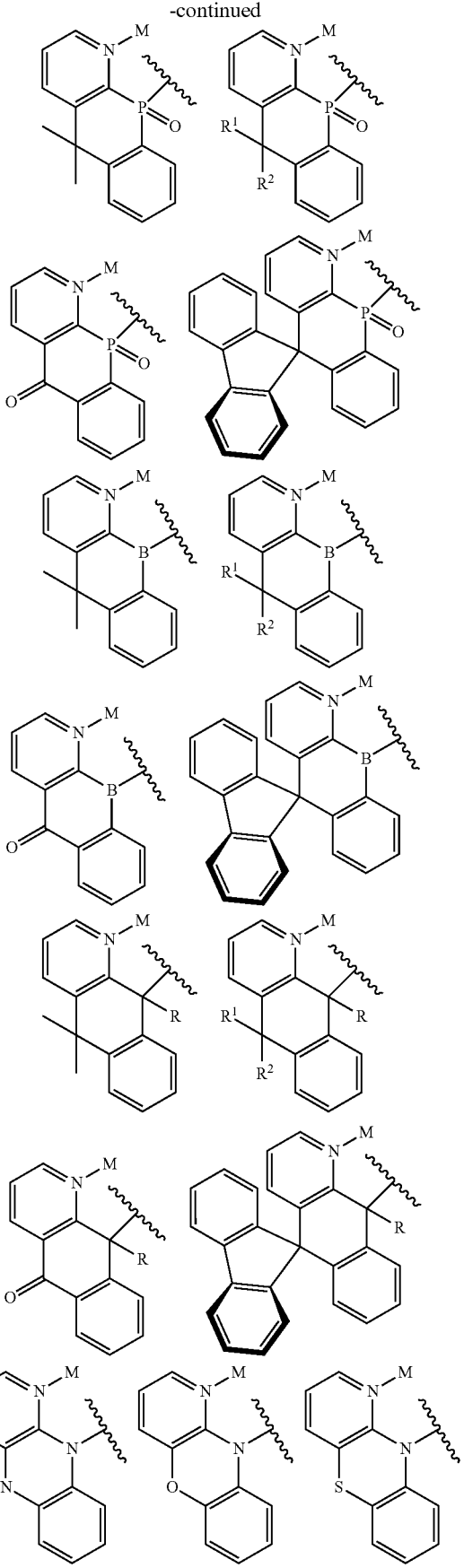

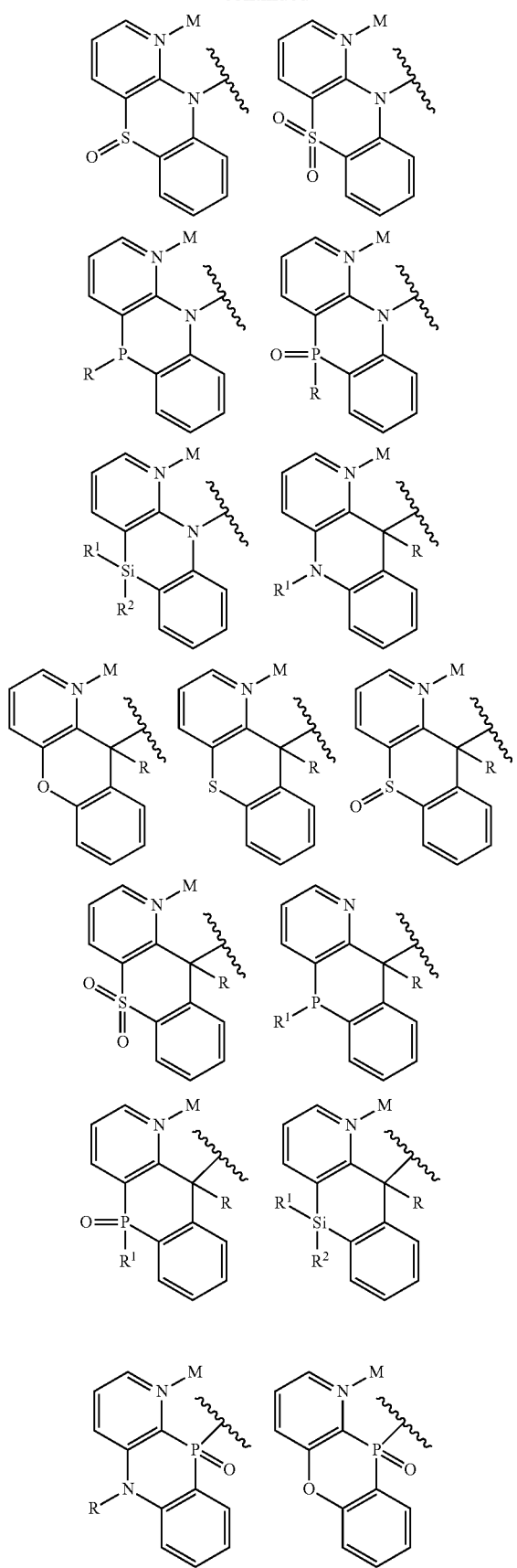
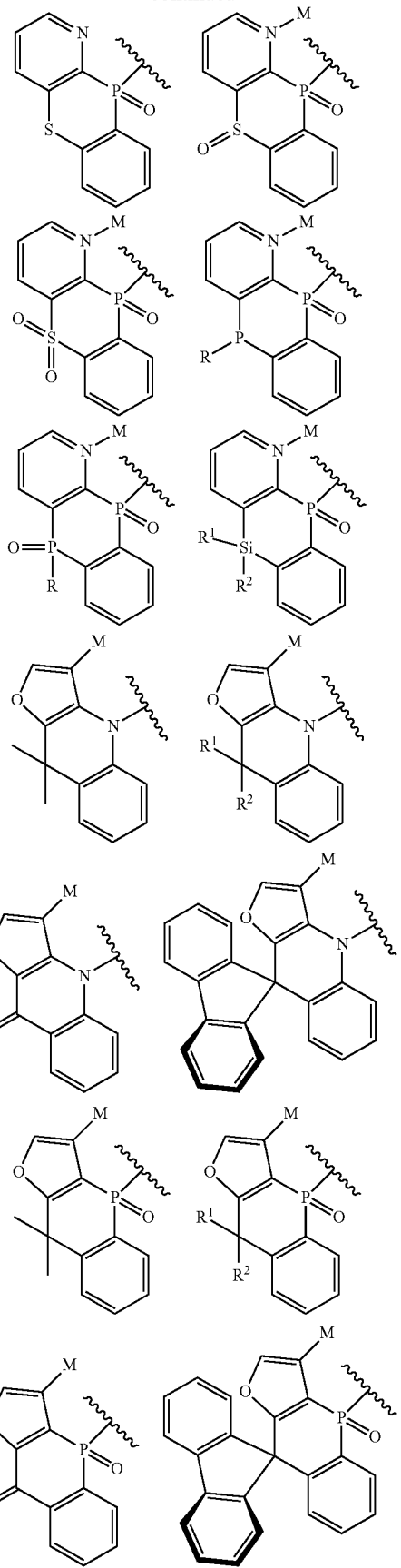

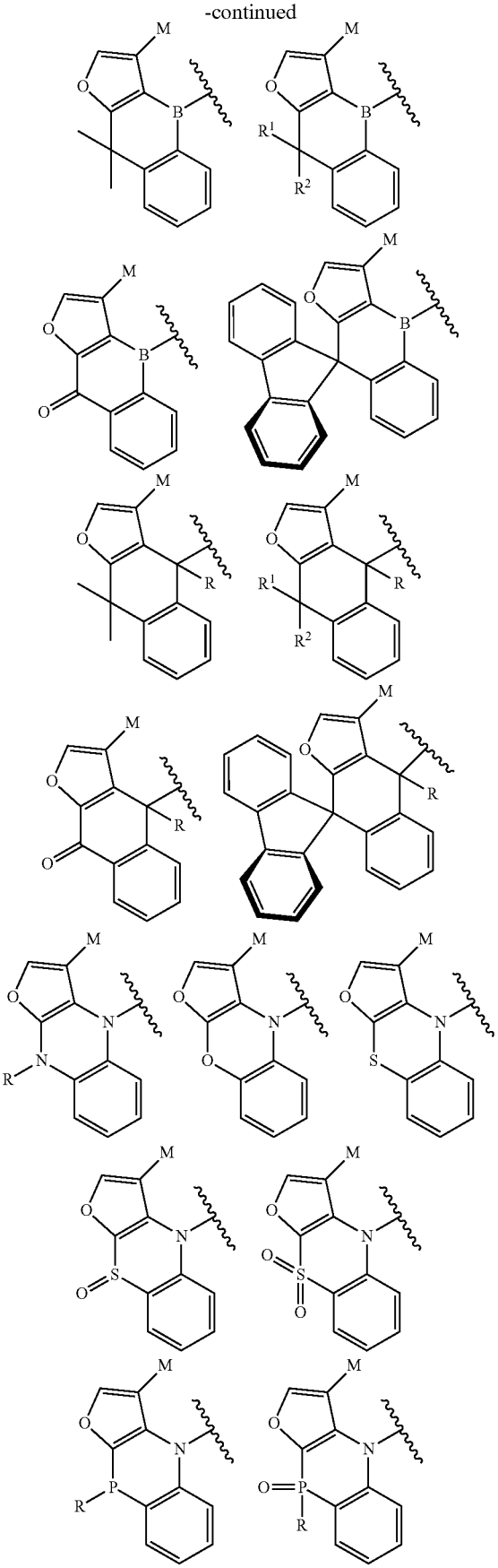
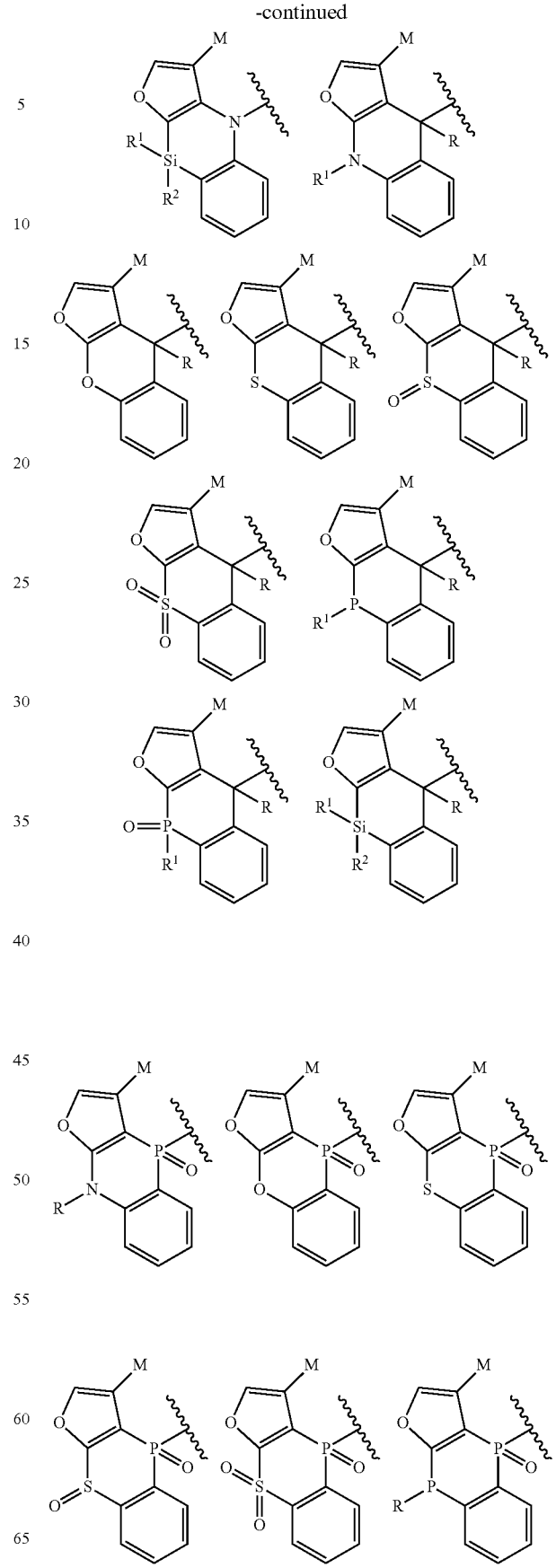

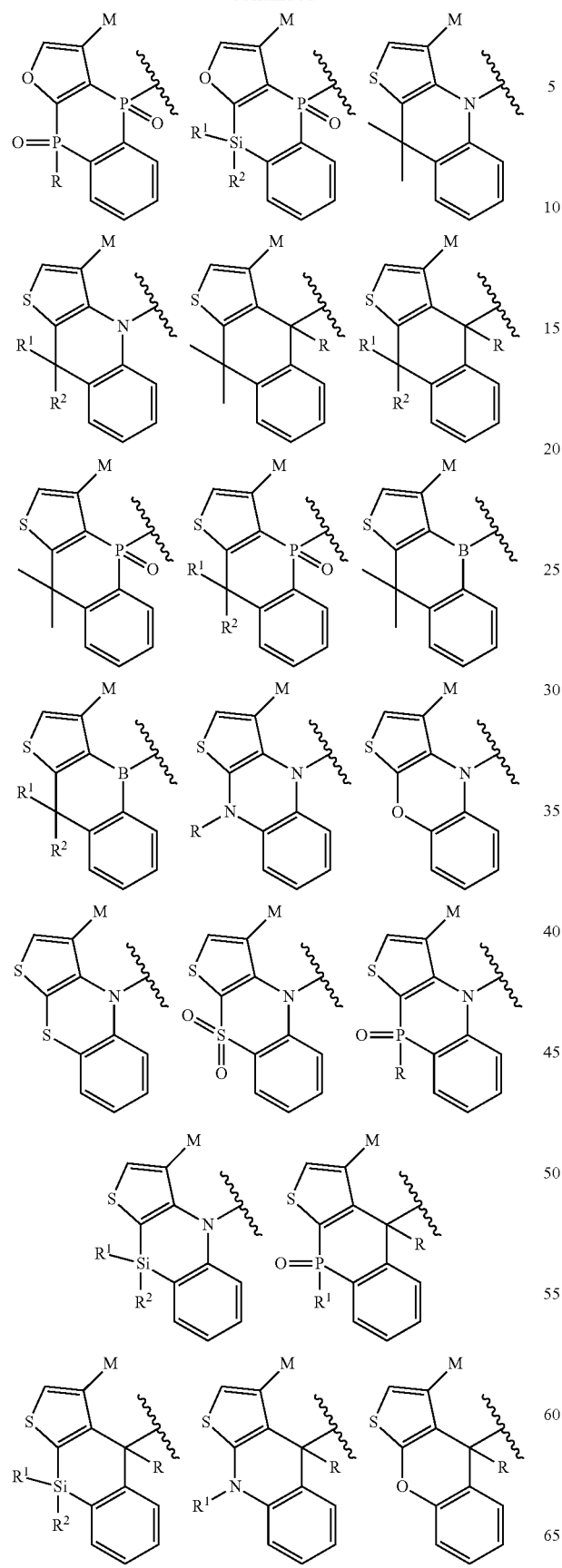
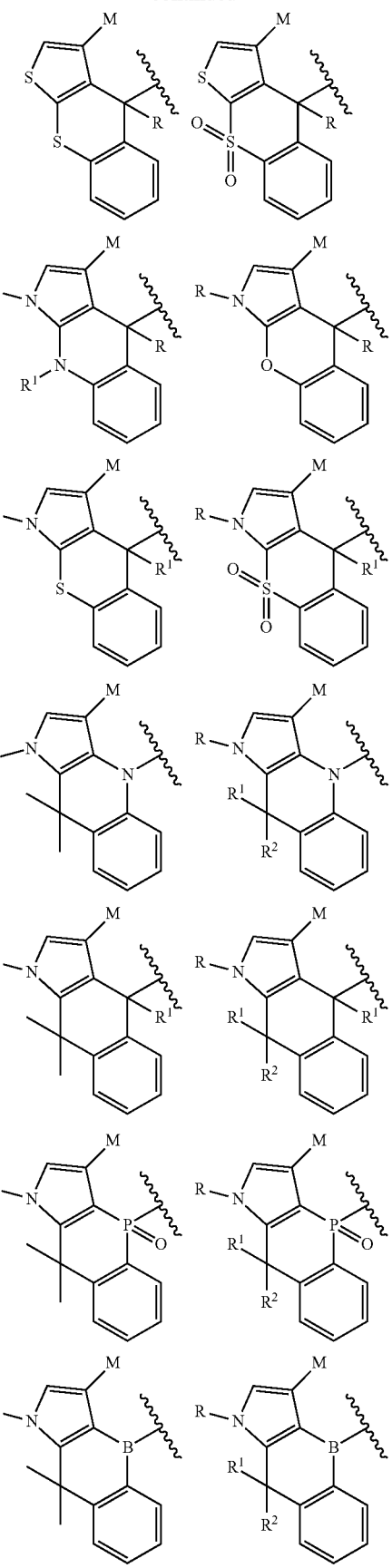

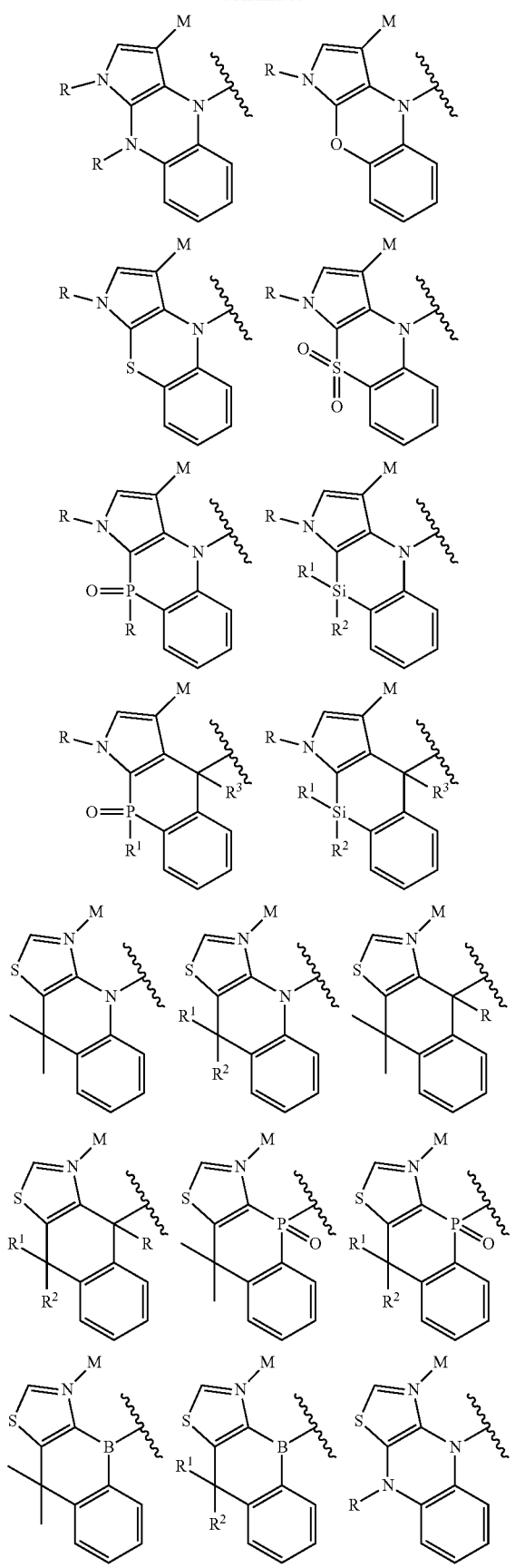
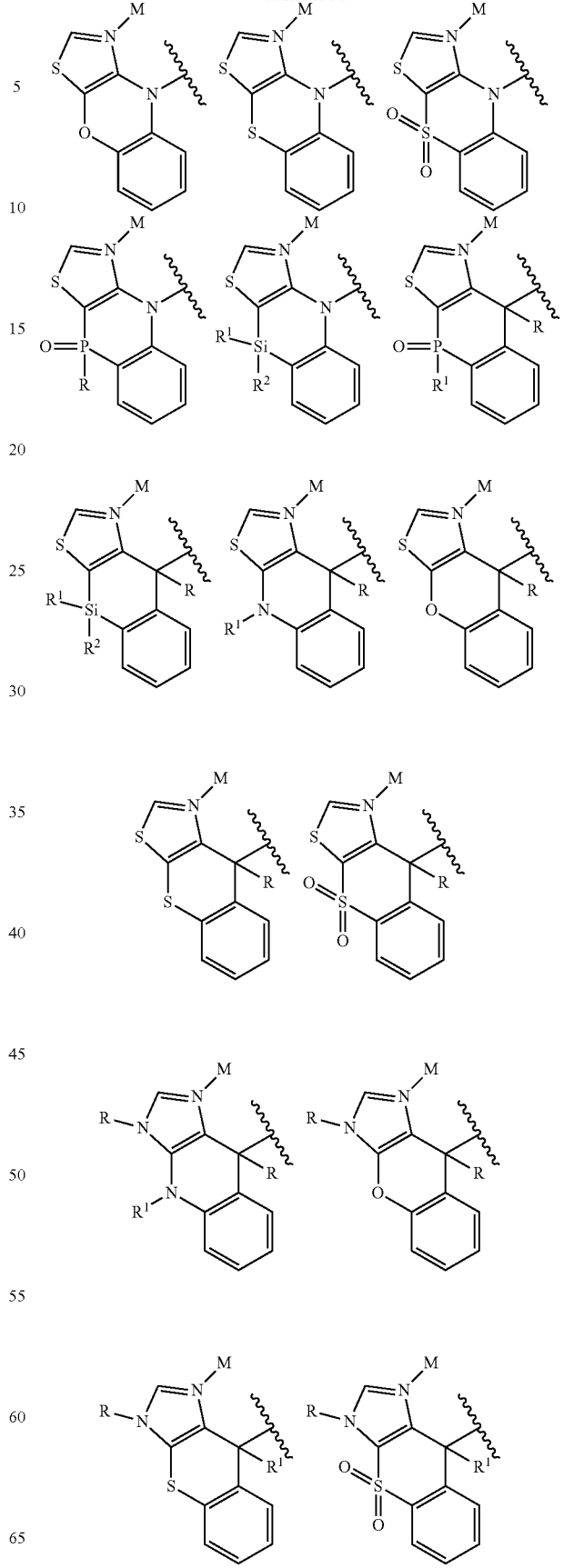

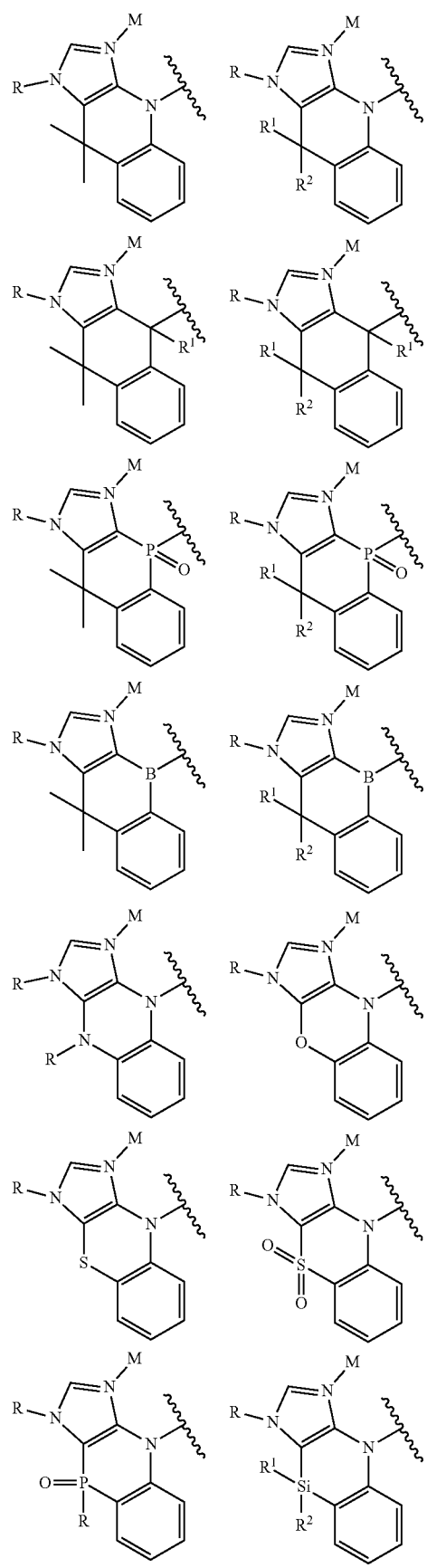
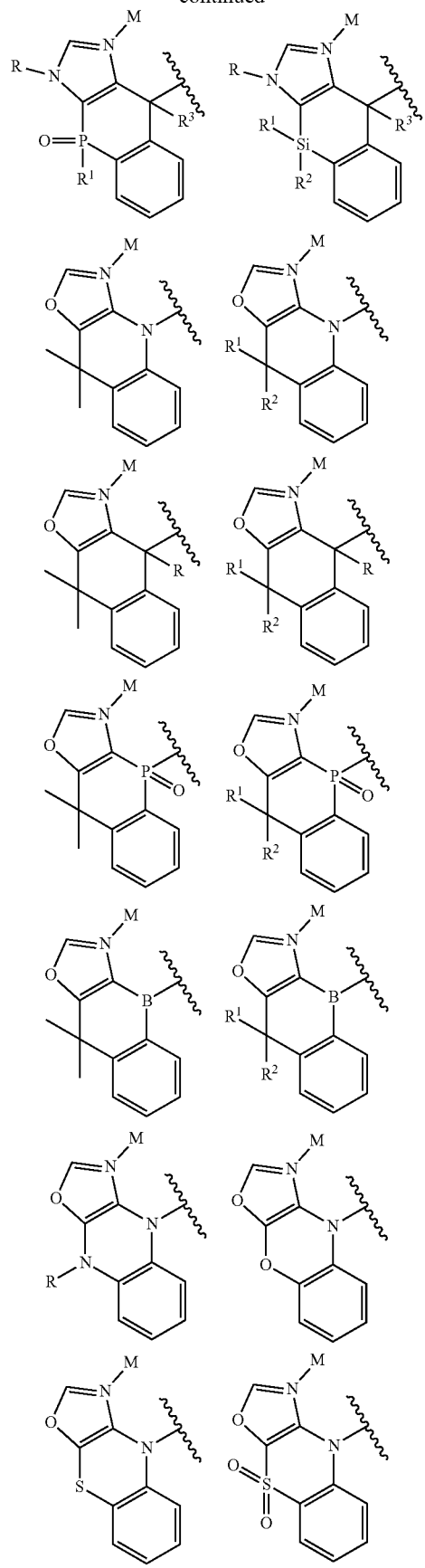

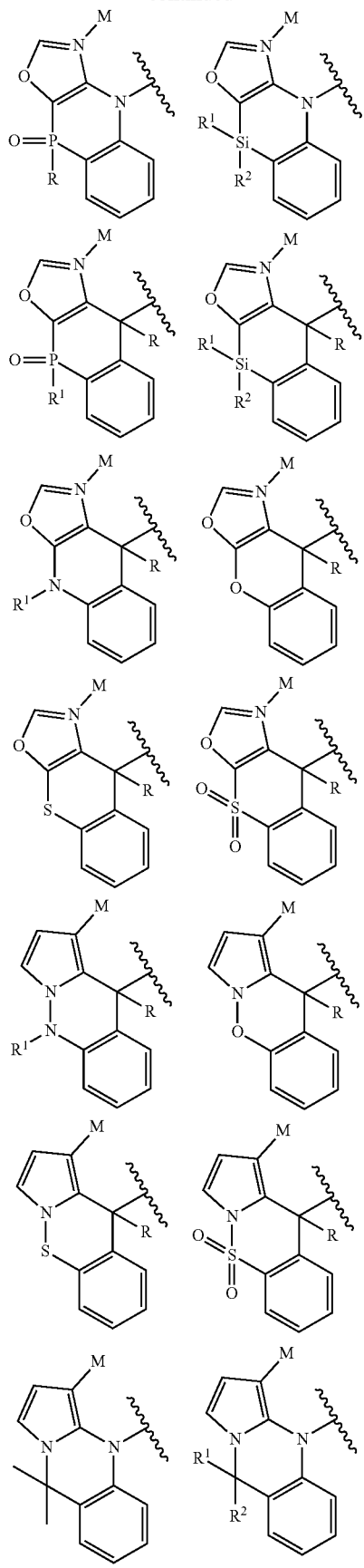
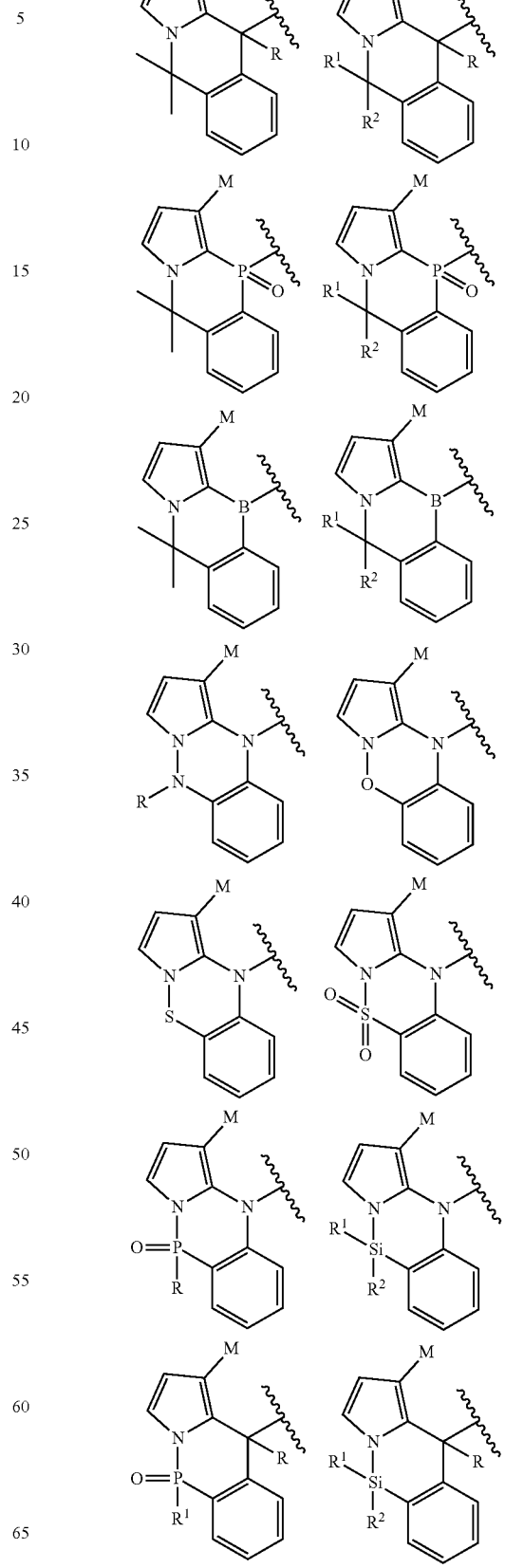

-continued

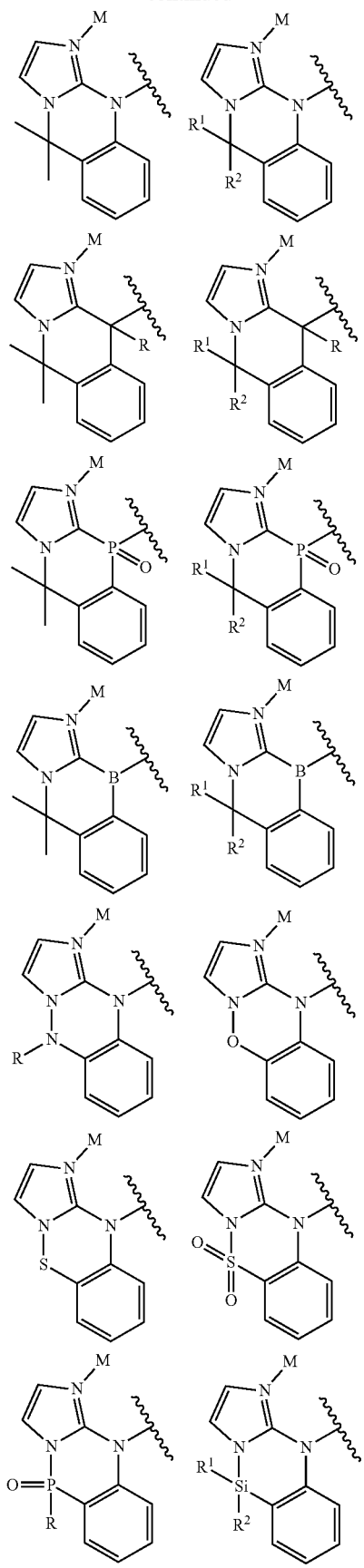

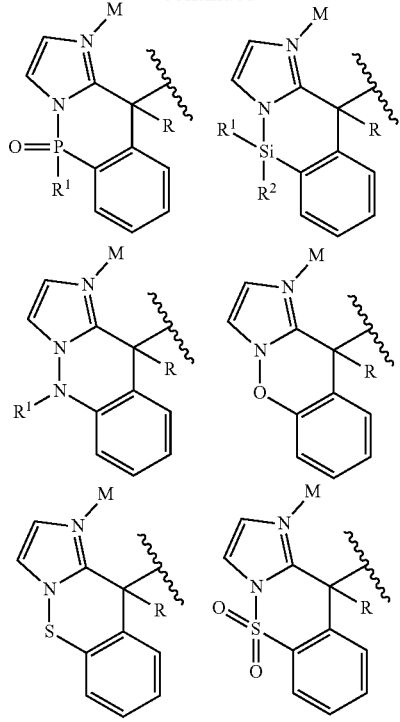

wherein each of R, $R^1$, $R^2$, and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

I. R Group

In one aspect, at least one $R^a$ is present. In another aspect, $R^a$ is absent.

In one aspect, $R^a$ is a mono-substitution. In another aspect, $R^a$ is a di-substitution. In yet another aspect, $R^a$ is a tri-substitution.

In one aspect, $R^a$ is connected to at least $L^1$. In another aspect, $R^b$ is connected to at least $L^2$. In yet another aspect, $R^c$ is connected to at least $L^3$. In one aspect, $R^d$ is connected to at least $L^4$.

In one aspect, $R^a$ is a di-substitution and the $R^a$'s are linked together. When the $R^a$'s are linked together the resulting structure can be a cyclic structure that includes a portion of the five- or six-membered cyclic structure as described herein. For example, a cyclic structure can be formed when the di-substitution is of $L^1$ and $L^2$ and the $R^a$'s are linked together.

In one aspect, each $R^a$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and two or more of $R^a$ are optionally linked together. In one aspect, at least one $R^a$ is halogen, hydroxyl; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl; or any conjugate or combination thereof, and two or more of $R^a$ are optionally linked together.

In one aspect, at least one $R^b$ is present. In another aspect, $R^b$ is absent.

In one aspect, $R^b$ is a mono-substitution. In another aspect, $R^b$ is a di-substitution. In yet another aspect, $R^b$ is a tri-substitution.

In one aspect, each $R^b$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and two or more of $R^b$ are optionally linked together. In one aspect, at least one $R^b$ is halogen, hydroxyl; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl; or any conjugate or combination thereof, and two or more of $R^b$ are optionally linked together.

In one aspect, at least one $R^c$ is present. In another aspect, $R^c$ is absent.

In one aspect, $R^c$ is a mono-substitution. In another aspect, $R^c$ is a di-substitution. In yet another aspect, $R^c$ is a tri-substitution.

In one aspect, each $R^c$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and two or more of $R^c$ are optionally linked together. In one aspect, at least one $R^c$ is halogen, hydroxyl; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl; or any conjugate or combination thereof, and two or more of $R^c$ are optionally linked together.

In one aspect, at least one $R^d$ is present. In another aspect, $R^d$ is absent.

In one aspect, $R^d$ is a mono-substitution. In another aspect, $R^d$ is a di-substitution. In yet another aspect, $R^d$ is a tri-substitution.

In one aspect, each $R^d$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and two or more of $R^d$ are optionally linked together. In one aspect, at least one $R^d$ is halogen, hydroxyl; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl; or any conjugate or combination thereof, and two or more of $R^d$ are optionally linked together.

In one aspect, at least one $R^e$ is present. In another aspect, $R^e$ is absent.

In one aspect, $R^e$ is a mono-substitution. In another aspect, $R^e$ is a di-substitution. In yet another aspect, $R^e$ is a tri-substitution.

In one aspect, each $R^e$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and two or more of $R^e$ are optionally linked together. In one aspect, at least one $R^e$ is halogen, hydroxyl; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl; or any conjugate or combination thereof, and two or more of $R^e$ are optionally linked together.

In one aspect, each of R, $R^1$, $R^2$, $R^3$, and $R^4$ is independently hydrogen, deuterium, halogen, hydroxyl, thiol, nitro, cyano, nitrile, isonitrile, sulfinyl, mercapto, sulfo, carboxyl, hydrazino, aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, substituted silyl, polymeric, or any conjugate or combination thereof. In another aspect, each of R, $R^1$, $R^2$, $R^3$, and $R^4$ is independently hydrogen, aryl, cycloalkyl, cycloalkenyl, heterocyclyl, heteroaryl, alkyl, alkenyl, alkynyl, halogen, hydroxyl, thiol, nitro, cyano, or amino. In another aspect, each of R, $R^1$, $R^2$, $R^3$, and $R^4$ is independently hydrogen, aryl, cycloalkyl, cycloalkenyl, heterocyclyl, heteroaryl, alkyl, alkenyl, or alkynyl.

J. Exemplary Compounds

In one aspect, metal complexes illustrated in this disclosure can comprise one or more of the following structures. In another aspect, they can also comprise other structures or portions thereof not specifically recited herein, and the present disclosure is not intended to be limited to those structures or portions thereof specifically recited.

Structure Pt-1
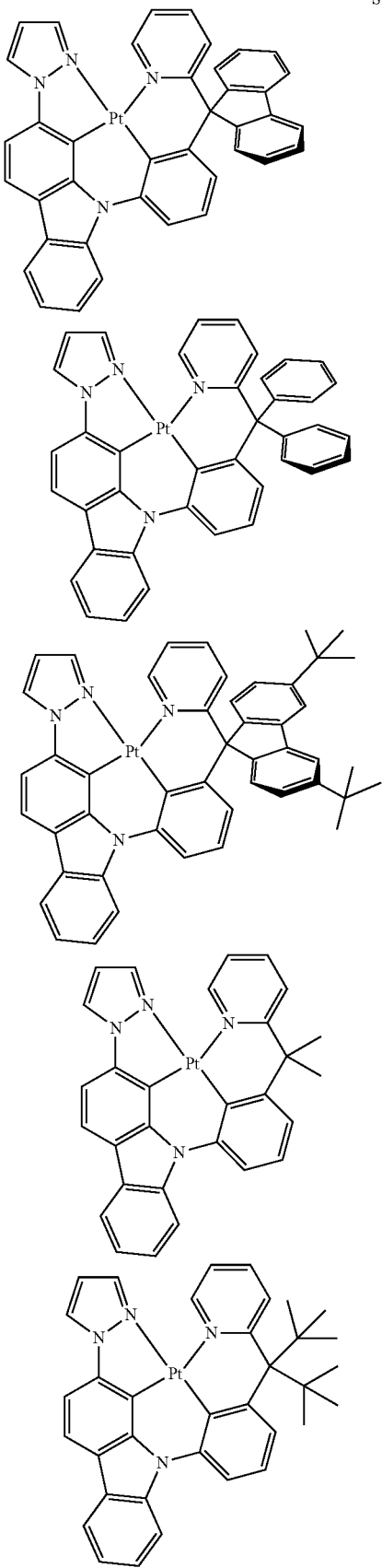

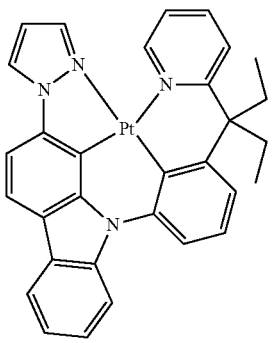

97
-continued
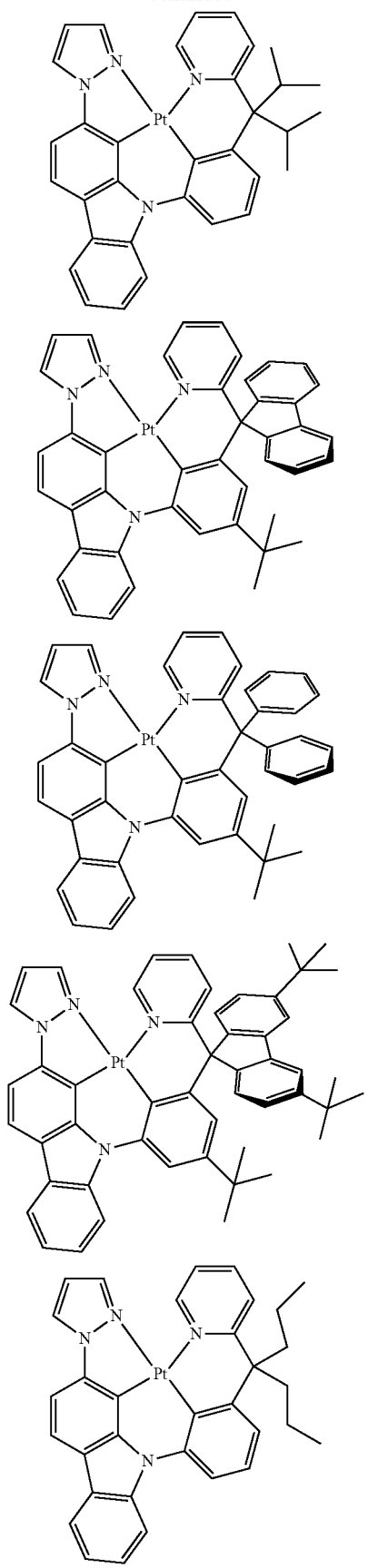
98
-continued
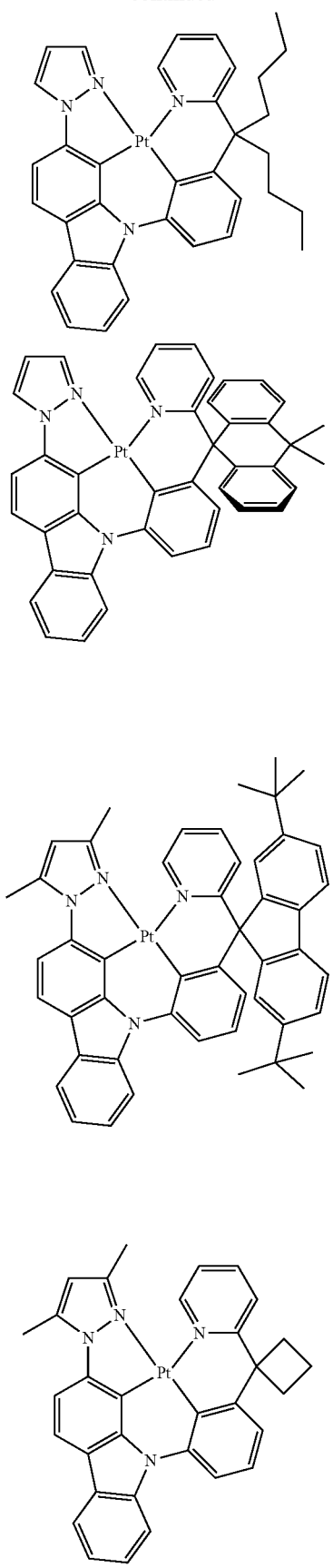

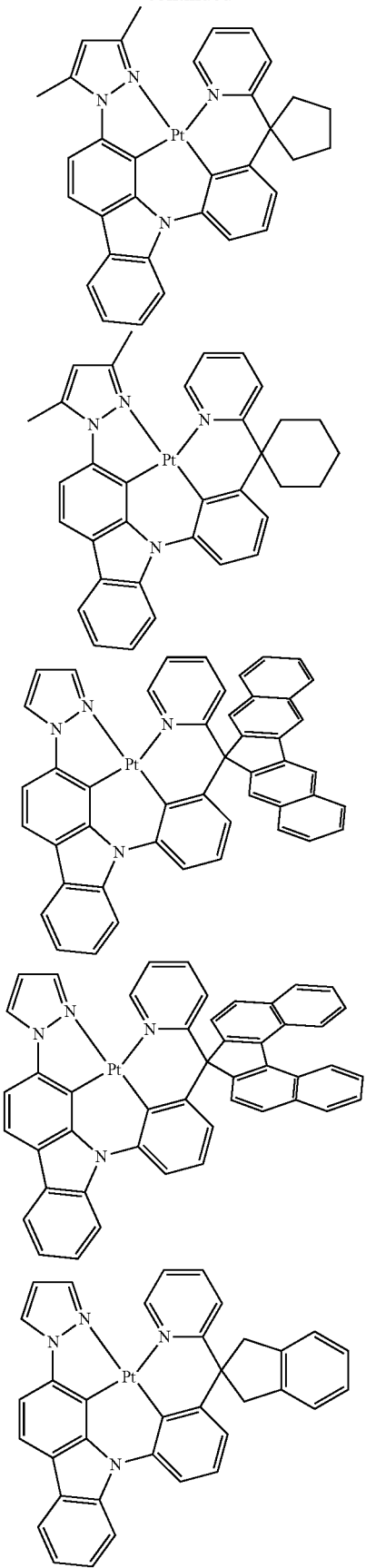
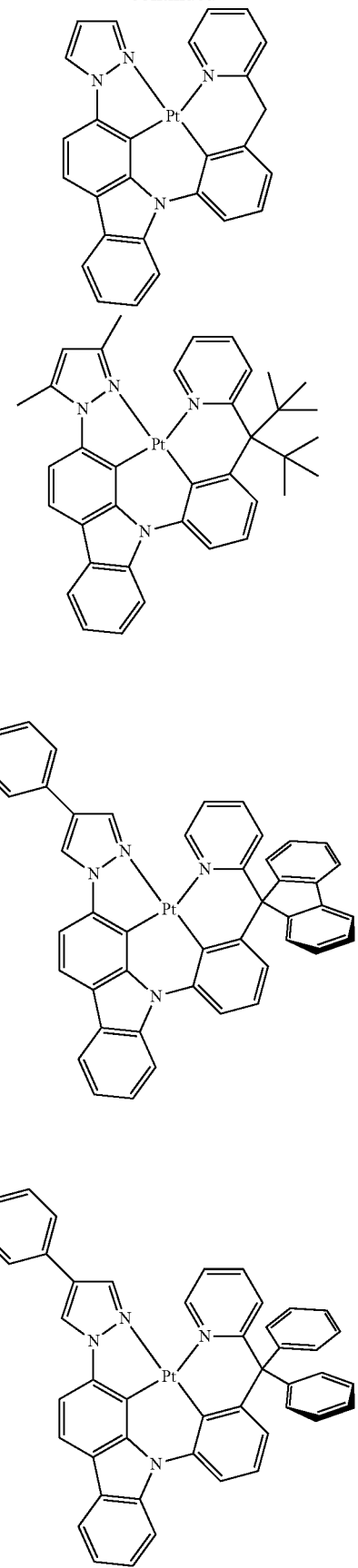

101
-continued
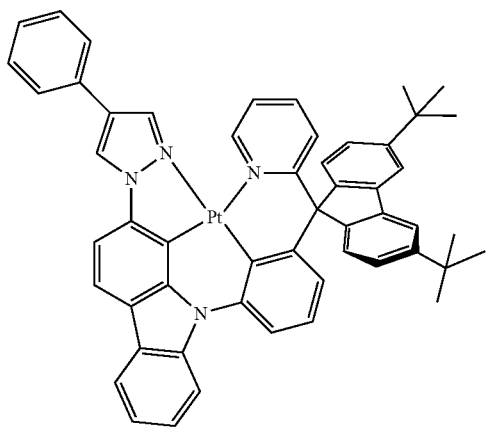
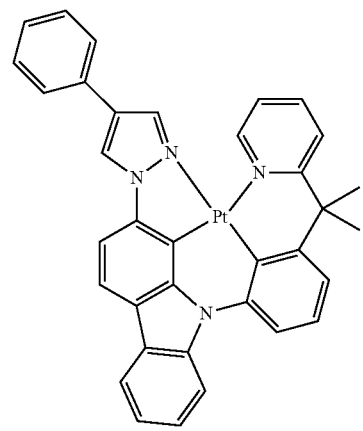
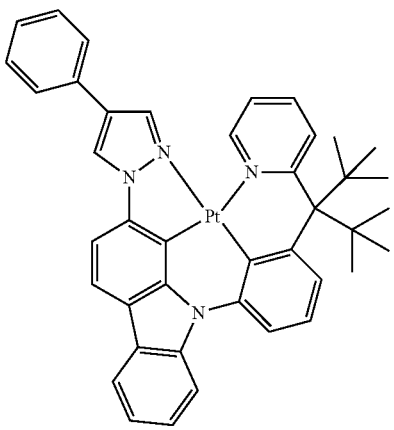
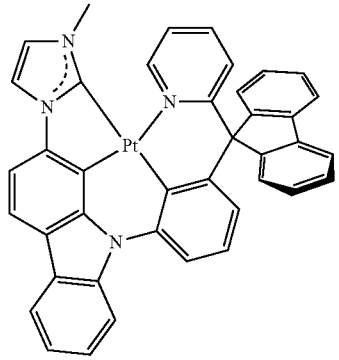
102
-continued
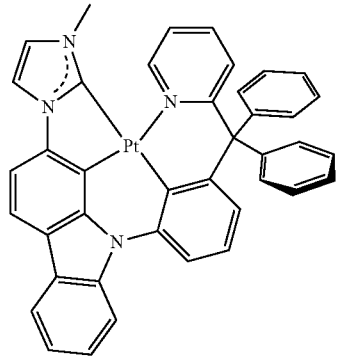
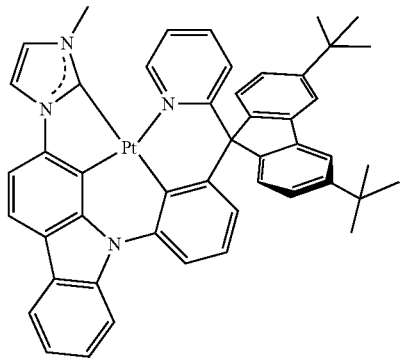
Structure Pt-2
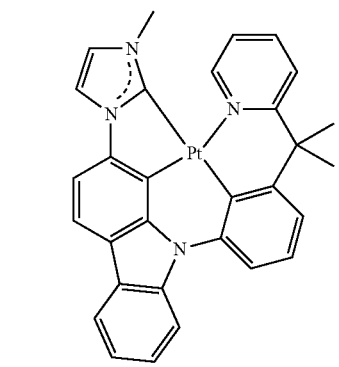
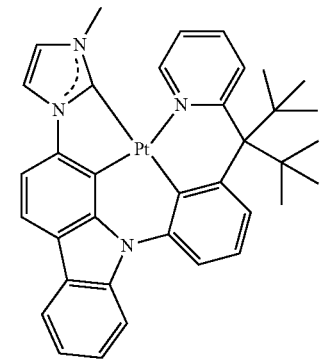

103
-continued
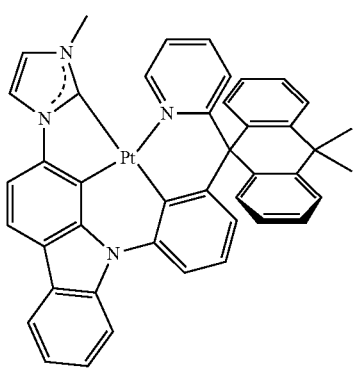
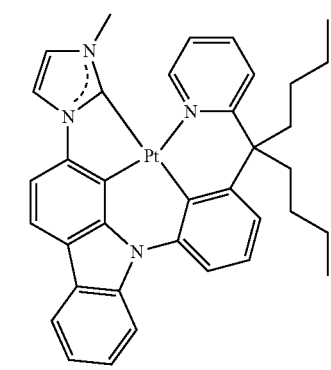
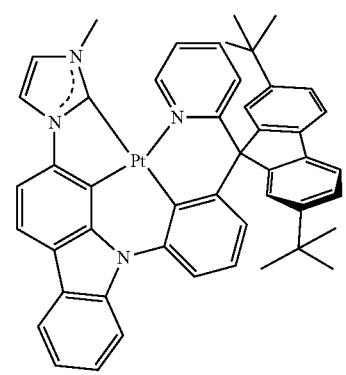
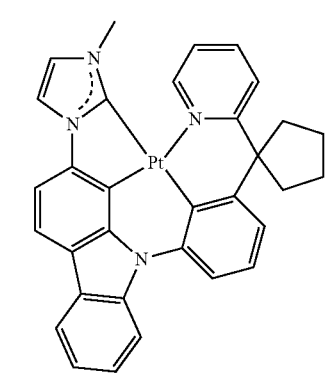
104
-continued
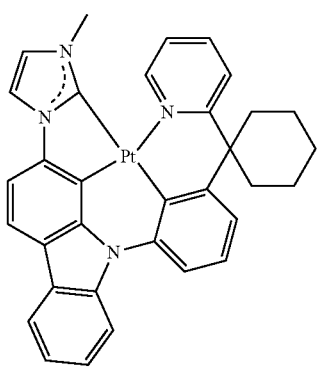
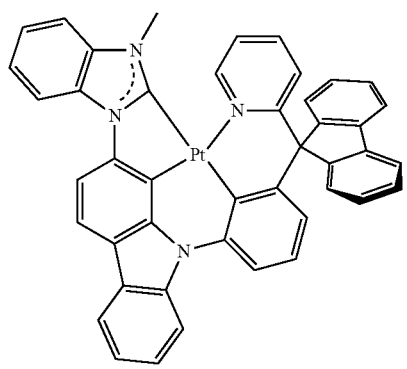
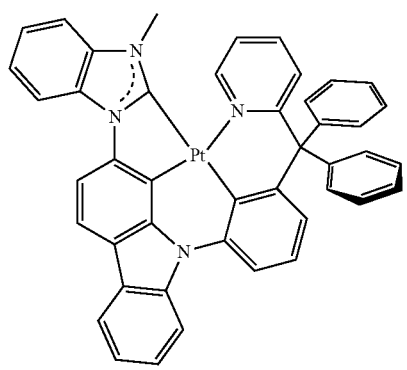
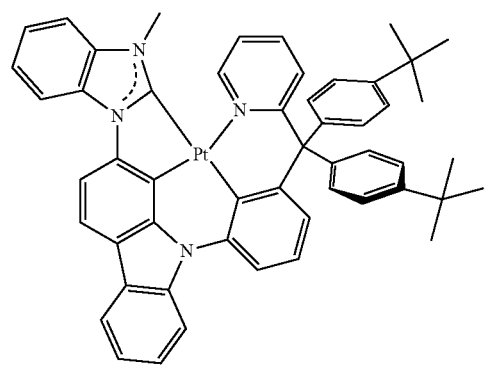

105
-continued
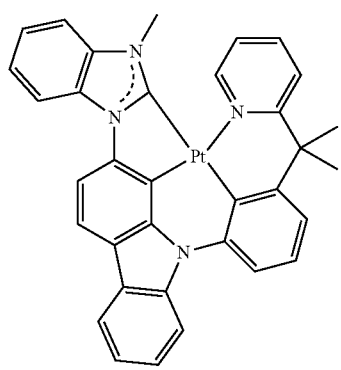
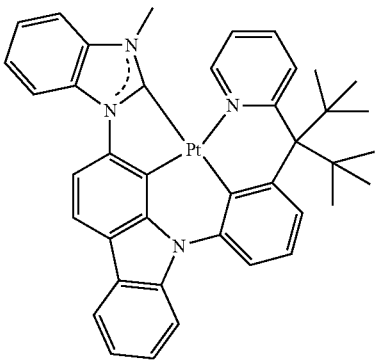
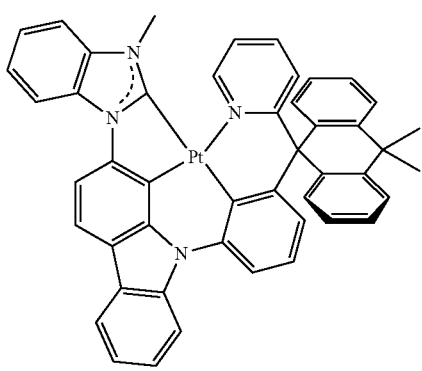
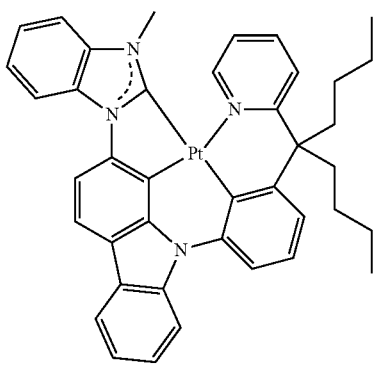
106
-continued
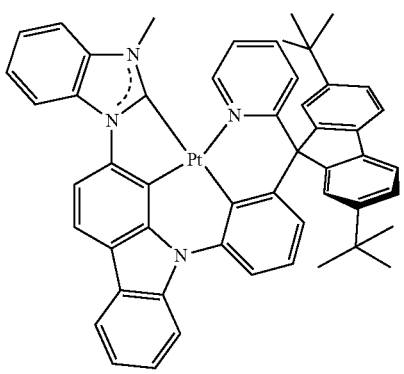
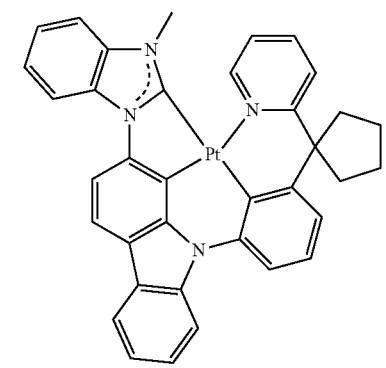
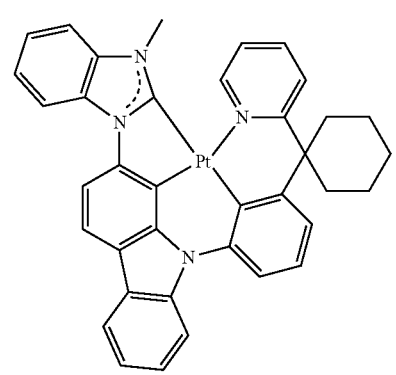
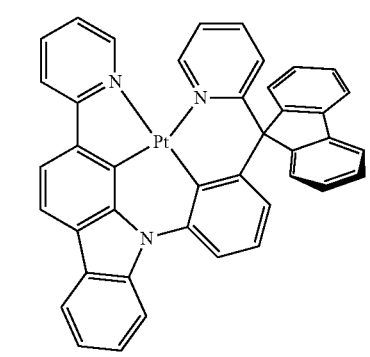

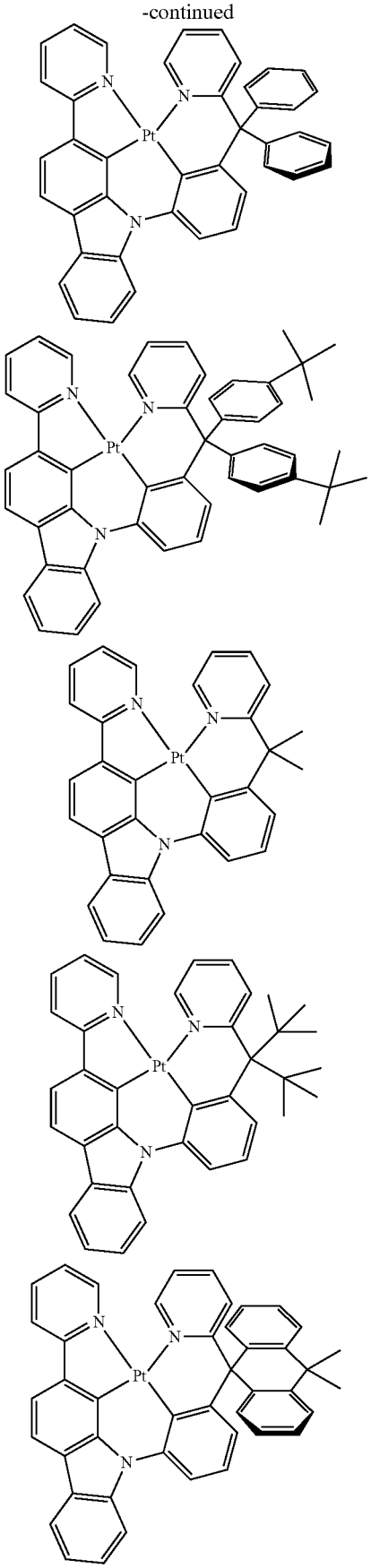
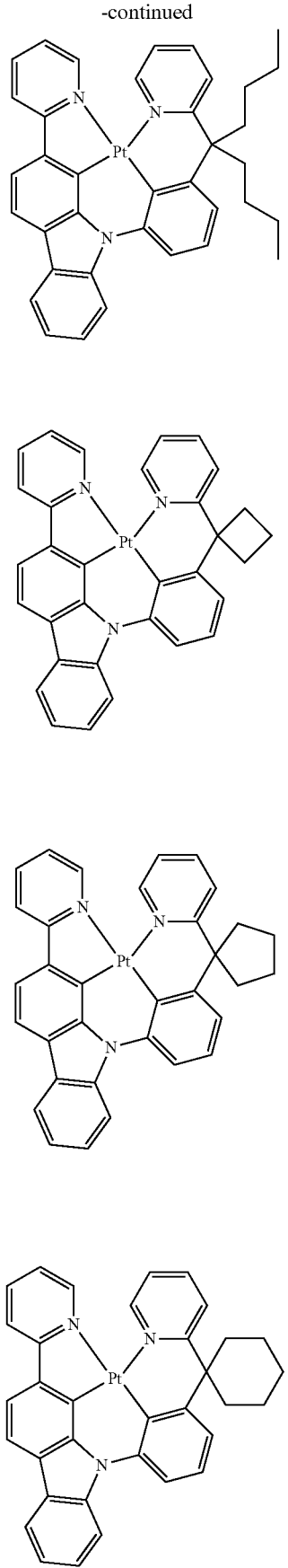

Structure Pt-3
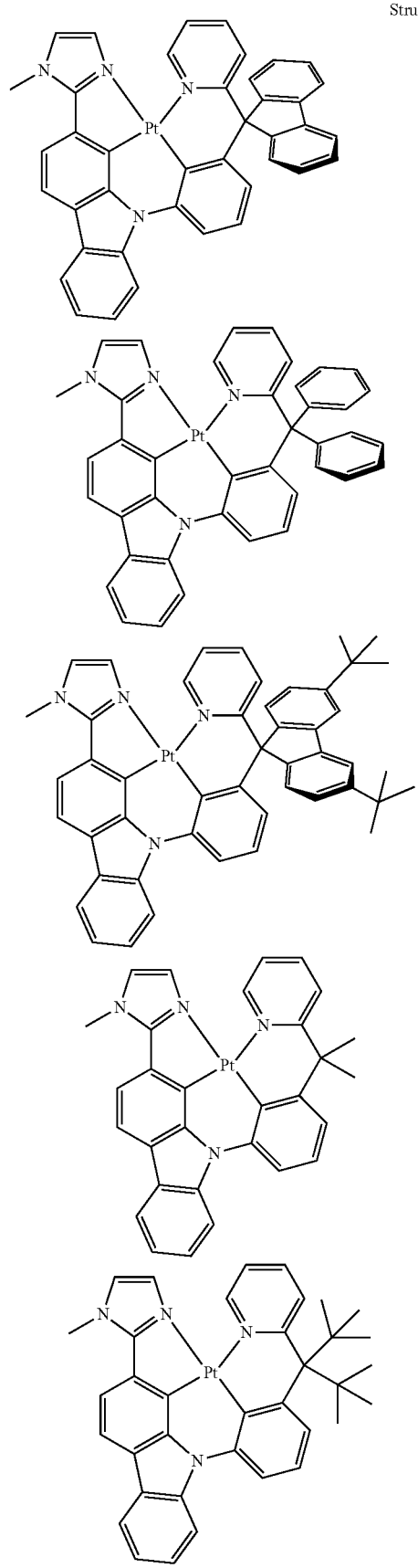
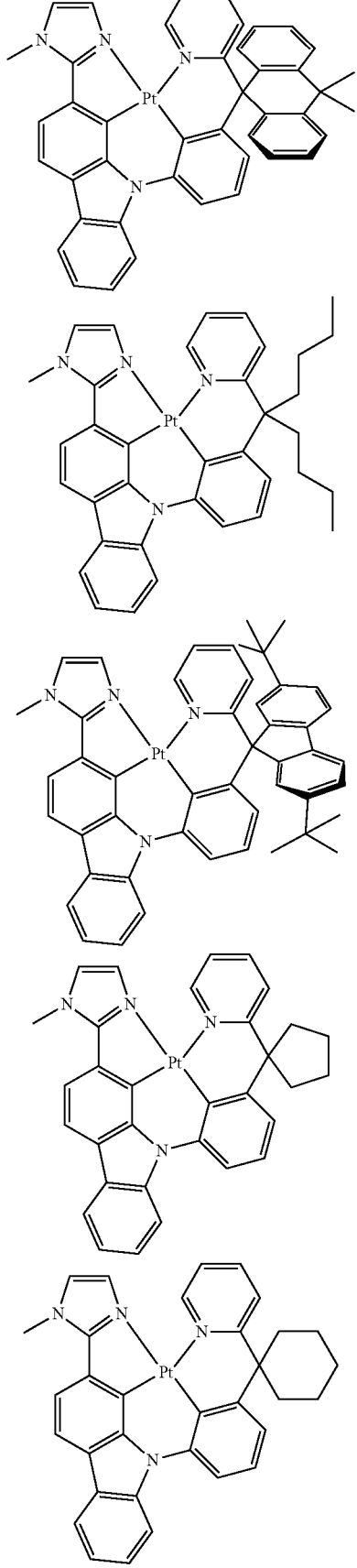

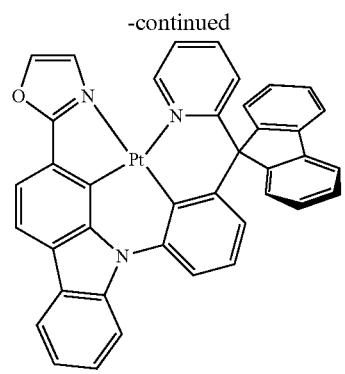
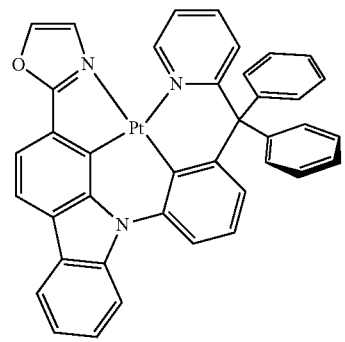
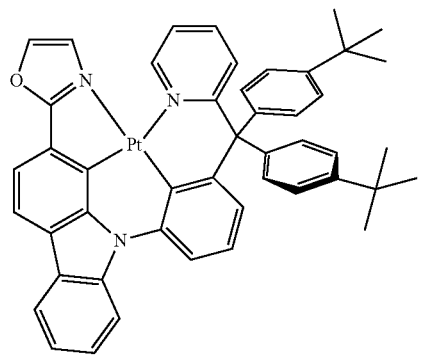
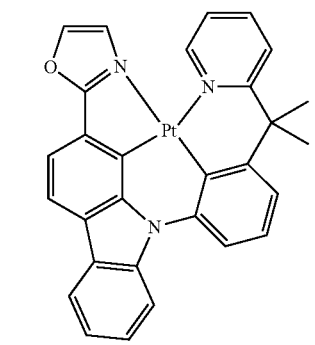
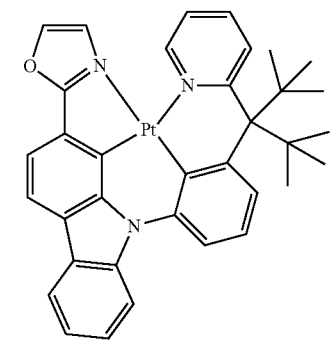
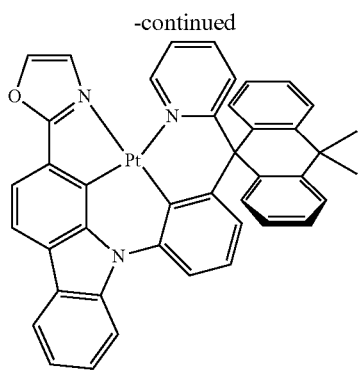
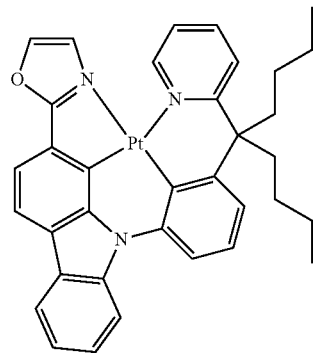
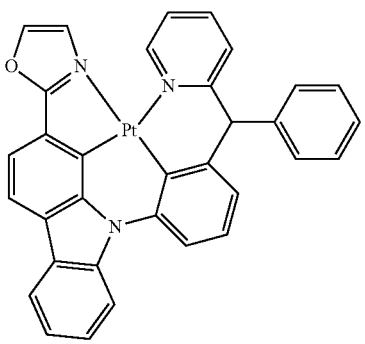
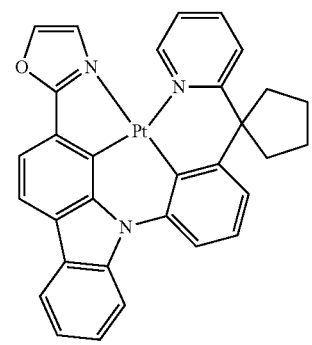
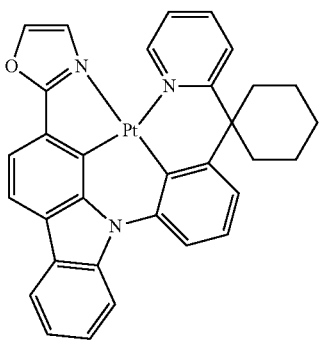

113
-continued
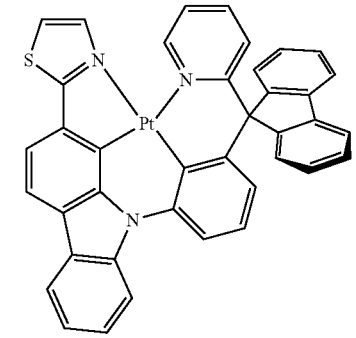
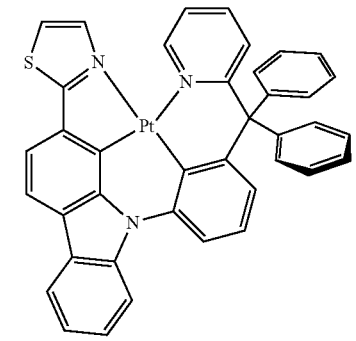
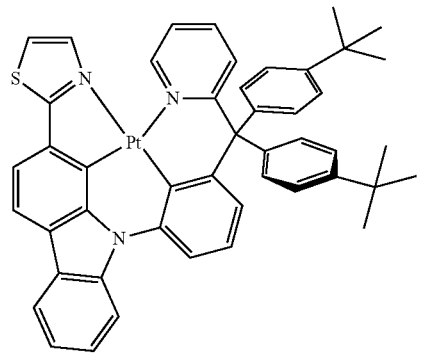
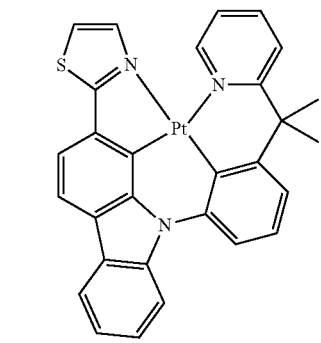
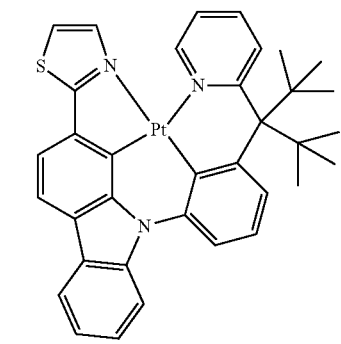
114
-continued
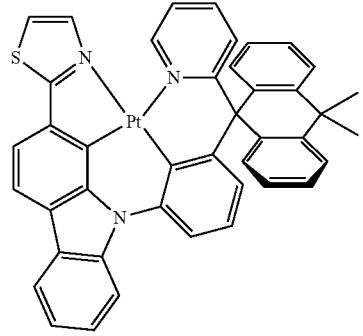
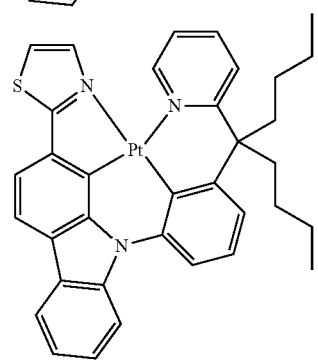
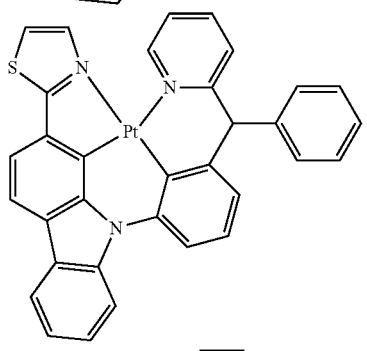
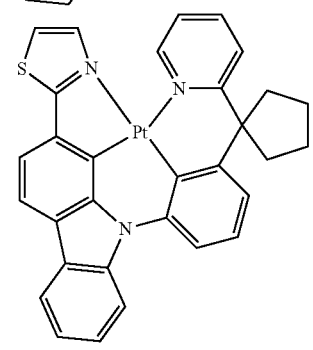
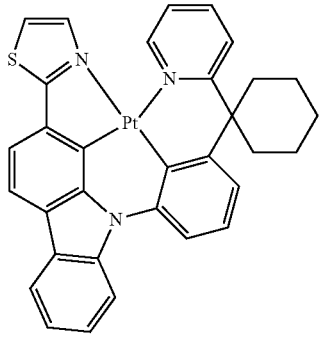

Structure Pt-4
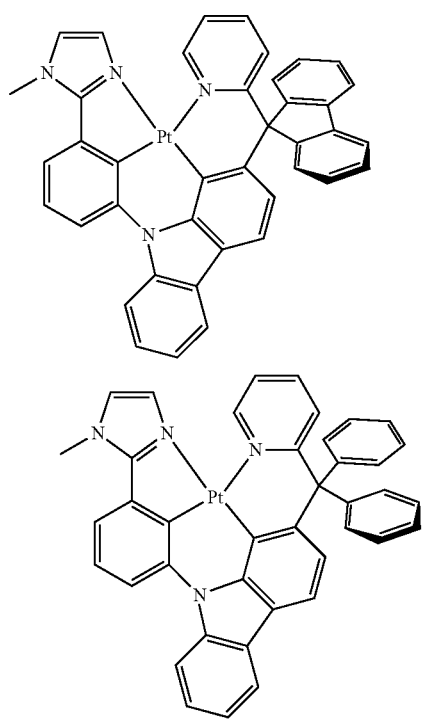
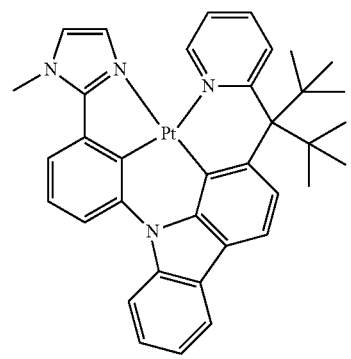
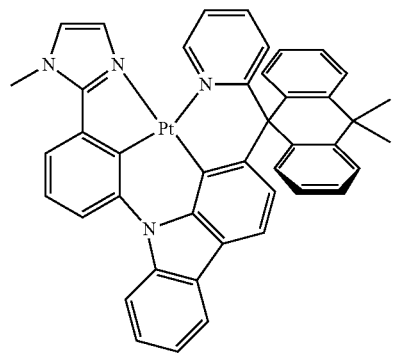
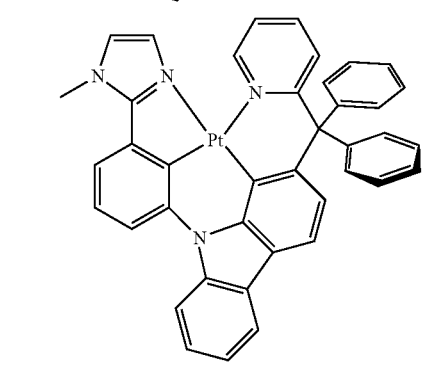
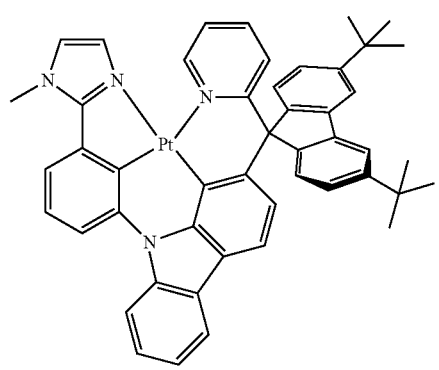
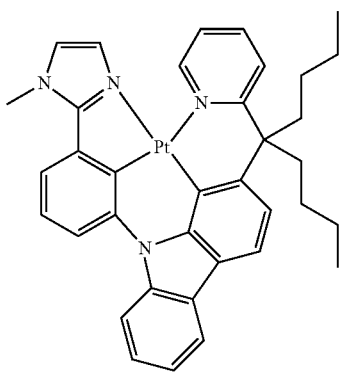
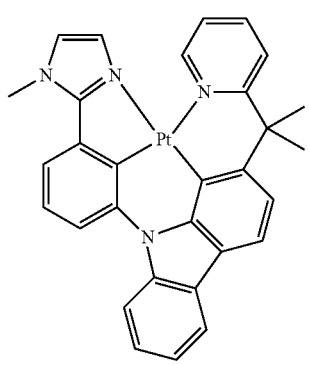
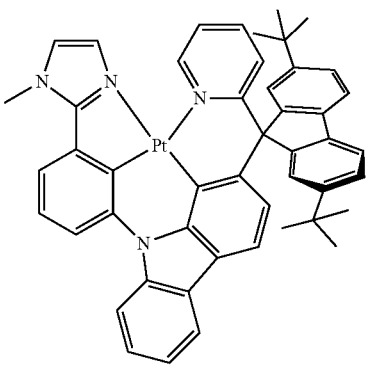

117
-continued
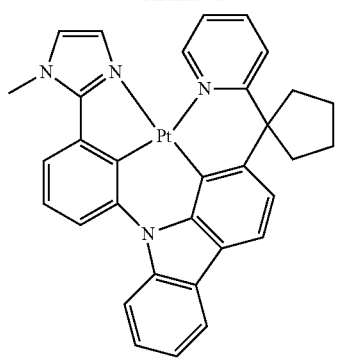
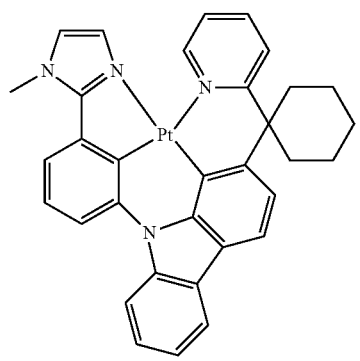
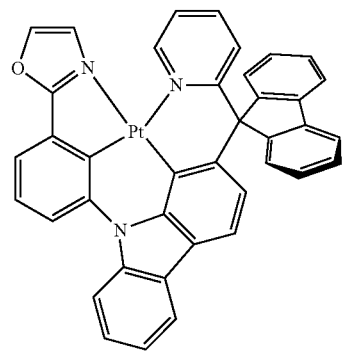
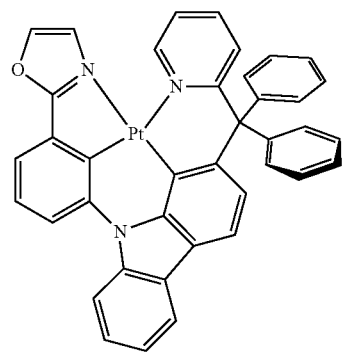
118
-continued
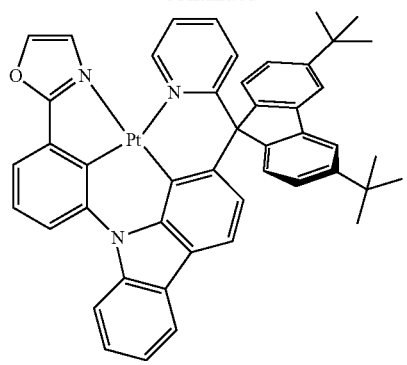
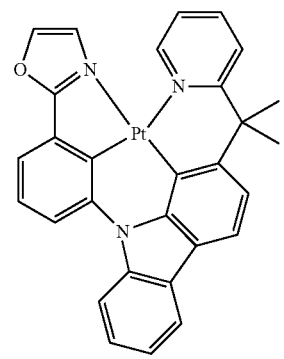
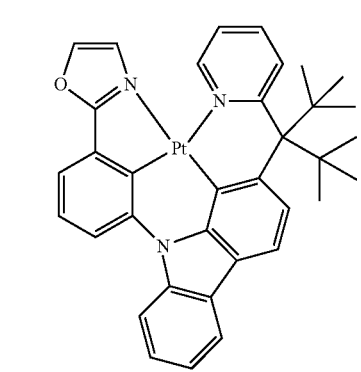
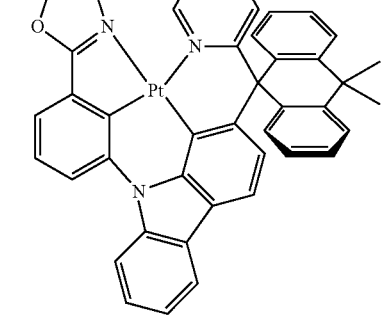

119
-continued
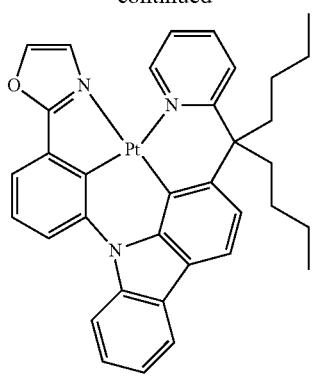
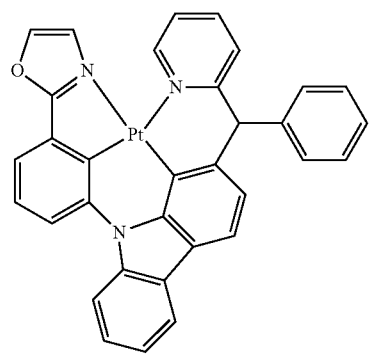
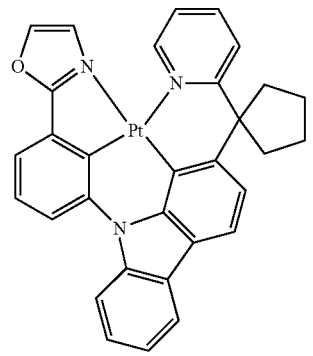
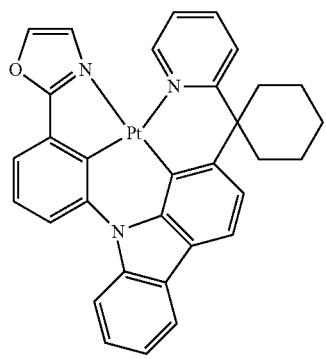
120
-continued
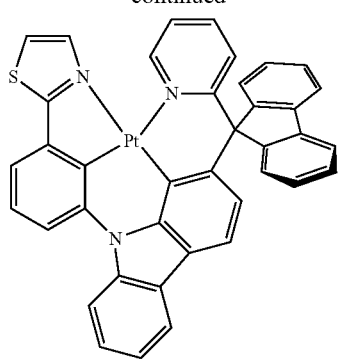
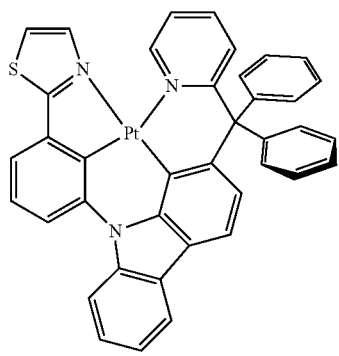
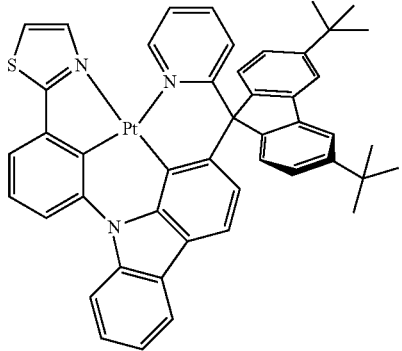
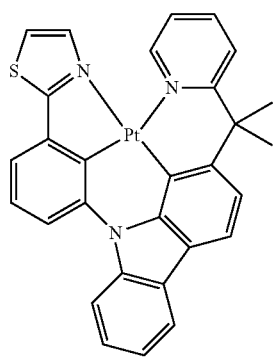

121
-continued
122
-continued
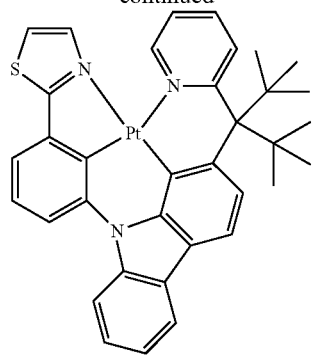
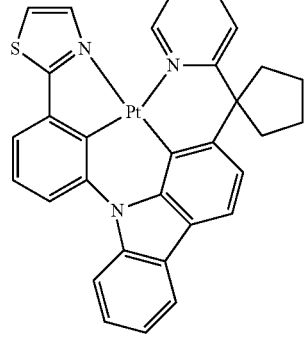
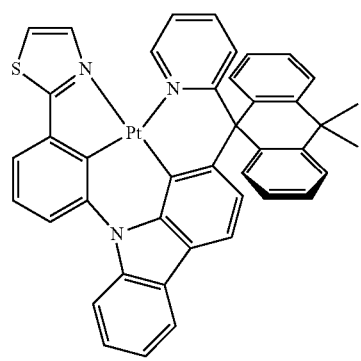
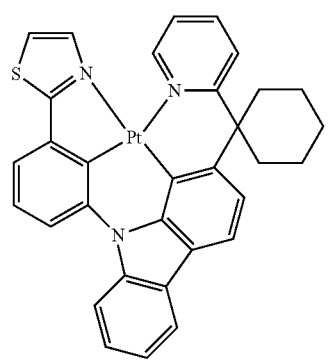
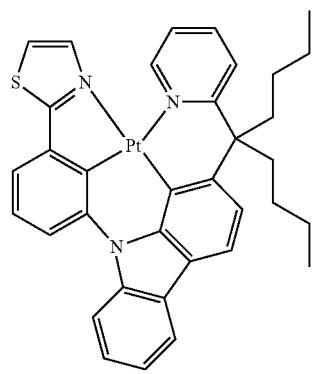
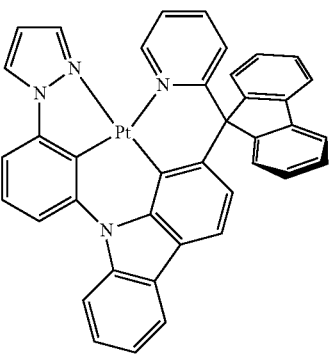
Structure Pt-5
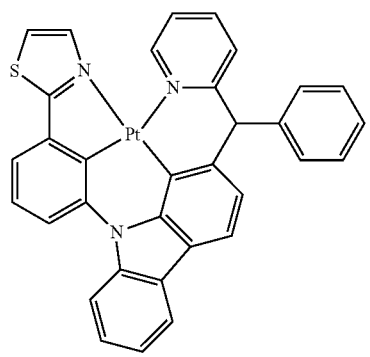
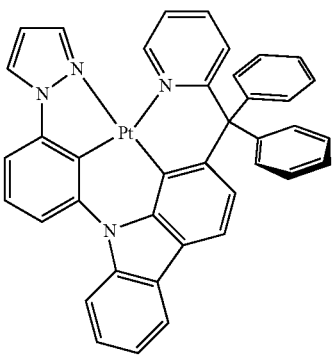

123
-continued
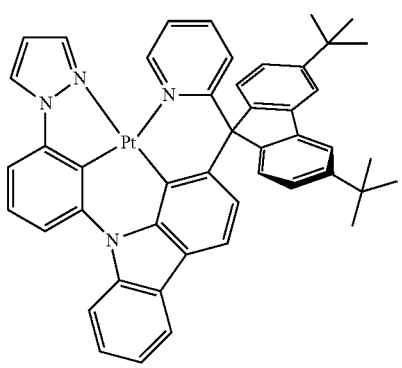
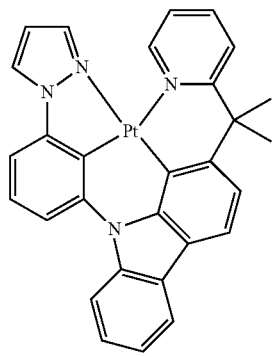
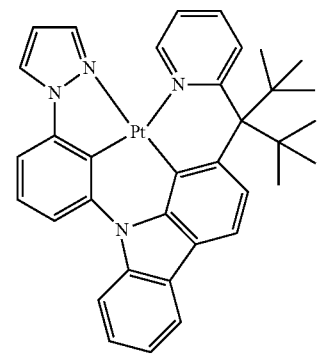
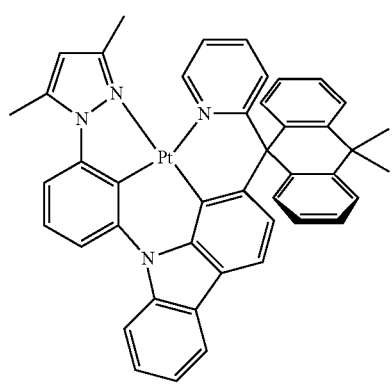
124
-continued
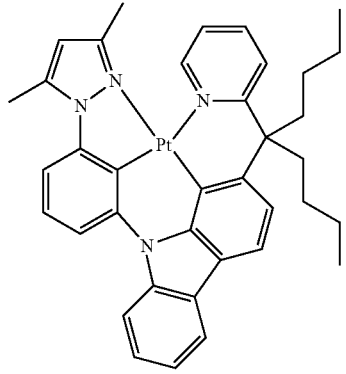
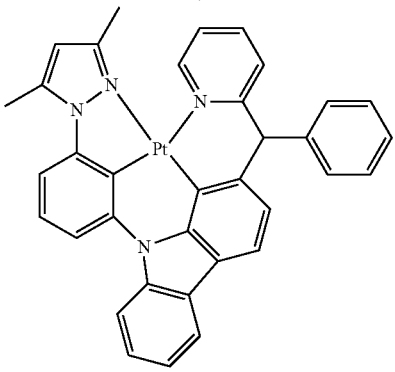
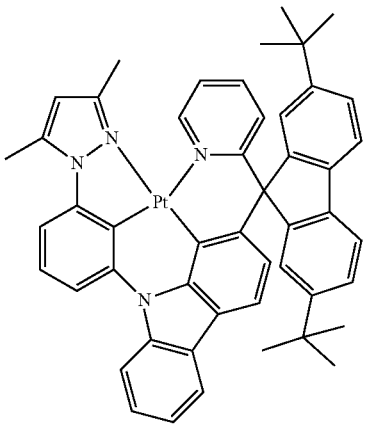
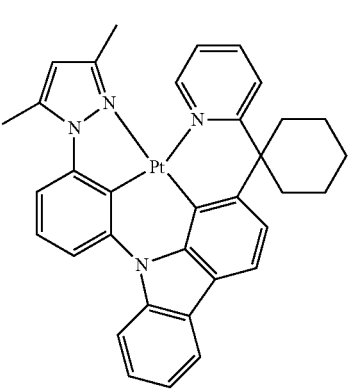

125
-continued
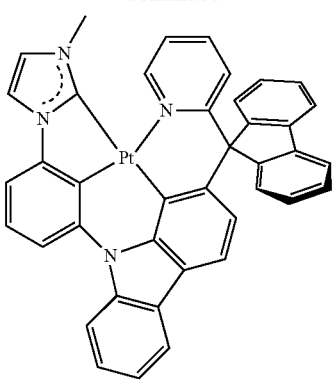
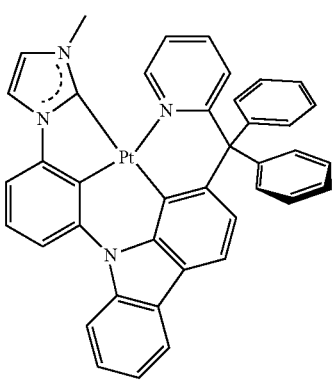
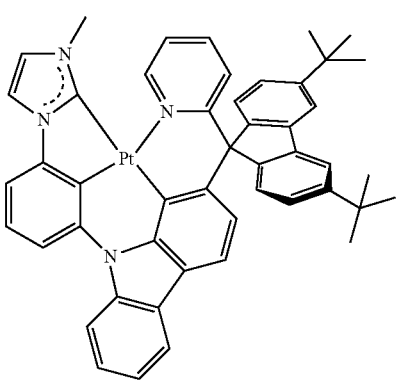
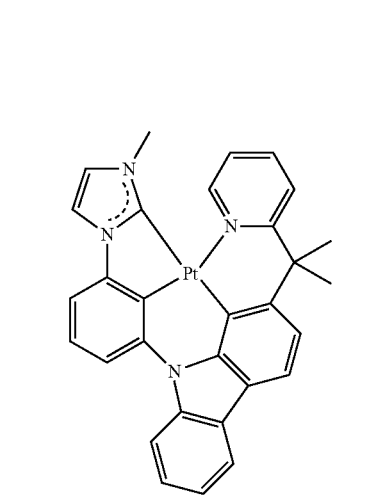
126
-continued
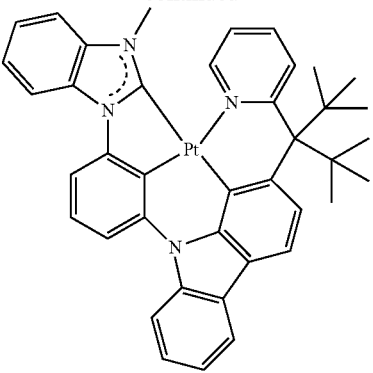
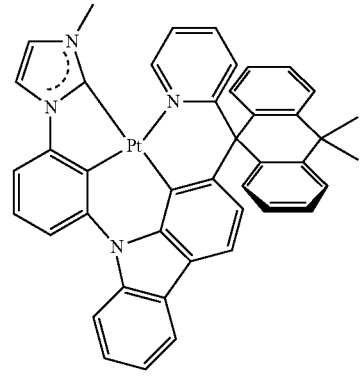
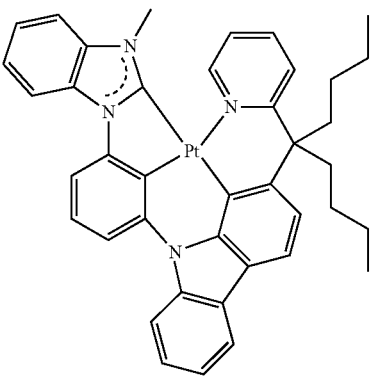
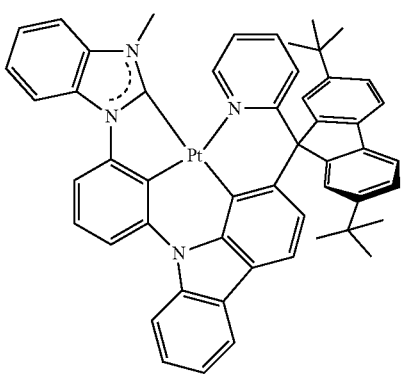

127
-continued
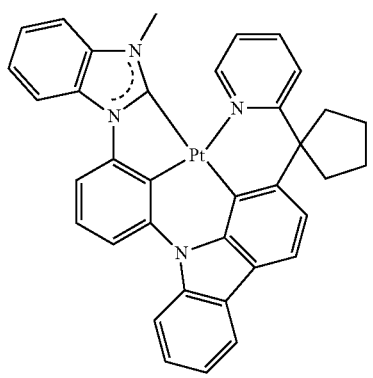
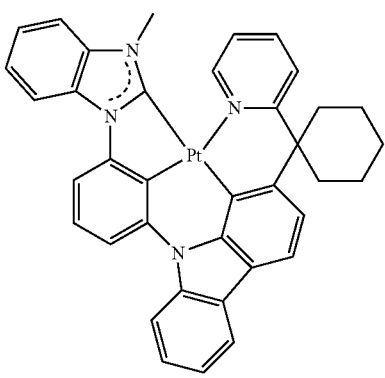
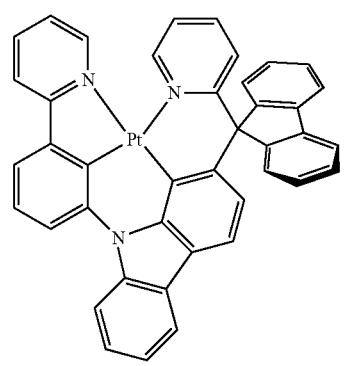
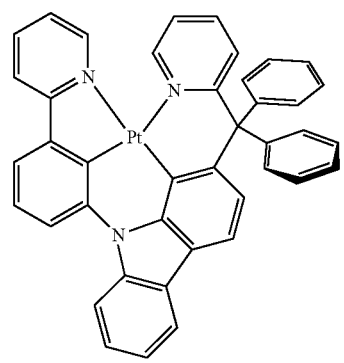
128
-continued
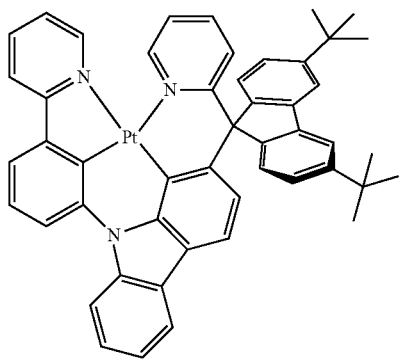
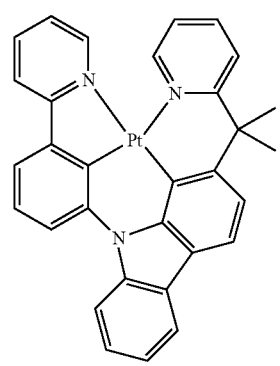
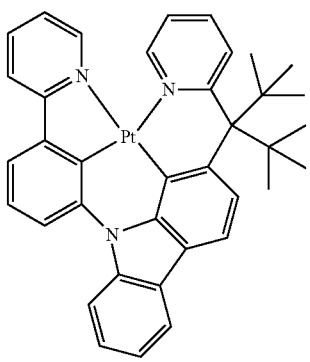
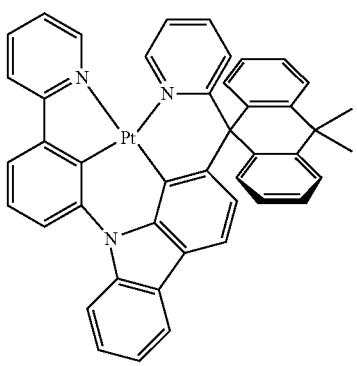

129
-continued
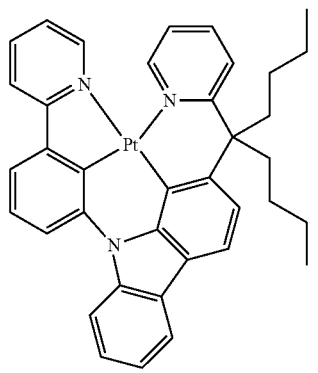
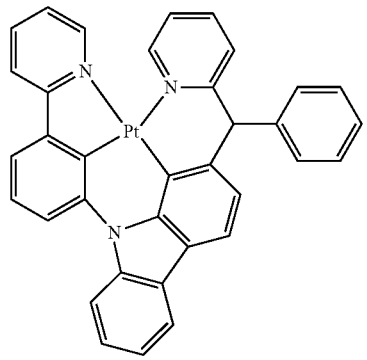
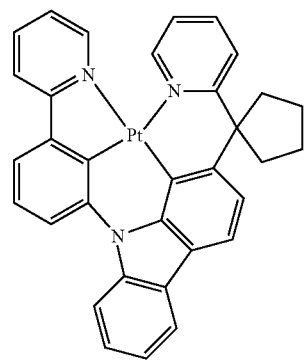
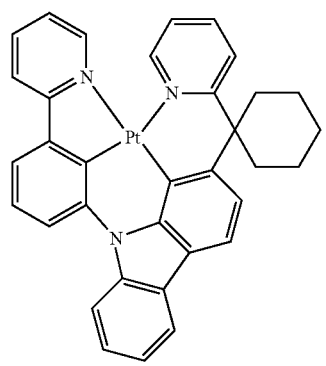
130
-continued
Structure Pt-6
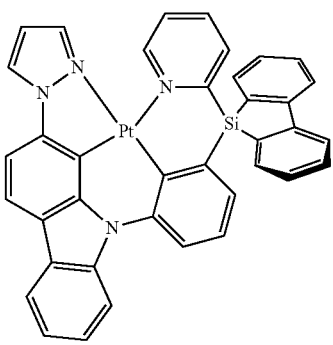
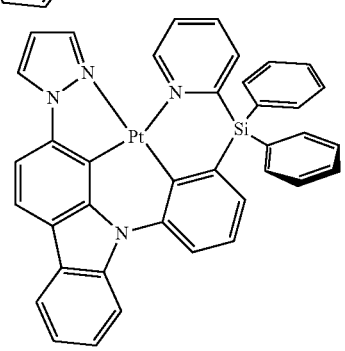
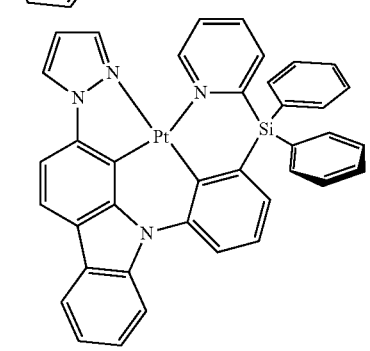
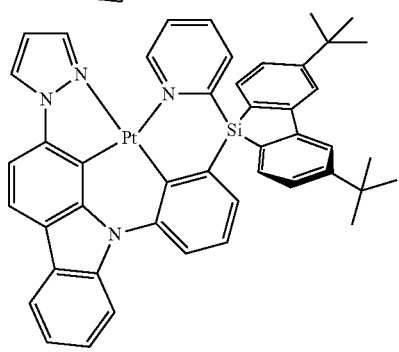
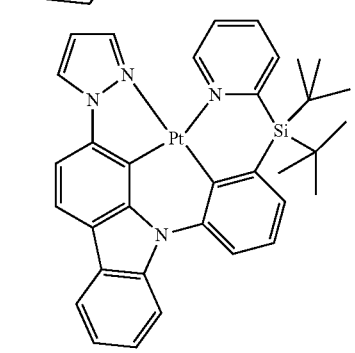
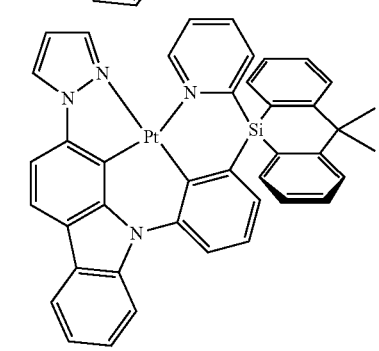

131
-continued
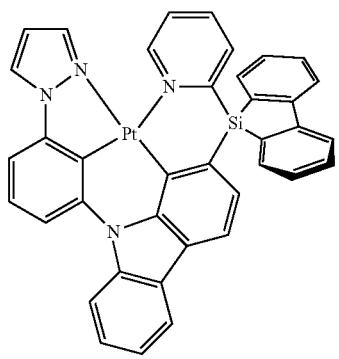
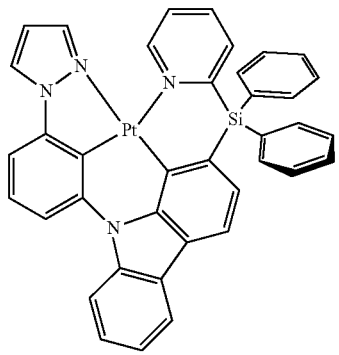
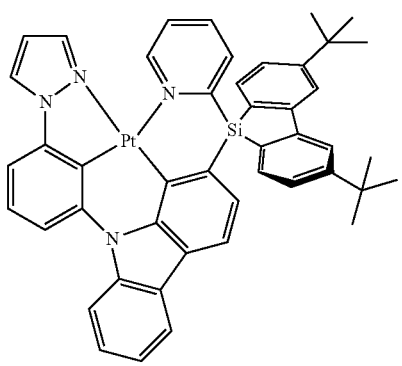
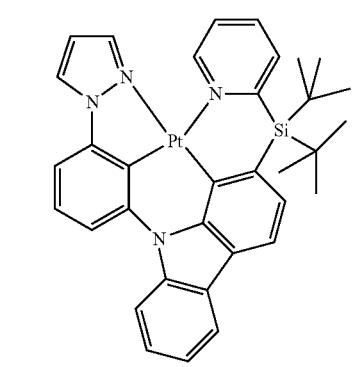
132
-continued
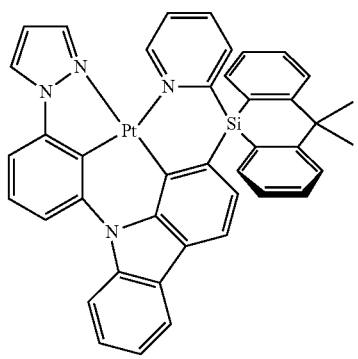
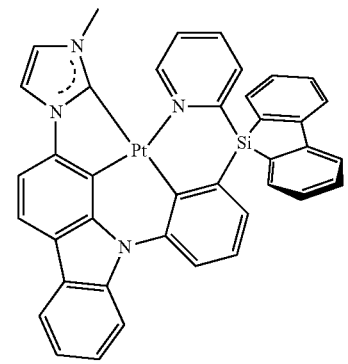
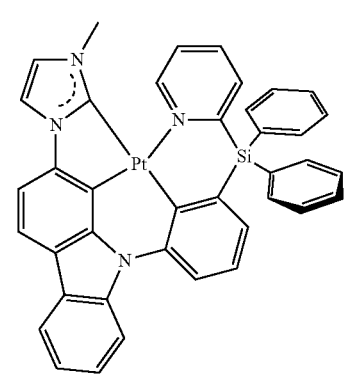
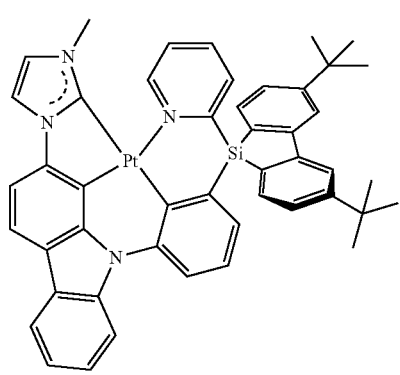

133
-continued
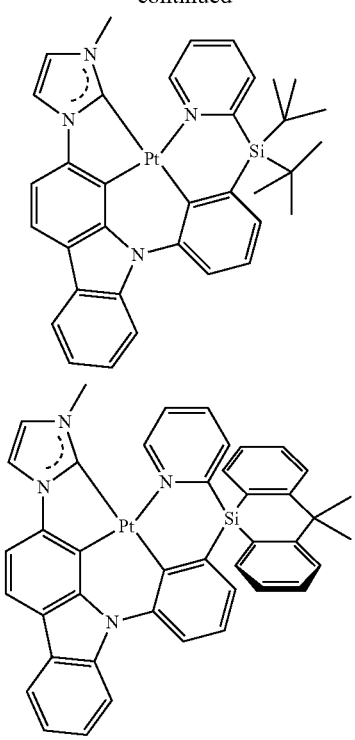
134
-continued
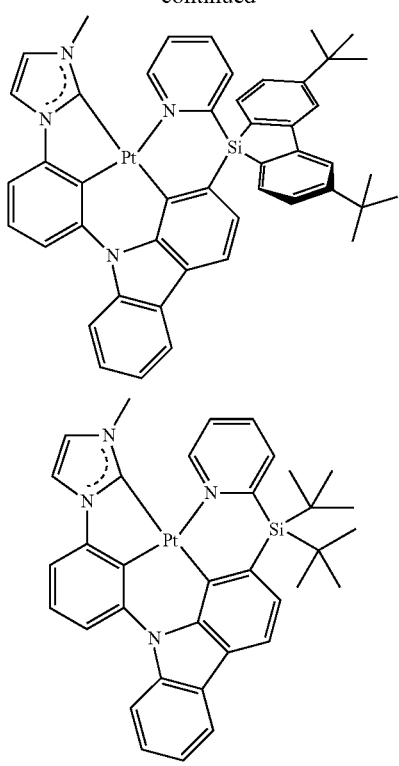
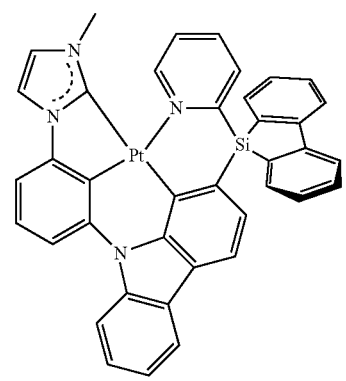
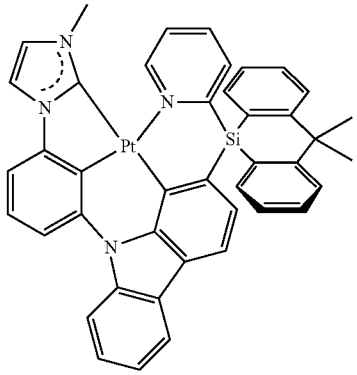
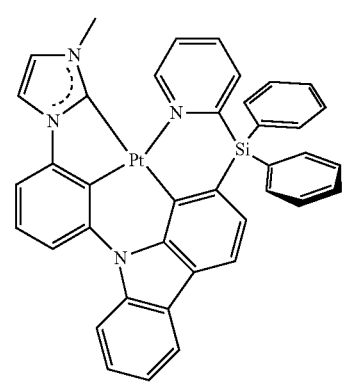
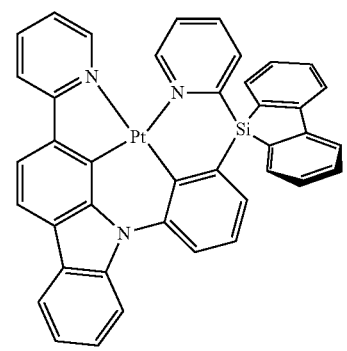

135
-continued
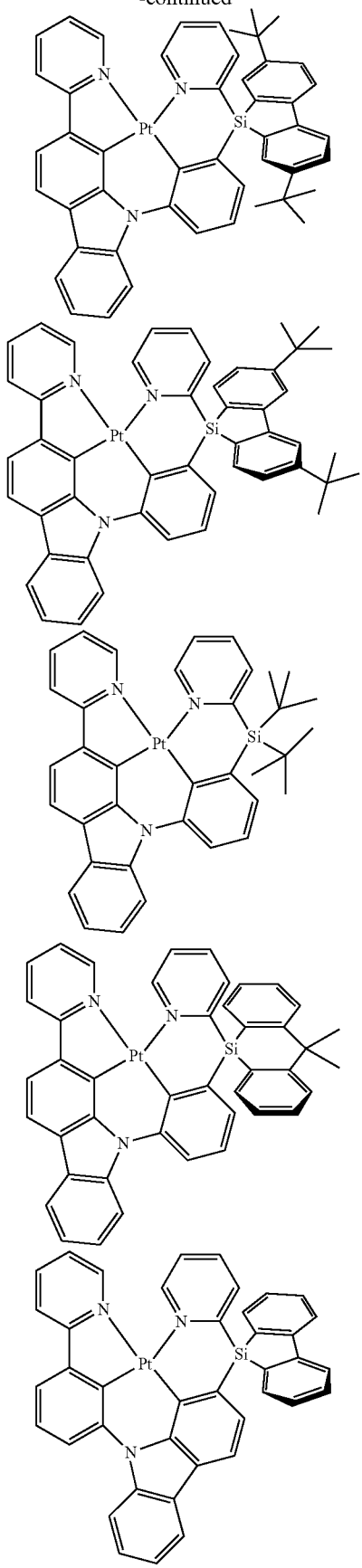
136
-continued
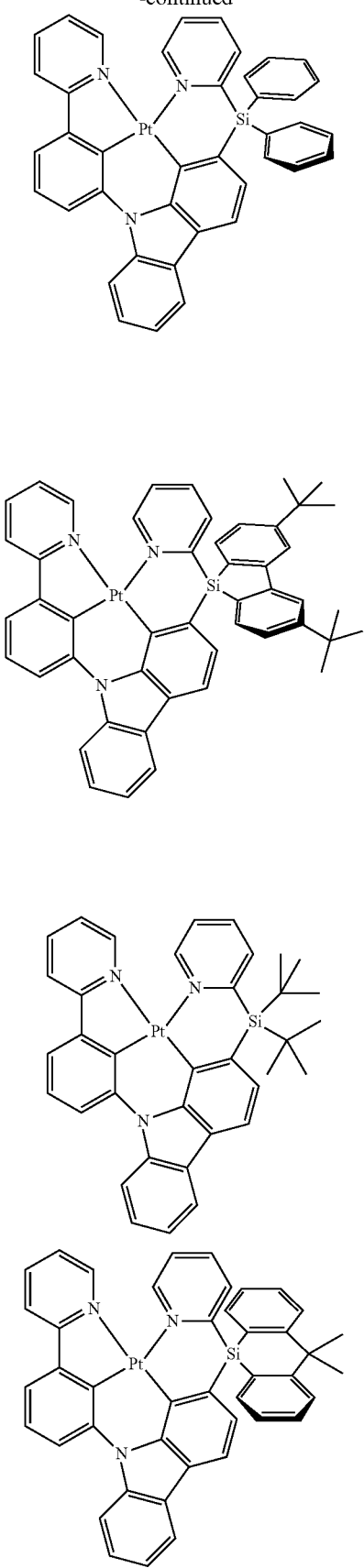

Structure Pt-7
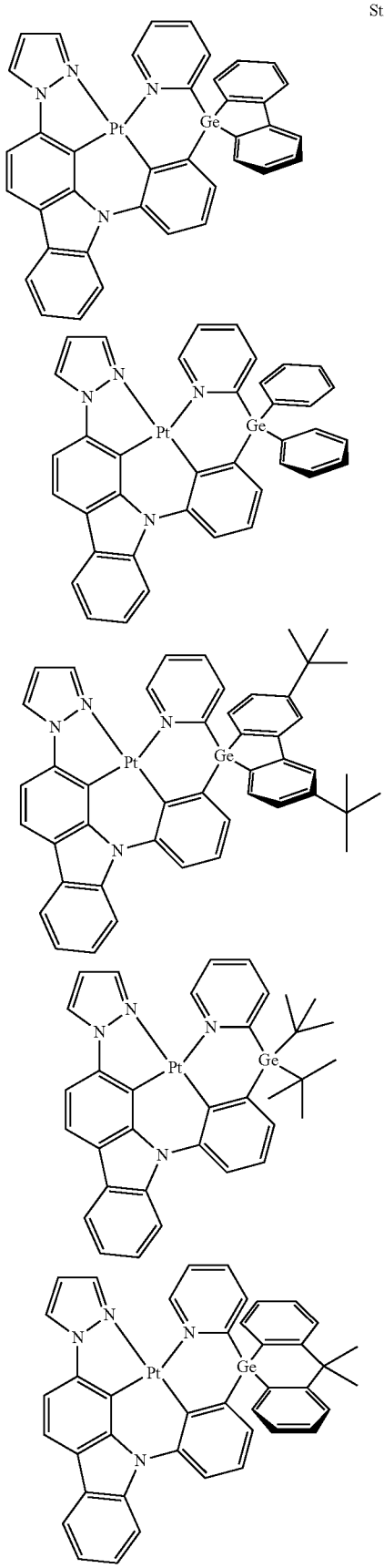
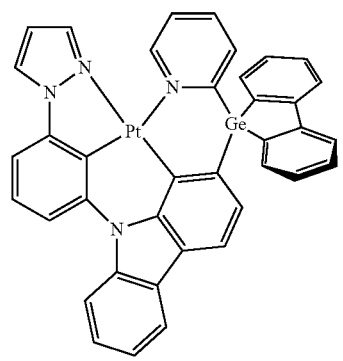
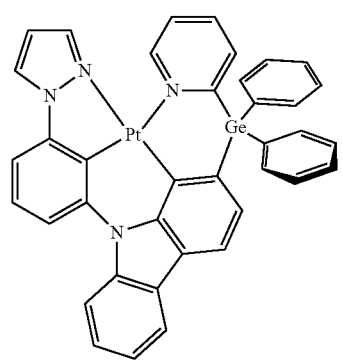
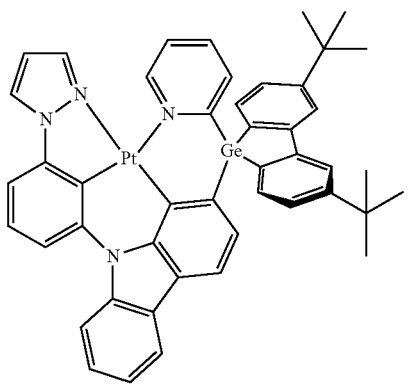
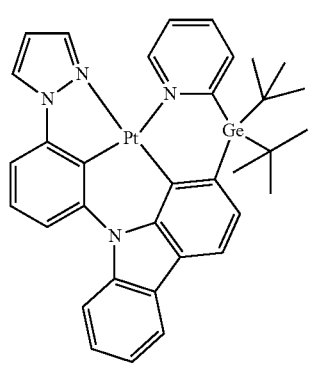

139
-continued
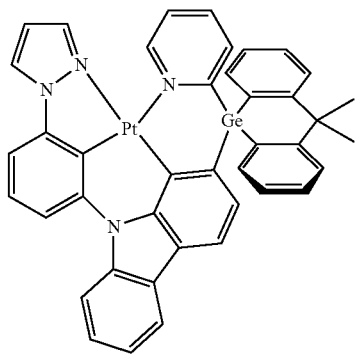
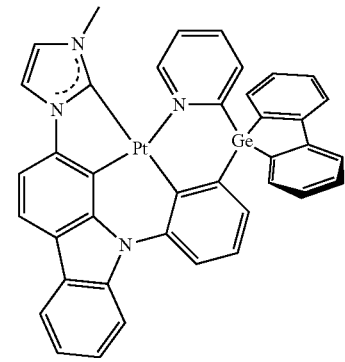
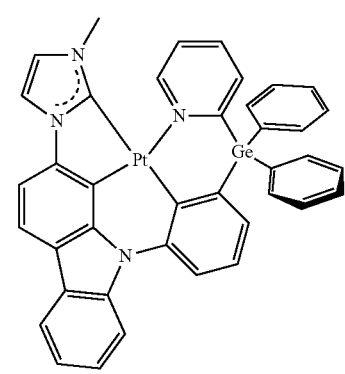
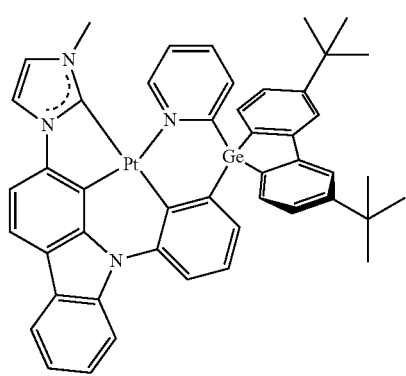
140
-continued
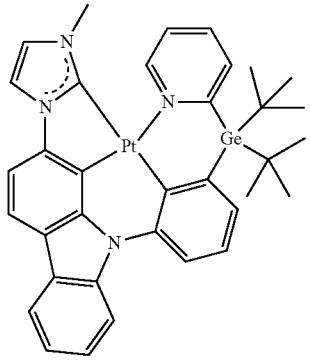
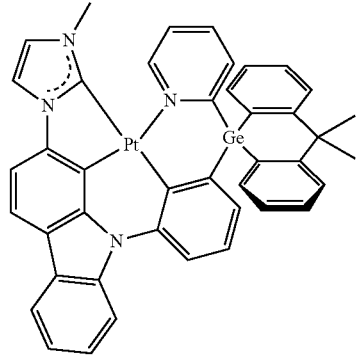
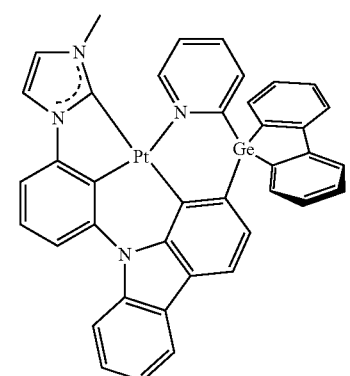
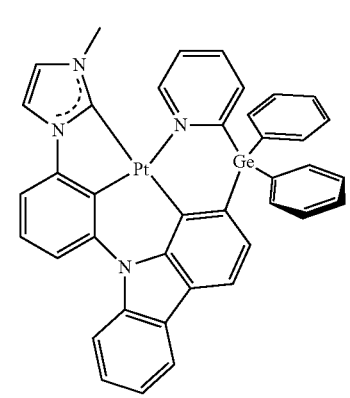

141
-continued
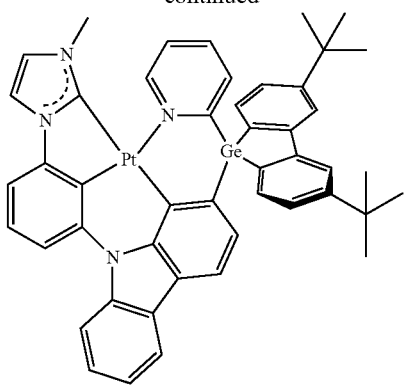
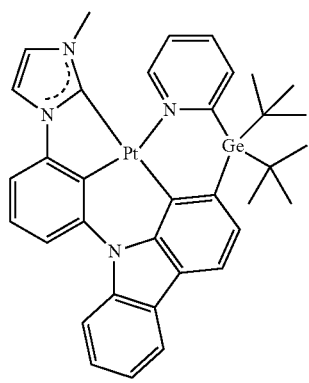
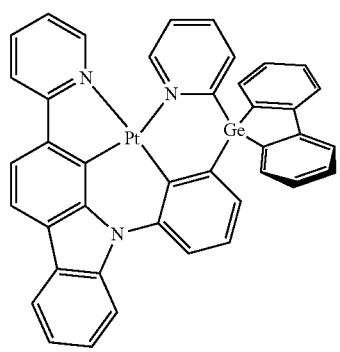
142
-continued
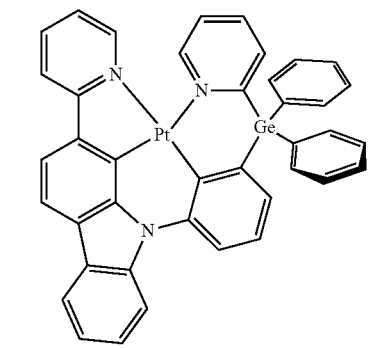
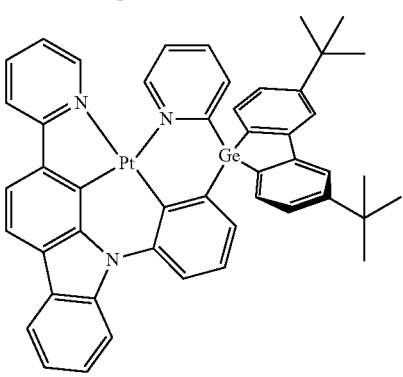
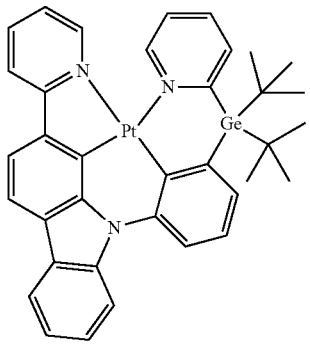
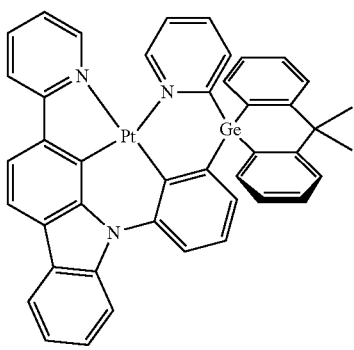

143
-continued
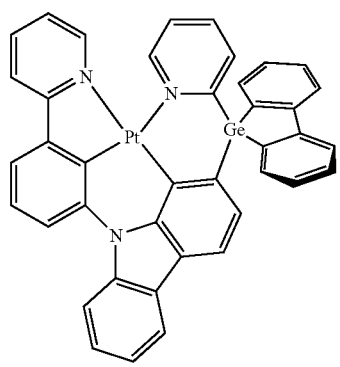
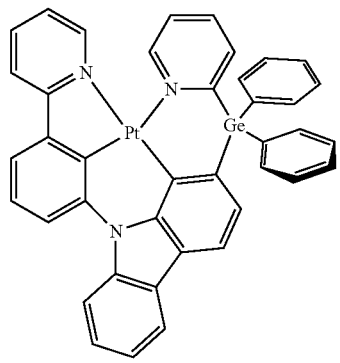
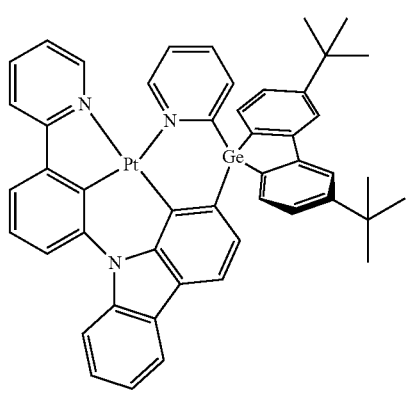
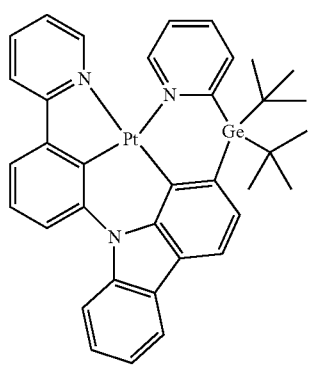
144
-continued
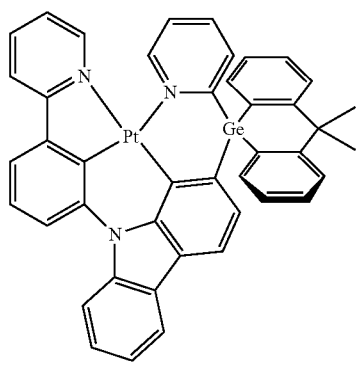
Structure Pt-8
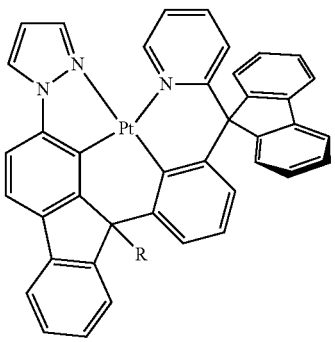
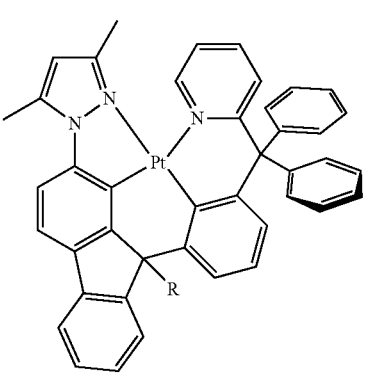
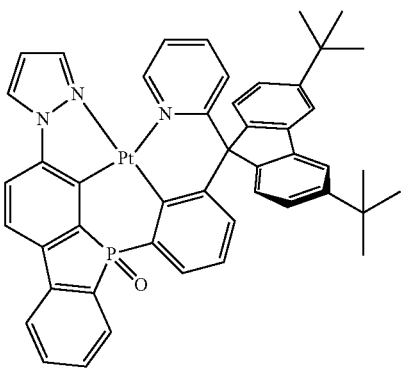

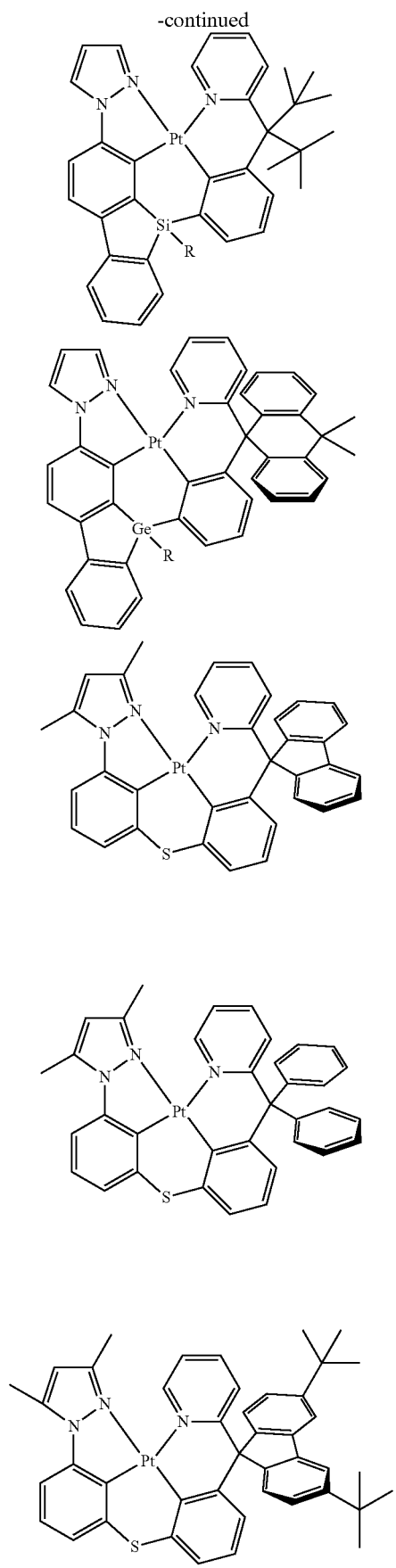

147
-continued
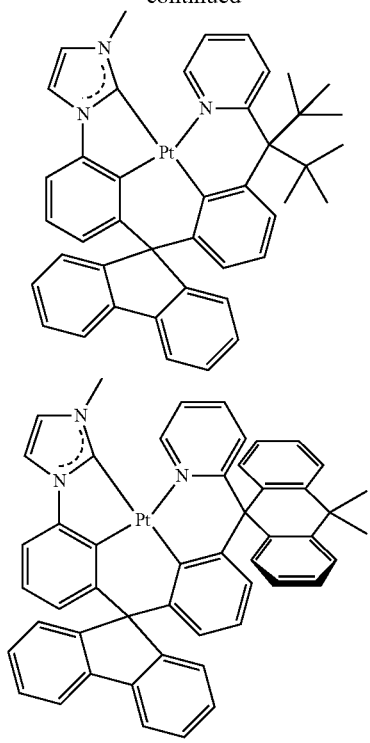
148
-continued
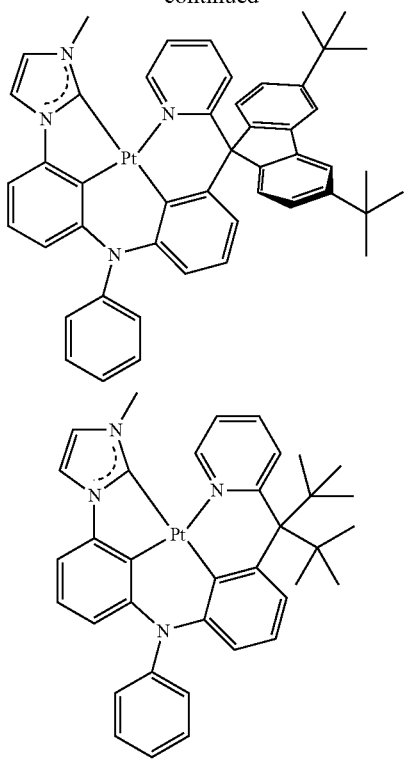
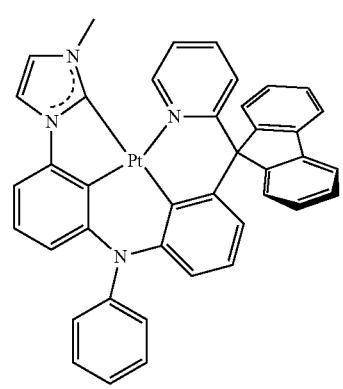
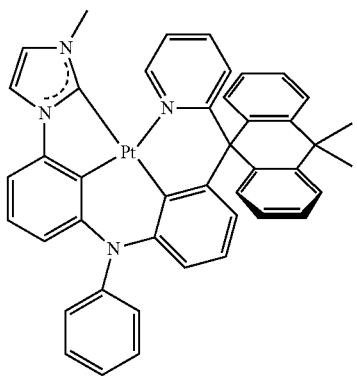
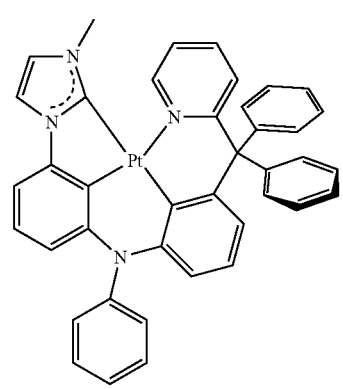
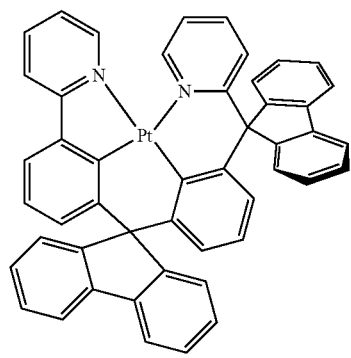

149
-continued
150
-continued
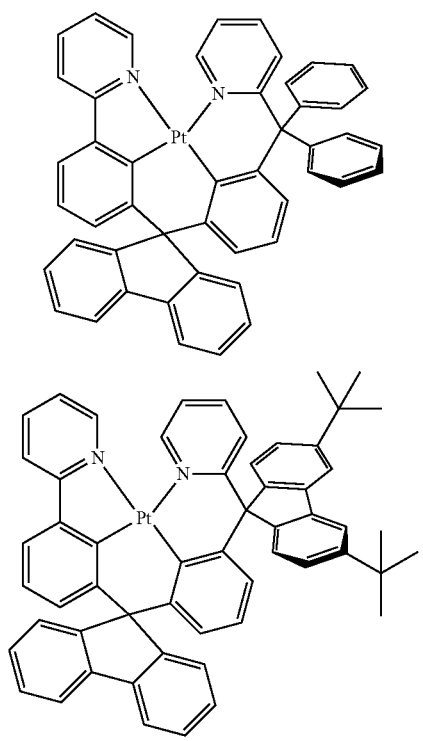
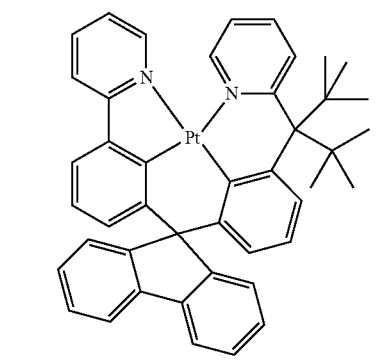
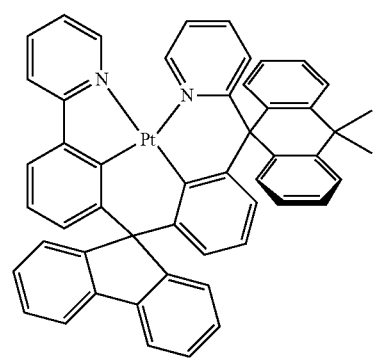
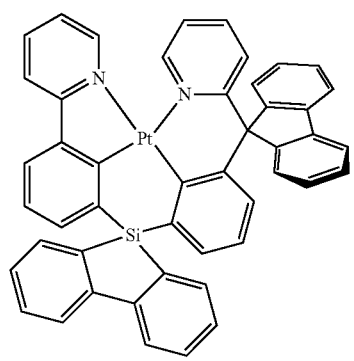
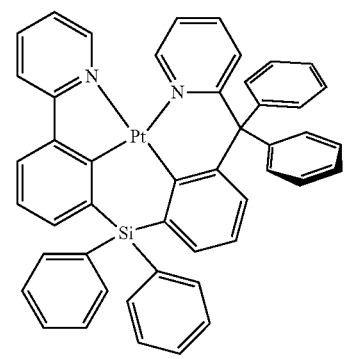
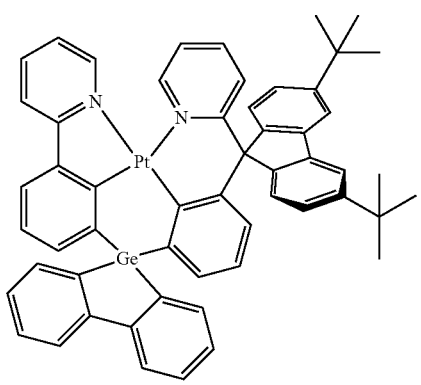
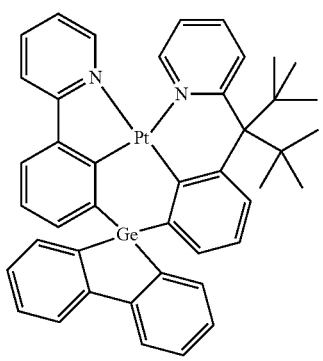

-continued
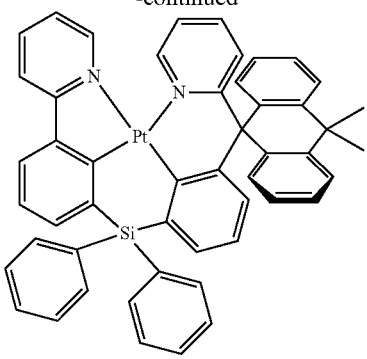
Structure Pt-9
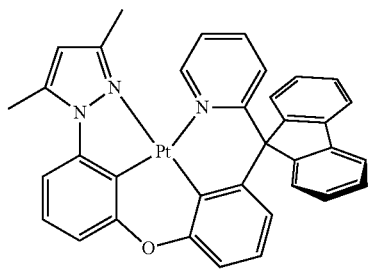
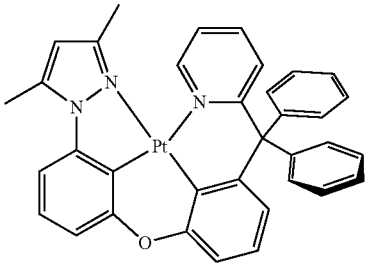
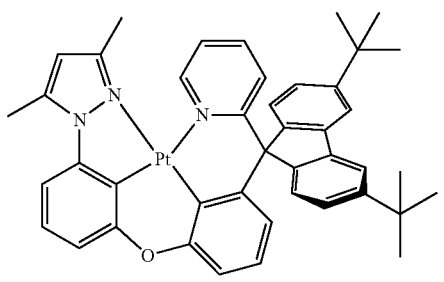
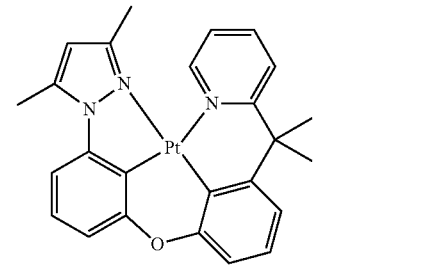
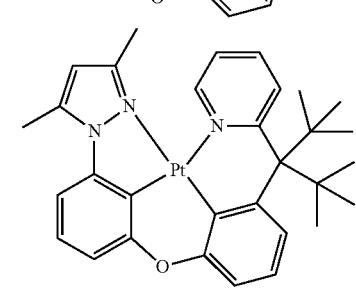
-continued
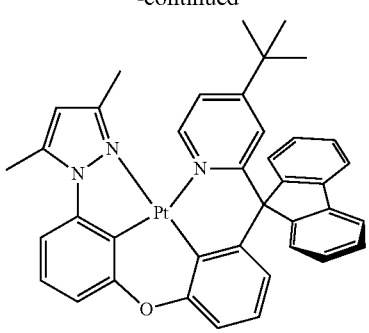
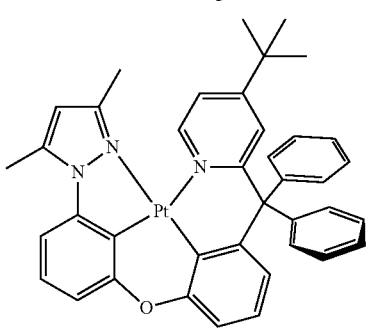
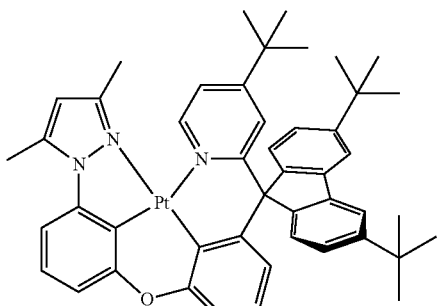
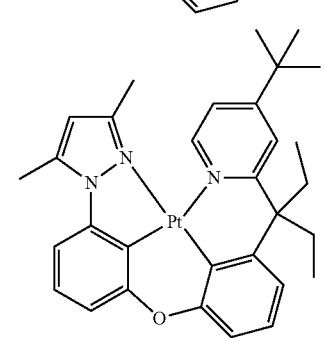
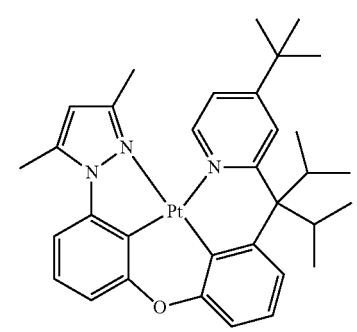

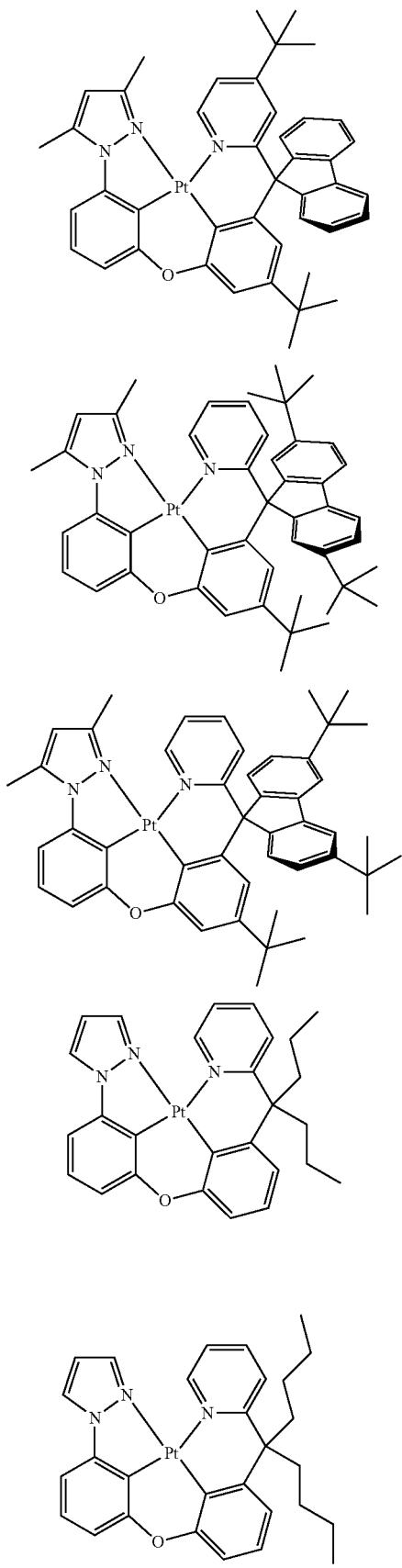
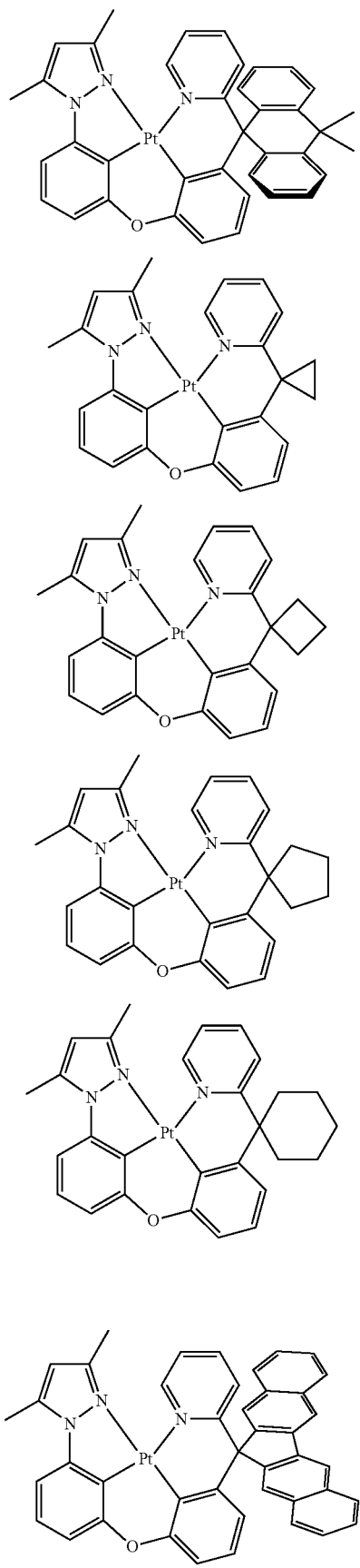

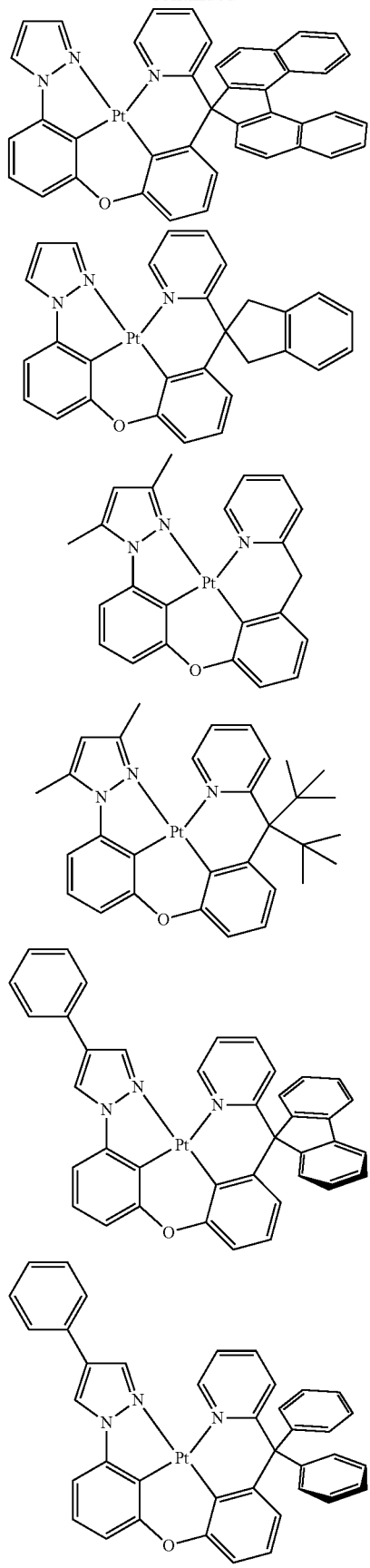
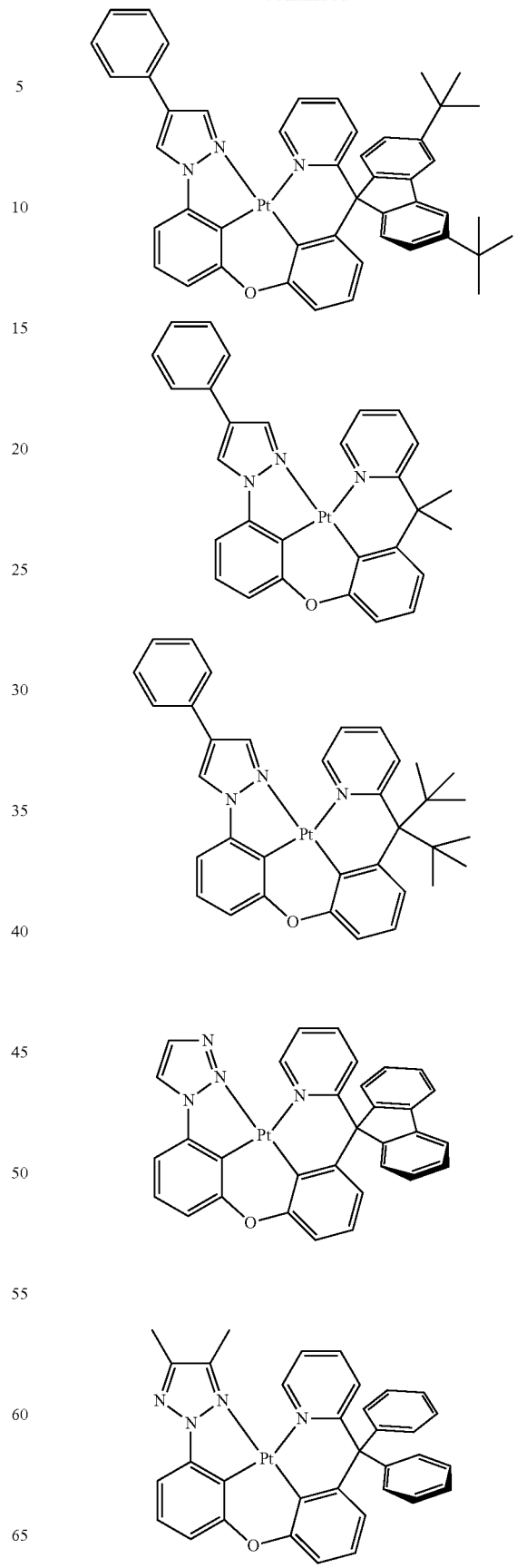

-continued
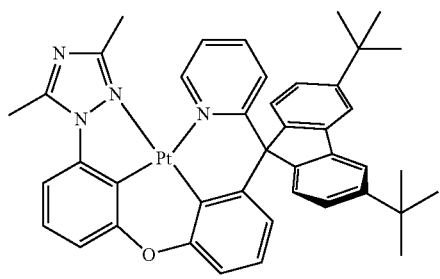
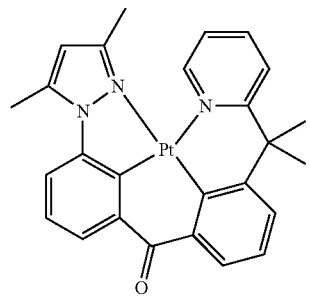
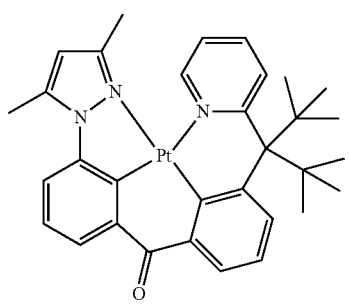
Structure Pt-10
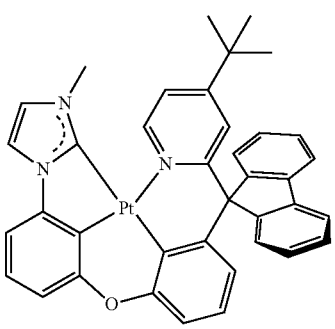
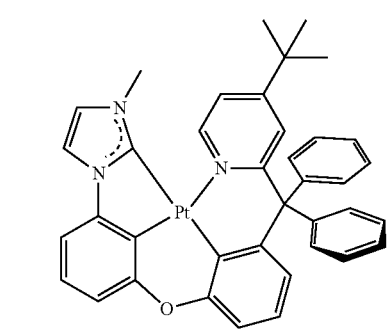
-continued
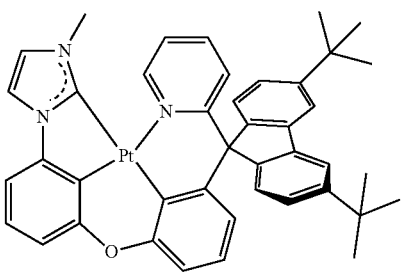
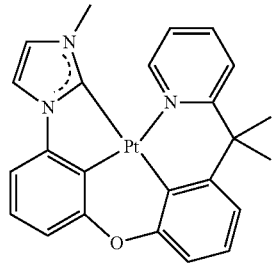
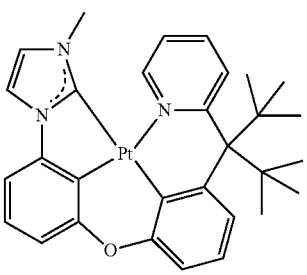
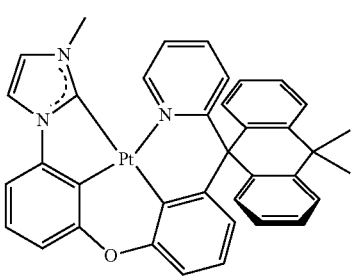
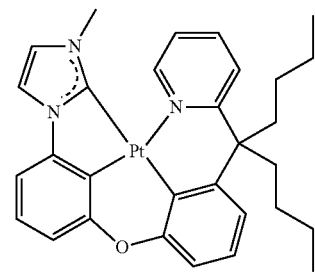
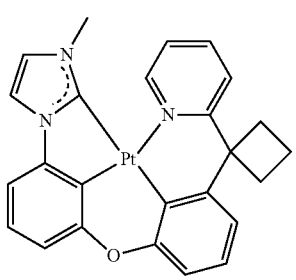

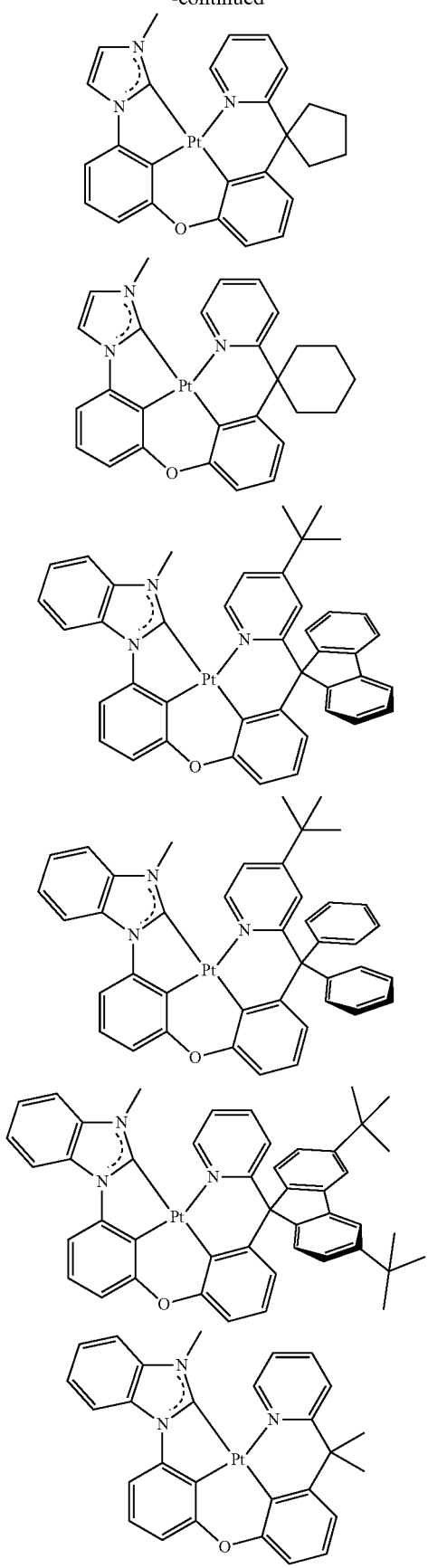
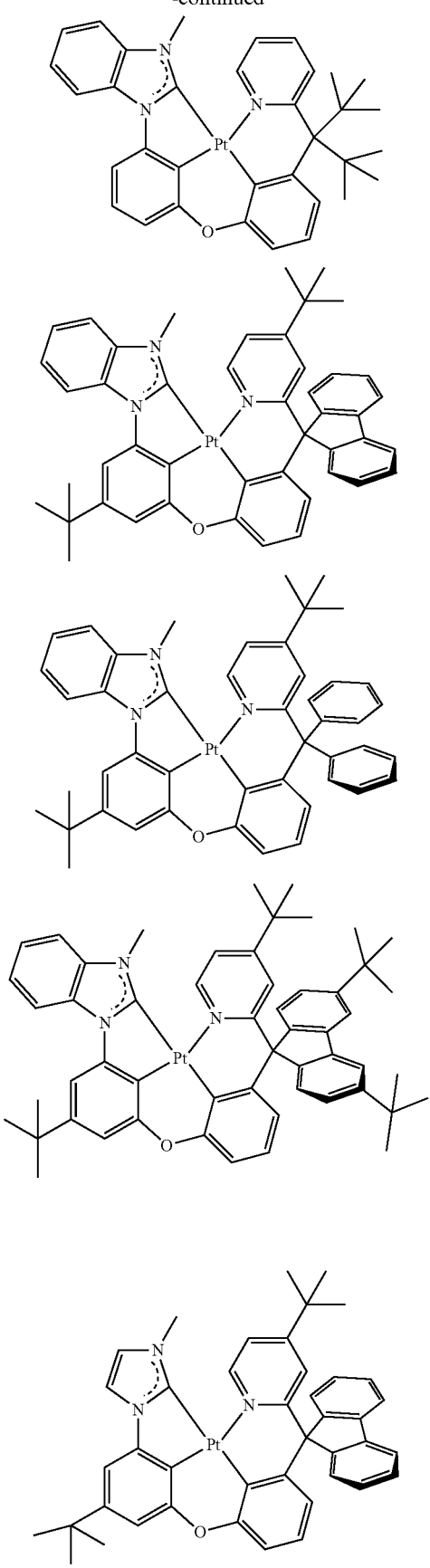

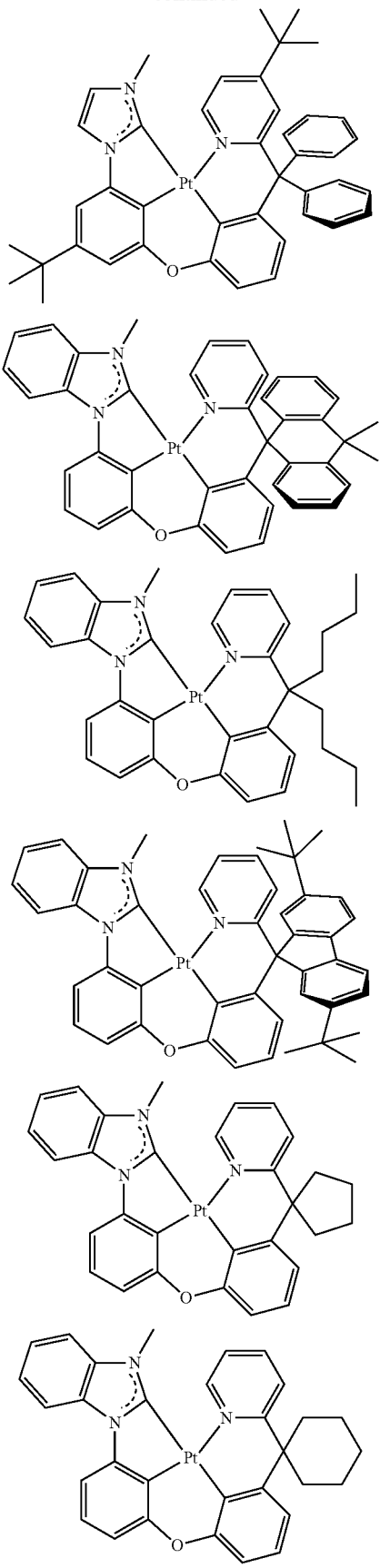
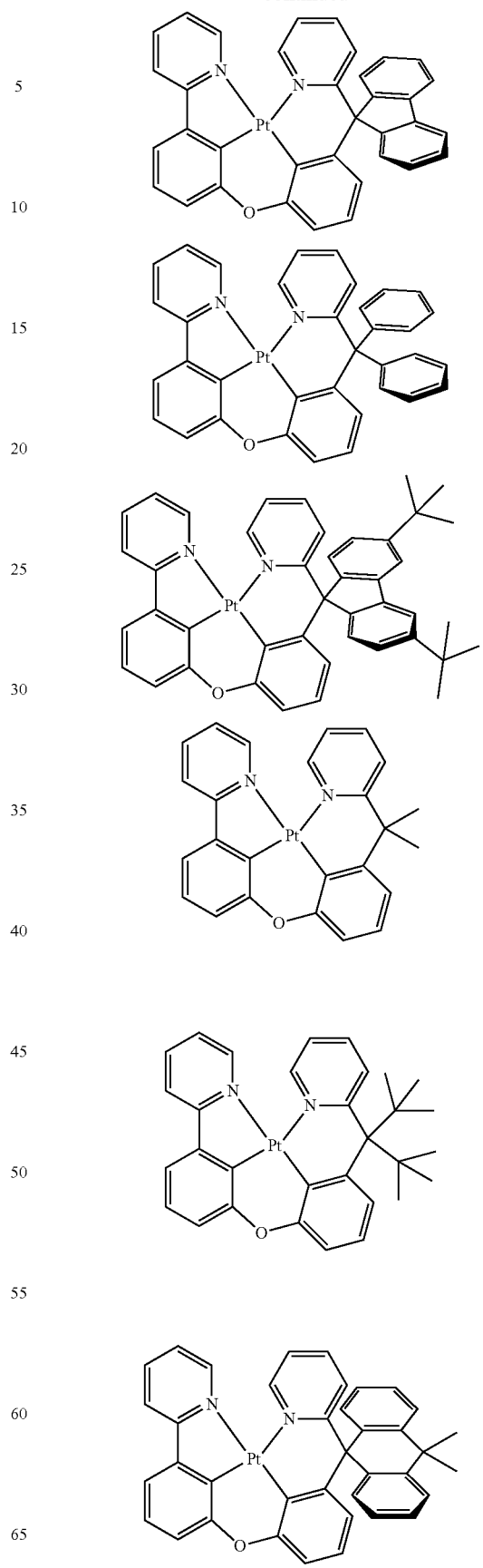

-continued
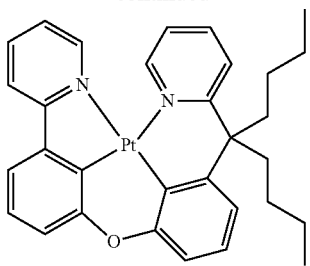
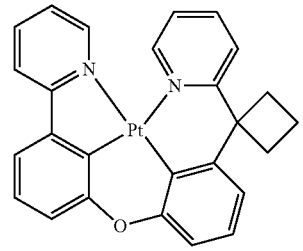
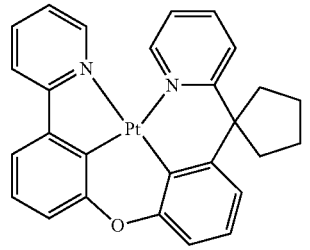
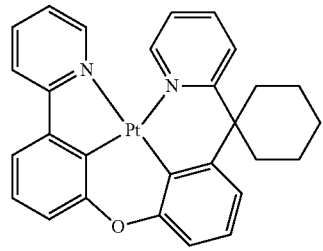
Structure Pt-11
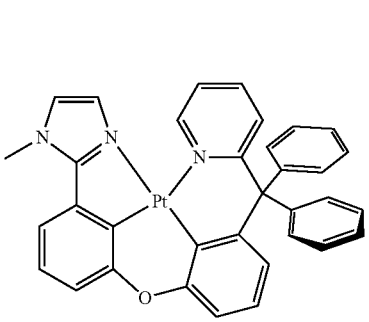
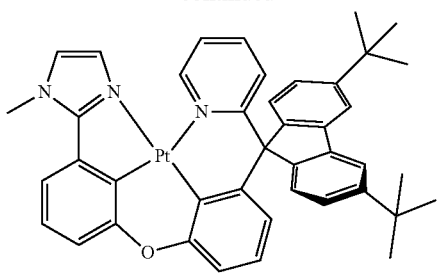
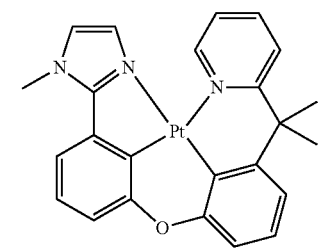
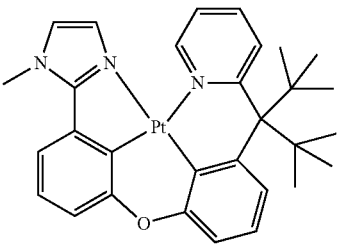
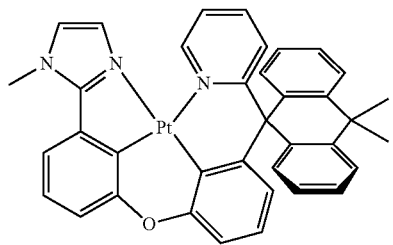
-continued
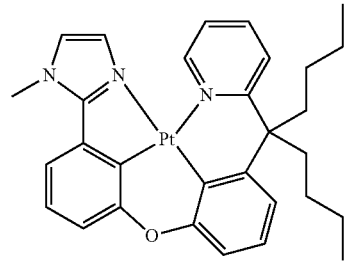
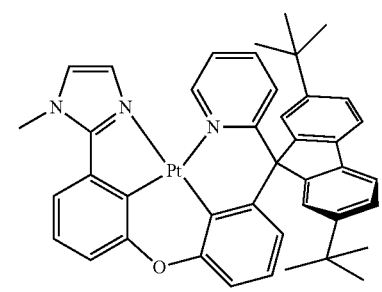

-continued
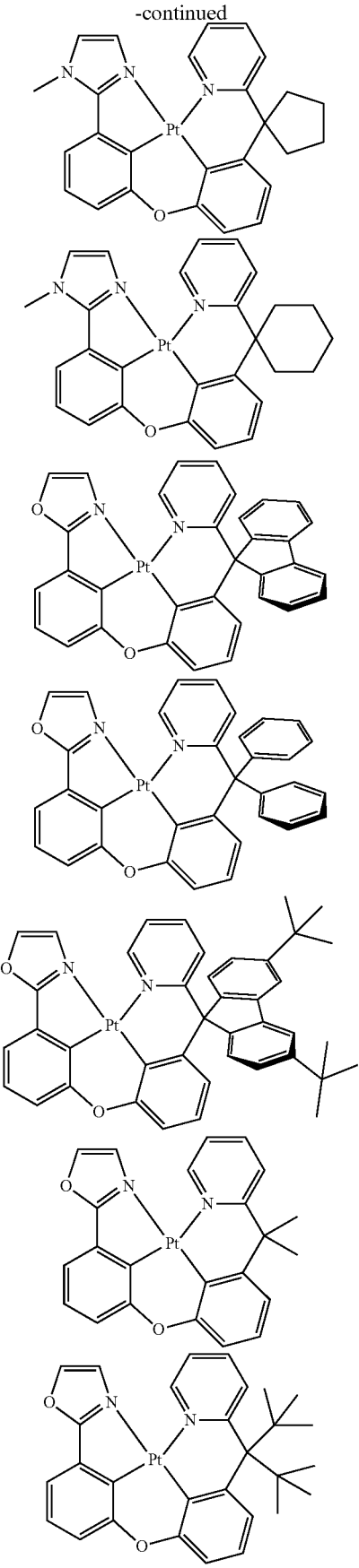
-continued
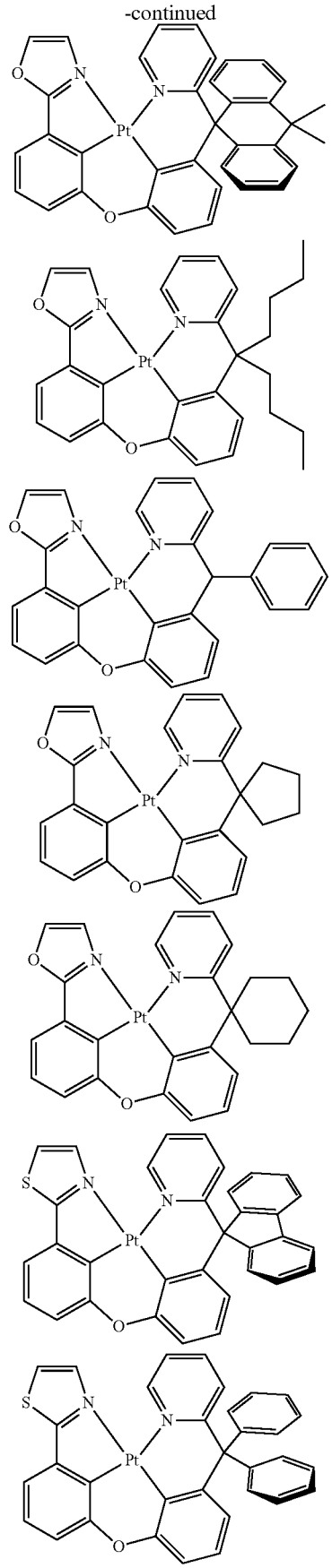

-continued
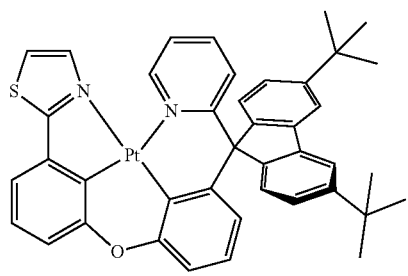
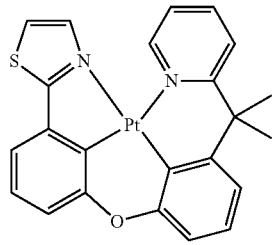
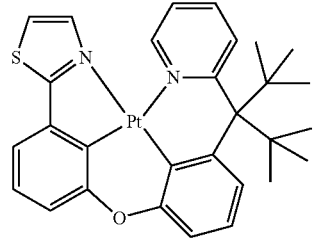
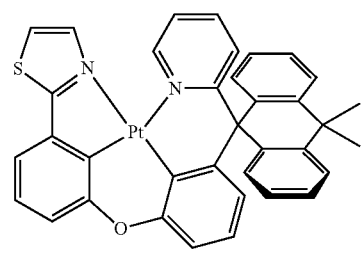
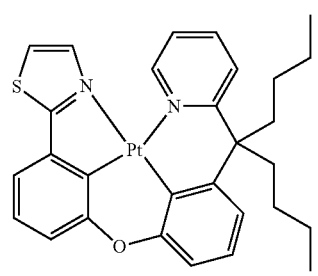
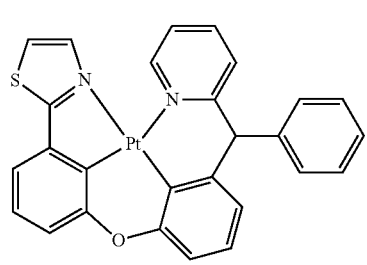
-continued
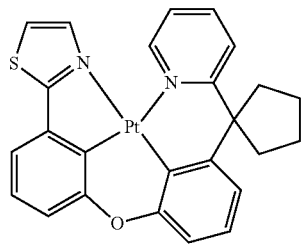
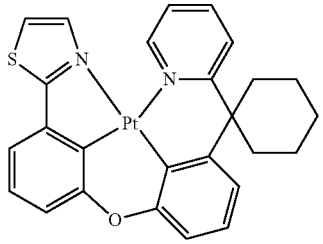
Structure Pt-12
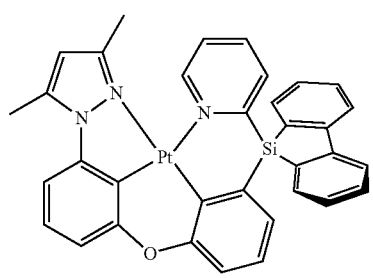
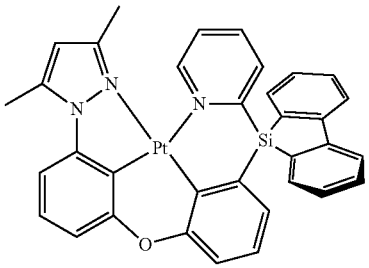
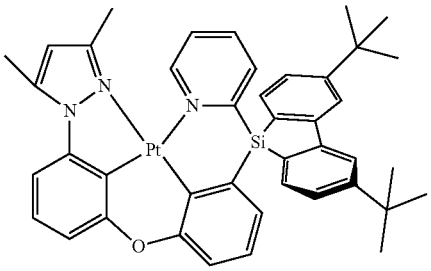
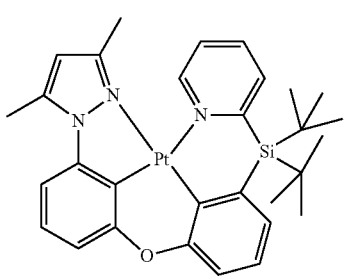

169
-continued
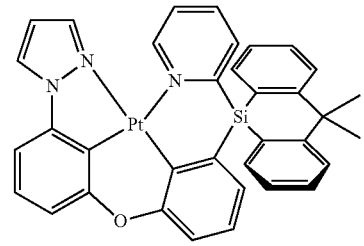
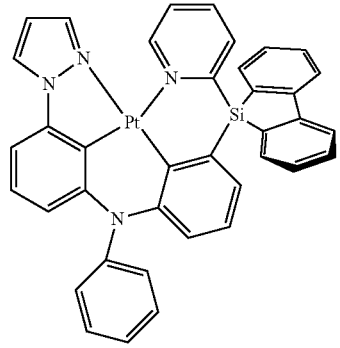
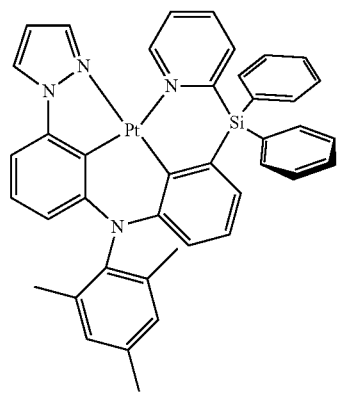
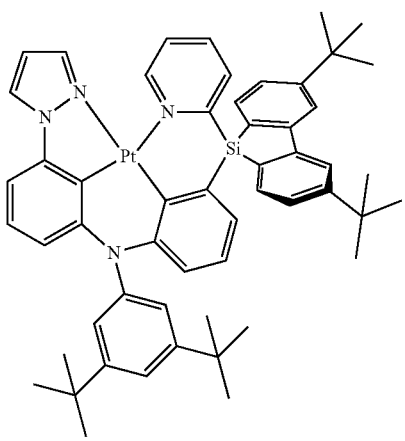
170
-continued
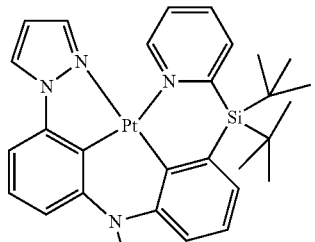
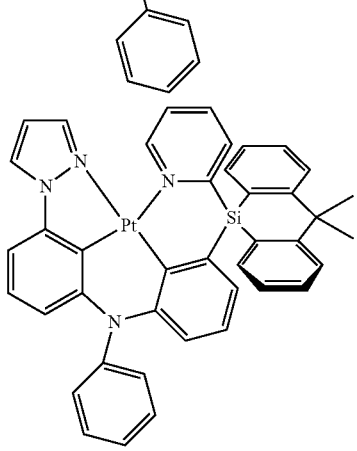
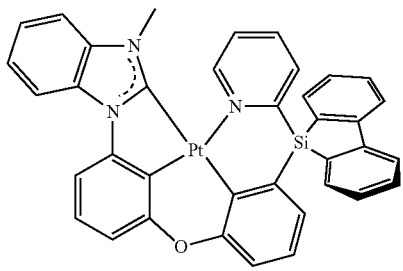
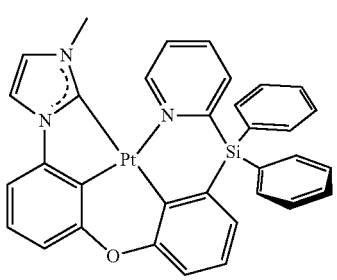


173
-continued
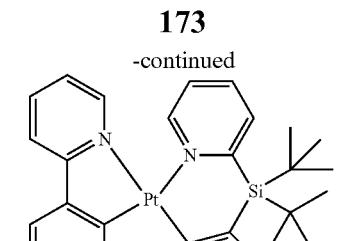

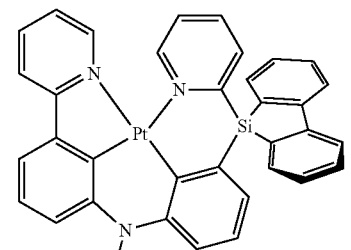
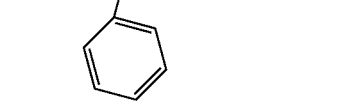
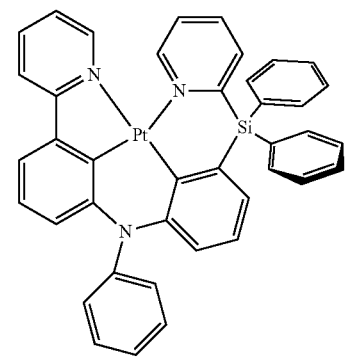
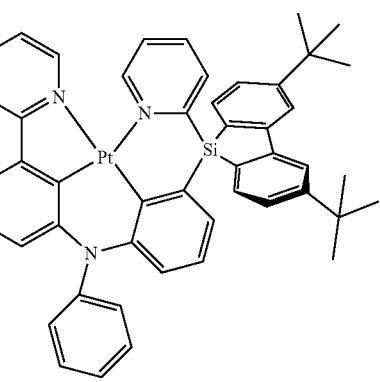
174
-continued
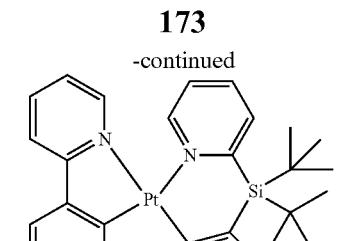
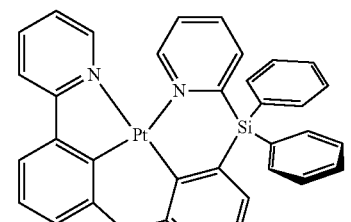
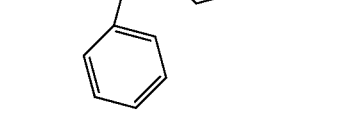
Structure Pt-13
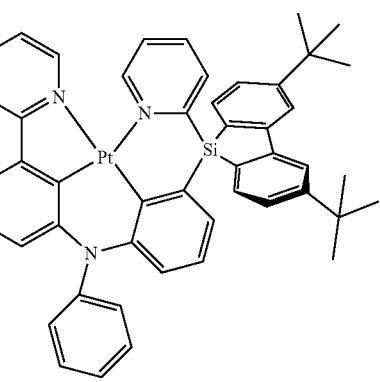

175
-continued
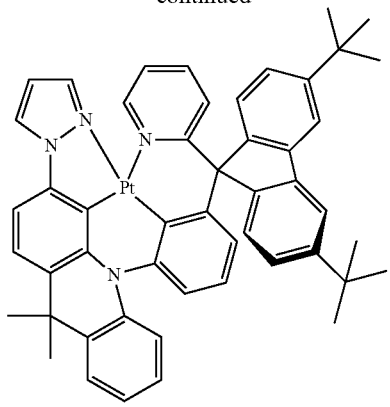
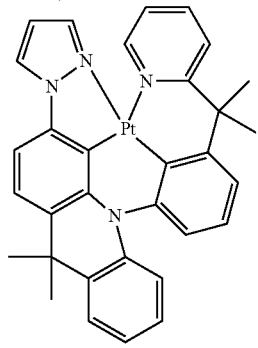
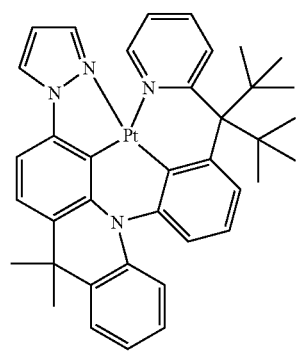
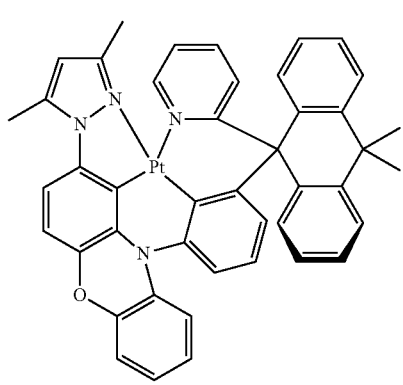
176
-continued
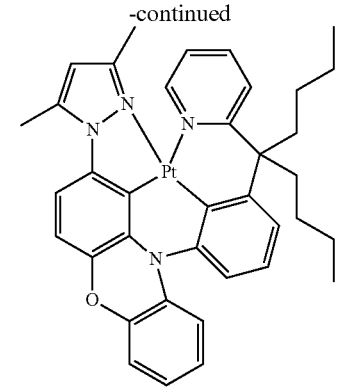
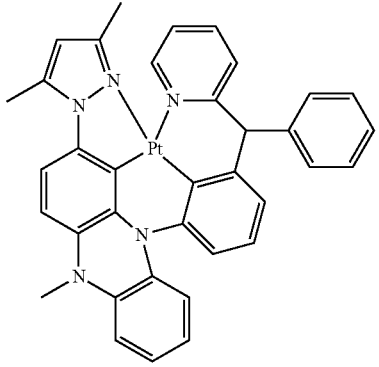
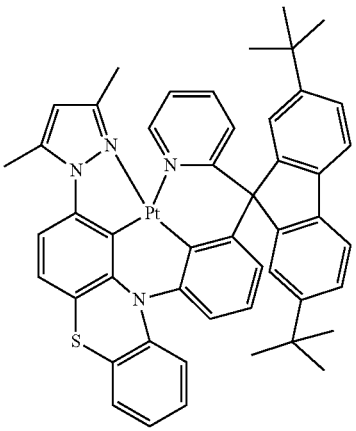
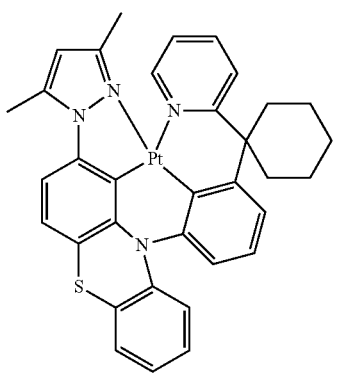

177 -continued
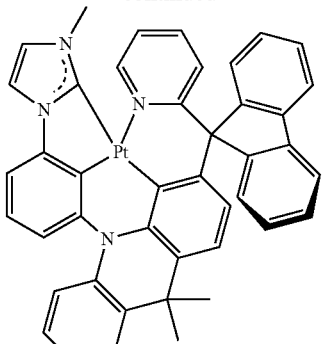
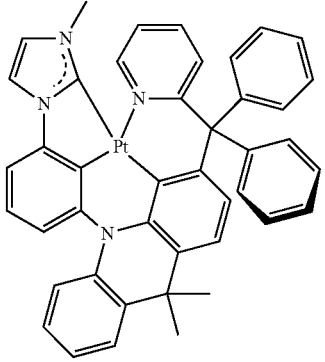
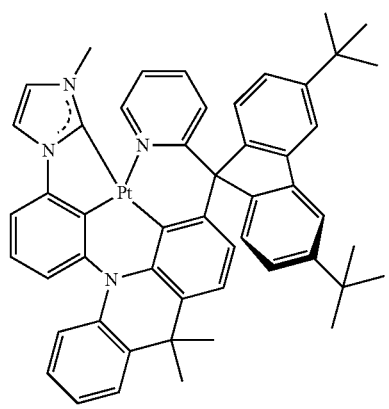
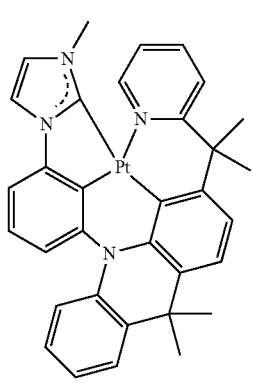
178 -continued
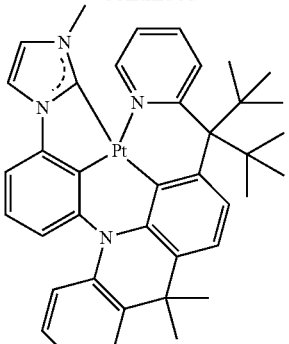
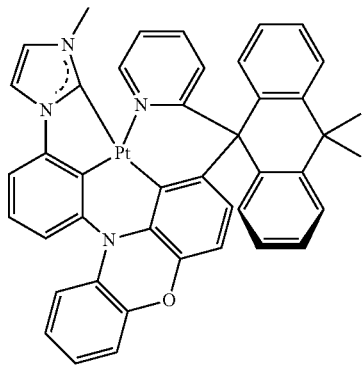
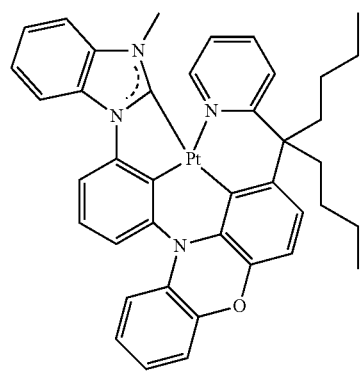
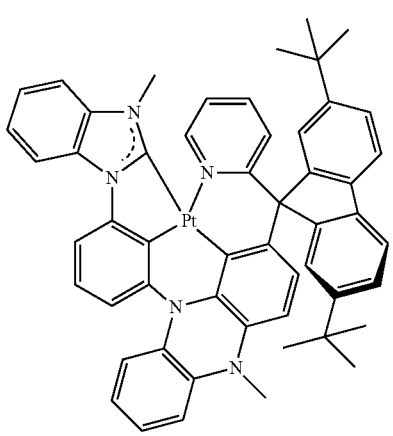

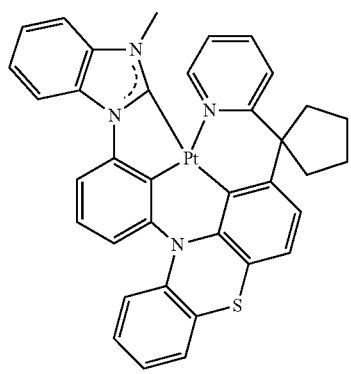
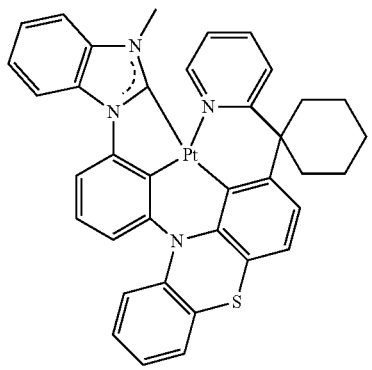
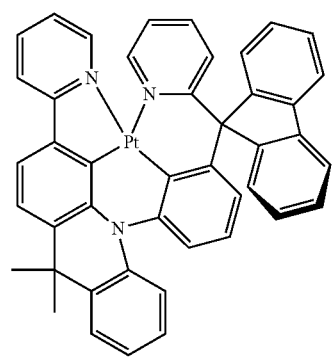
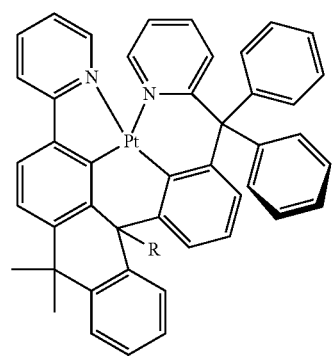
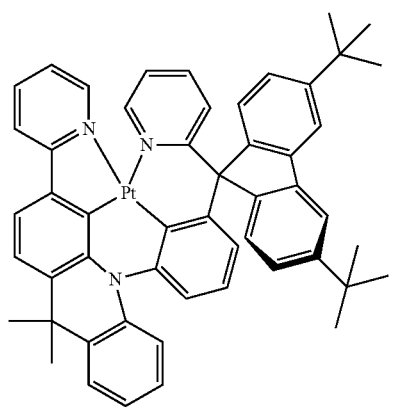
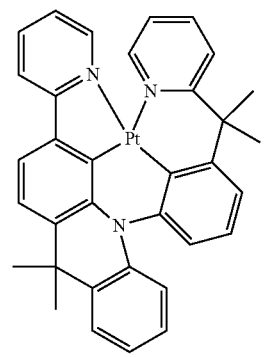
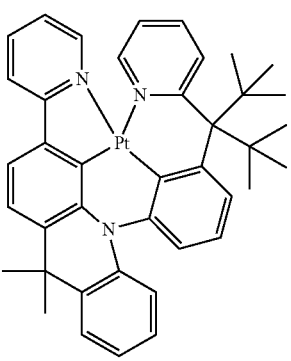
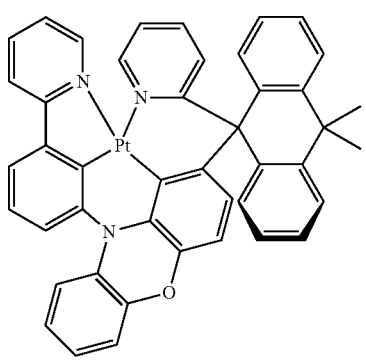

181
-continued
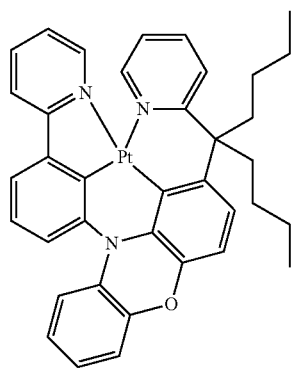
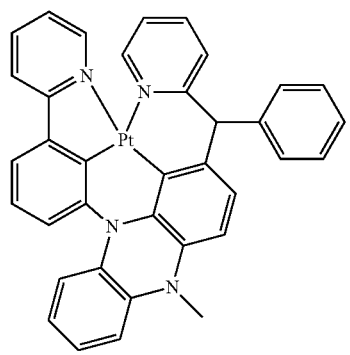
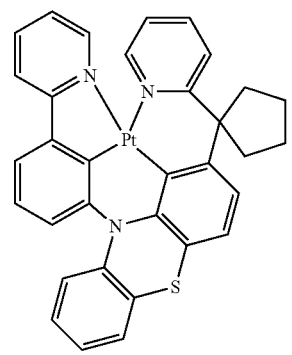
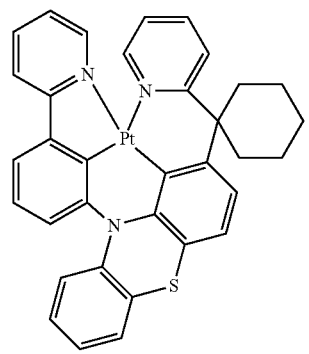
182
-continued
Structure Pt-14
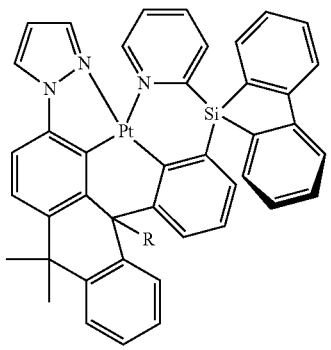
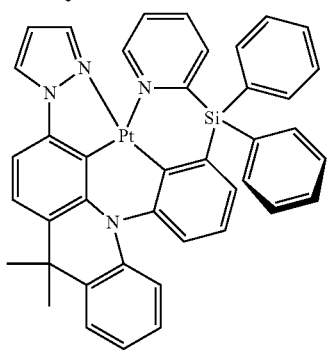
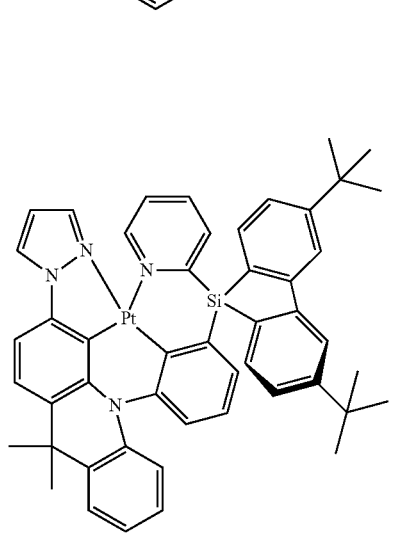
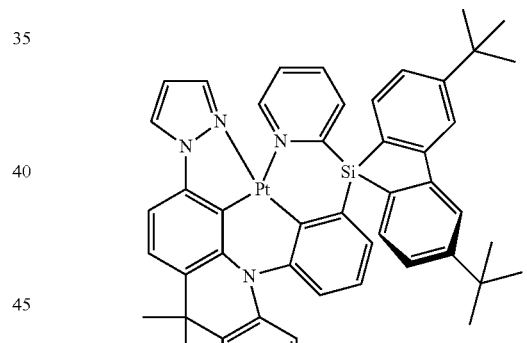

-continued
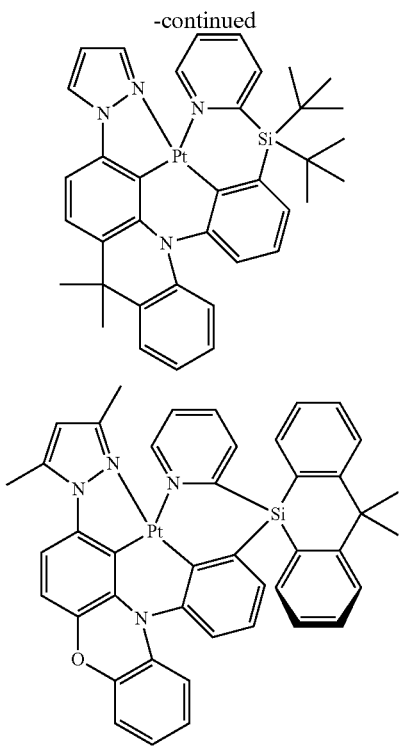
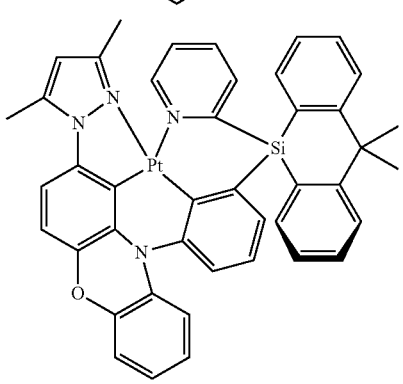
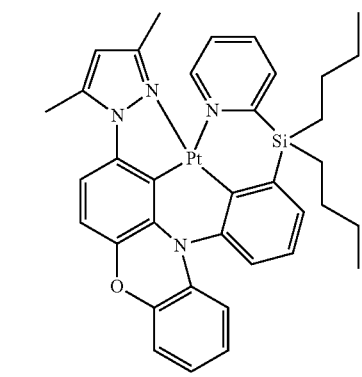

-continued
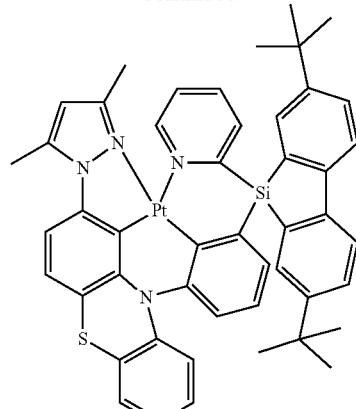
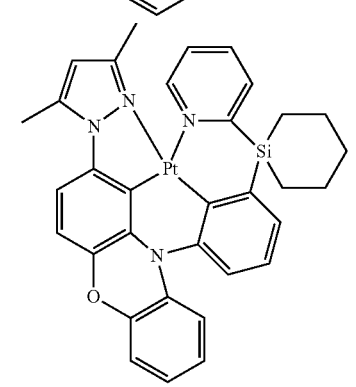
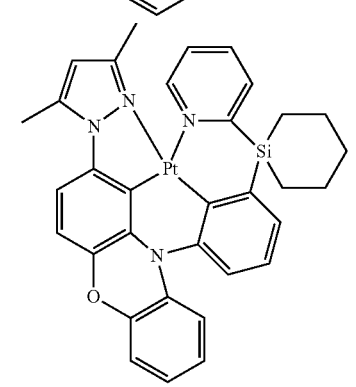
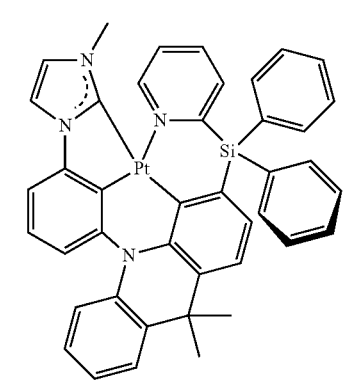

185
-continued
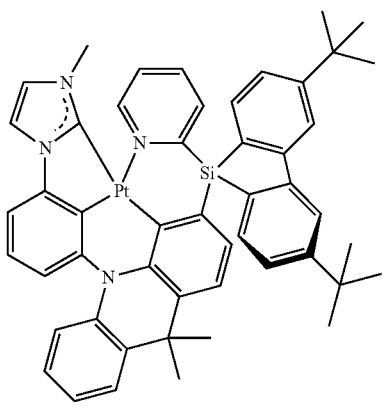
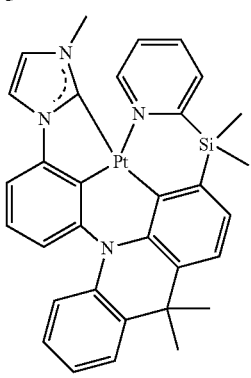
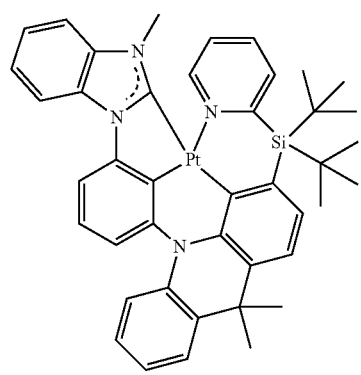
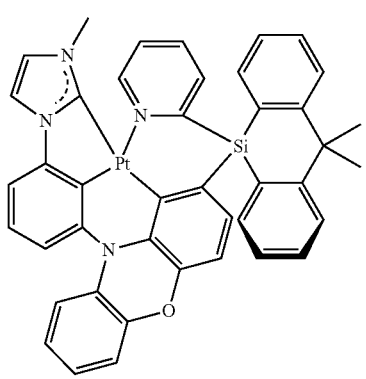
186
-continued
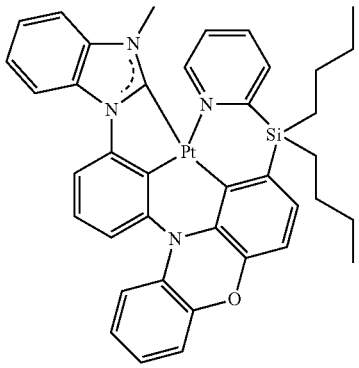
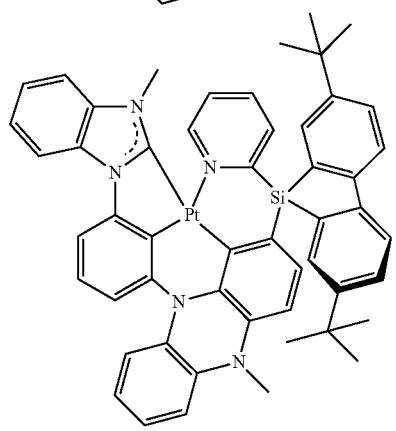
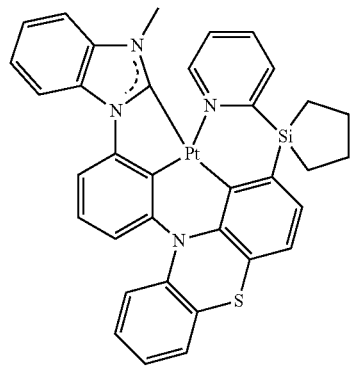
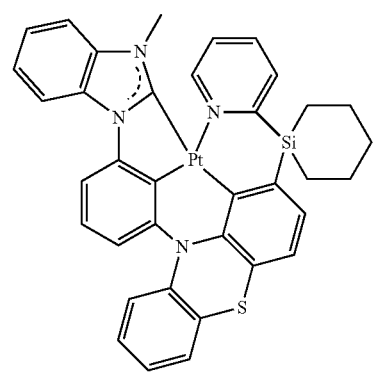

187
-continued
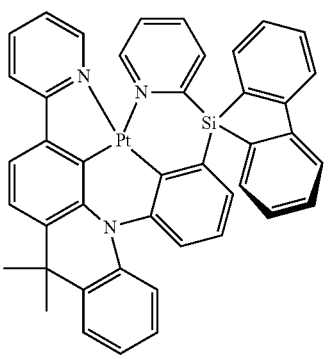
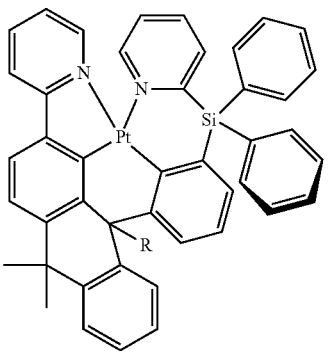
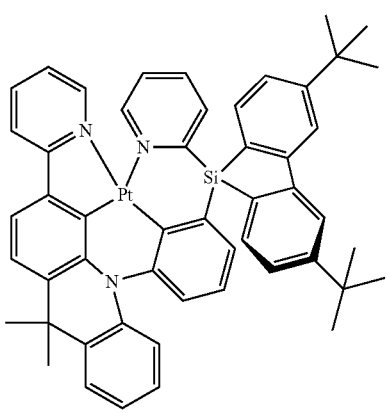
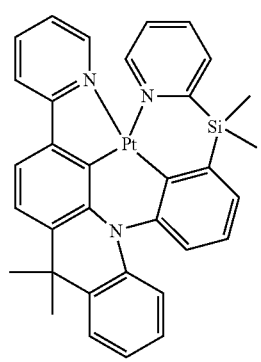
188
-continued
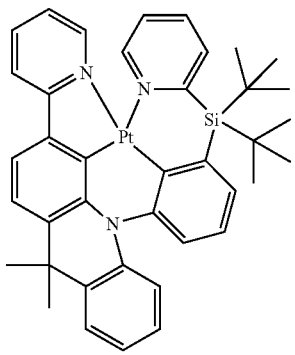
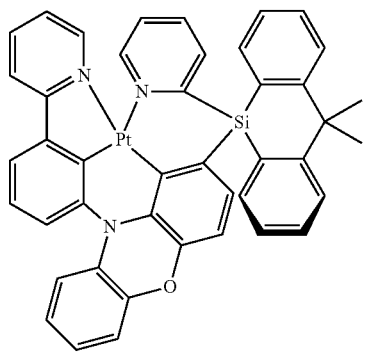
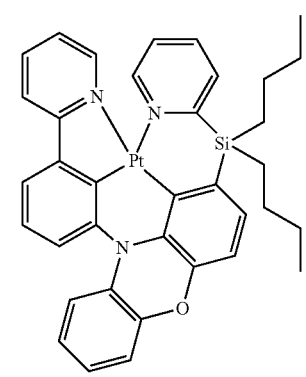
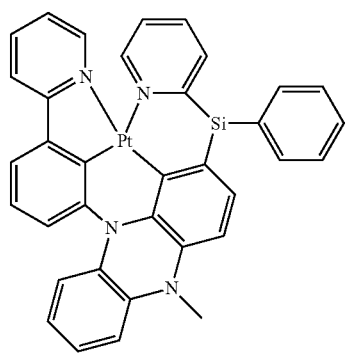

189
-continued
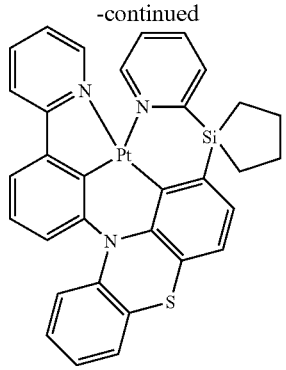
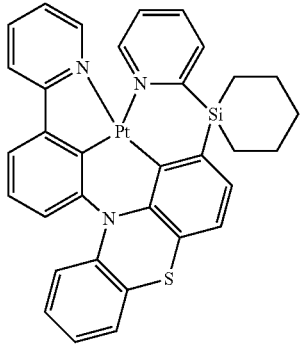
Structure Pt-15
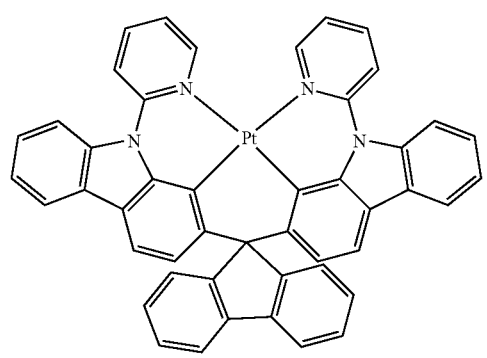
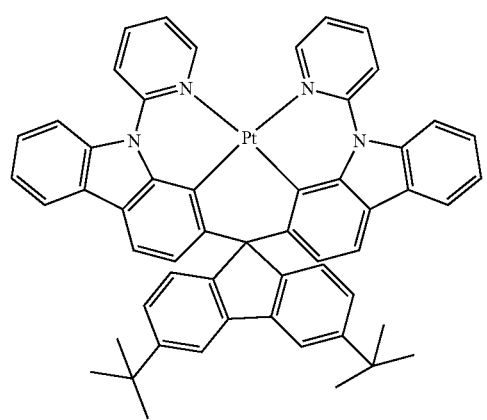
190
-continued
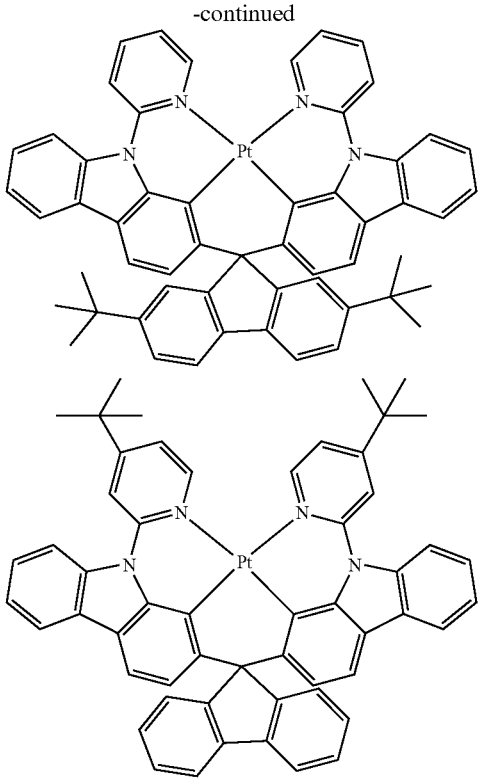
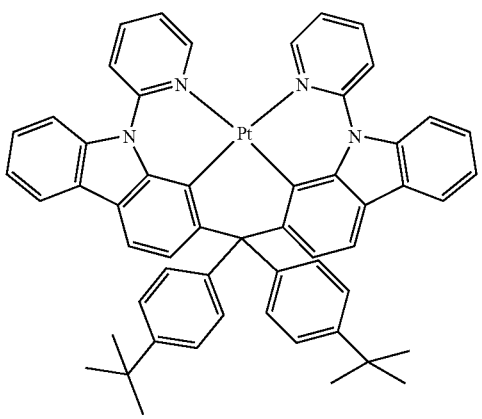
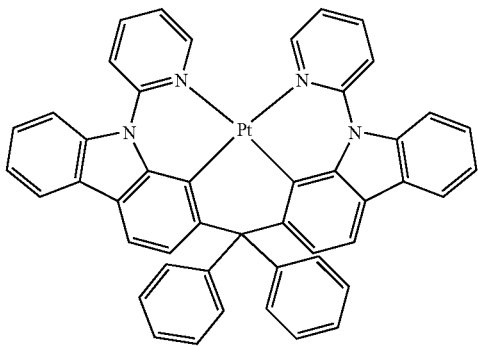

-continued
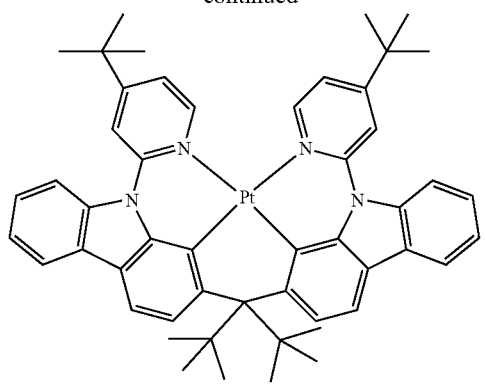
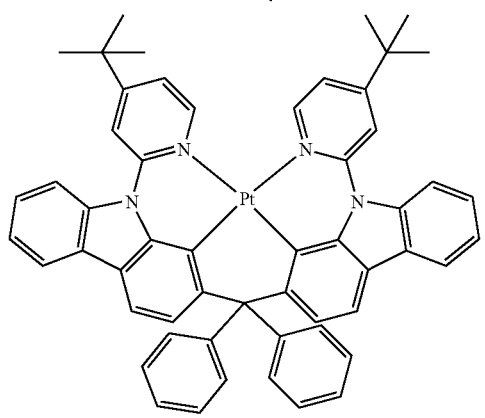
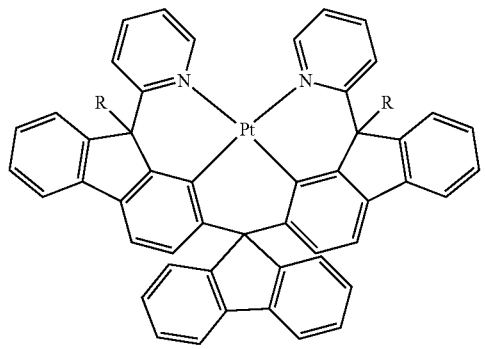
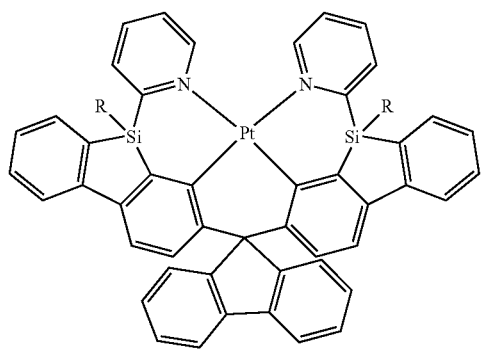
-continued
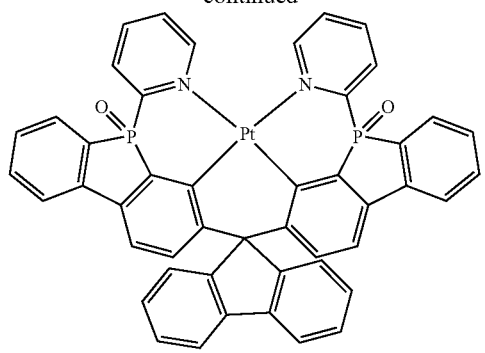
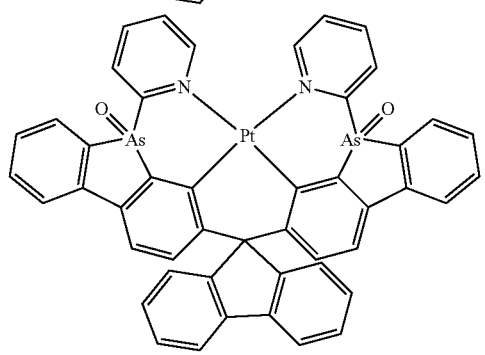
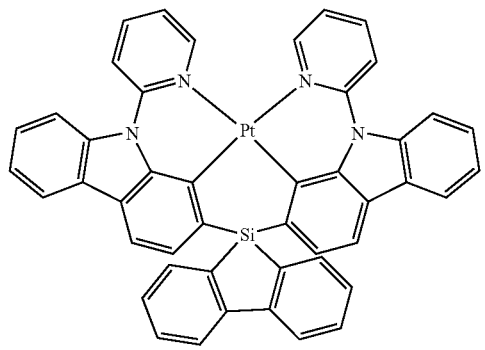
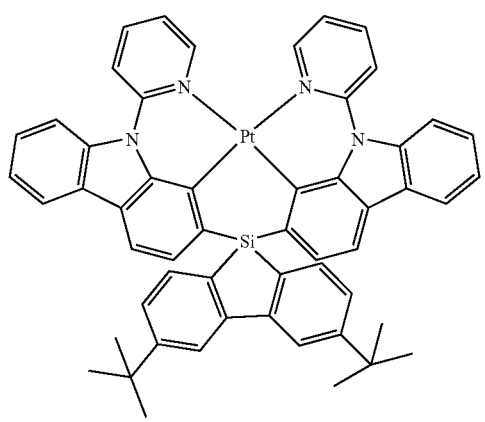

193
-continued
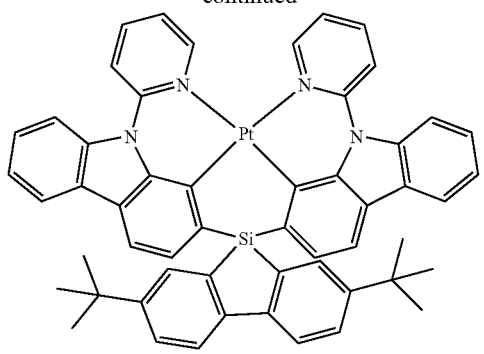
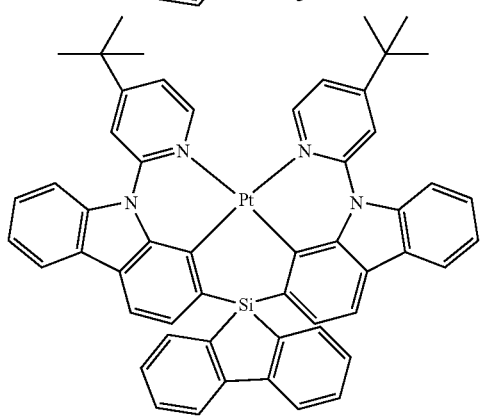
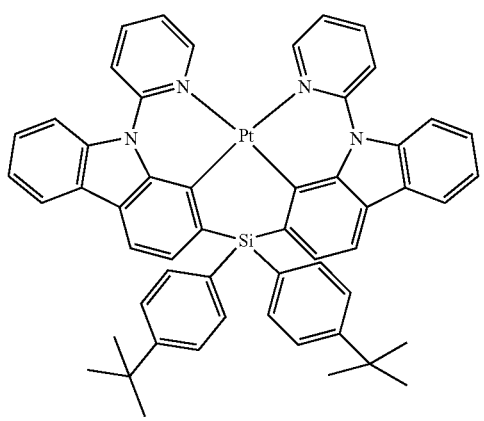
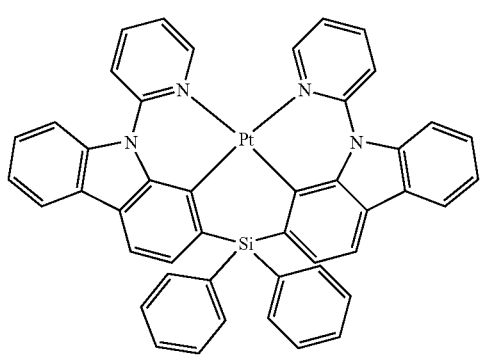
194
-continued
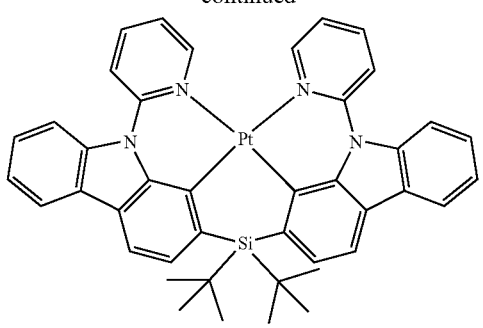
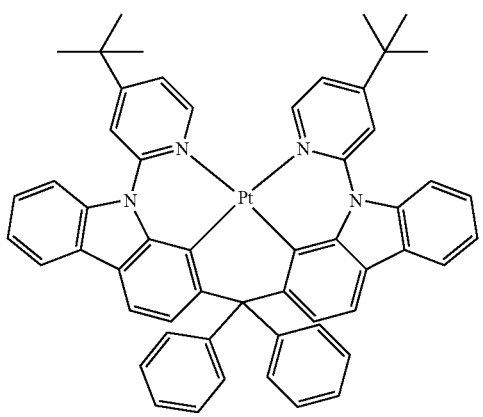
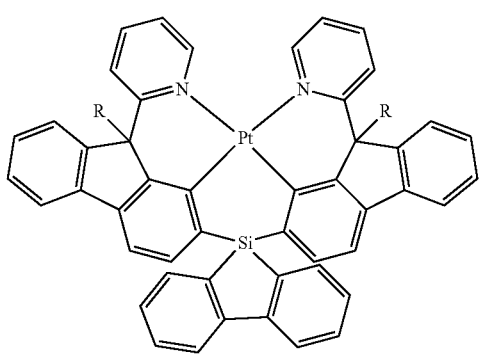
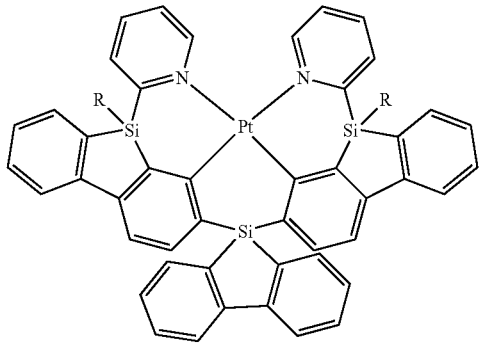

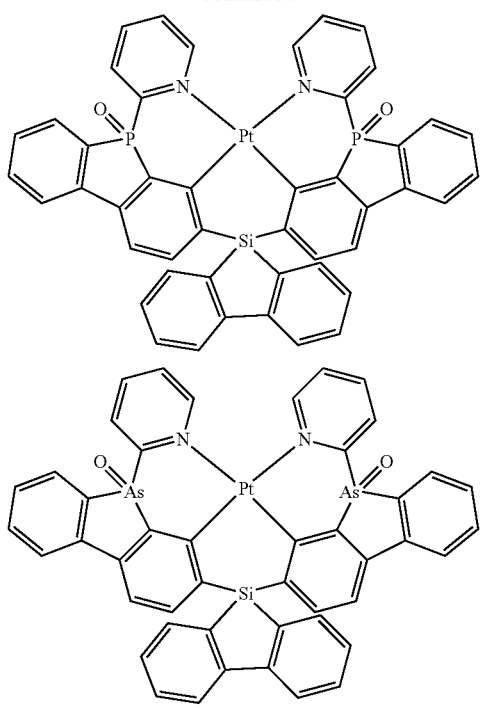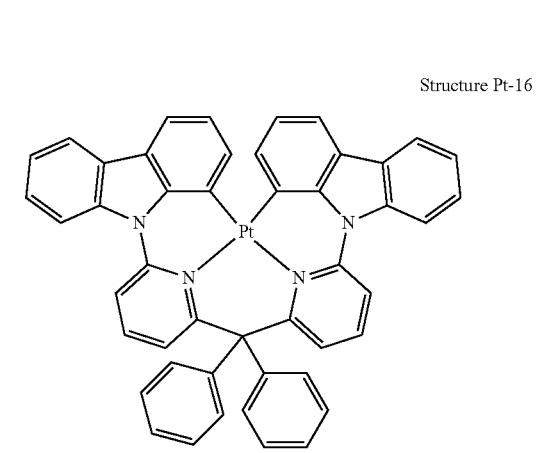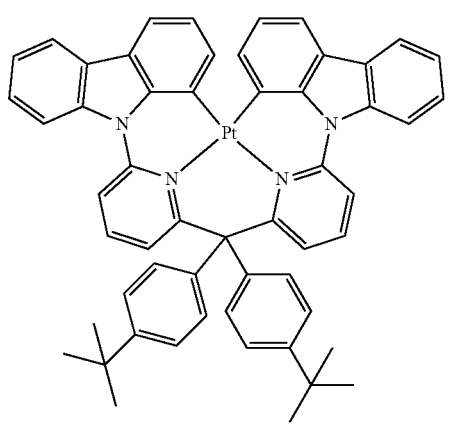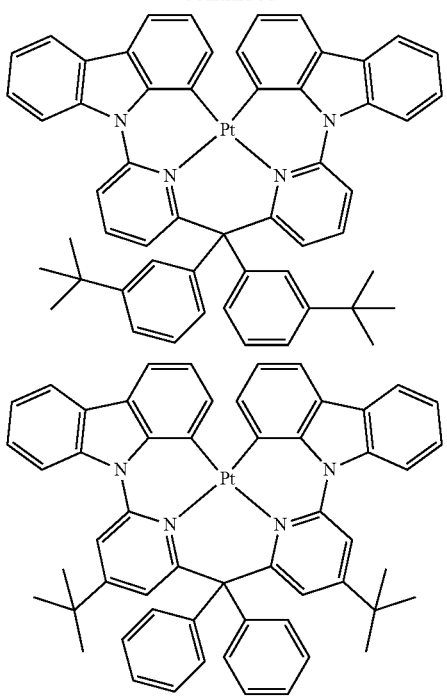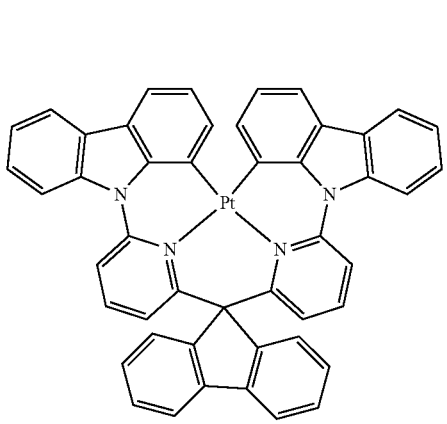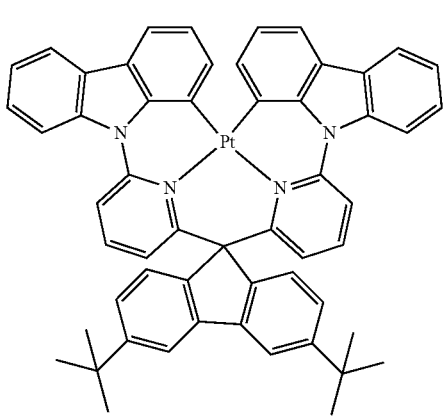
Structure Pt-16

197
-continued
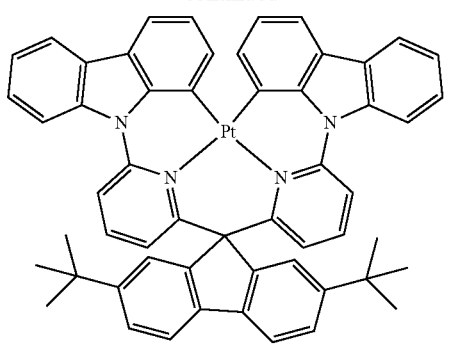
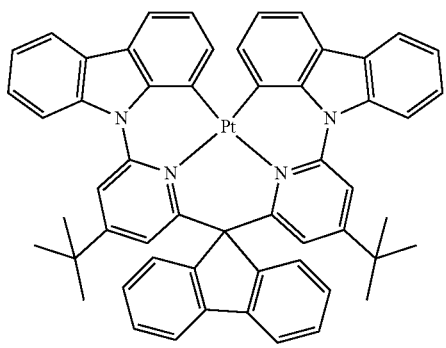
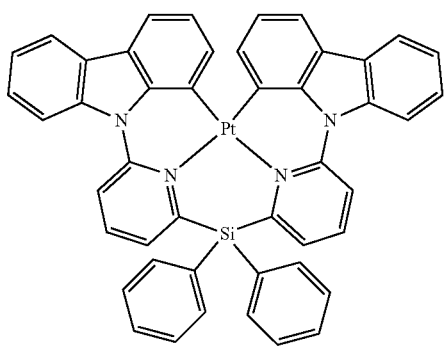
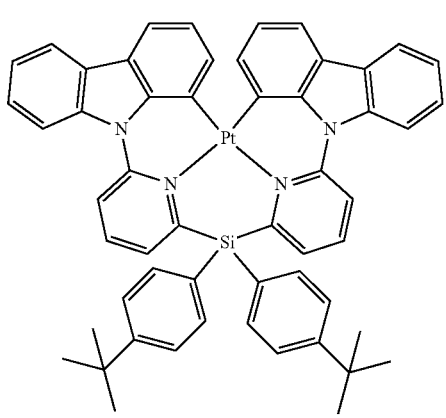
198
-continued
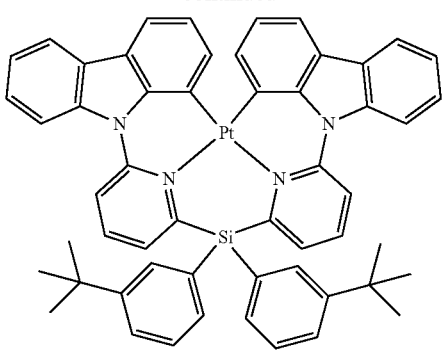
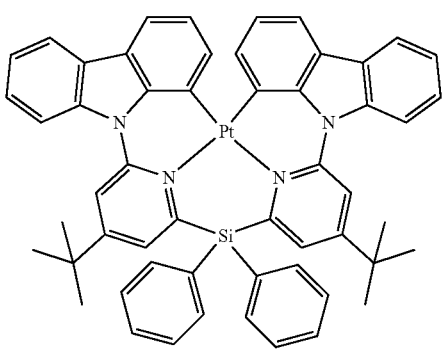
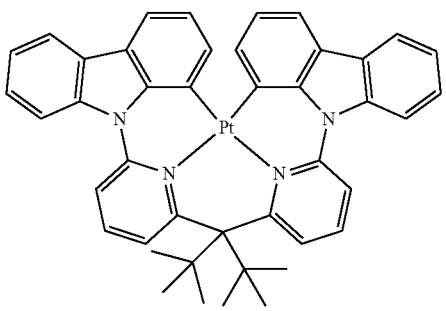
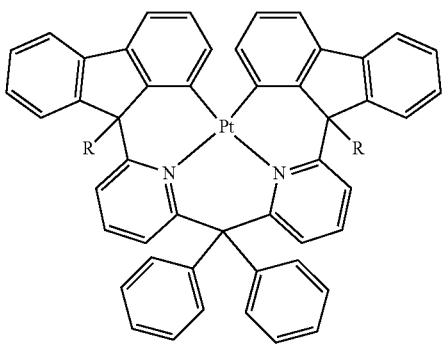
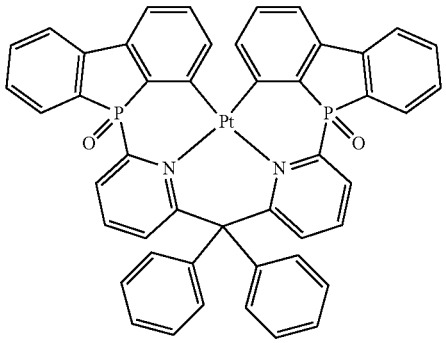

199
-continued
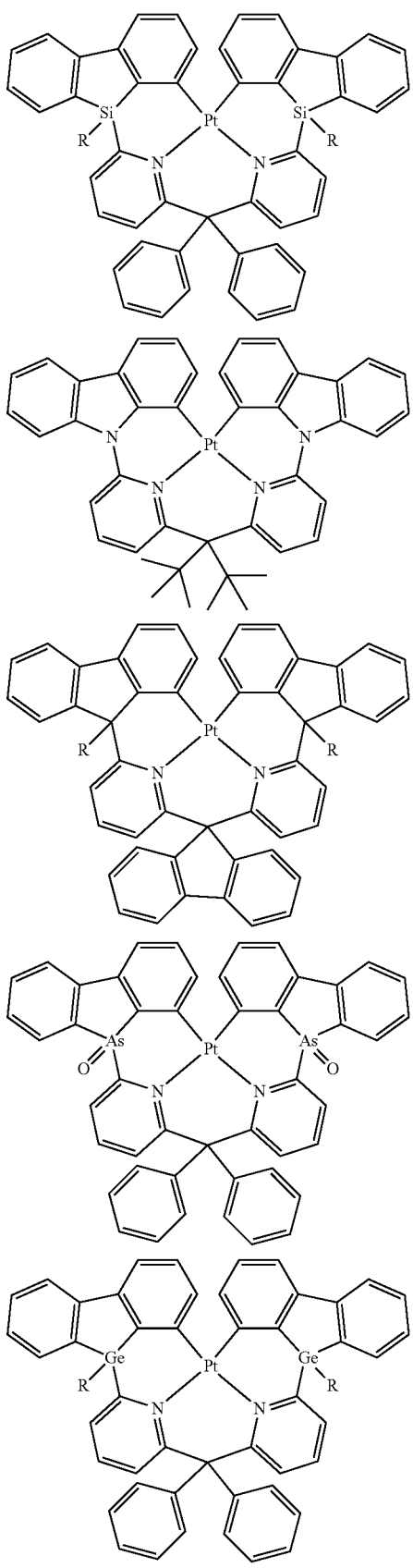
200
-continued
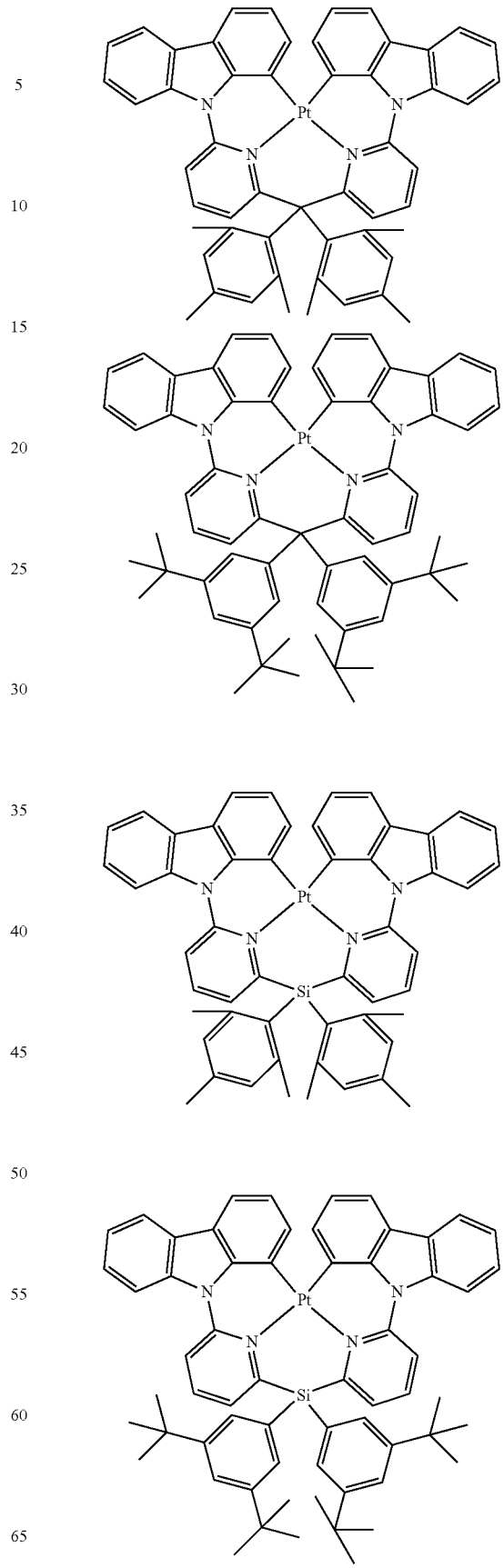

-continued
Structure Pt-17
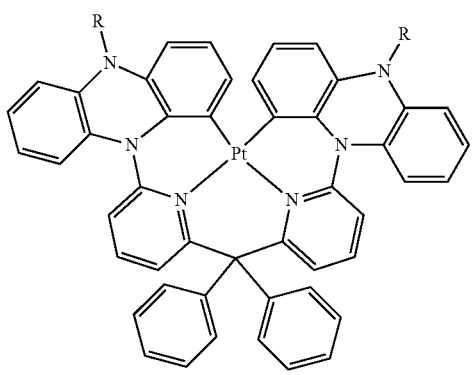
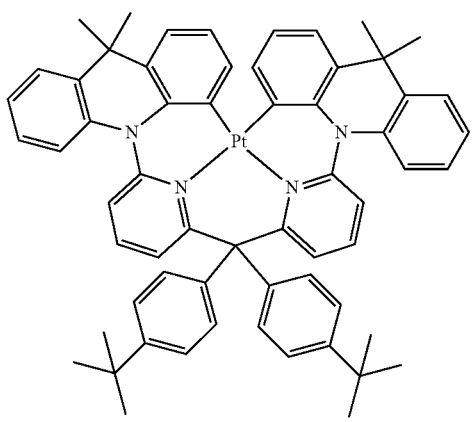
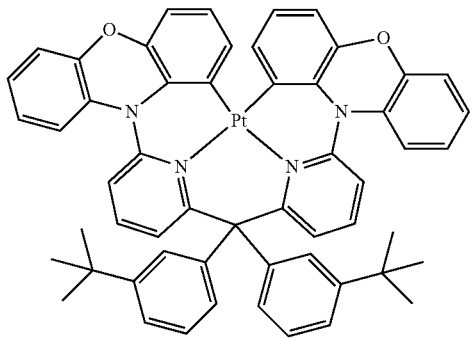
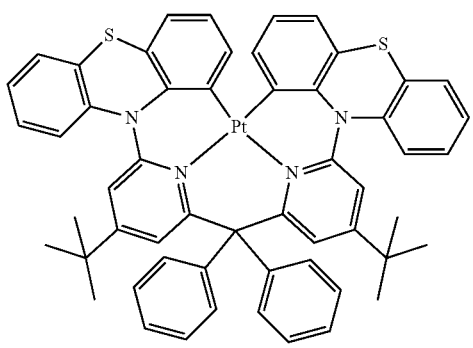
-continued
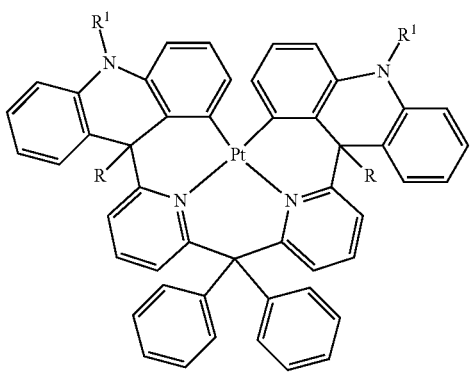
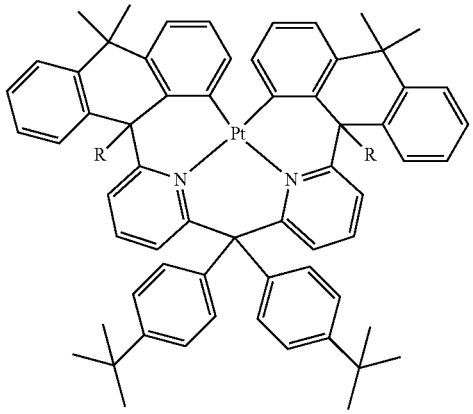
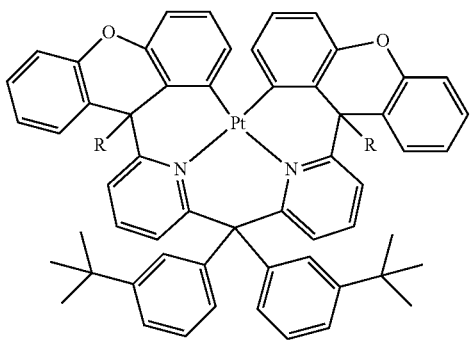
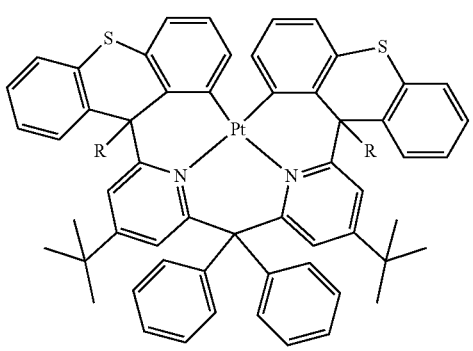

203
-continued
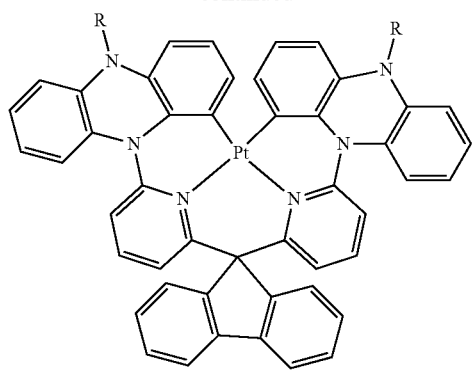
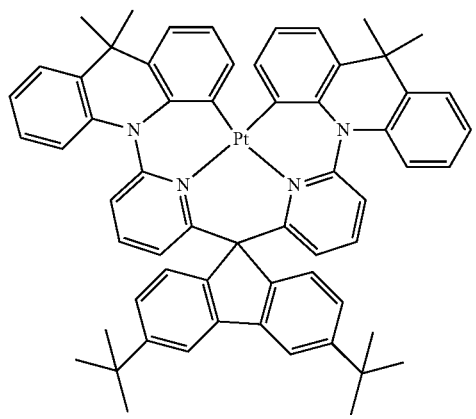
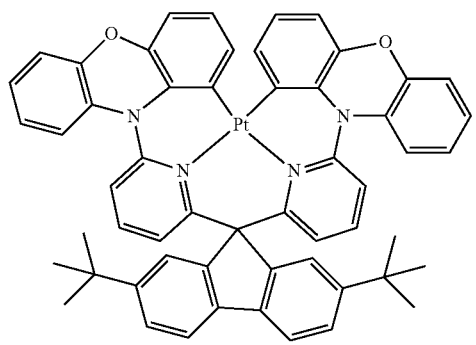
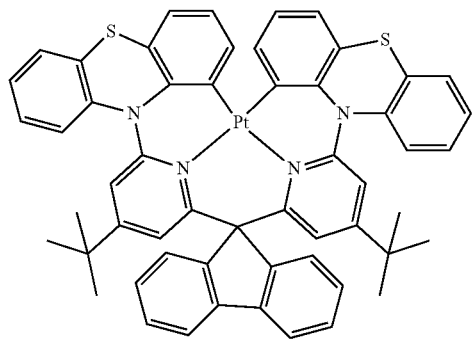
204
-continued
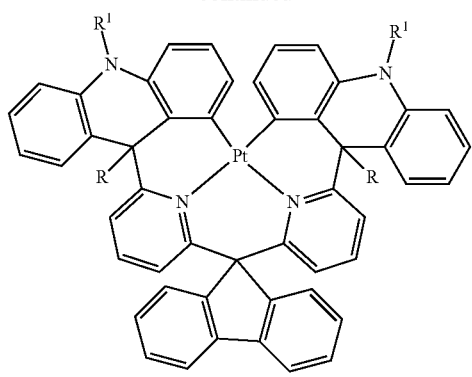
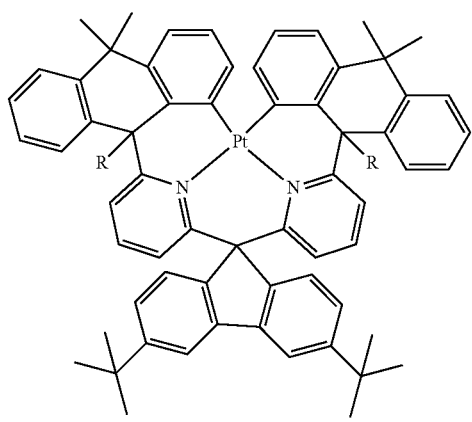
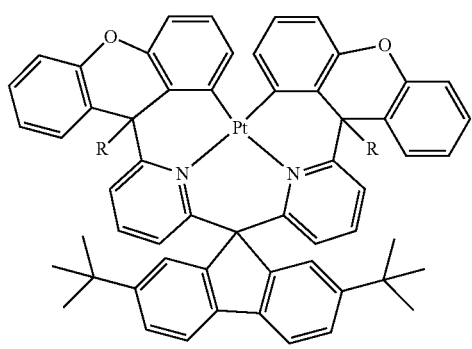
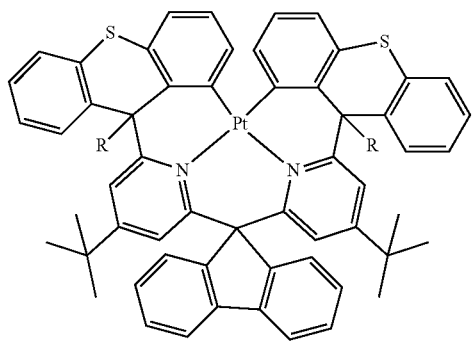

205
-continued
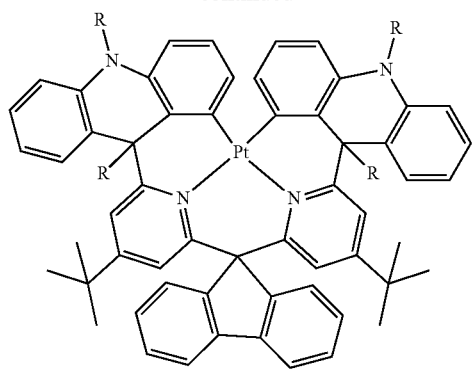
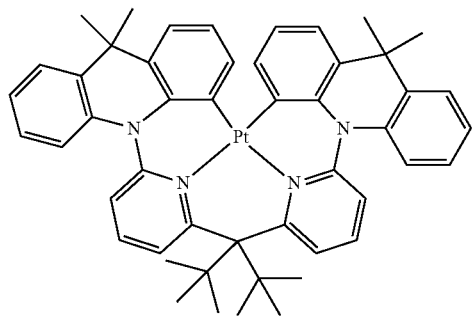
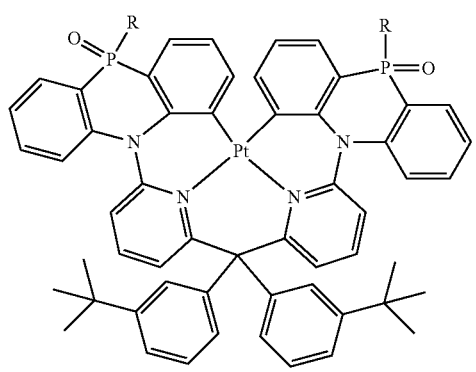
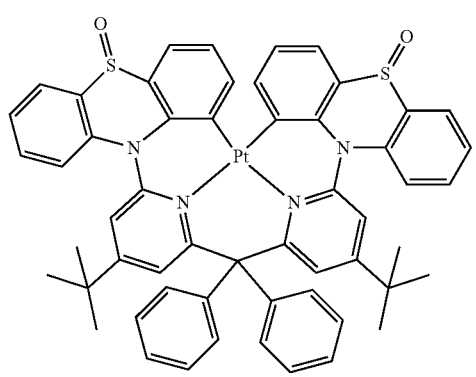
206
-continued
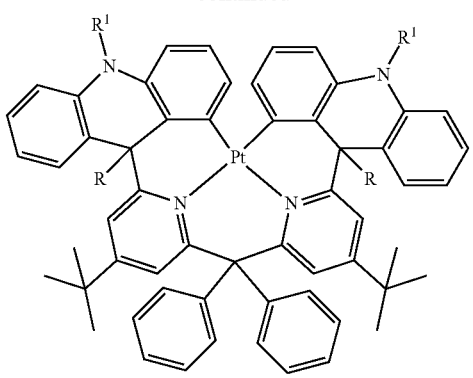
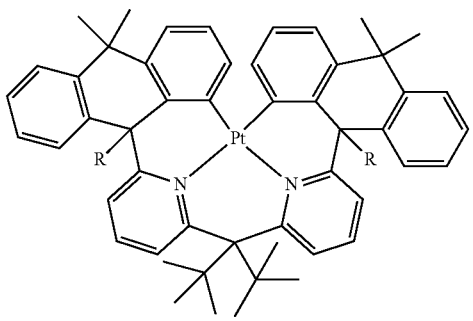
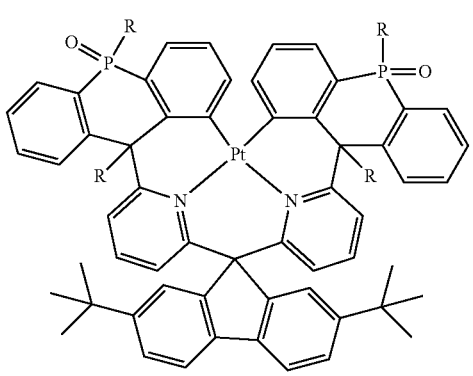
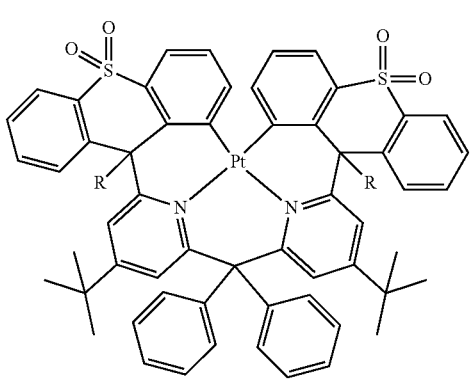

Structure Pt-18
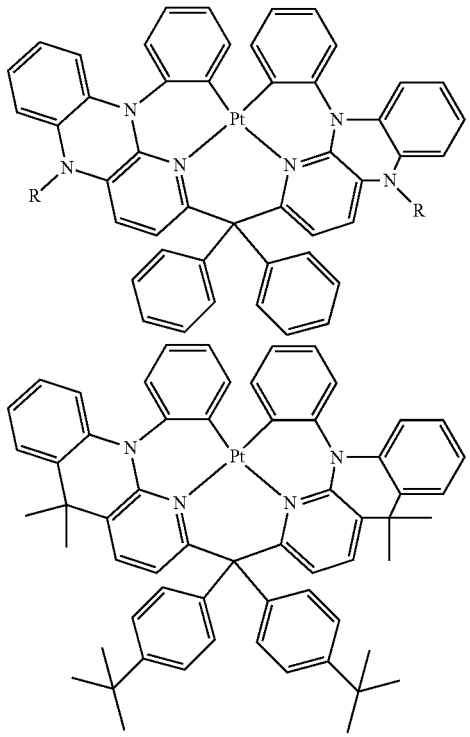
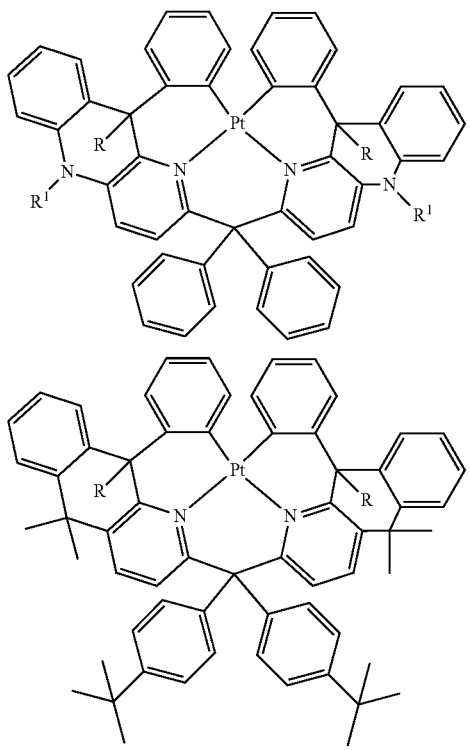
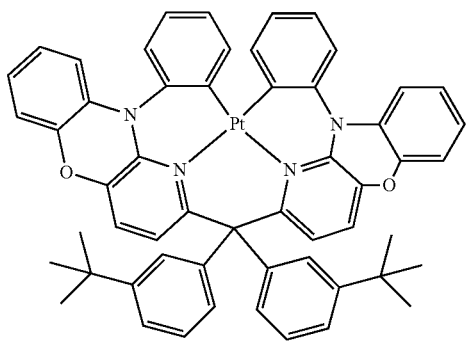
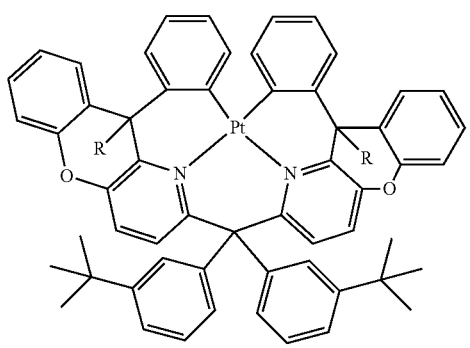
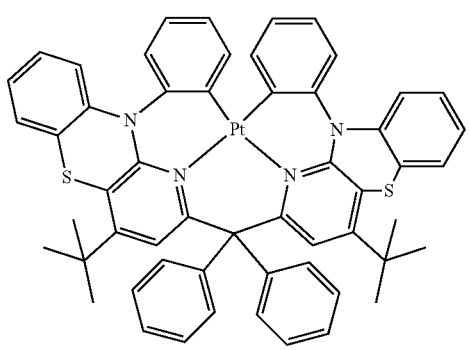
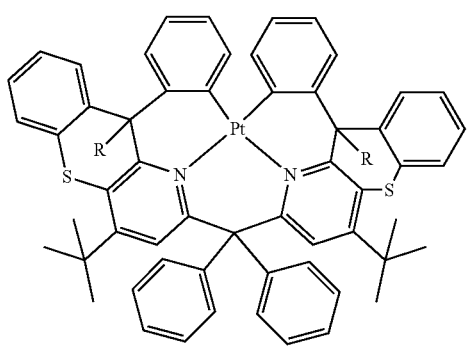

209
-continued
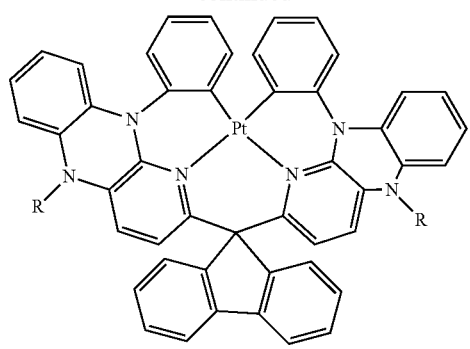
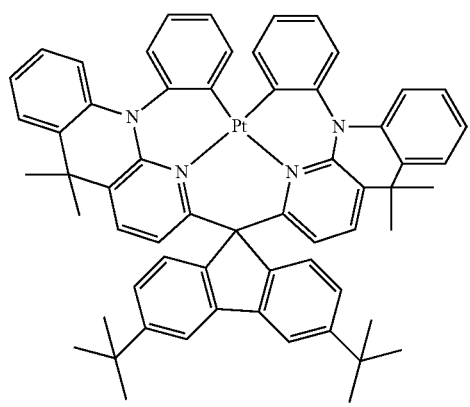
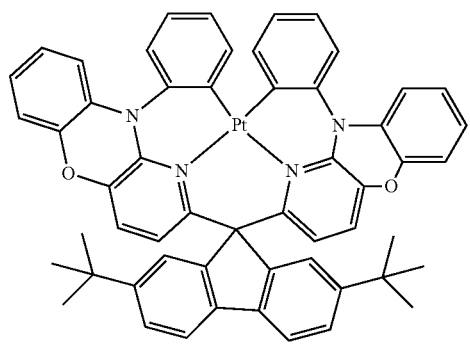
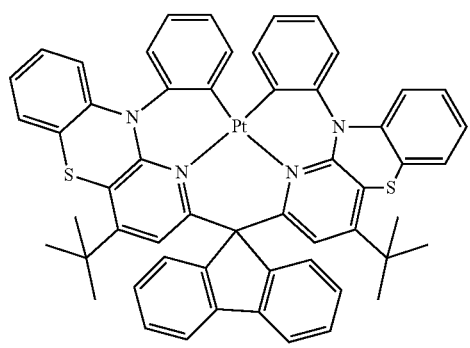
210
-continued
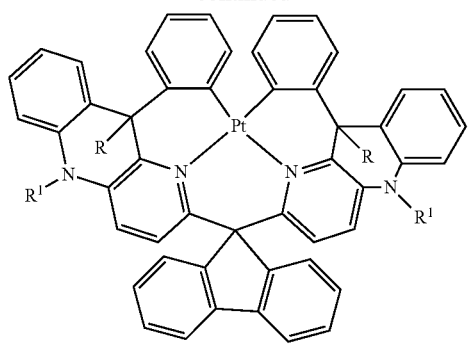
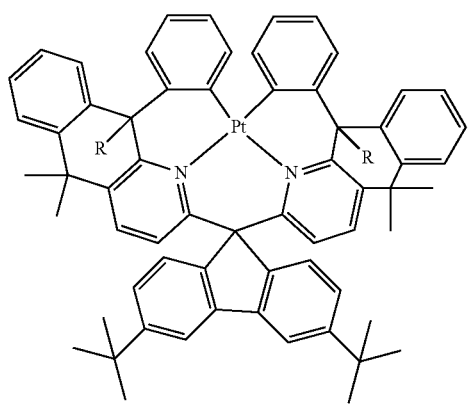
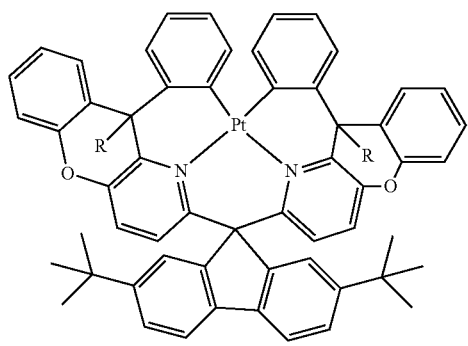
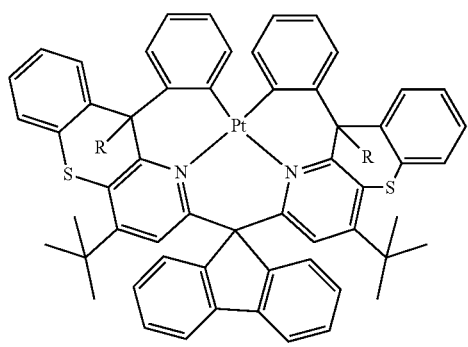

211
-continued
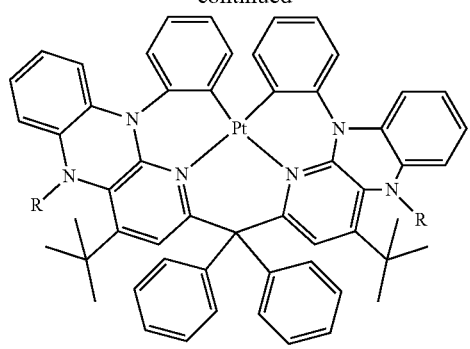
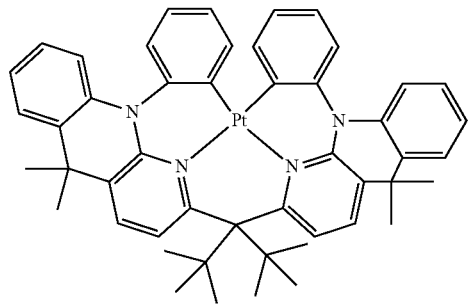
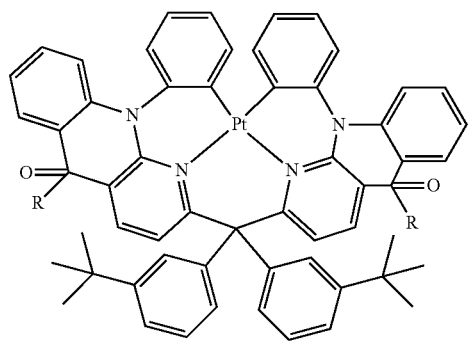
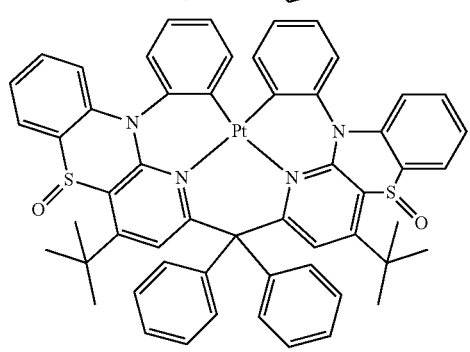
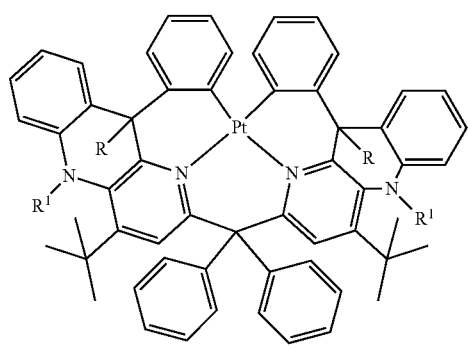
212
-continued
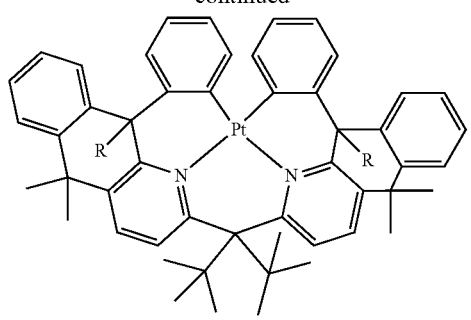
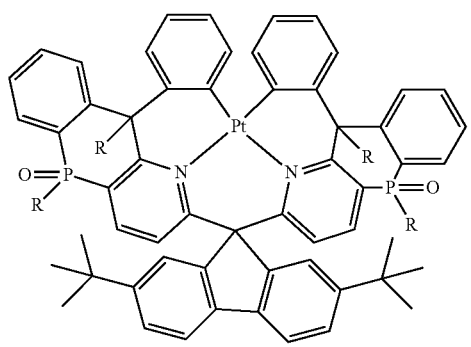
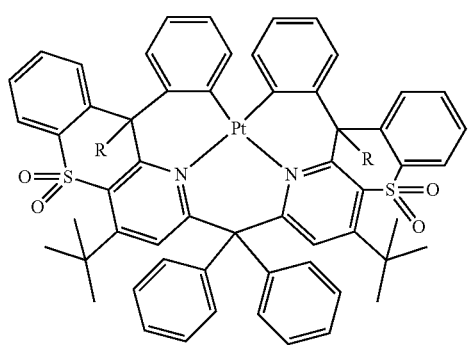
Structure Pd-1
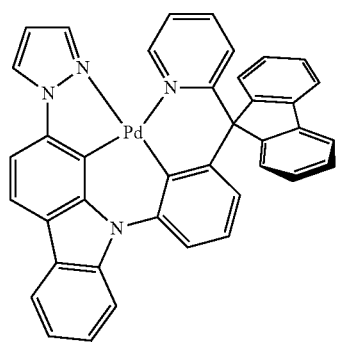

213
-continued
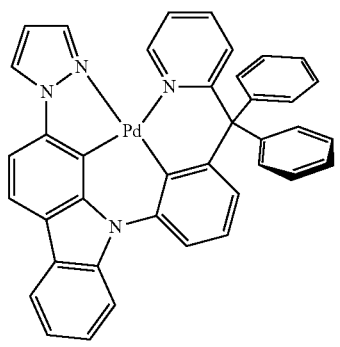
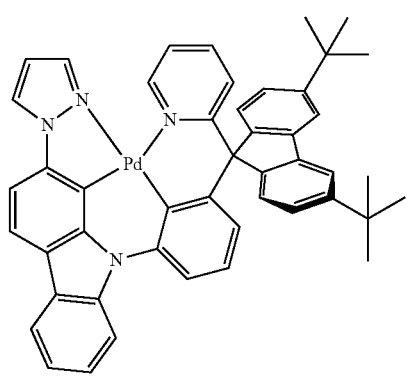
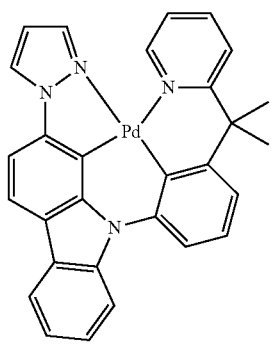
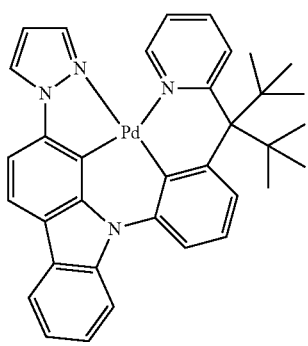
214
-continued
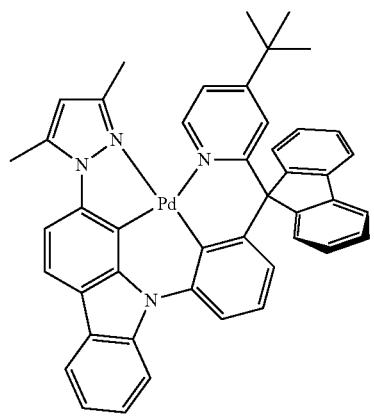
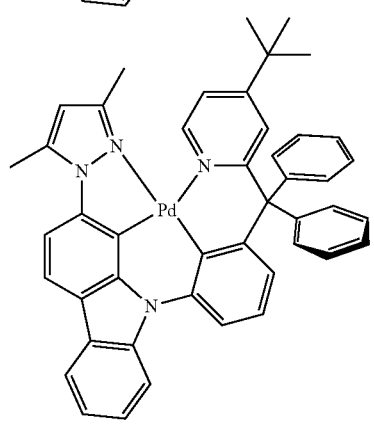
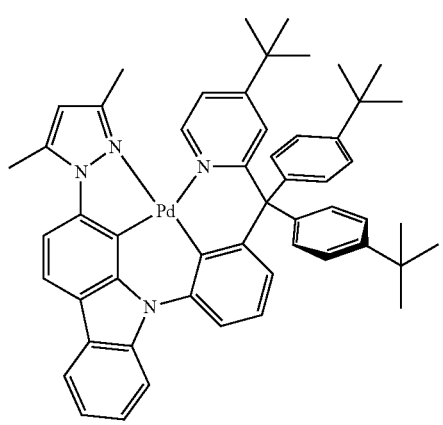
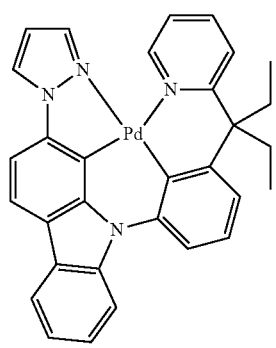

215
-continued
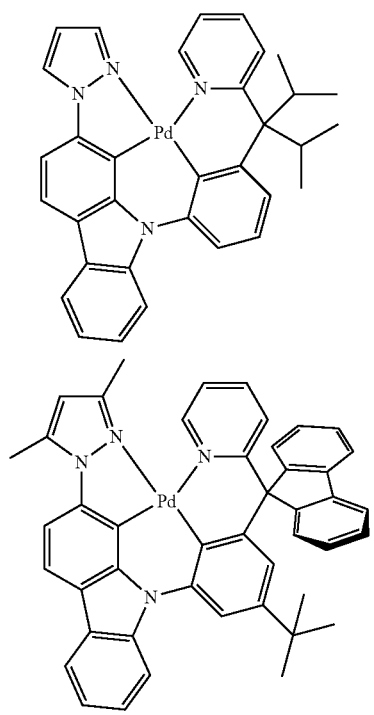
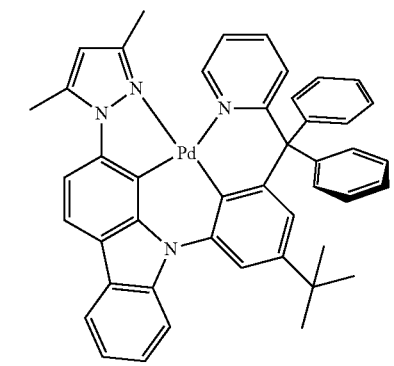
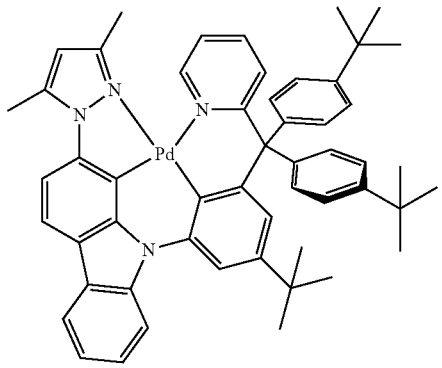
216
-continued
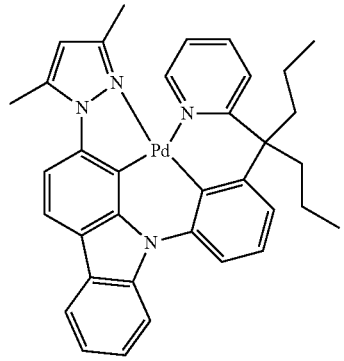
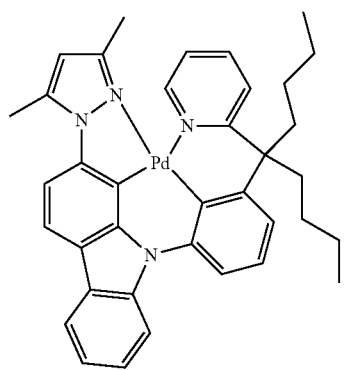
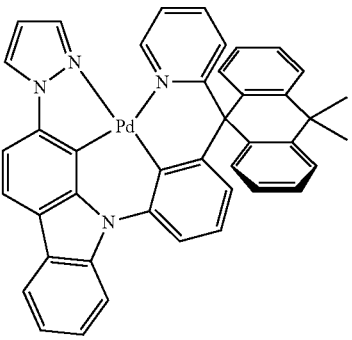
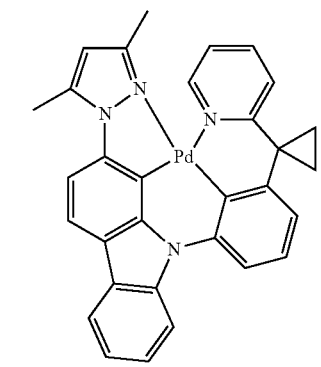

217
-continued
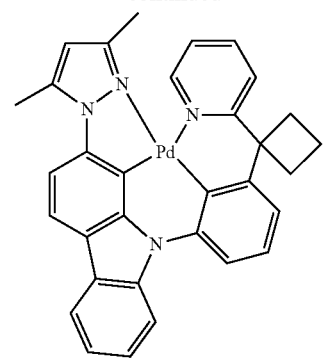
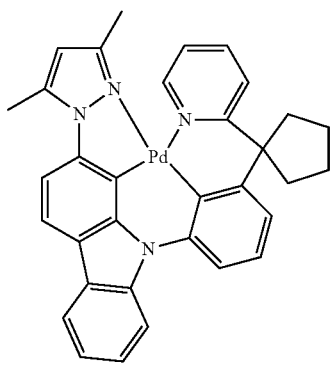
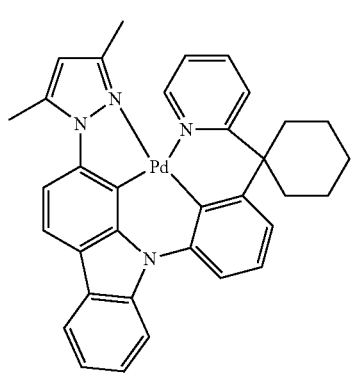
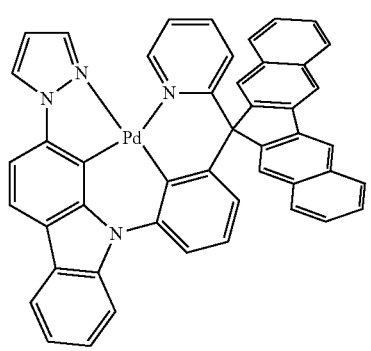
218
-continued
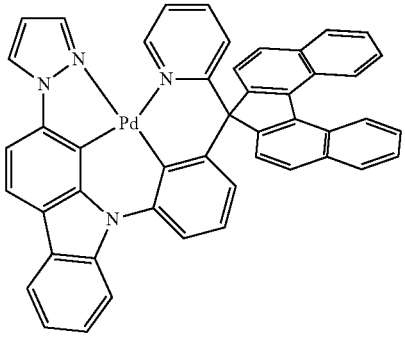
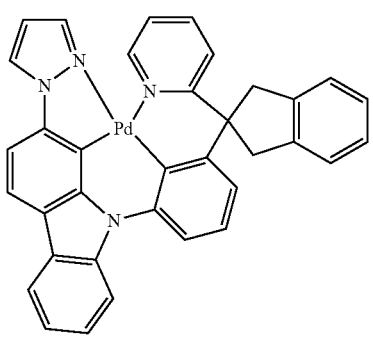
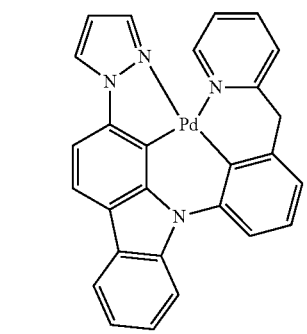
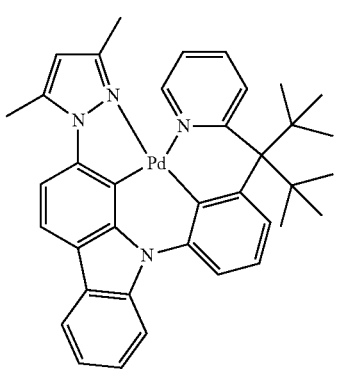

219
-continued
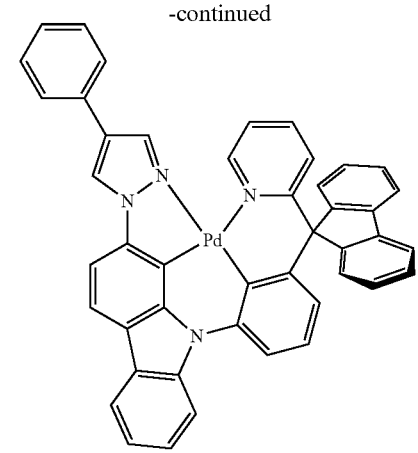
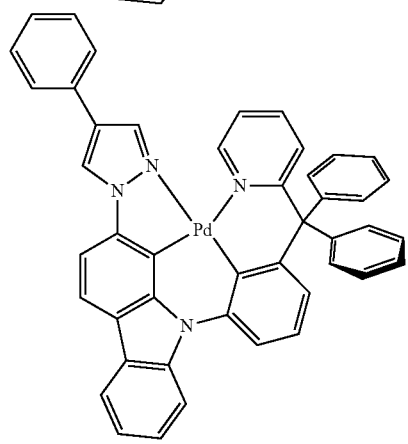
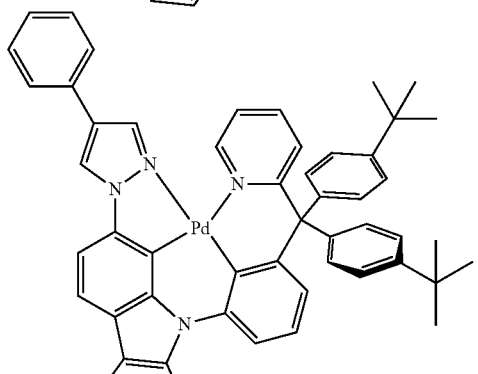
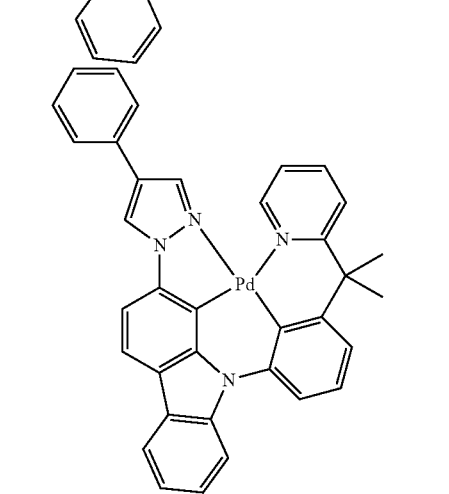
220
-continued
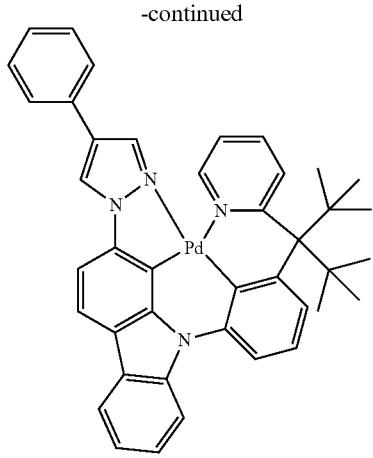
Structure Pd-2
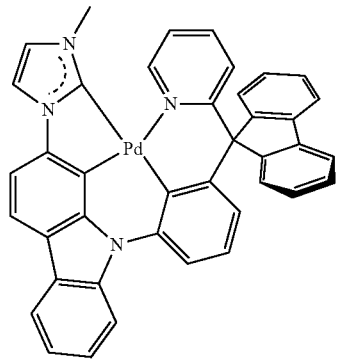
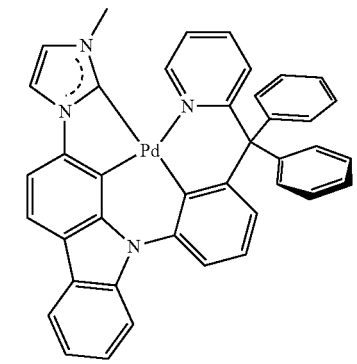
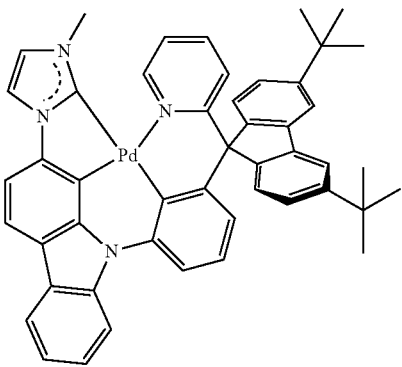

221
-continued
222
-continued
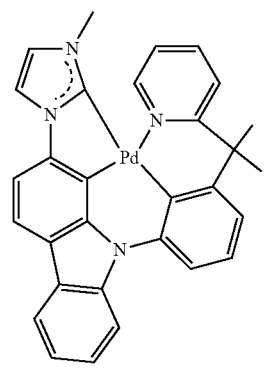
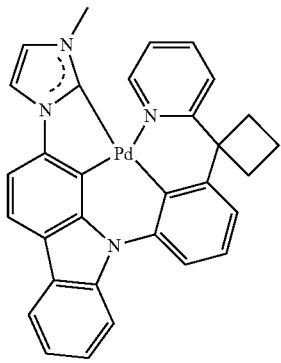
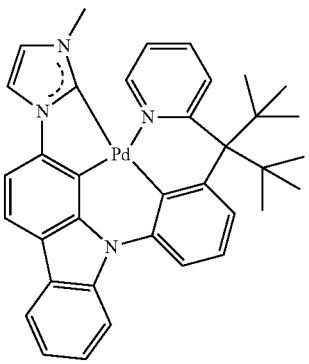
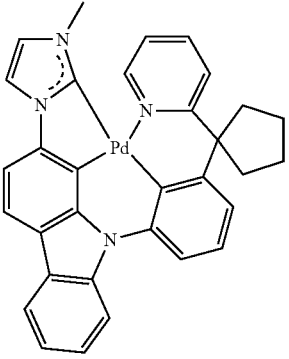
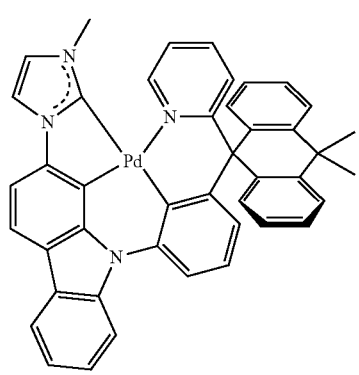
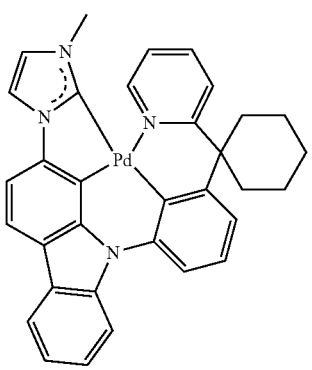
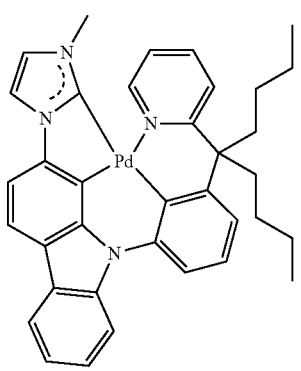
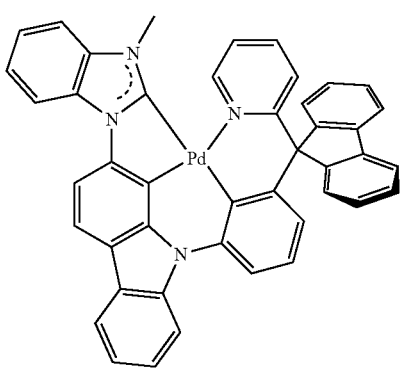

223
-continued
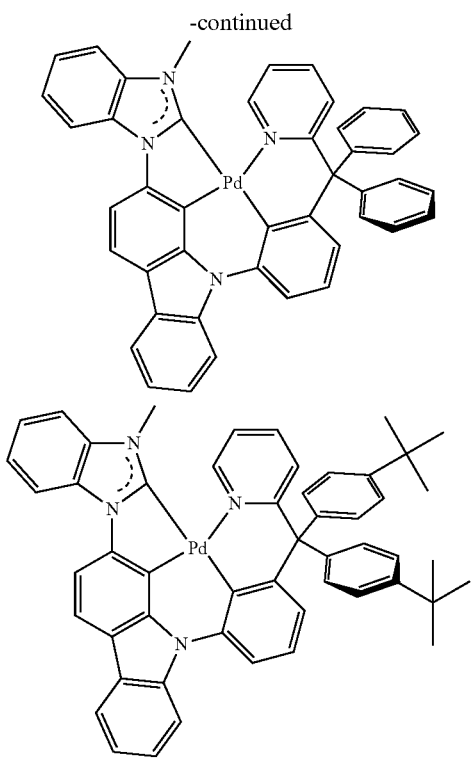
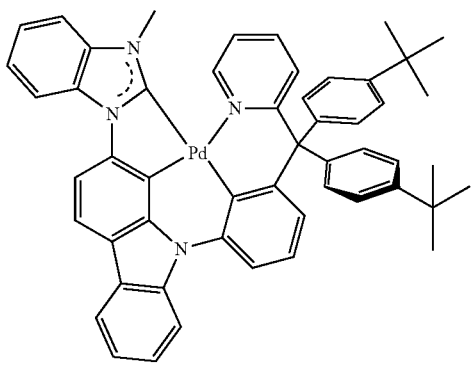
224
-continued
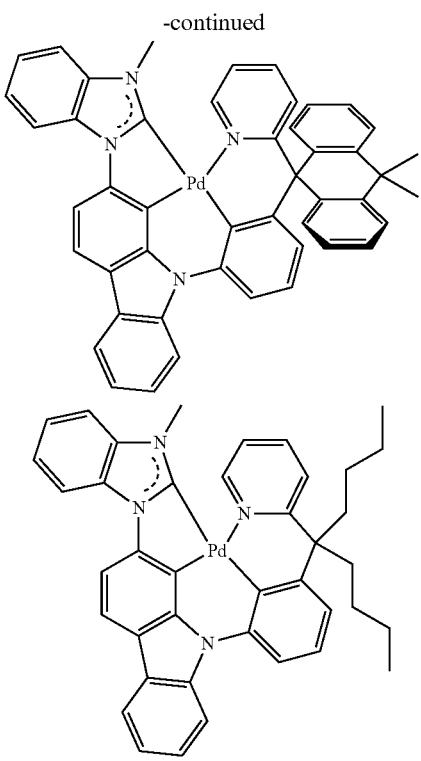
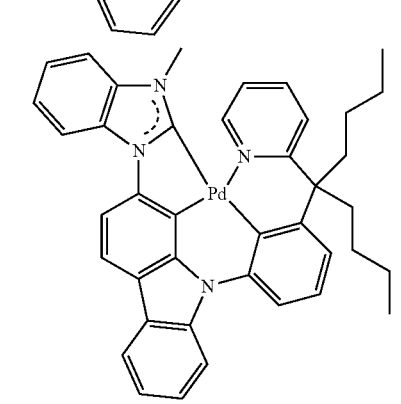
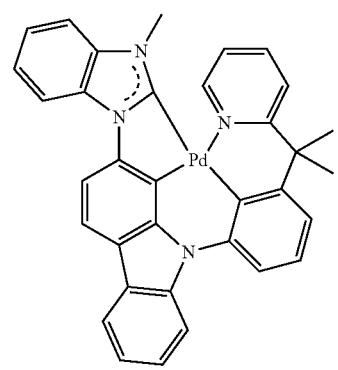
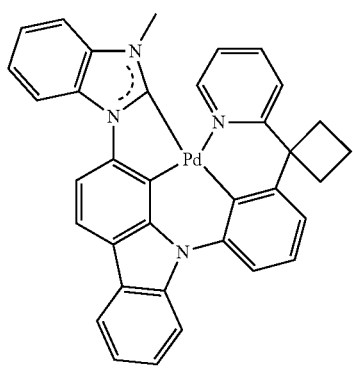
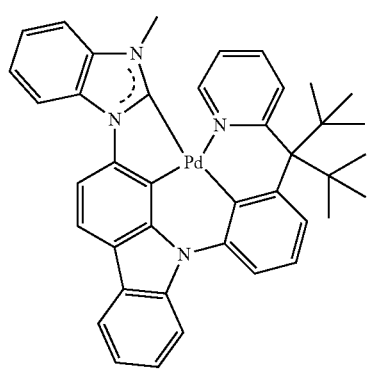
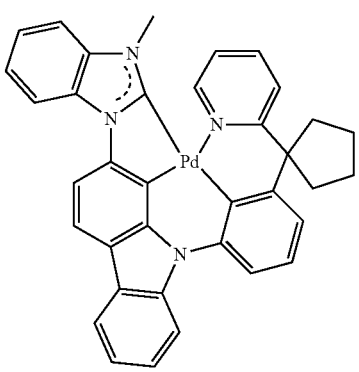

225
-continued
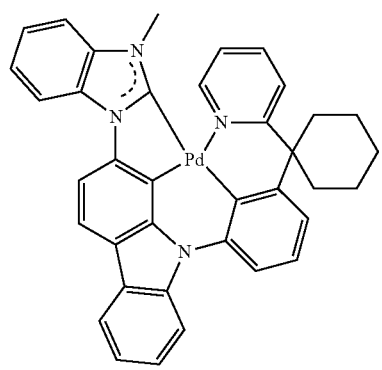
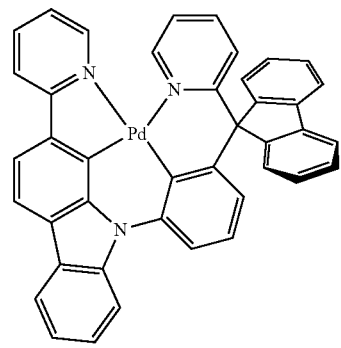
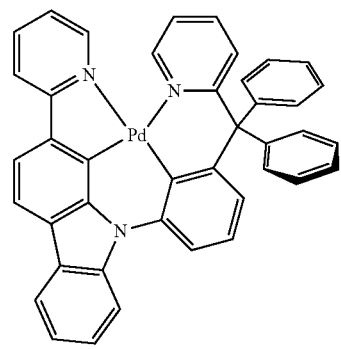
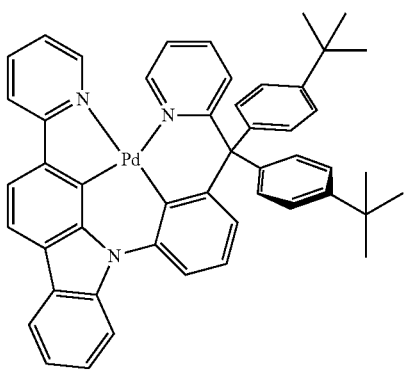
226
-continued
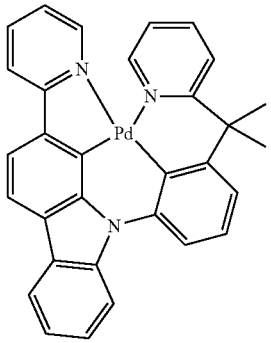
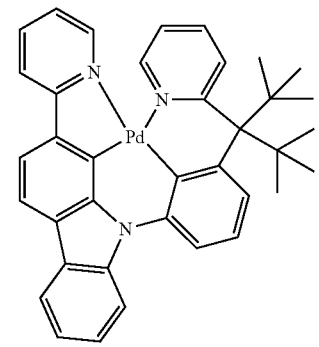
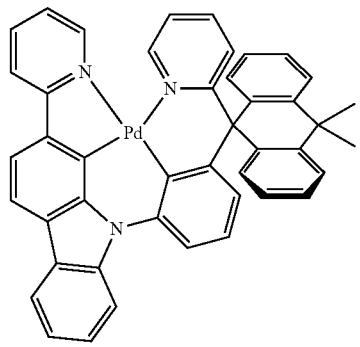
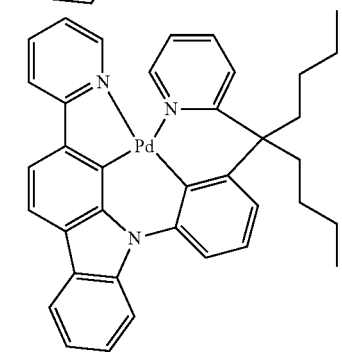
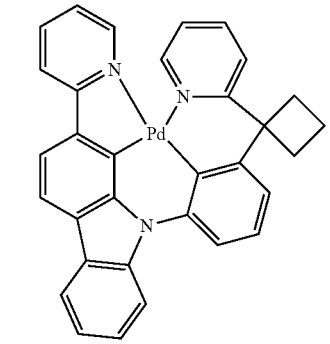

227
-continued
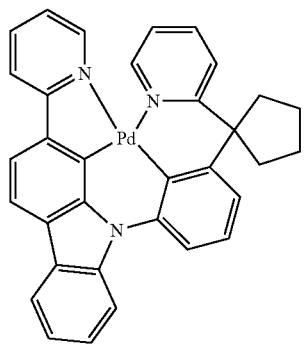
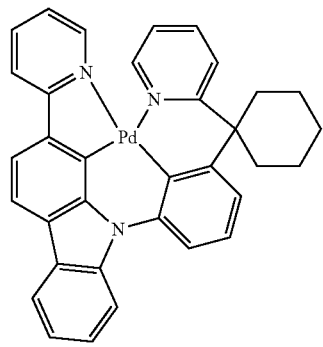
Structure Pd-3
228
-continued
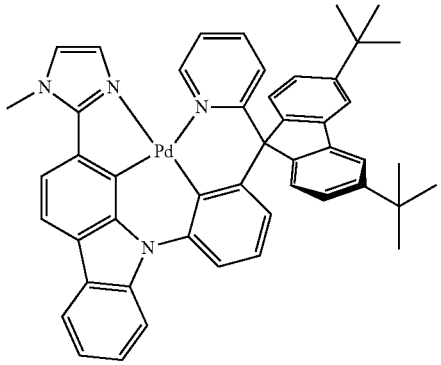
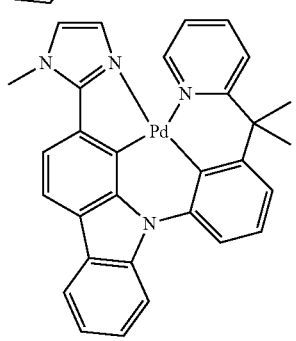
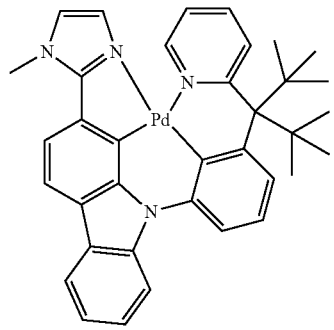
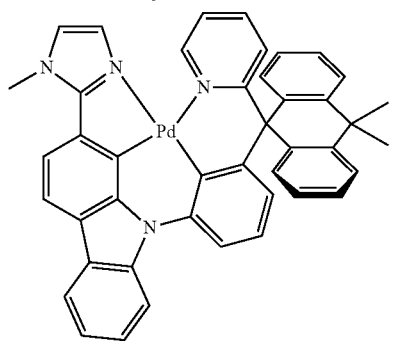
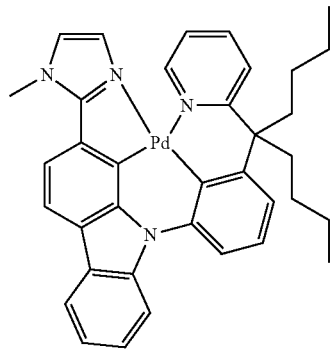

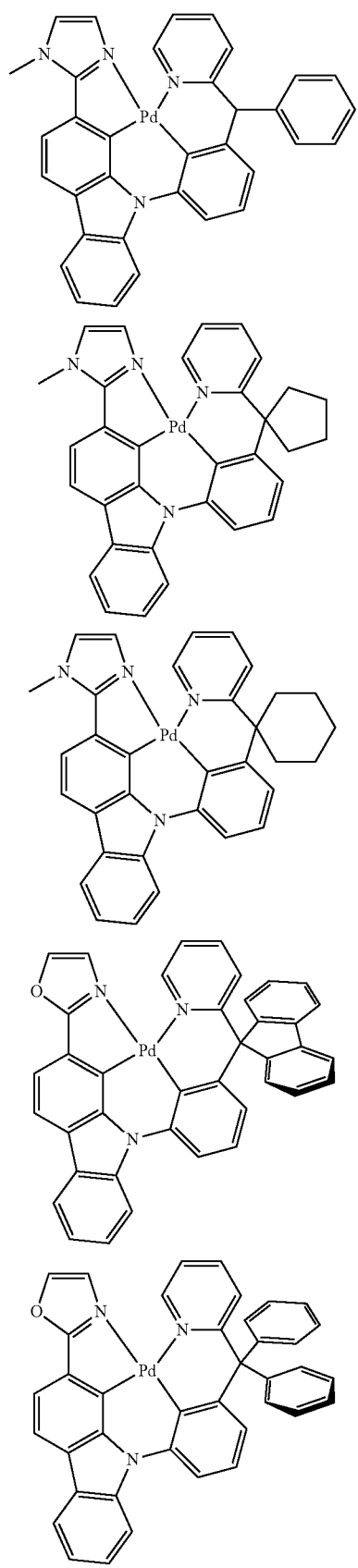
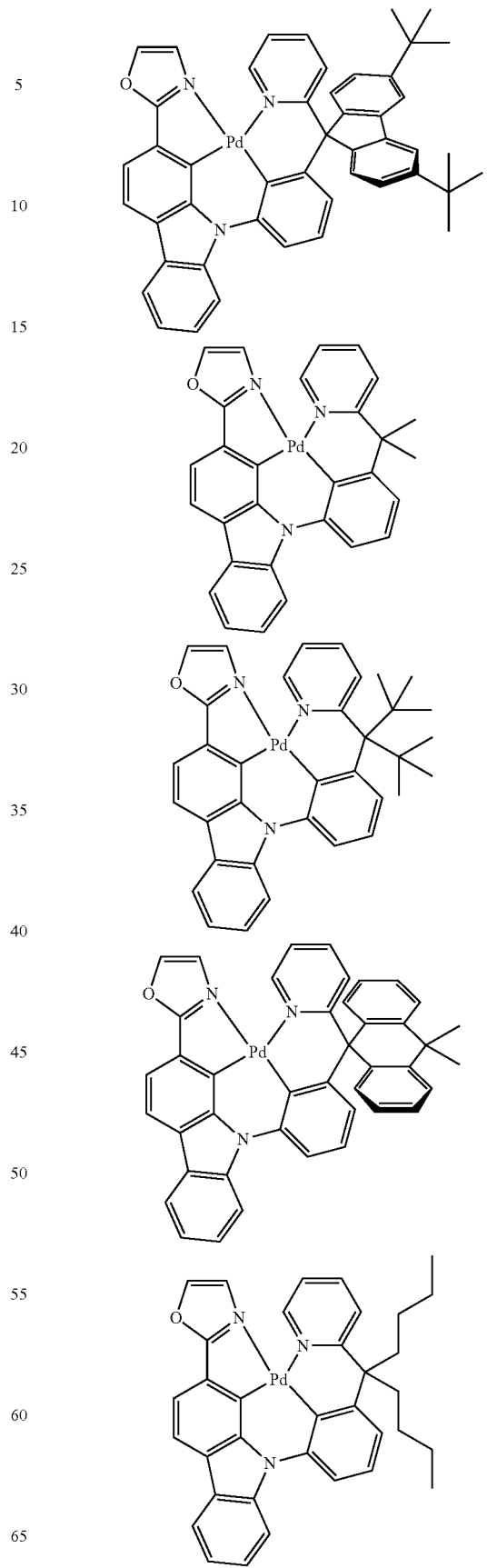

-continued
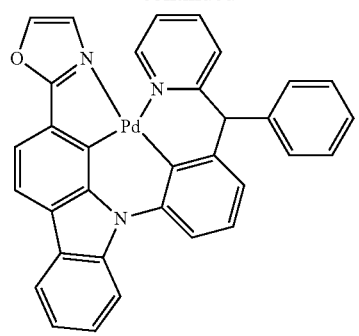
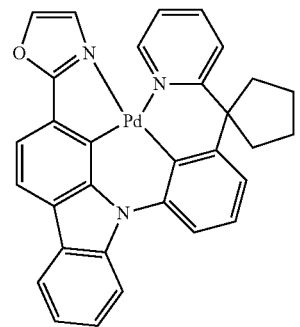
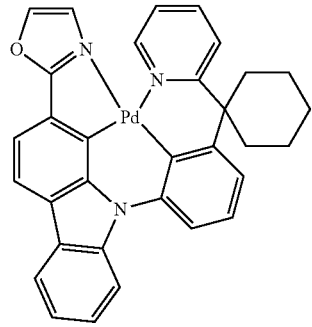
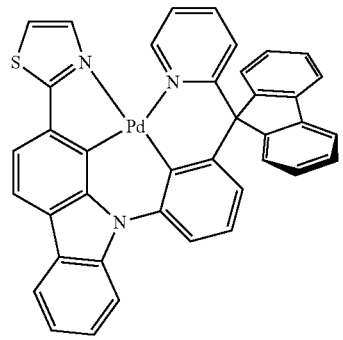
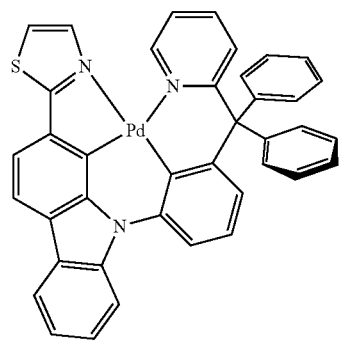
-continued
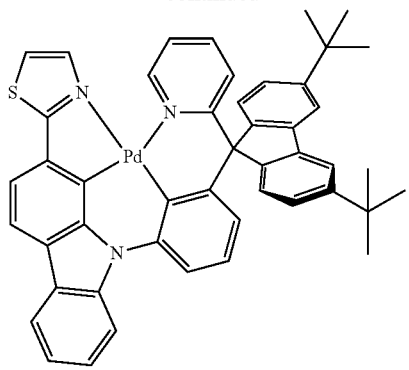
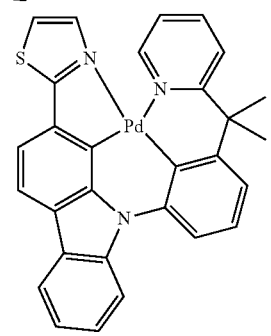
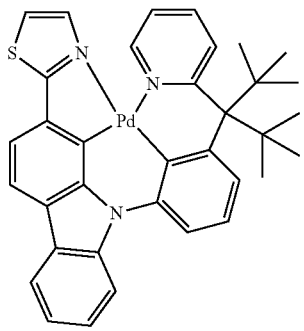
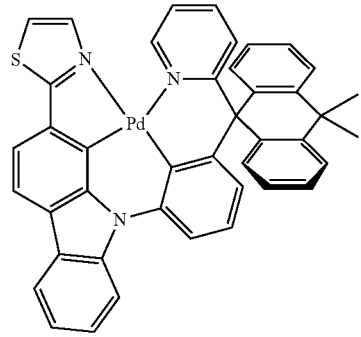
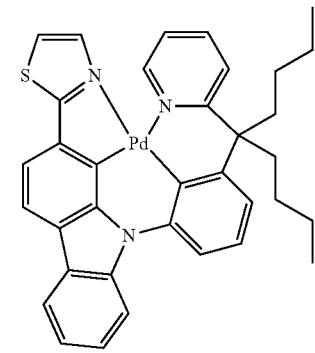

233
-continued
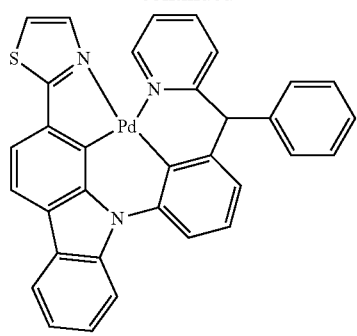
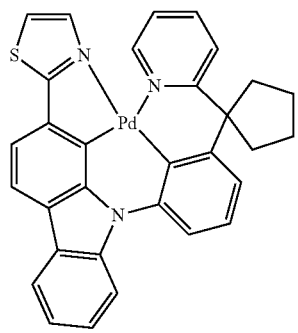
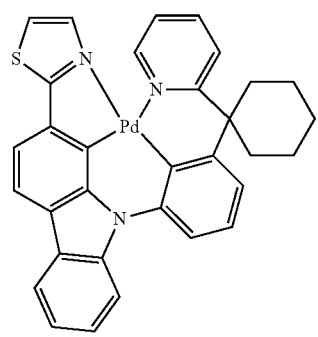
Structure Pd-4
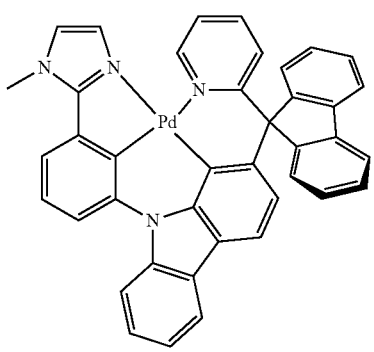
234
-continued
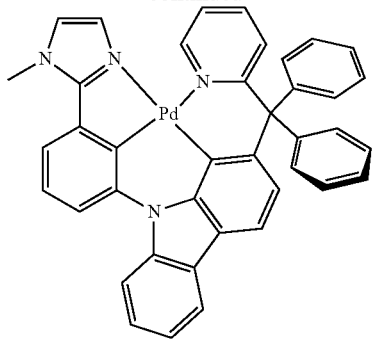
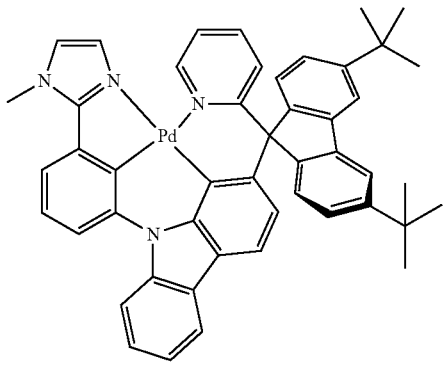
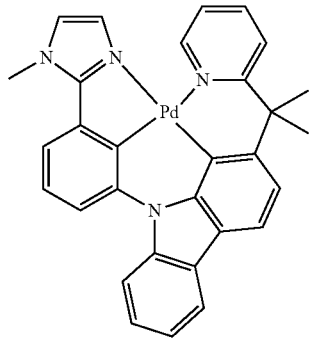
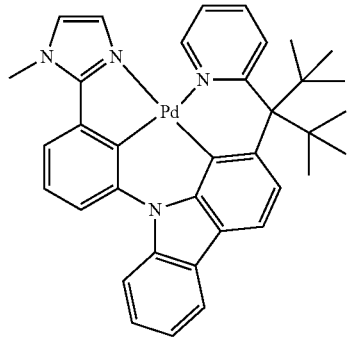
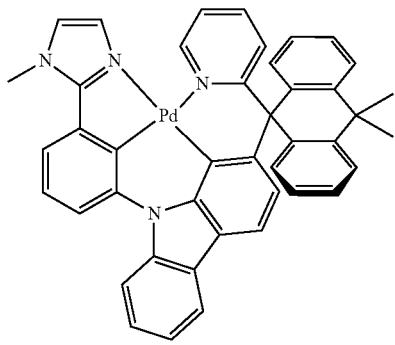

235
-continued
236
-continued
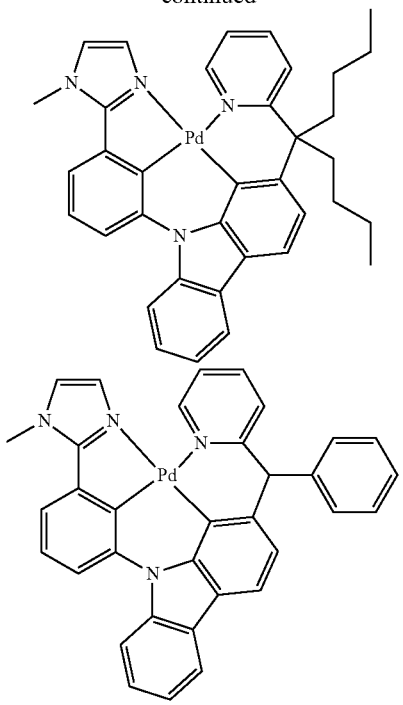
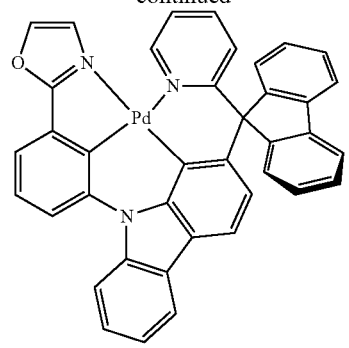
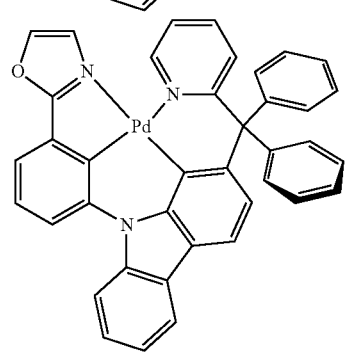
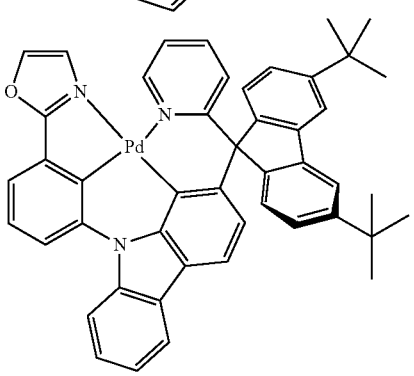
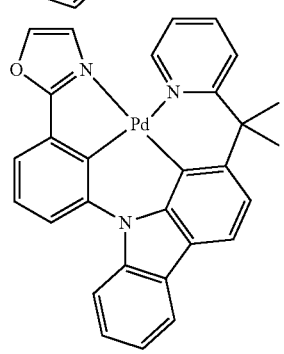
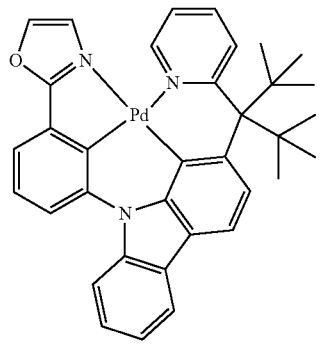

237
-continued
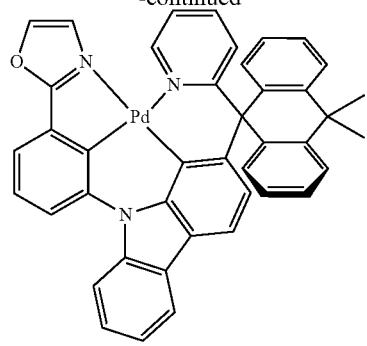
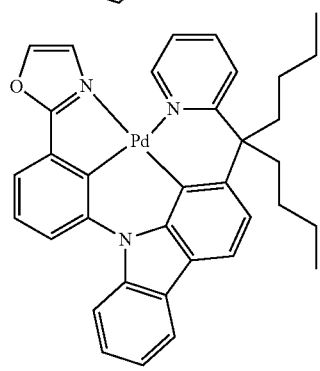
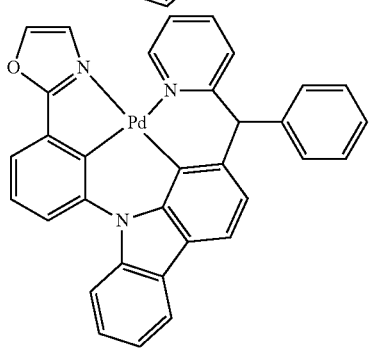
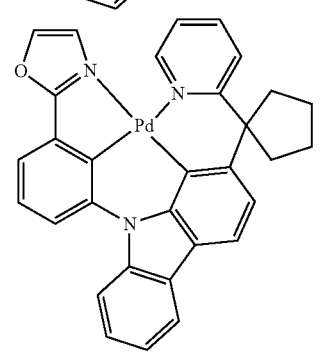
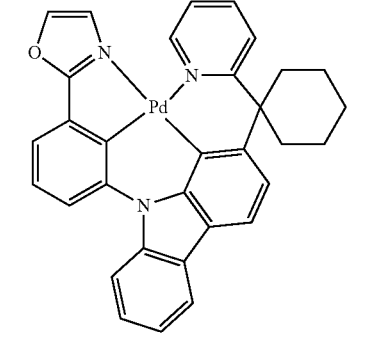
238
-continued
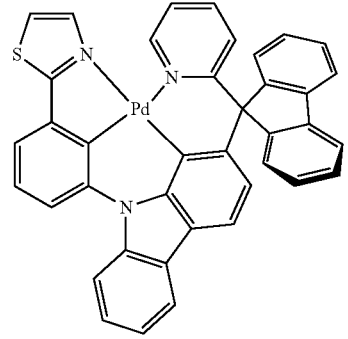
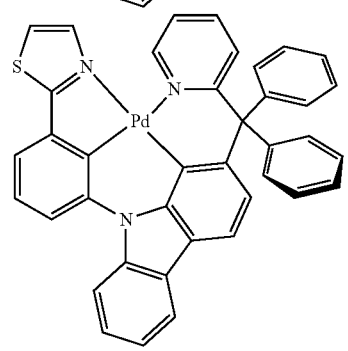
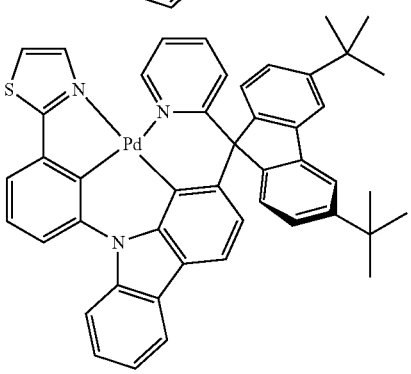
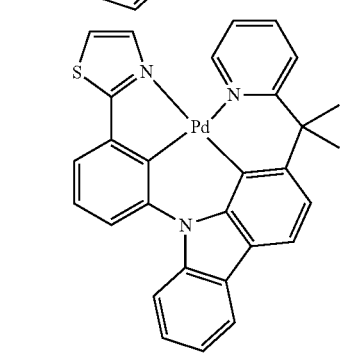
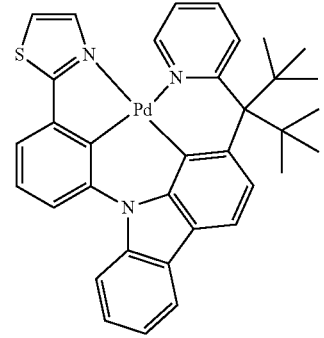

-continued
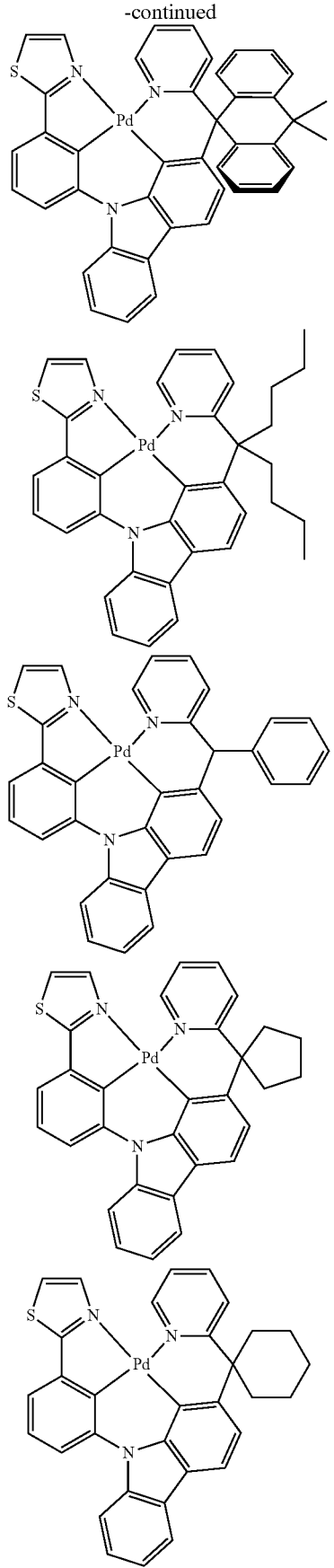
-continued
Structure Pd-5
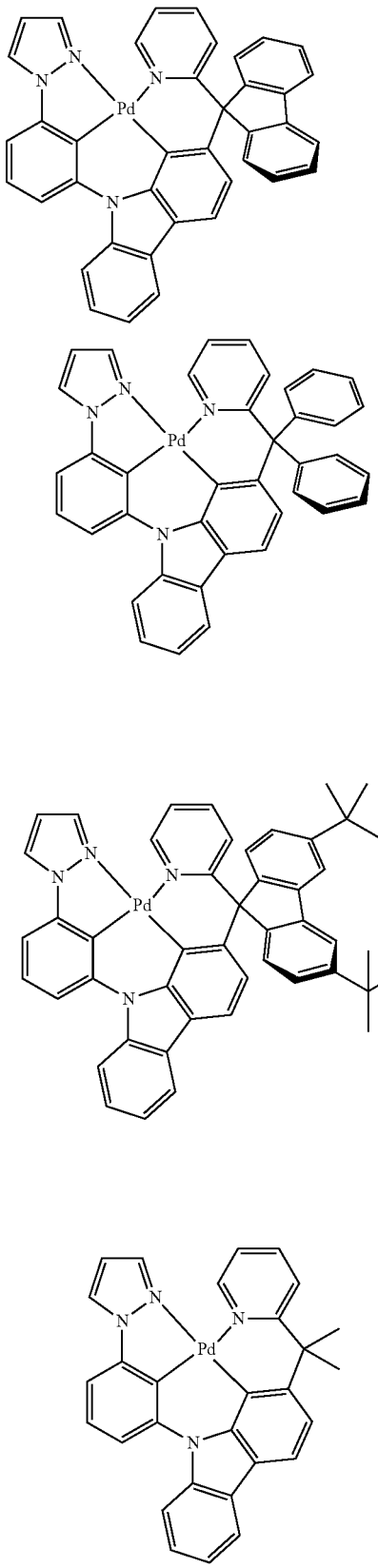

241
-continued
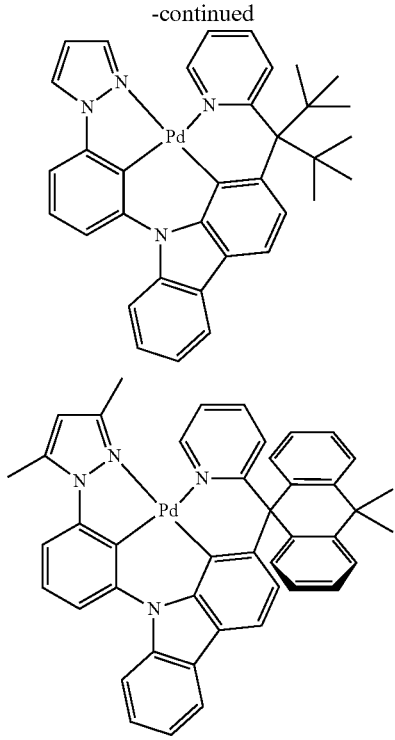
242
-continued
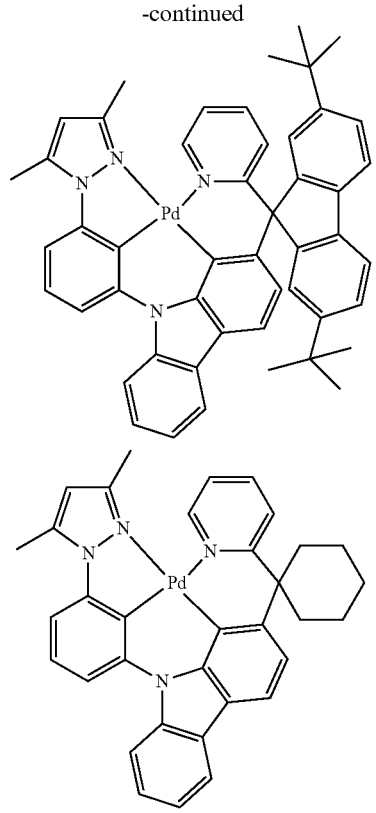
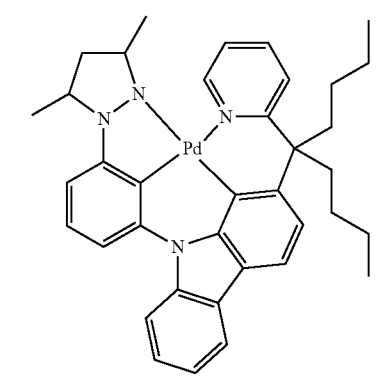
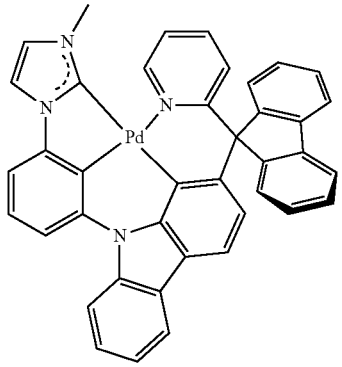
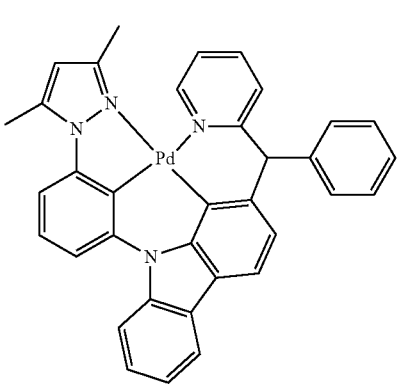
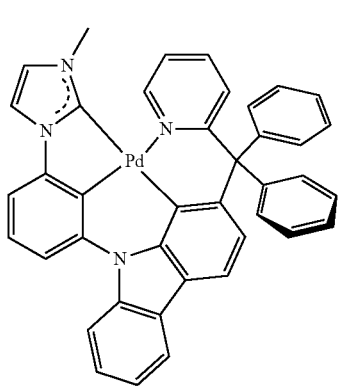

243
-continued
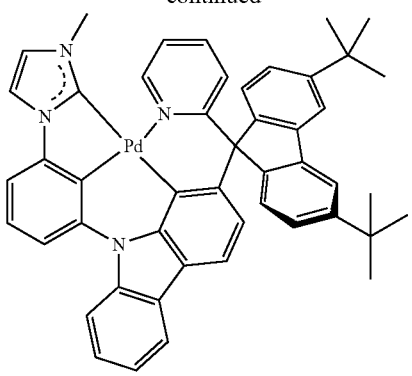
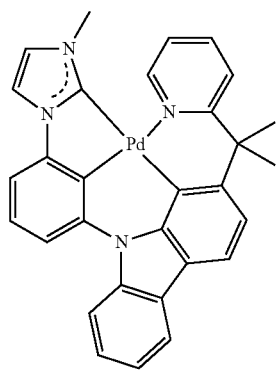
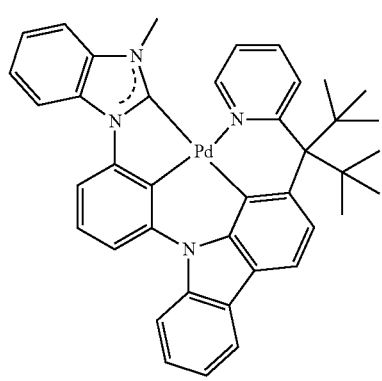
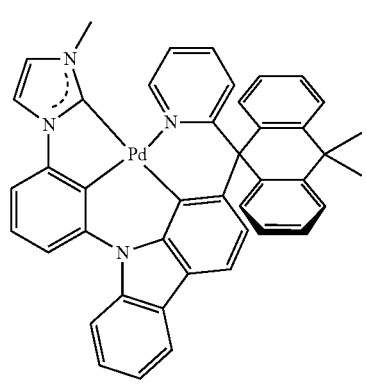
244
-continued
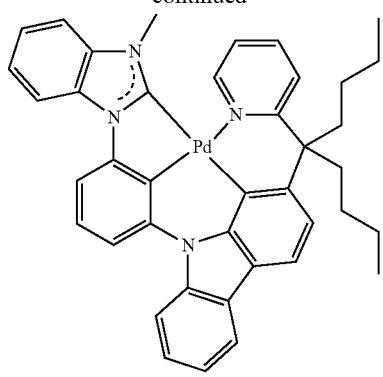
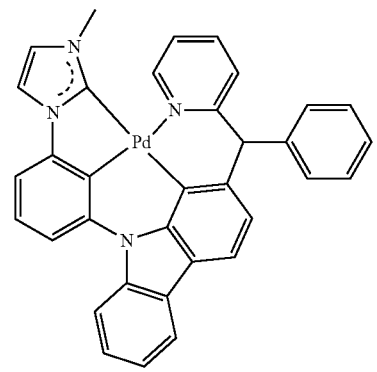
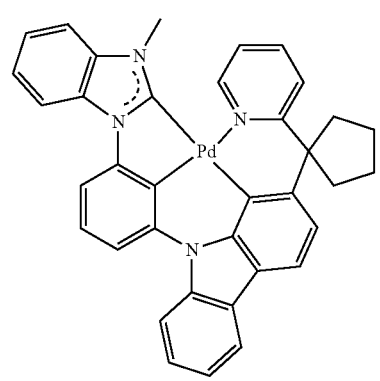
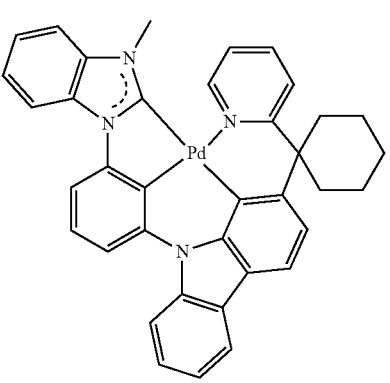

245
-continued
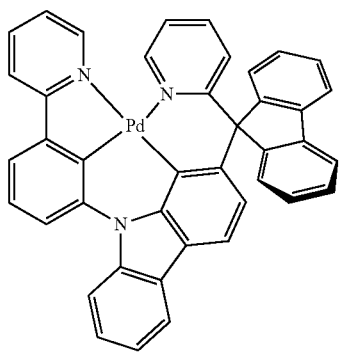
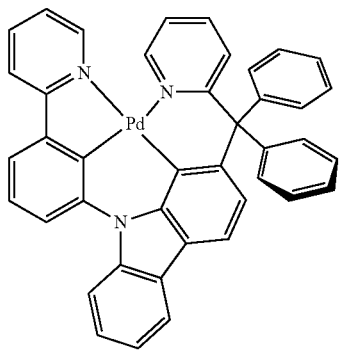
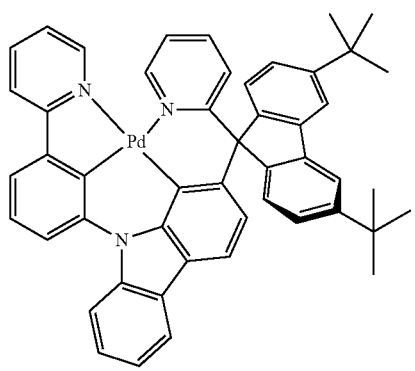
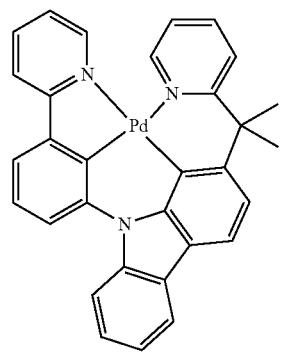
246
-continued
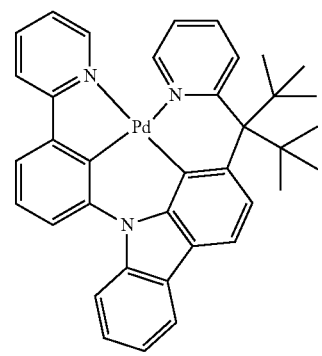
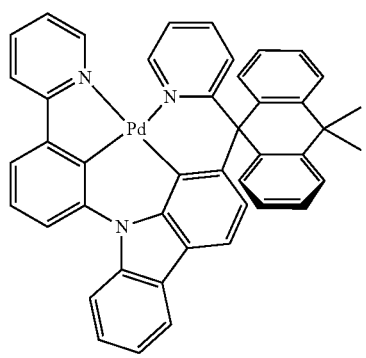
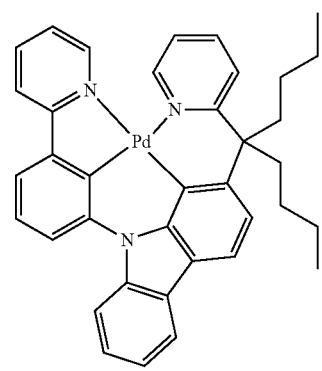
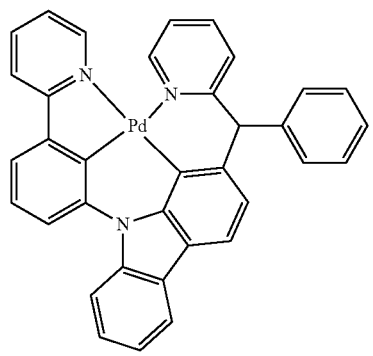

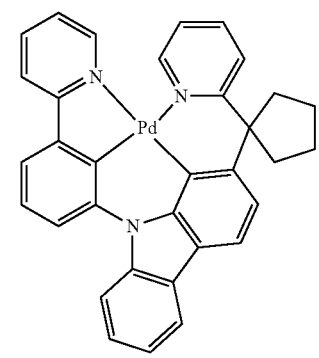
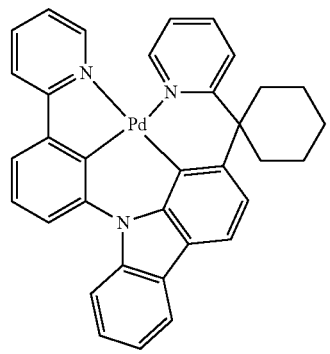
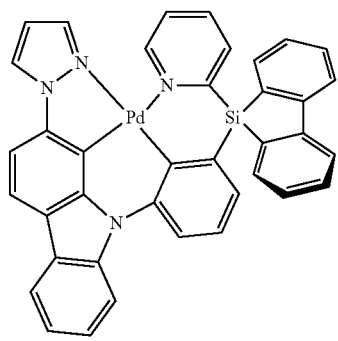
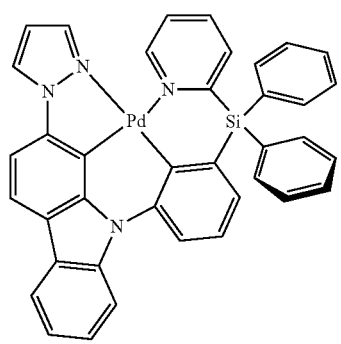
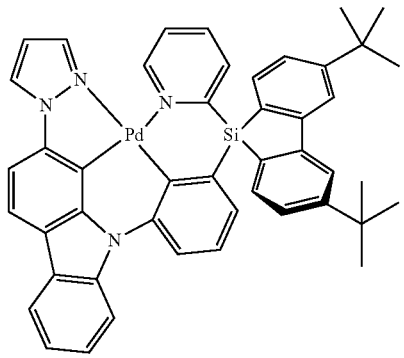
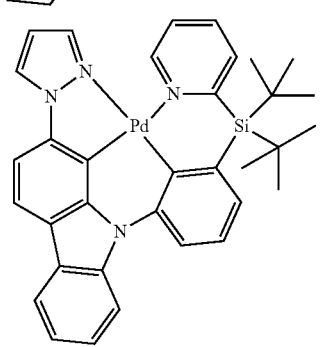
Structure Pd-6
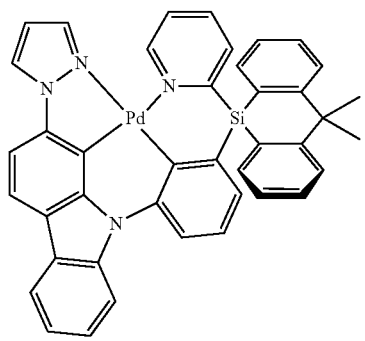
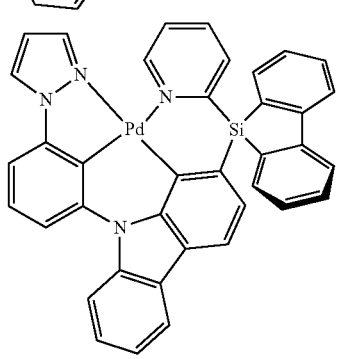
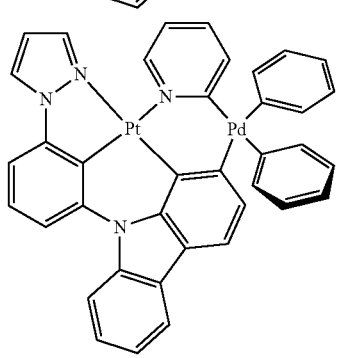

249
-continued
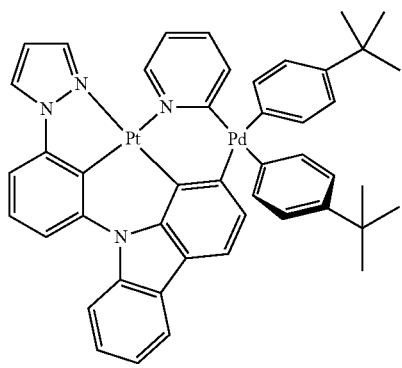
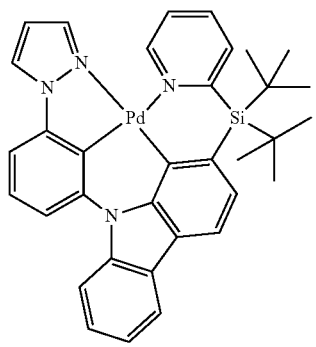
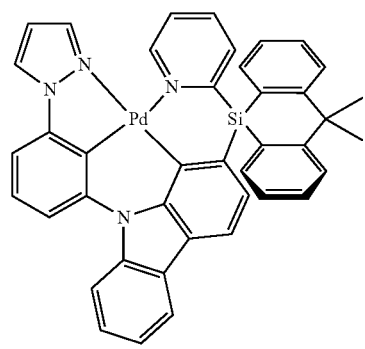
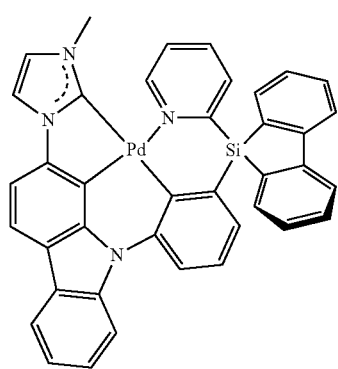
250
-continued
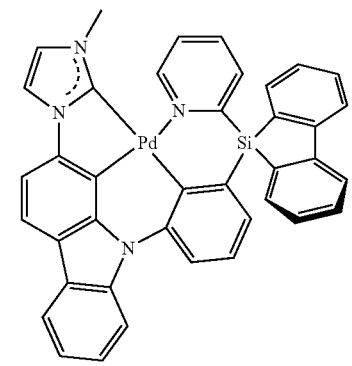
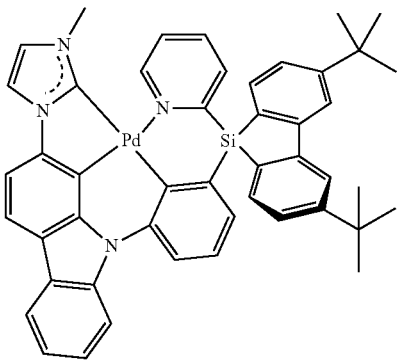
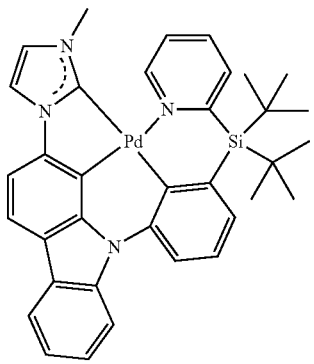
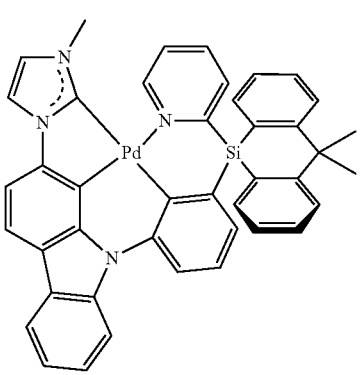

251
-continued
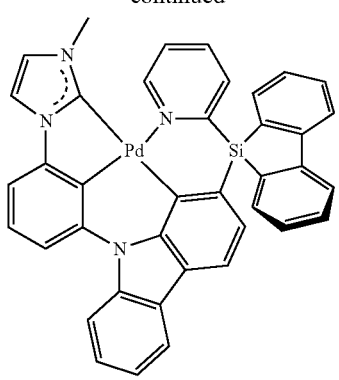
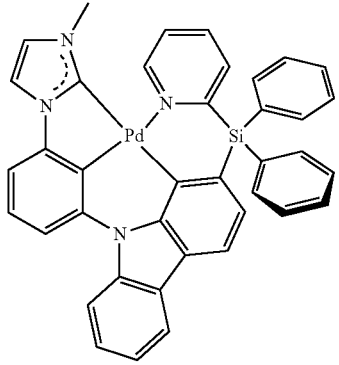
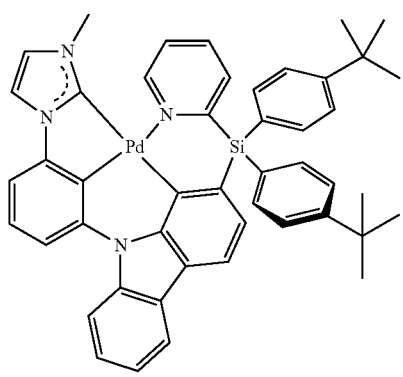
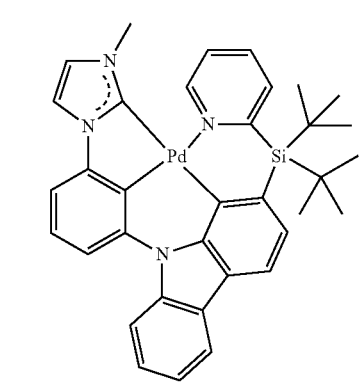
252
-continued
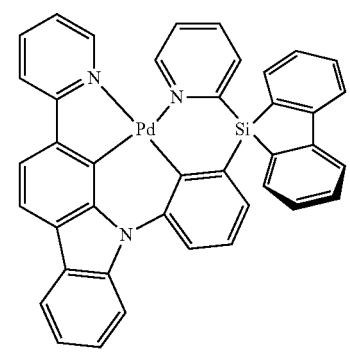
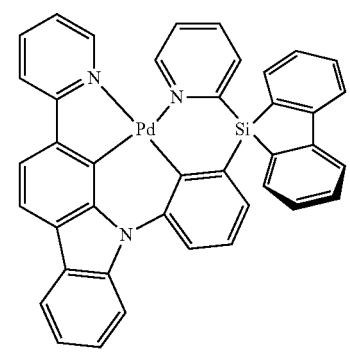
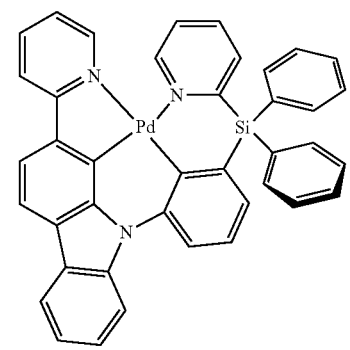
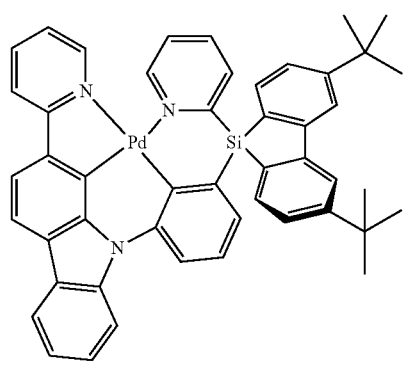

253
-continued

254
-continued

Structure Pd-7

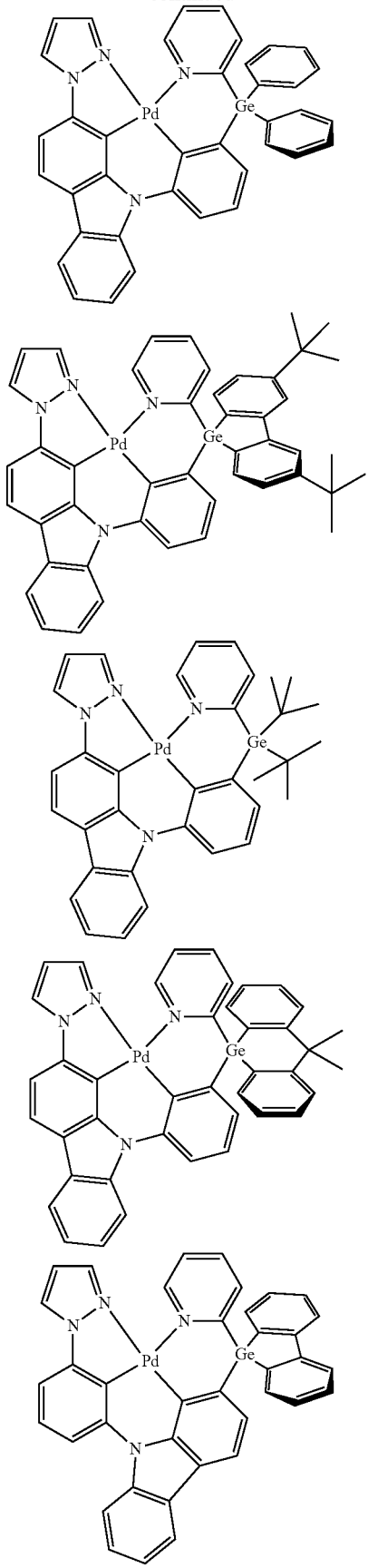

257
-continued
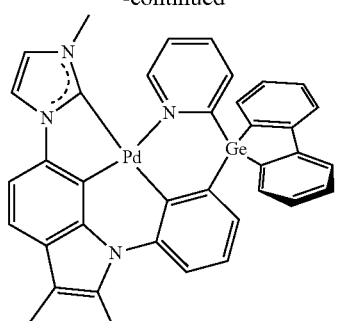
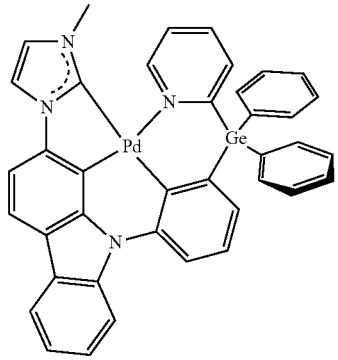
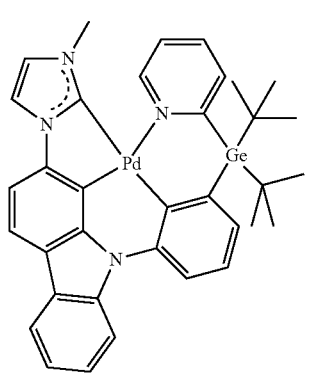
258
-continued
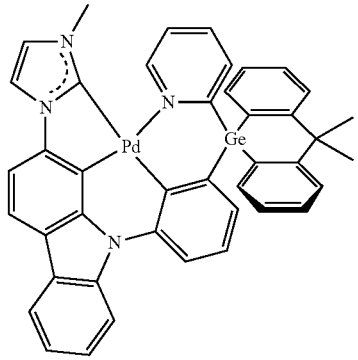
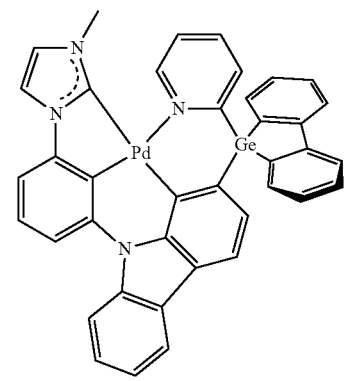
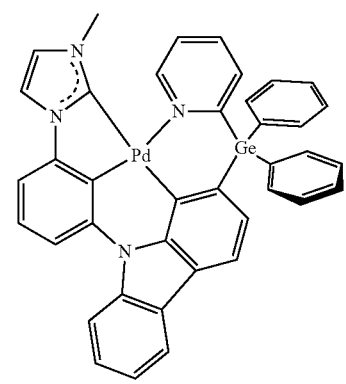
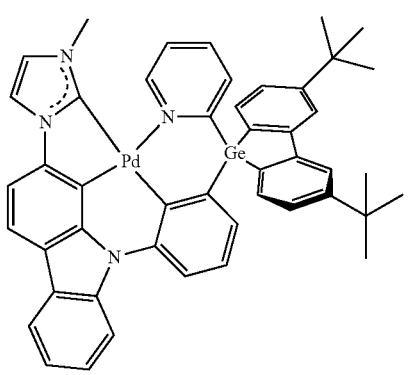
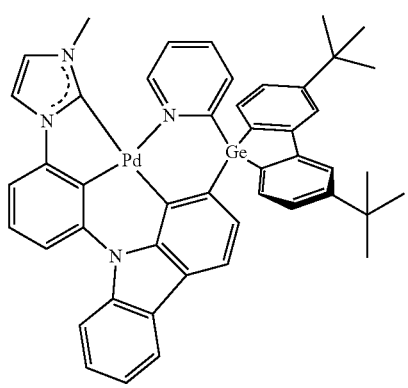

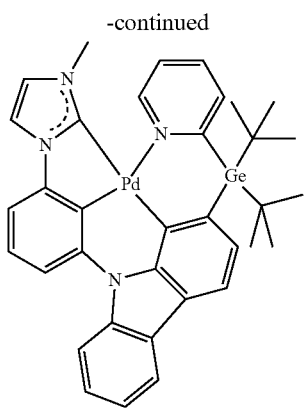
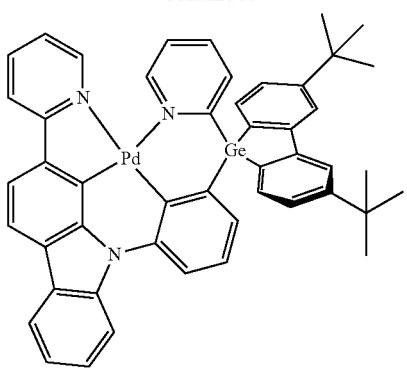
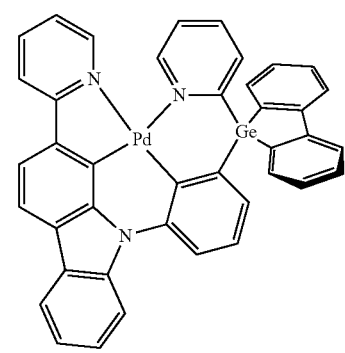
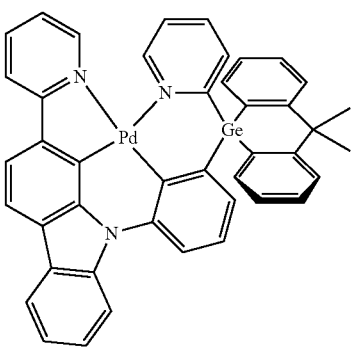
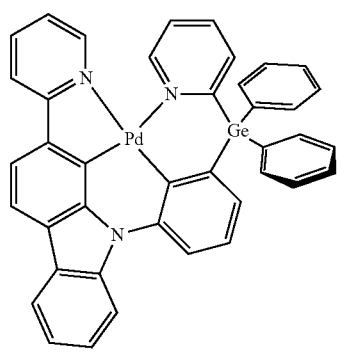
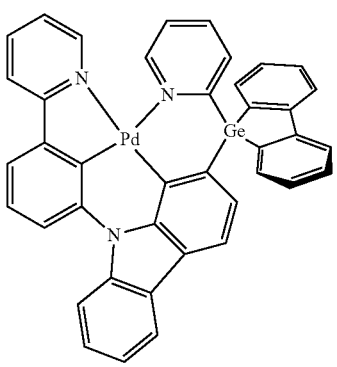

-continued
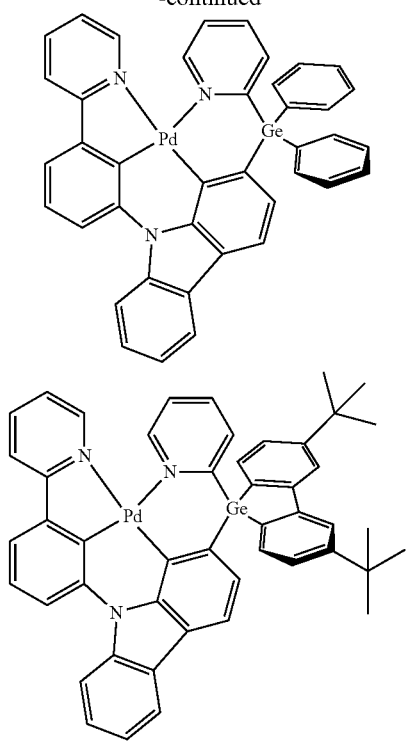
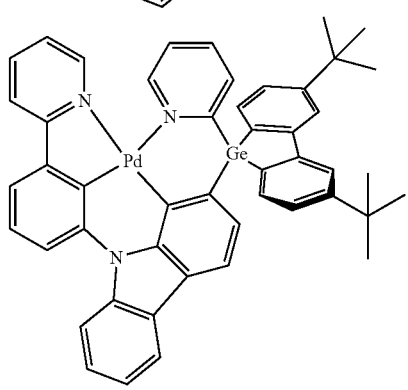
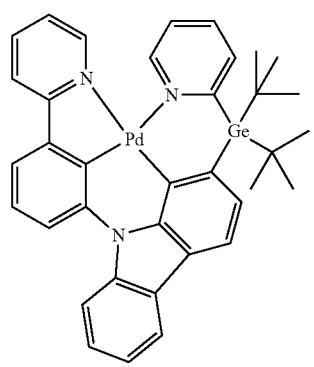
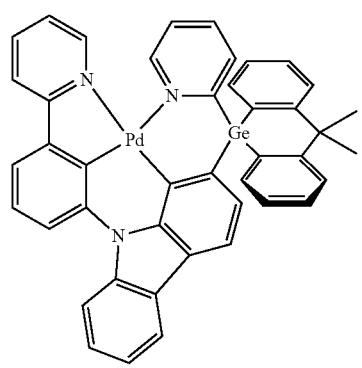
-continued
Structure Pd-8
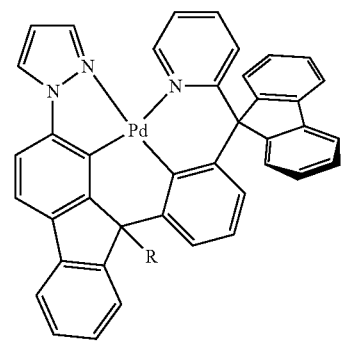
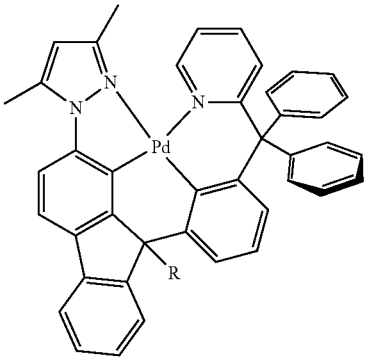
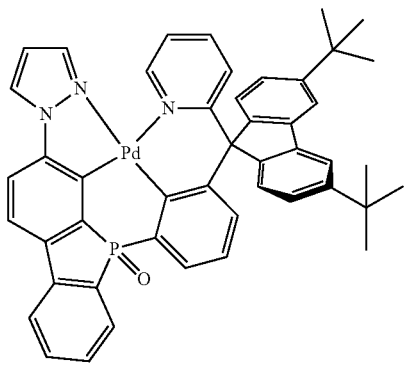
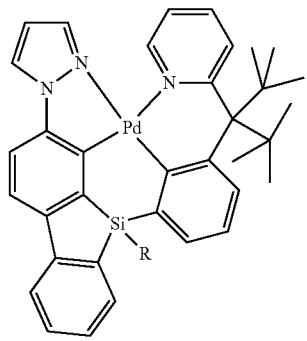

263
-continued
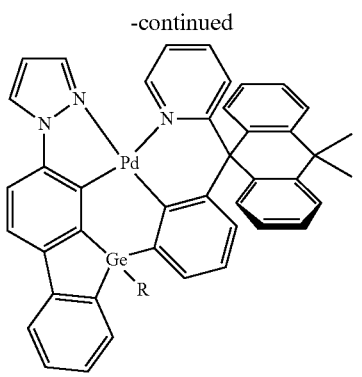
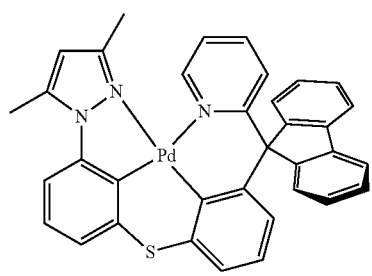
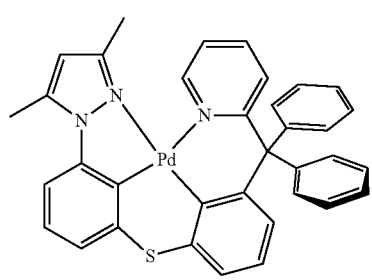
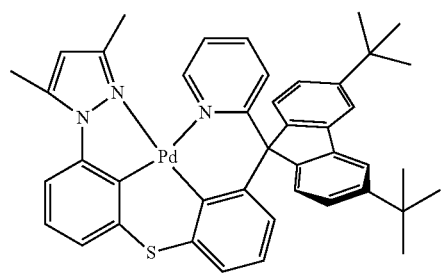
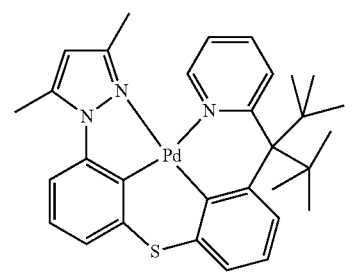
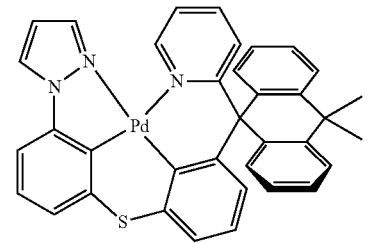
264
-continued
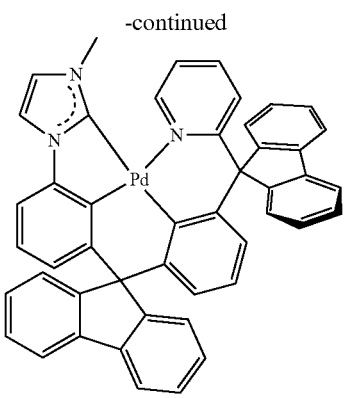
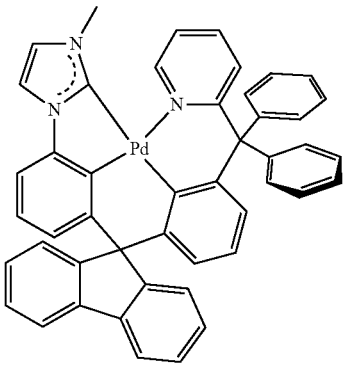
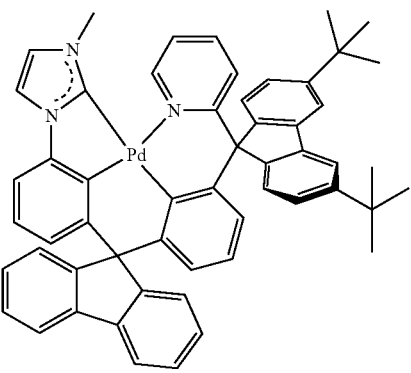
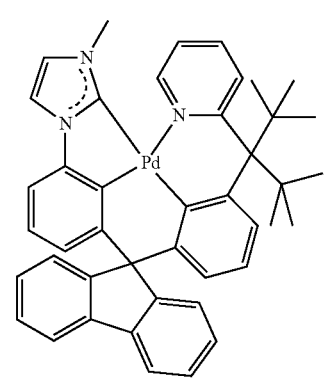

265
-continued
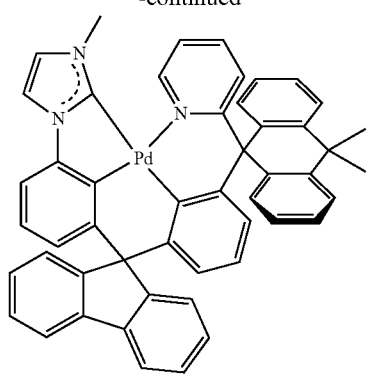
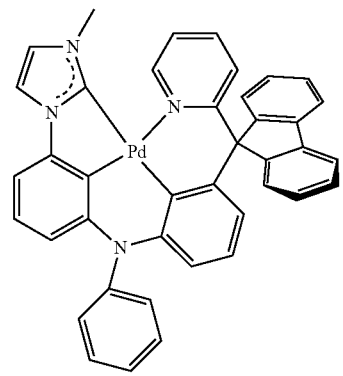
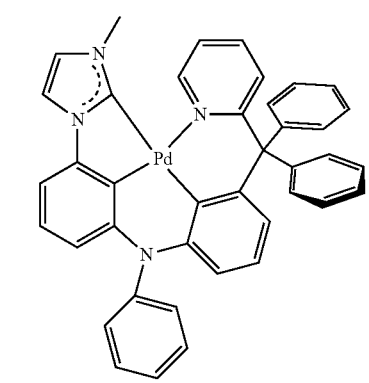
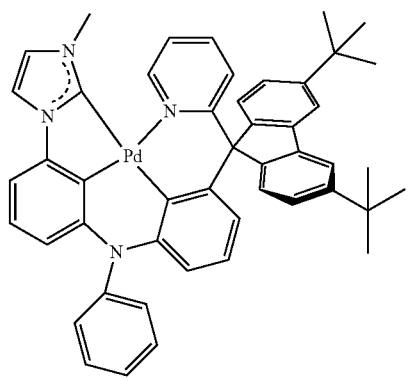
266
-continued
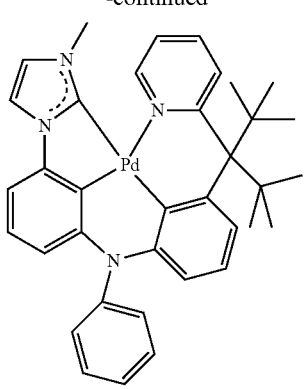
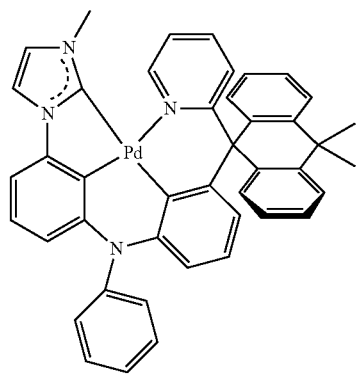
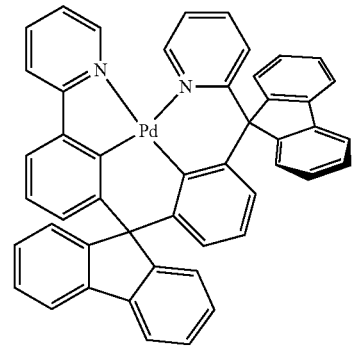
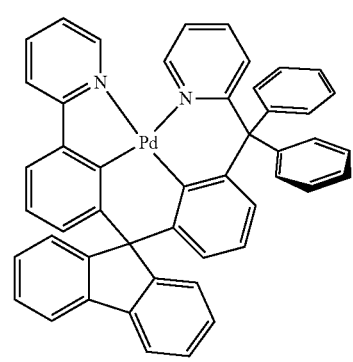

267
-continued
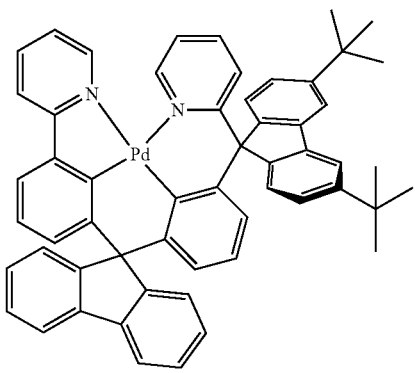
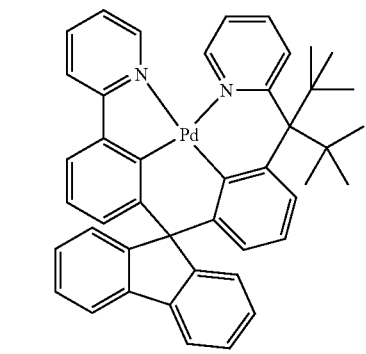
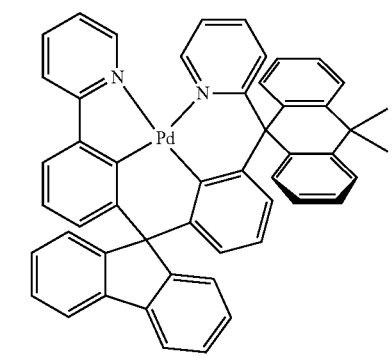
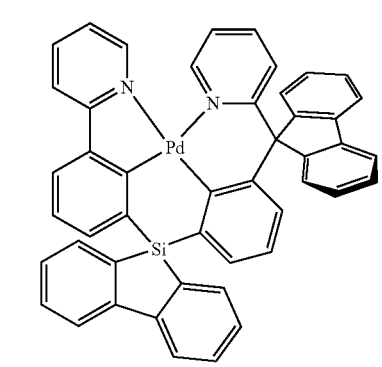
268
-continued
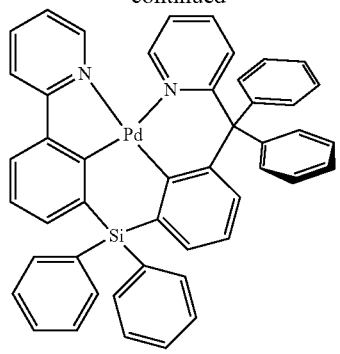
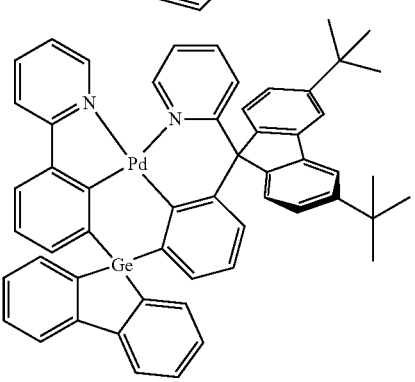
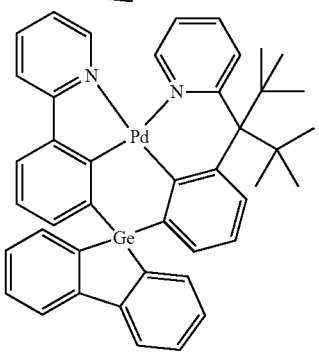
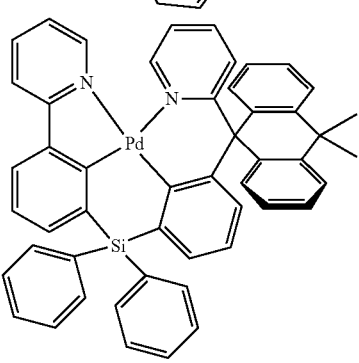
Structure Pd-9
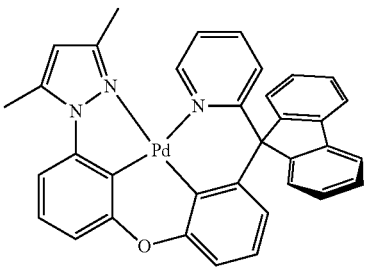

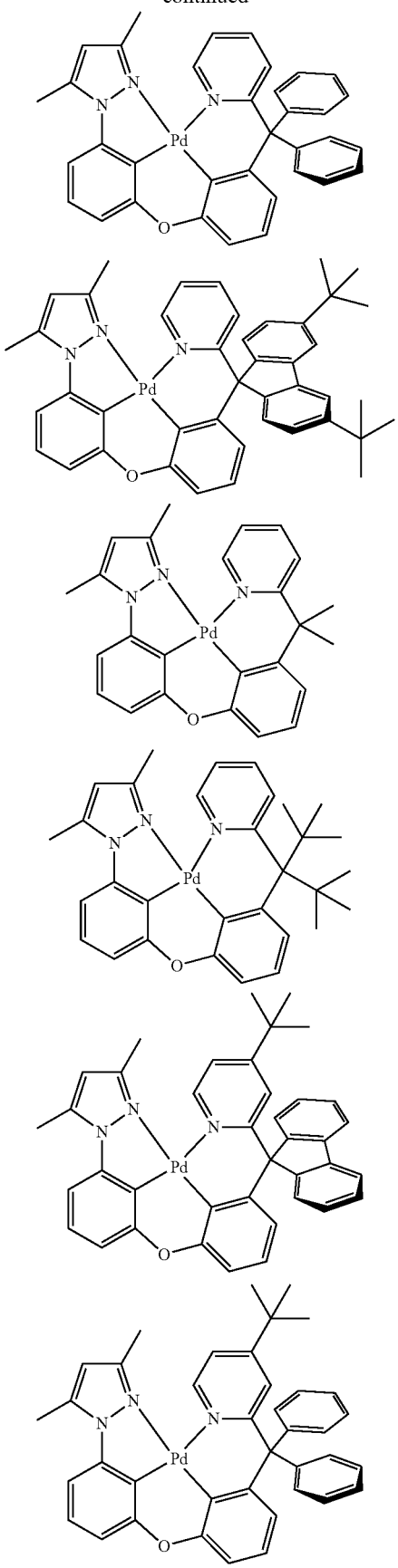
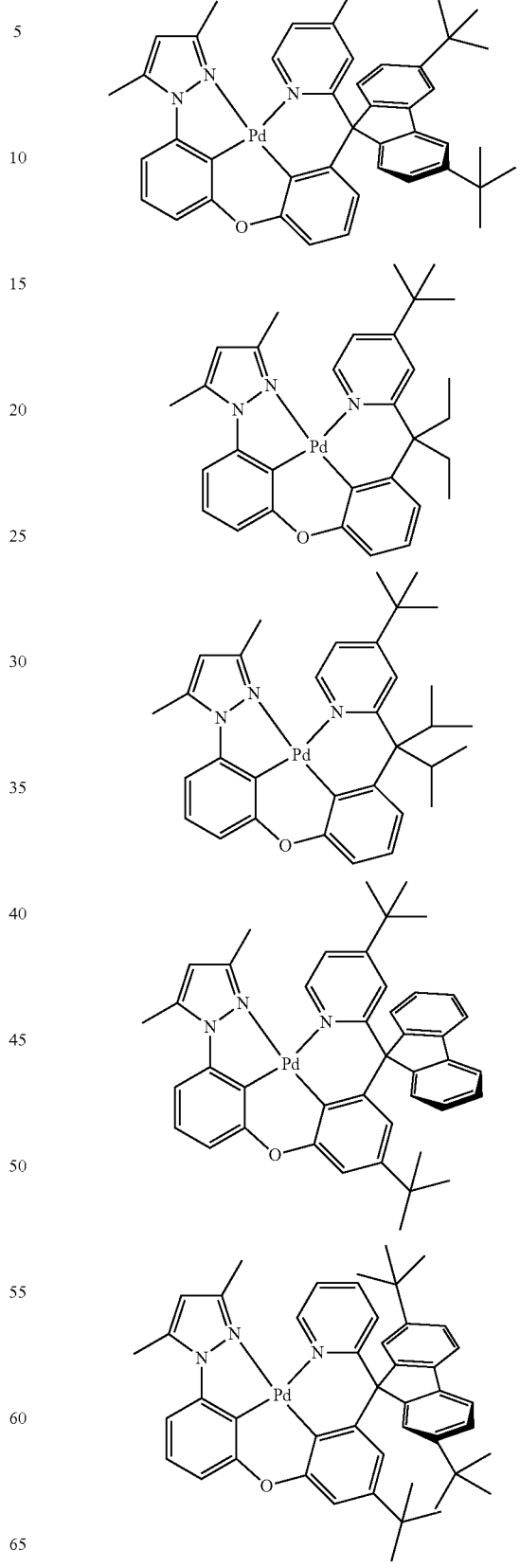

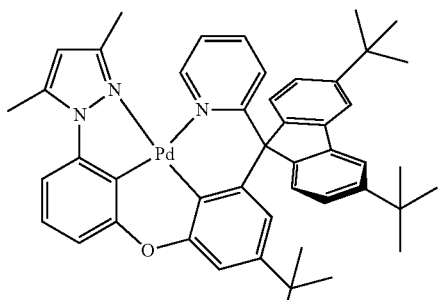
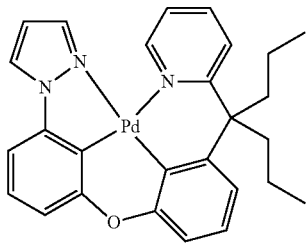
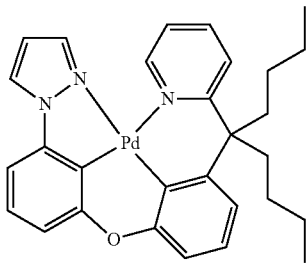
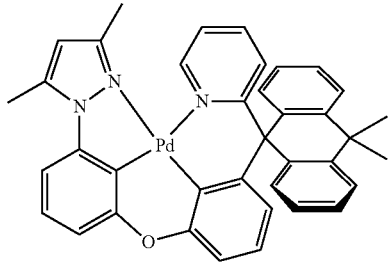
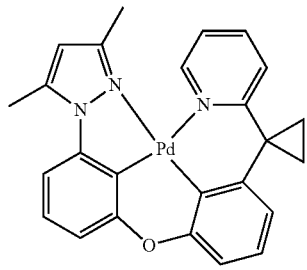
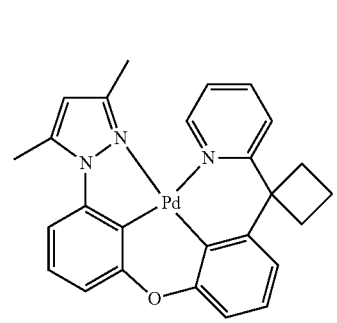
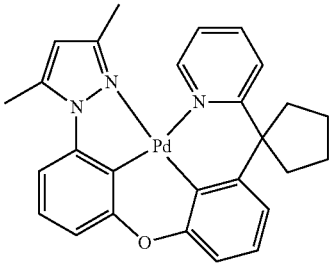
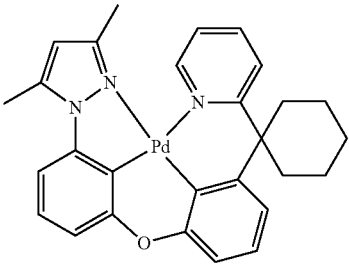
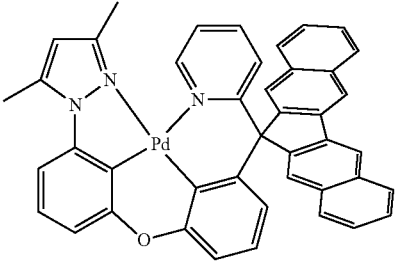
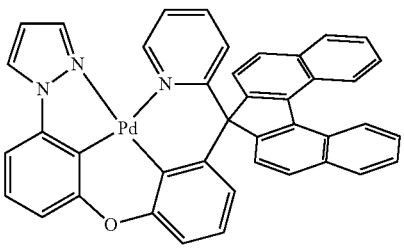
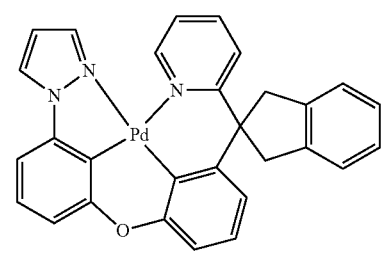
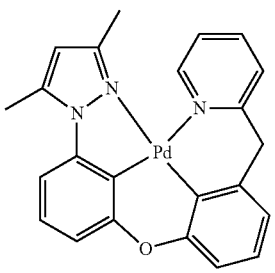

273
-continued
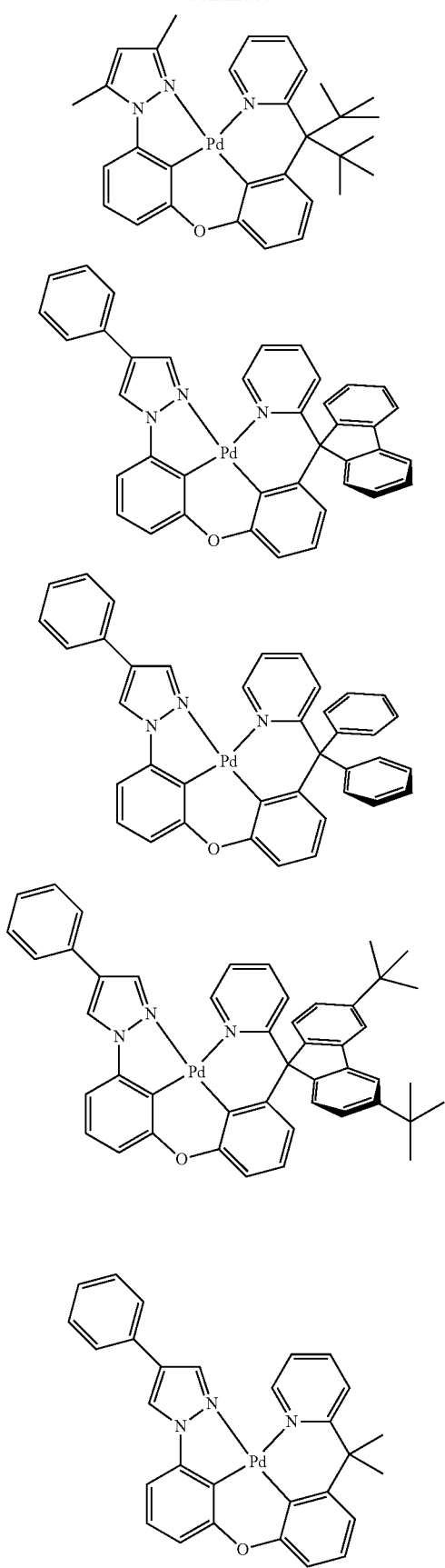
274
-continued
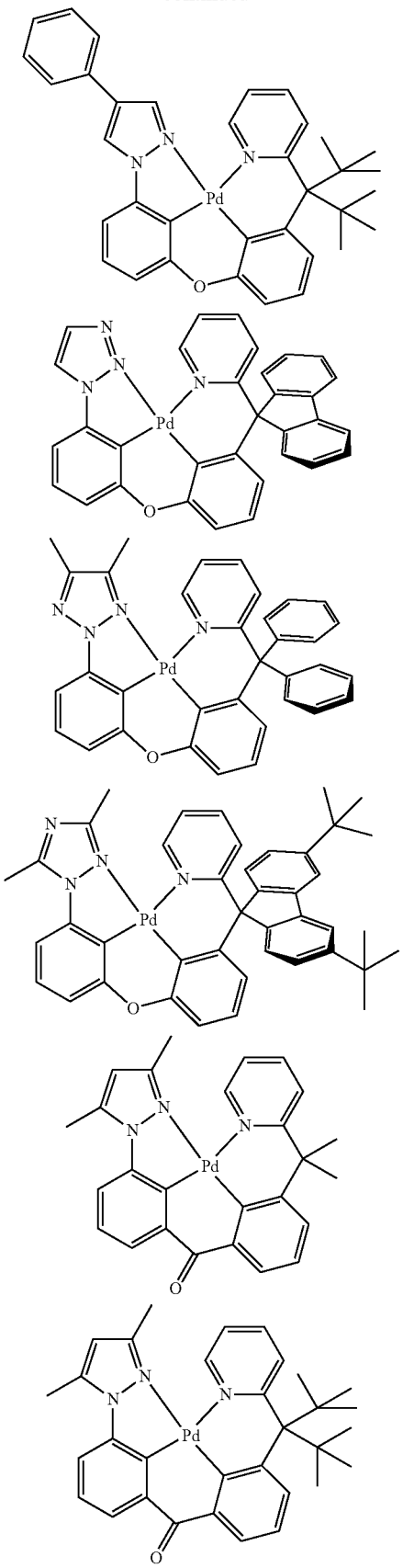

Structure Pd-10
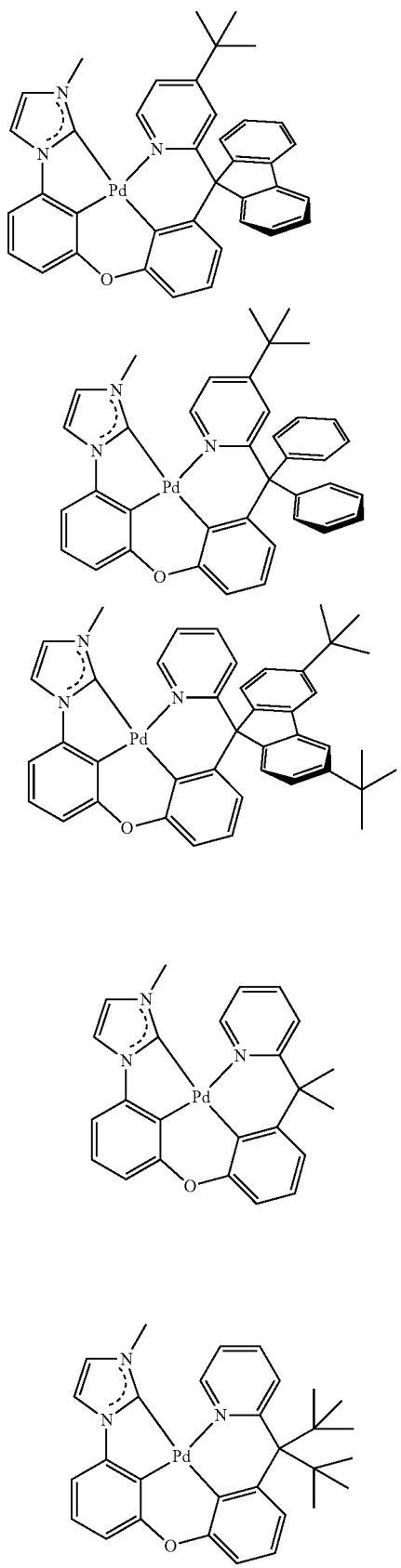
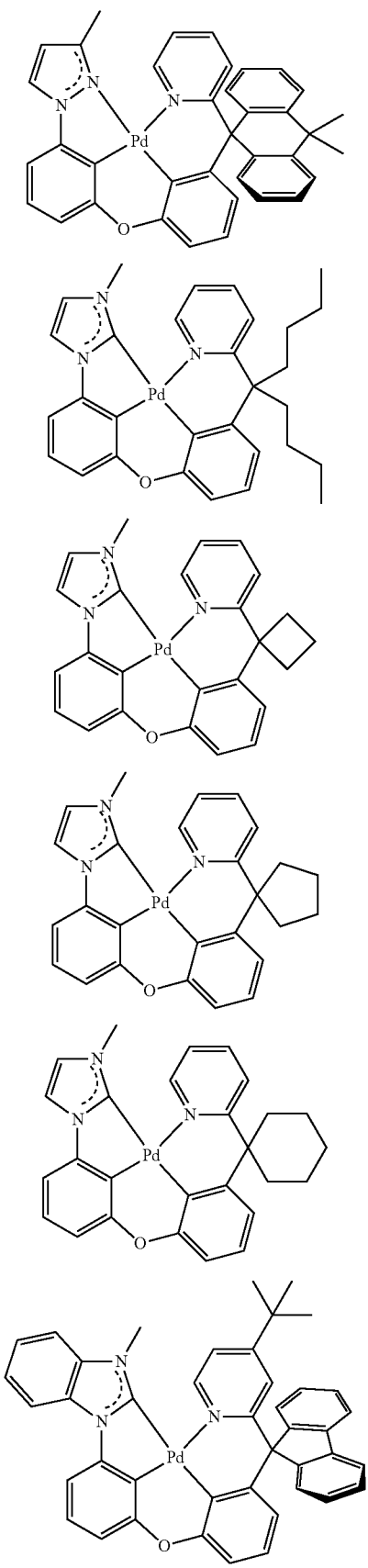

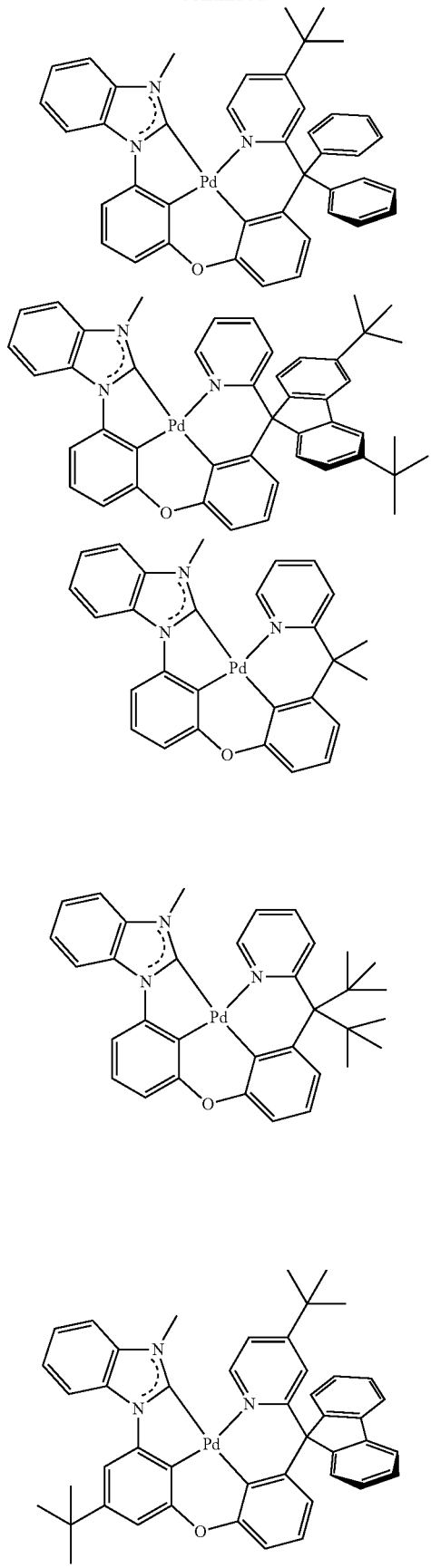
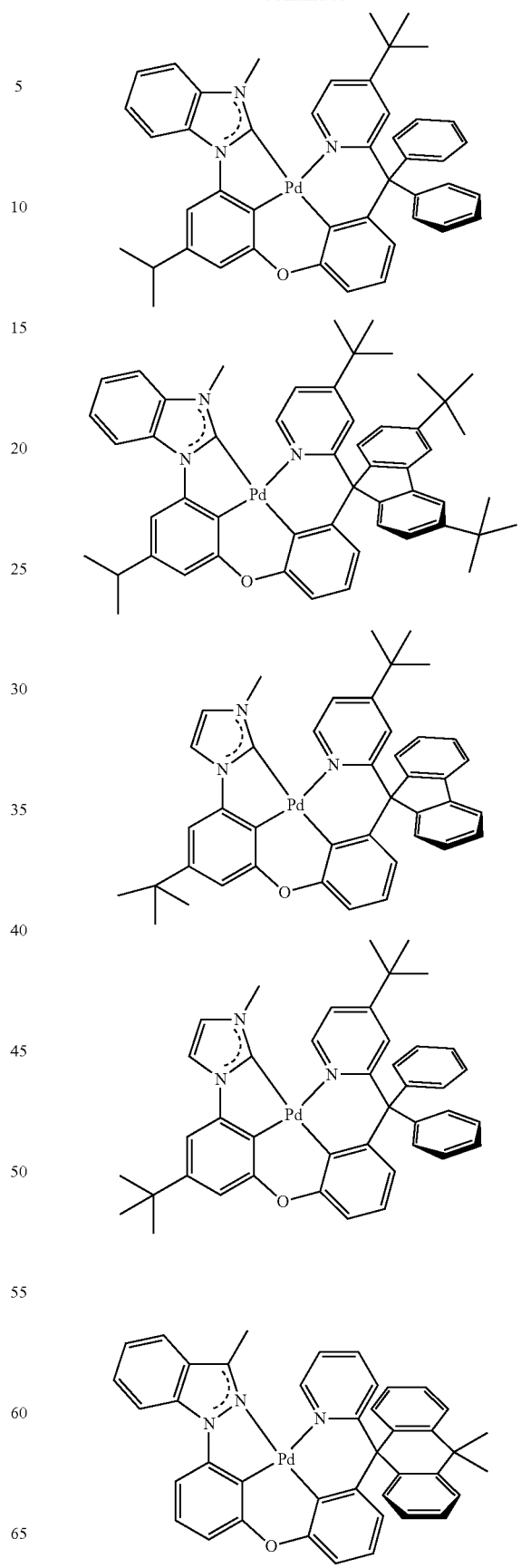

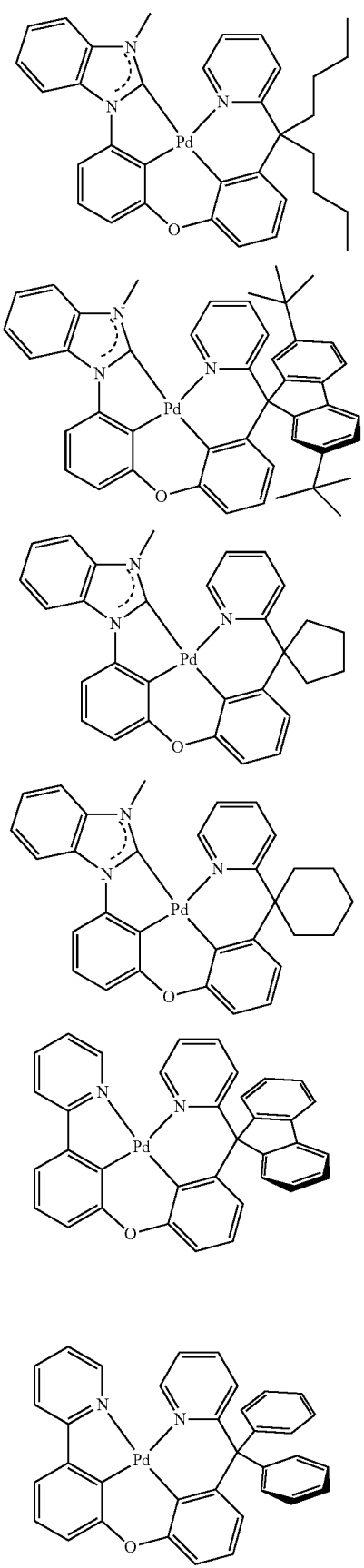
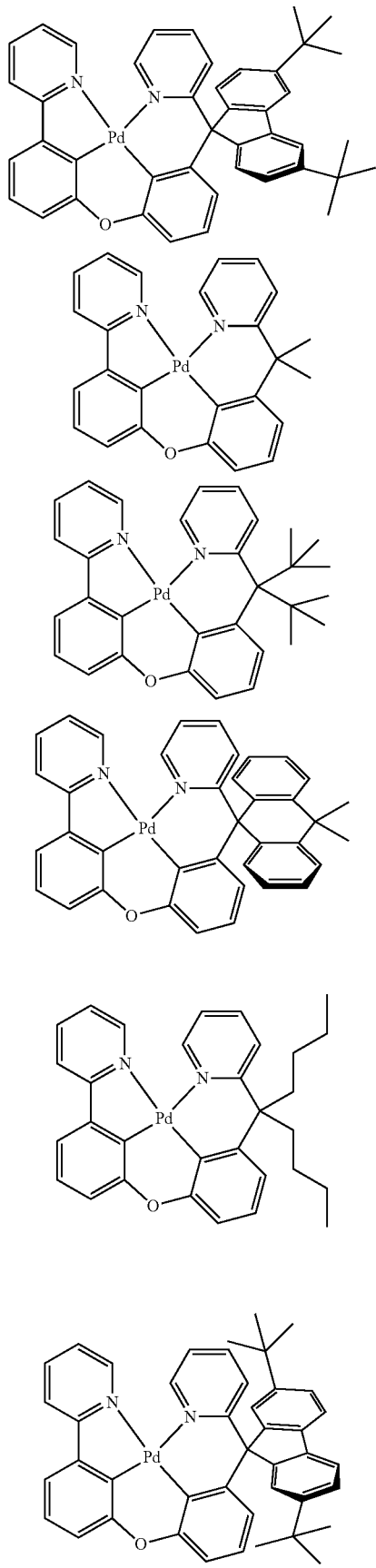

281
-continued
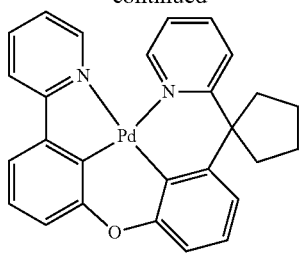
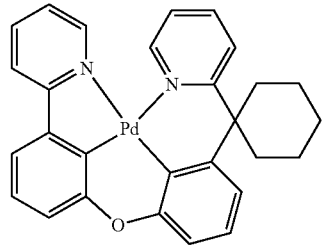
Structure Pd-11
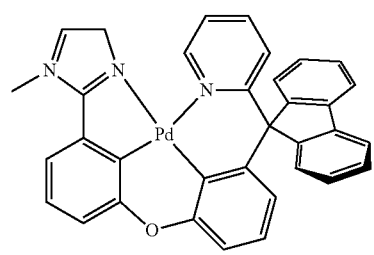
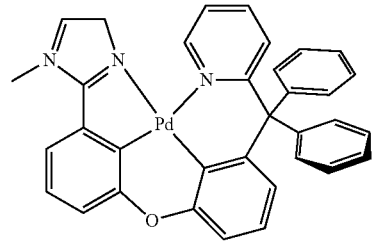
282
-continued
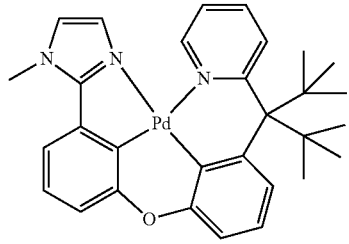
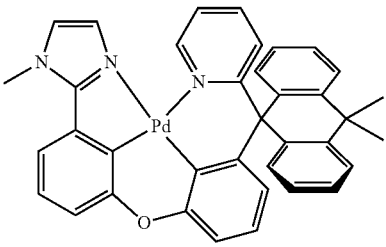
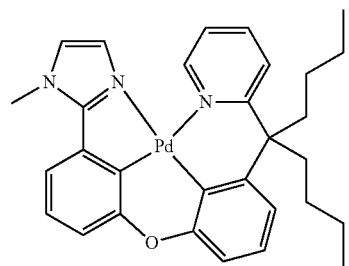
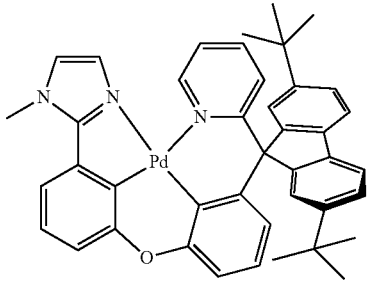
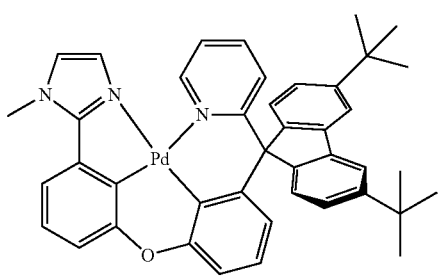
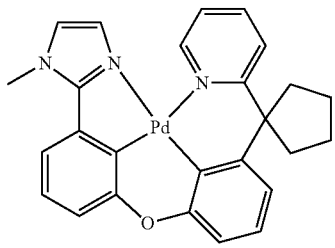
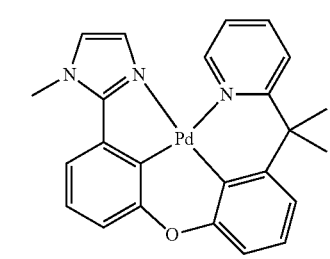
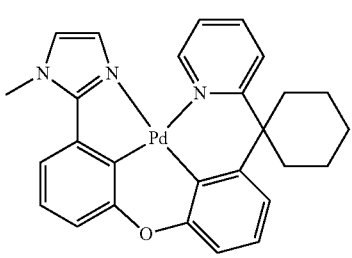

283
-continued
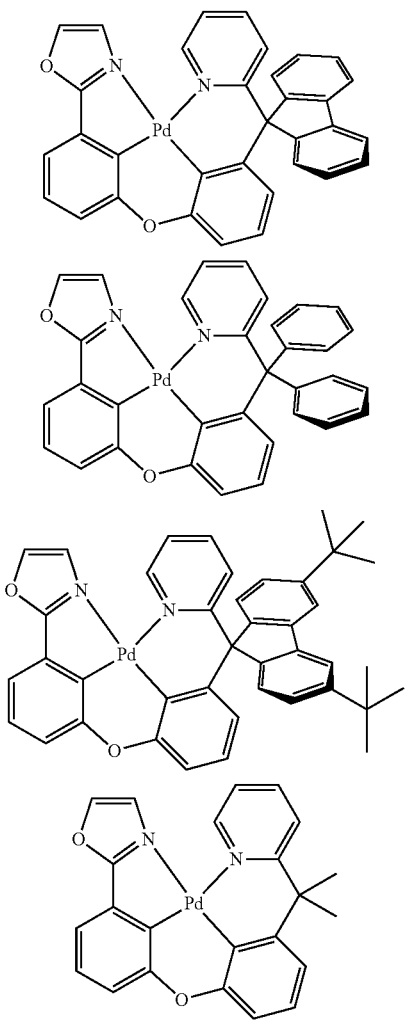
284
-continued
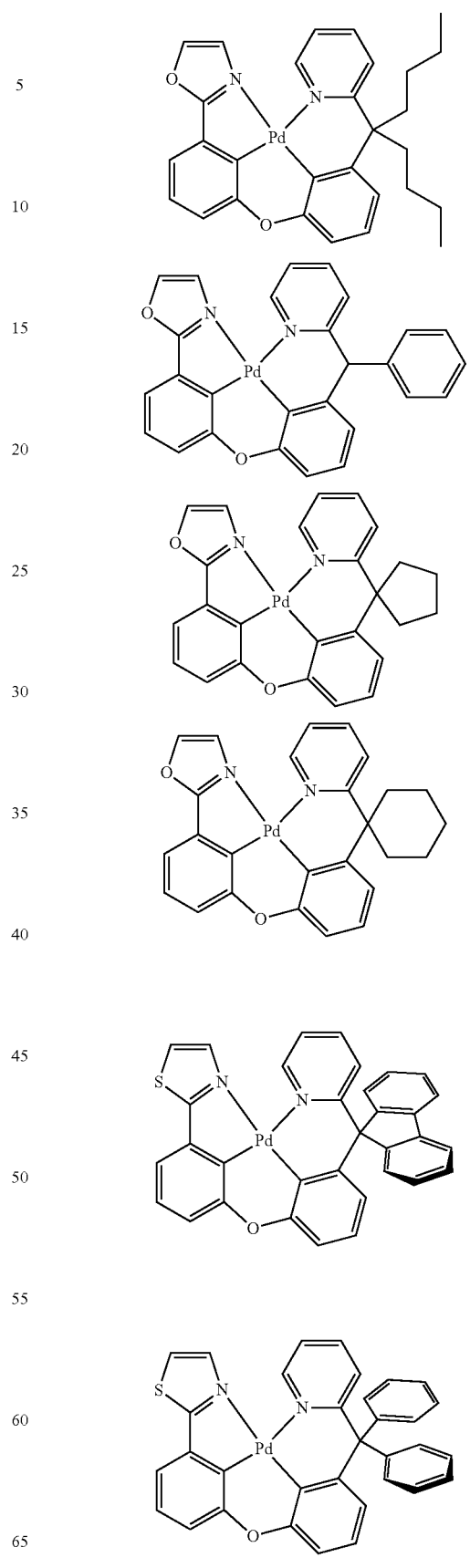

285
-continued
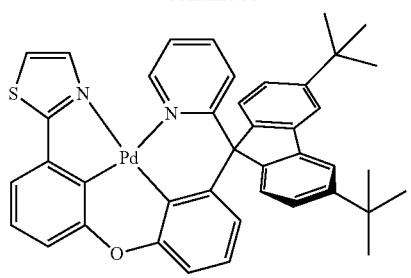
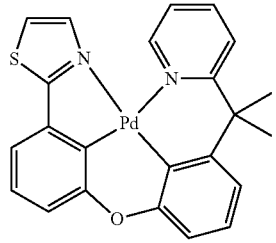
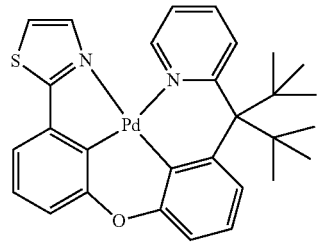
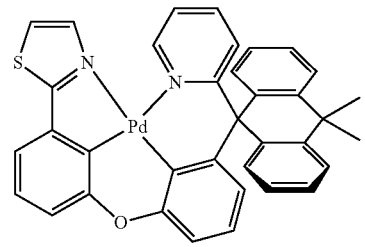
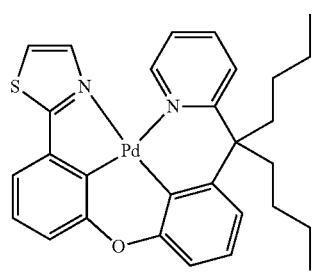
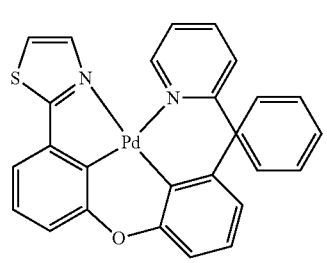
286
-continued
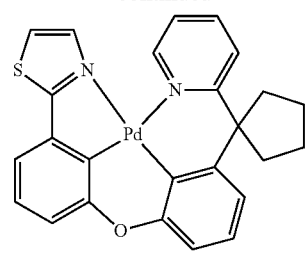
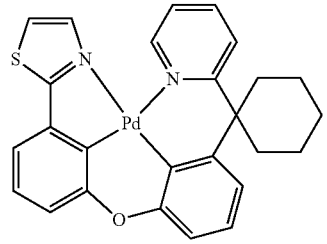
Structure Pd-12
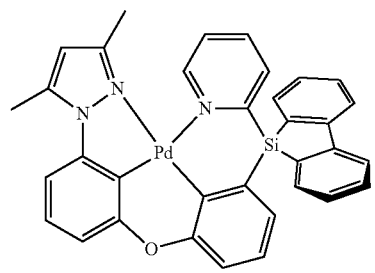
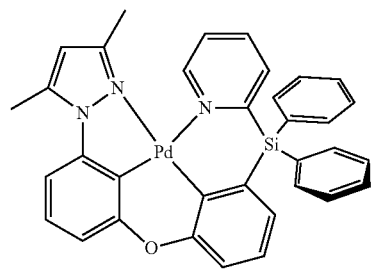
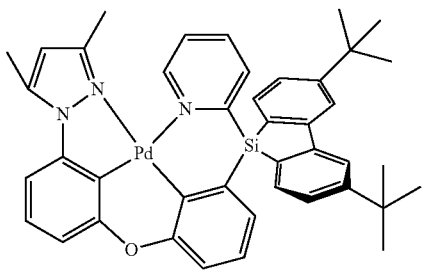
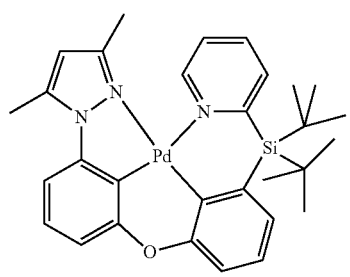

287
-continued
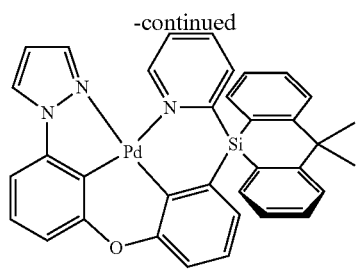
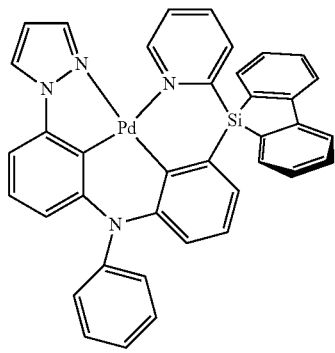
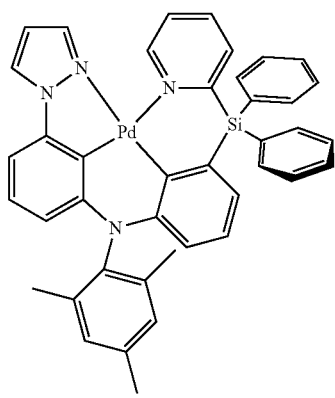
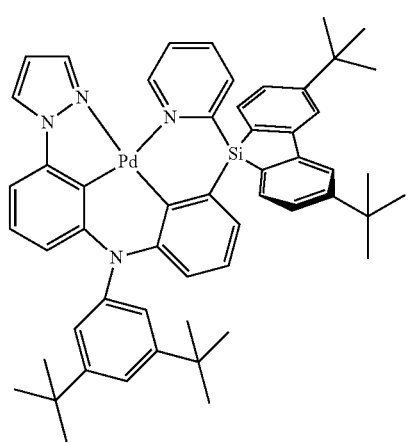
288
-continued
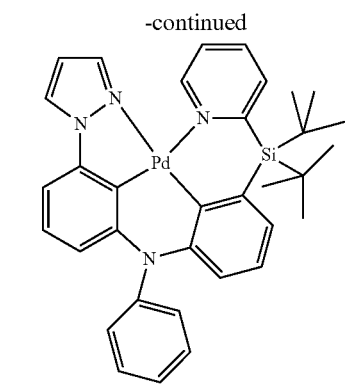
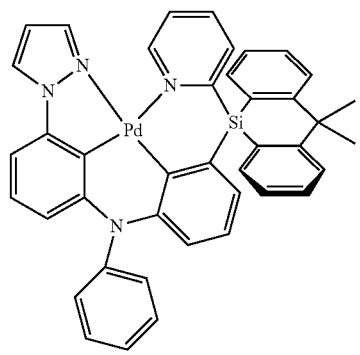
1p;2p
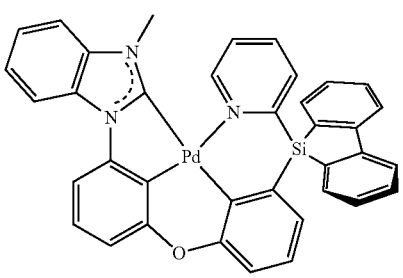
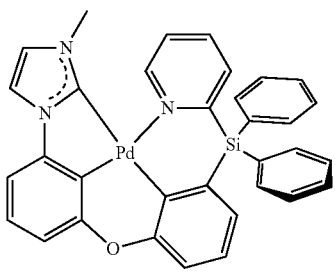
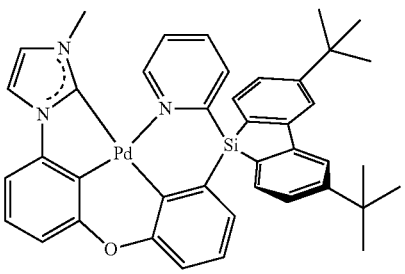

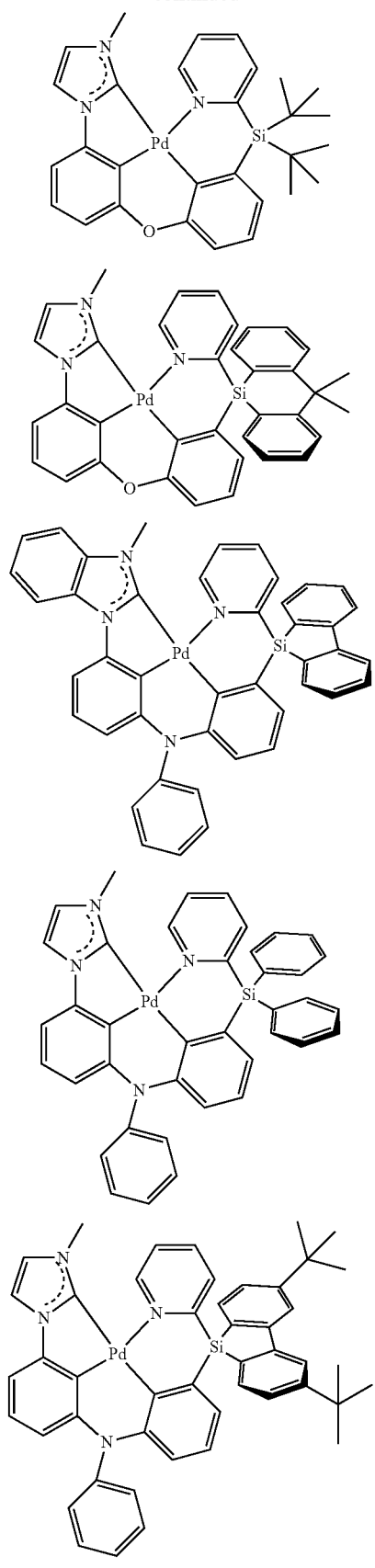
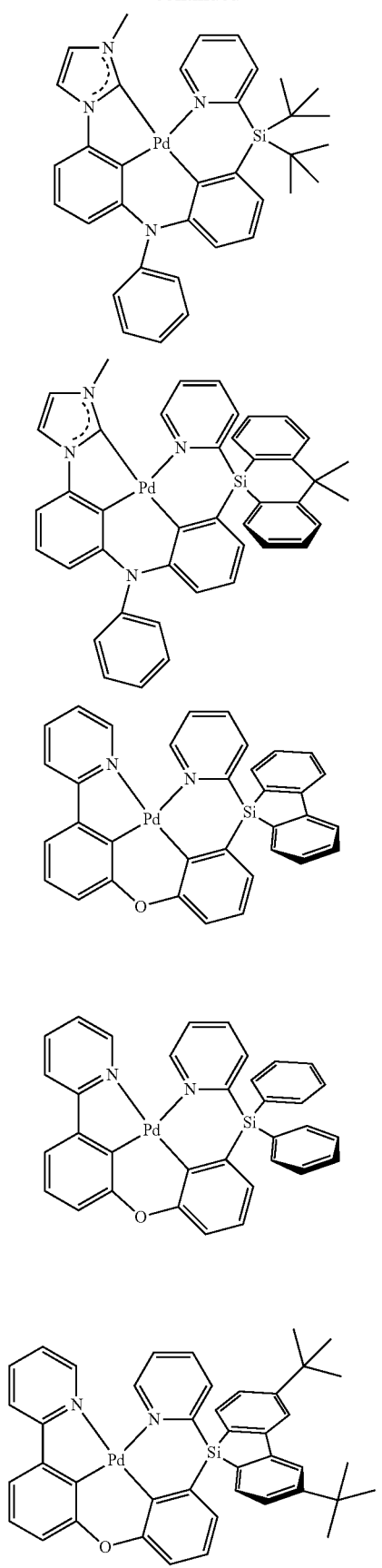

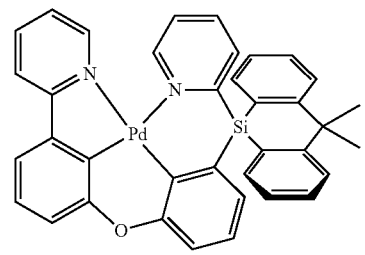
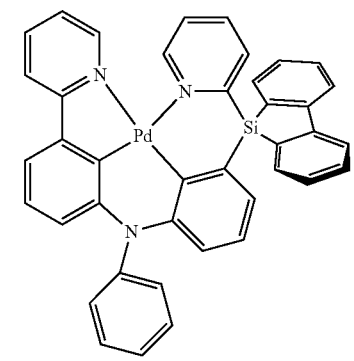
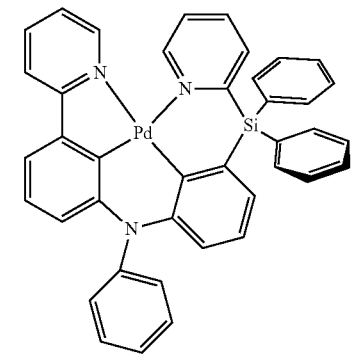
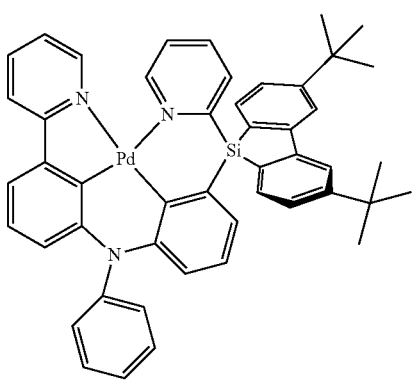
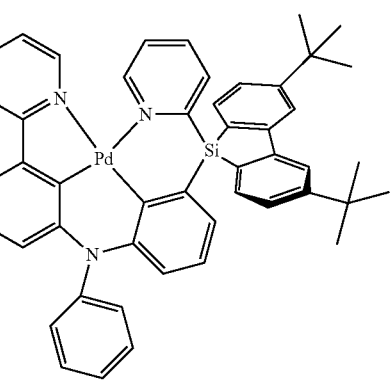
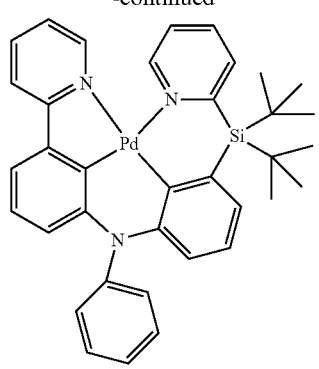
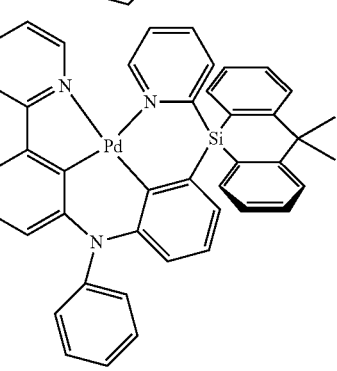
Structure Pd-13
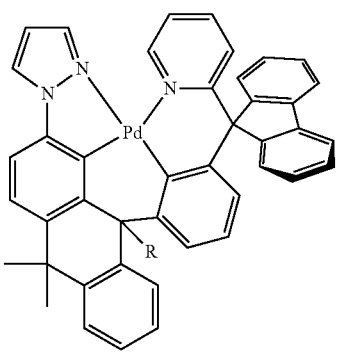
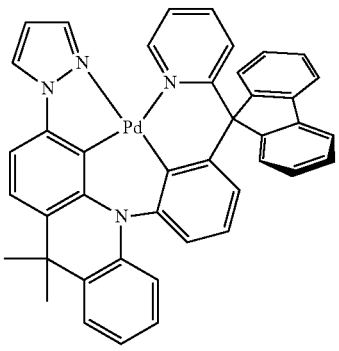

293
-continued
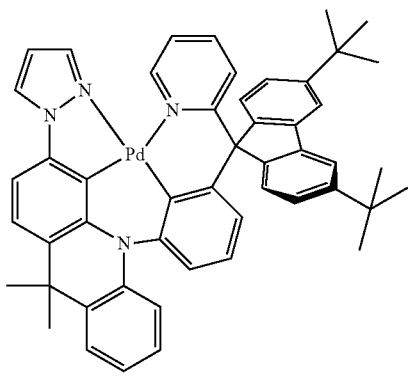
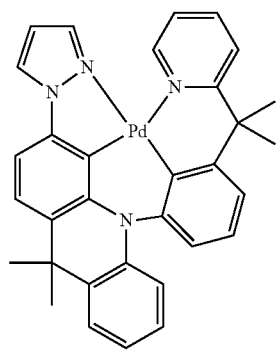
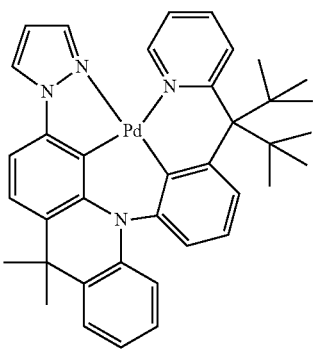
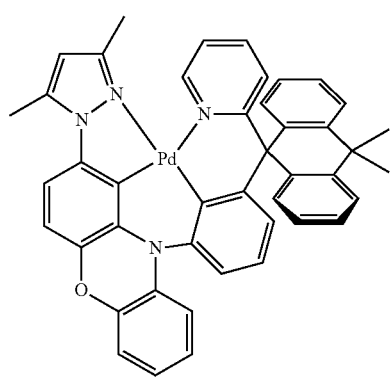
294
-continued
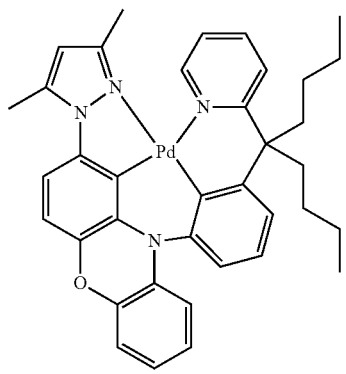
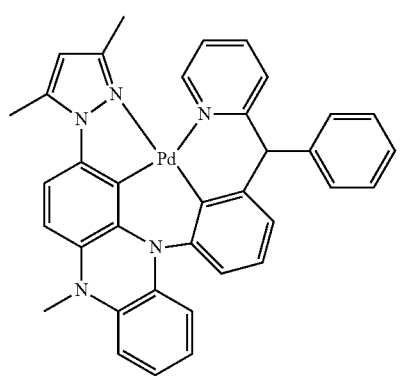
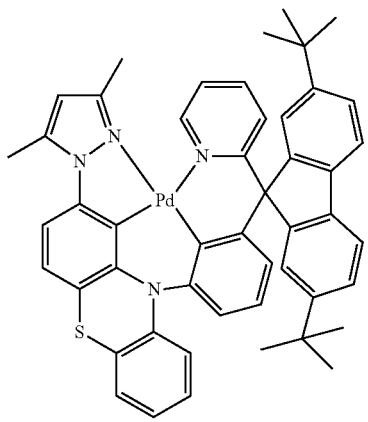
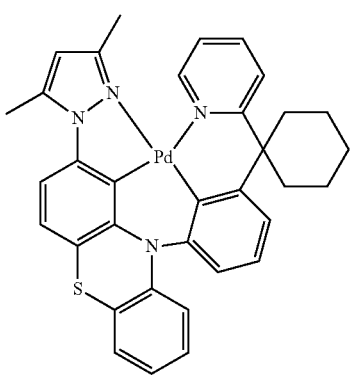

295
-continued
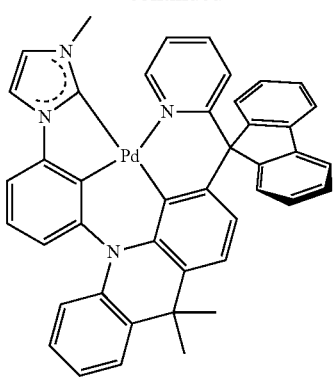
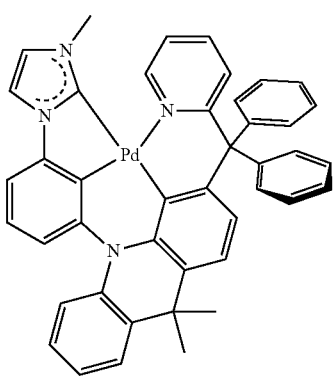
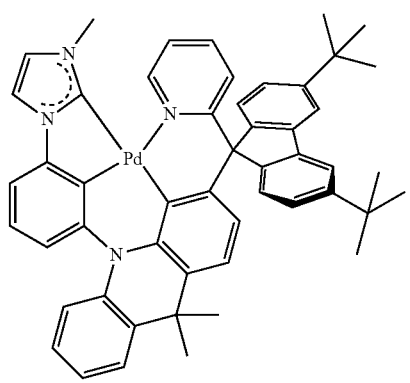
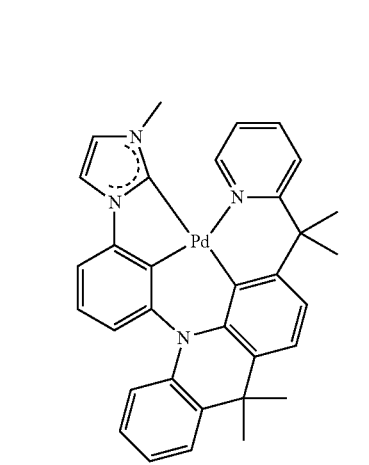
296
-continued
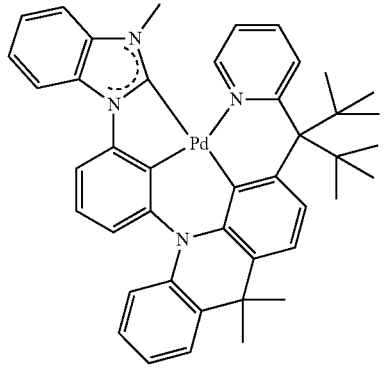
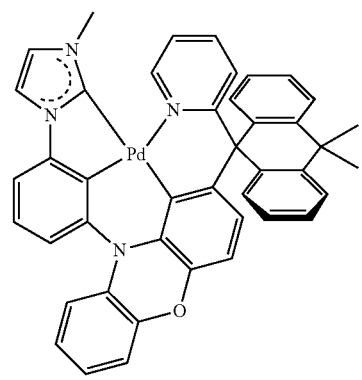
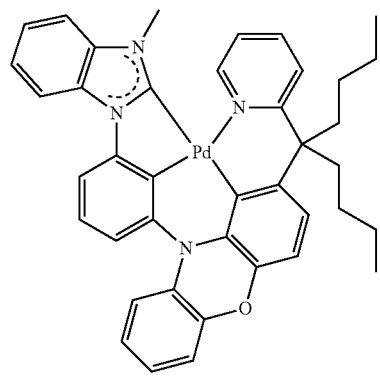
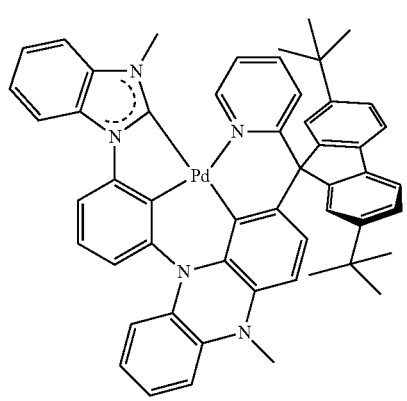

297
-continued
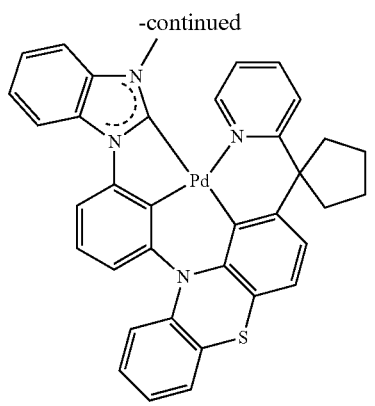
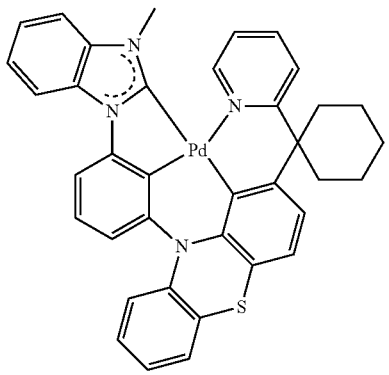
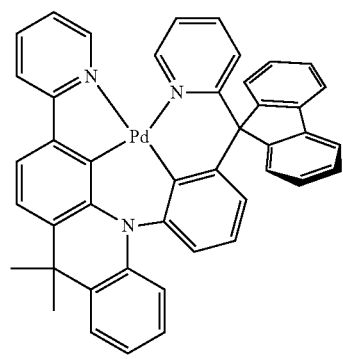
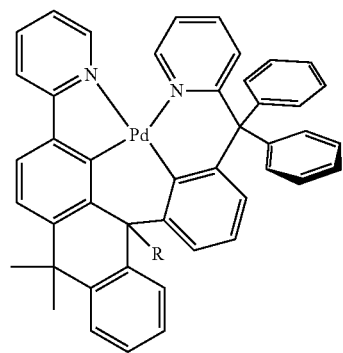
298
-continued
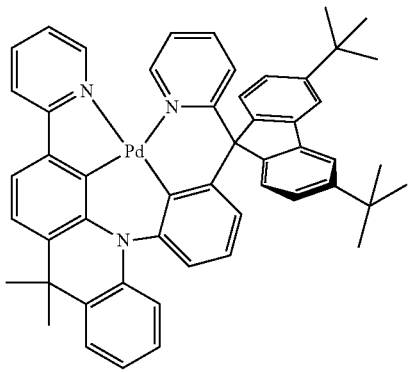
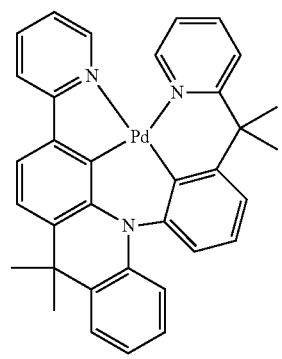
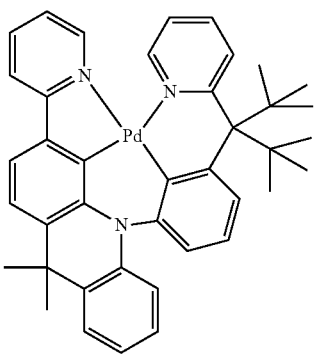
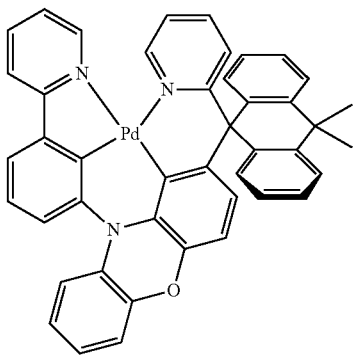

299
-continued
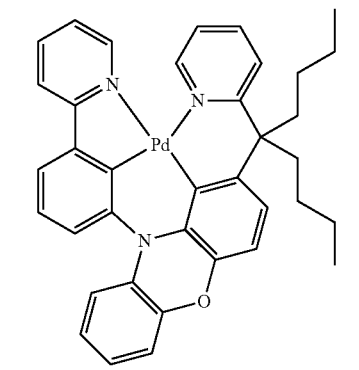
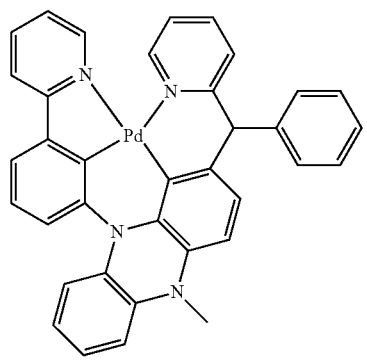
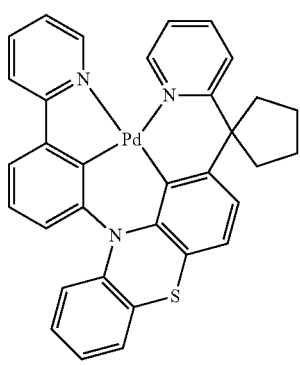
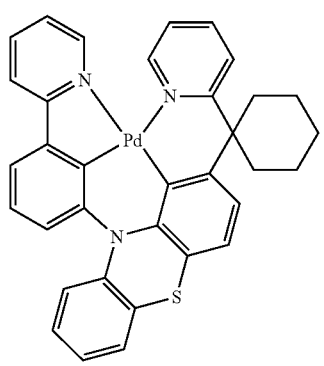
300
-continued
Structure Pd-14
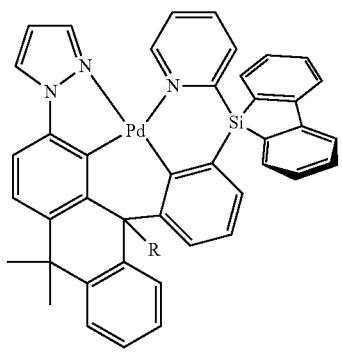
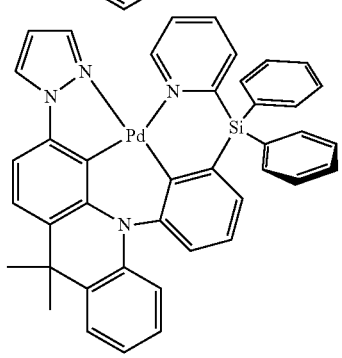
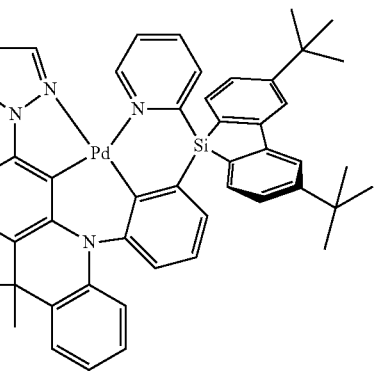
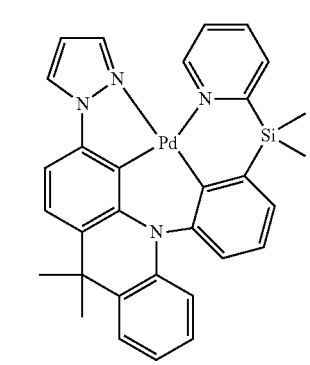

301
-continued
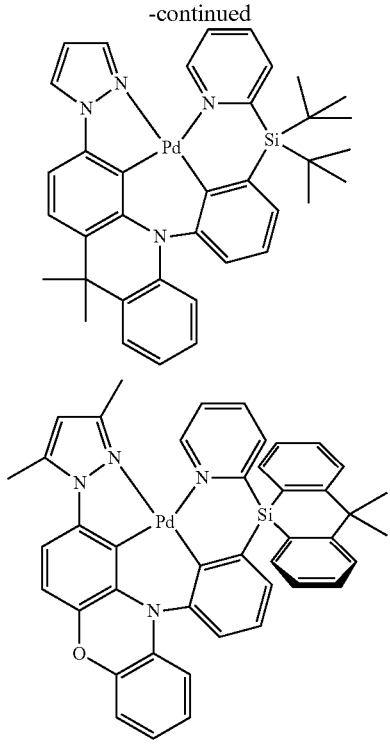
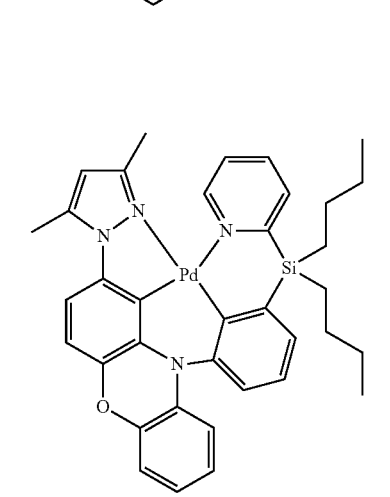
302
-continued
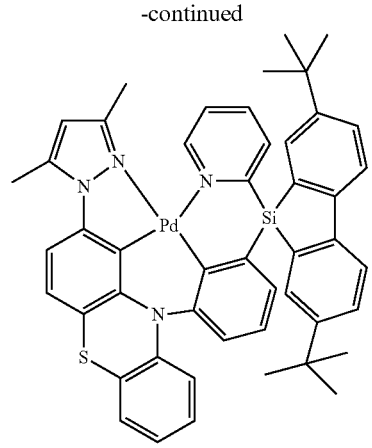
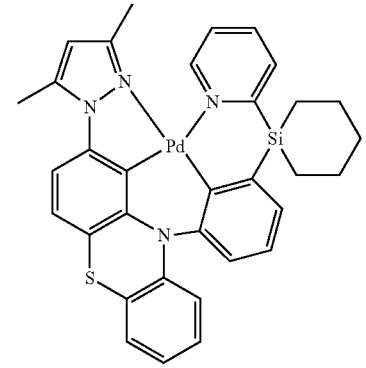
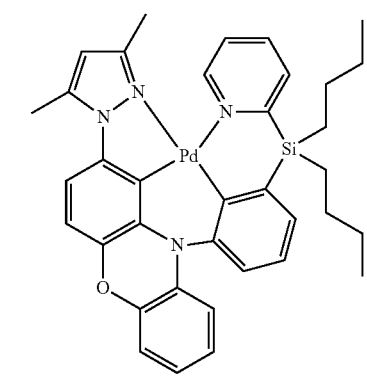
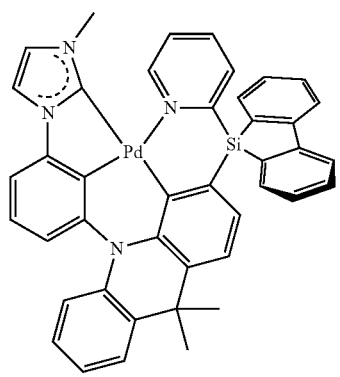
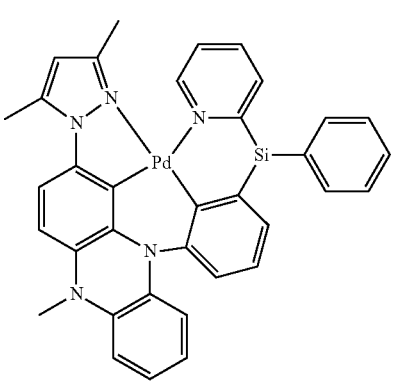
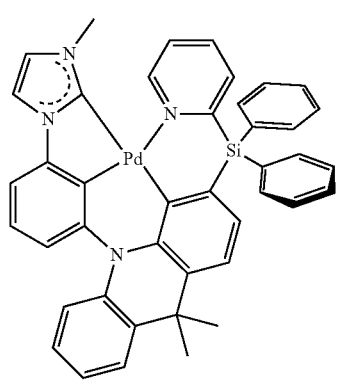

303
-continued
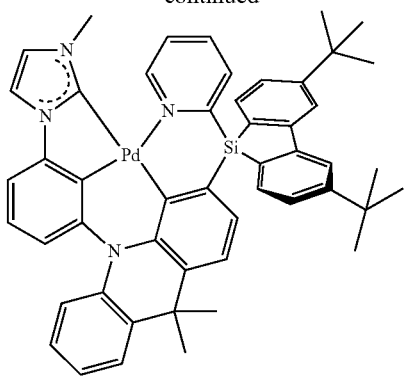
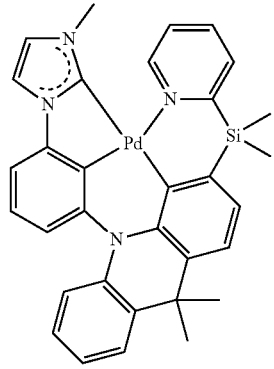
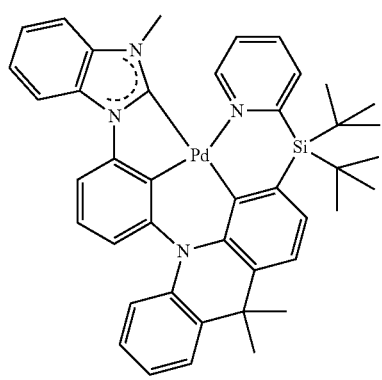
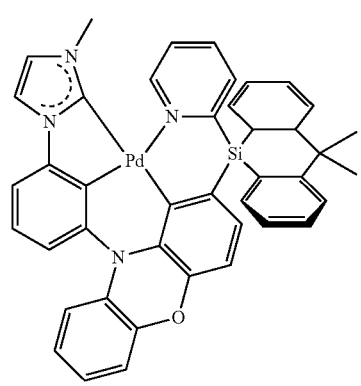
304
-continued
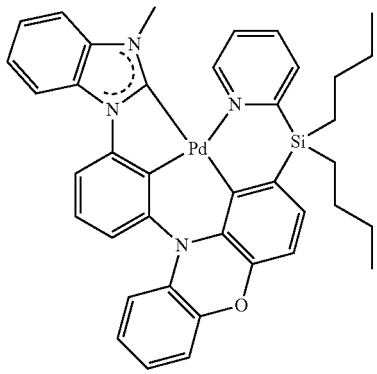
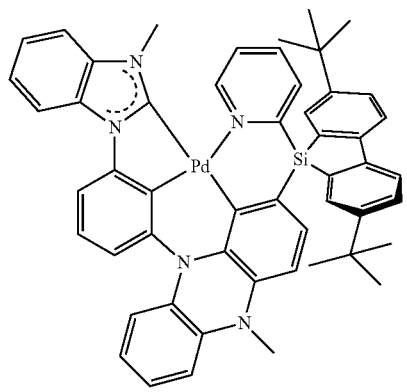
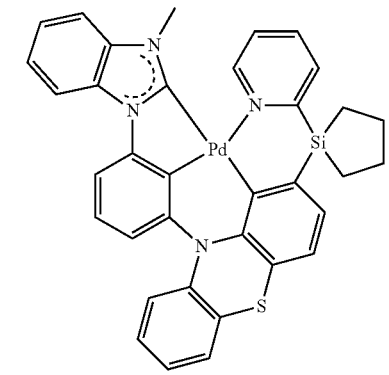
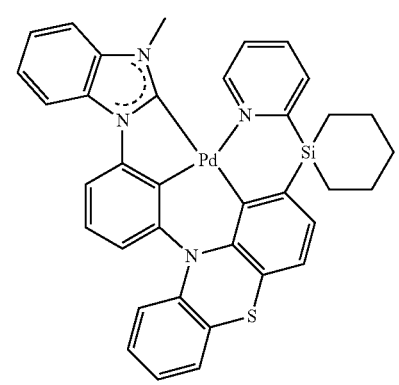

305
-continued

306
-continued

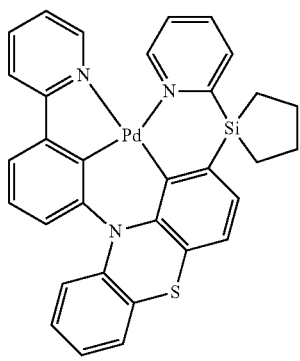
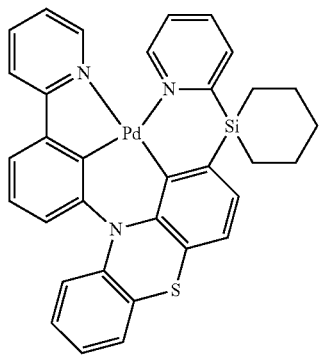
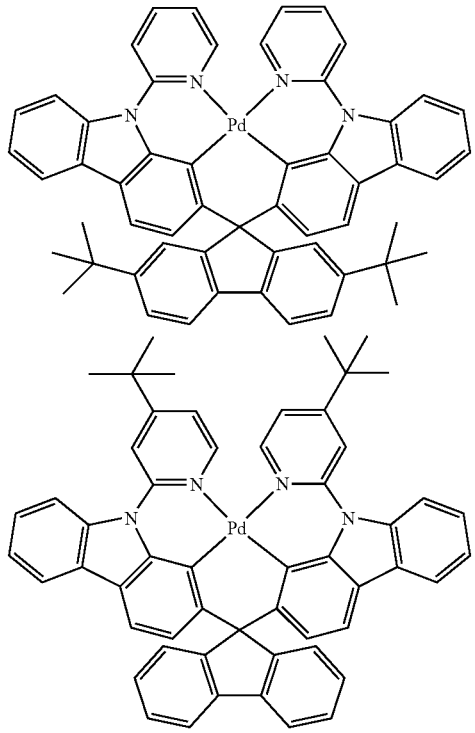
Structure Pd-15
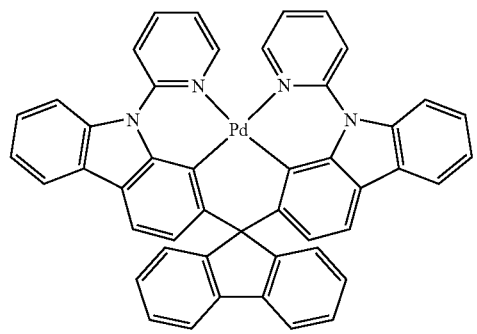
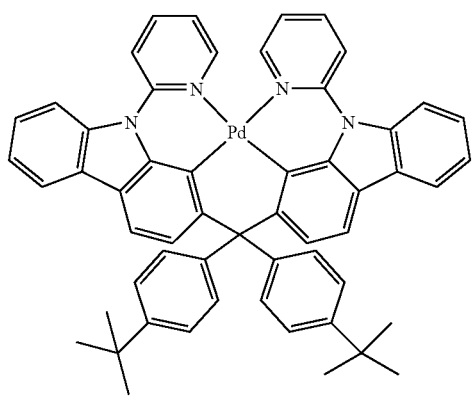
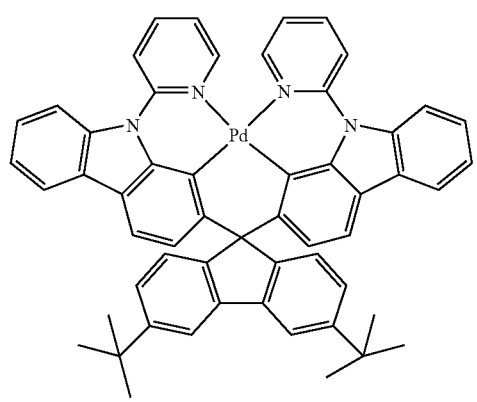
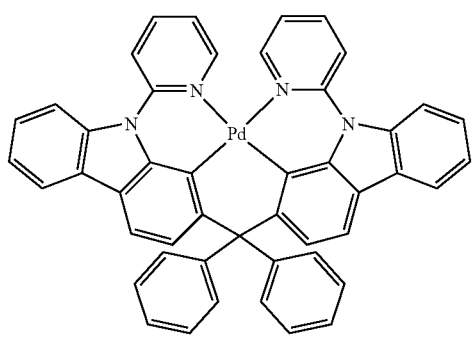

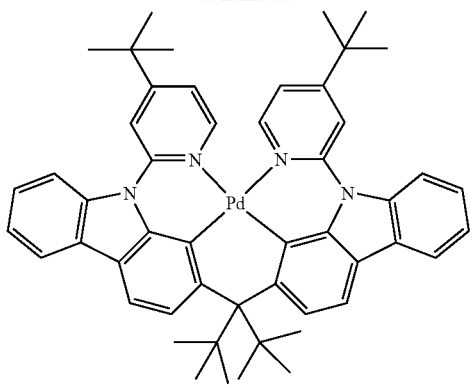
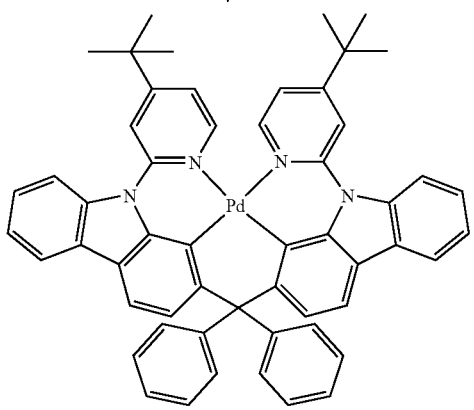
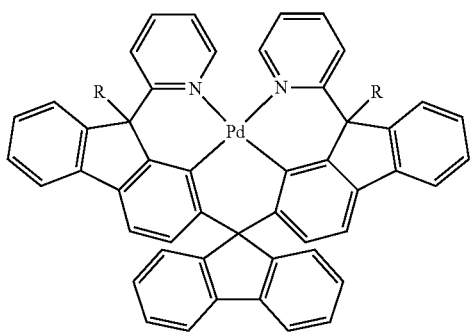
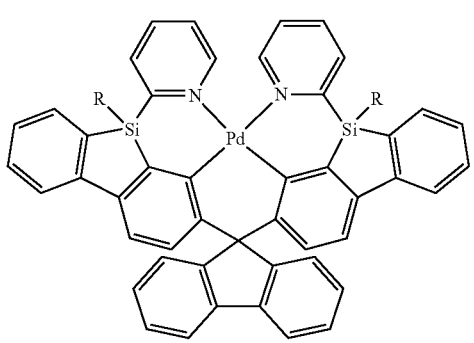
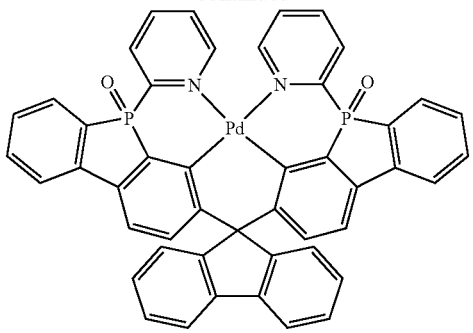
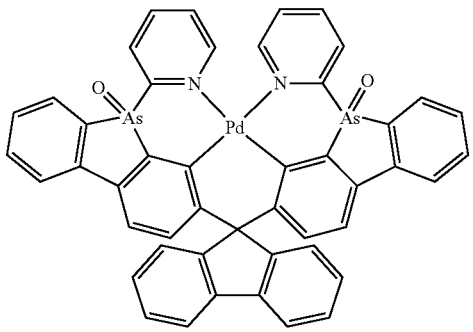
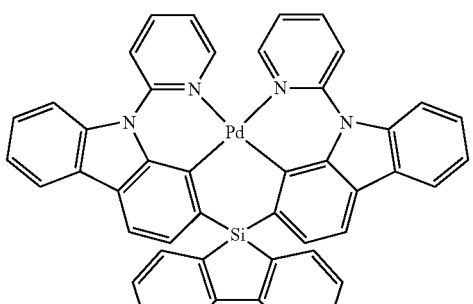
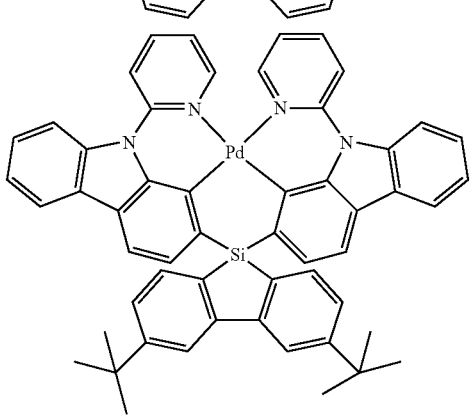
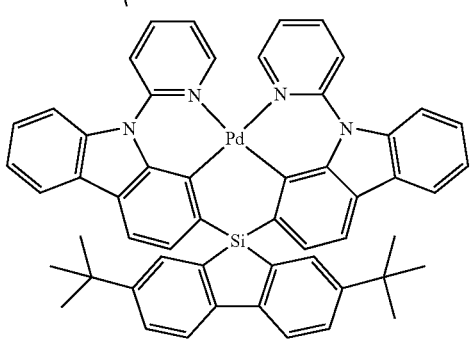

311
-continued
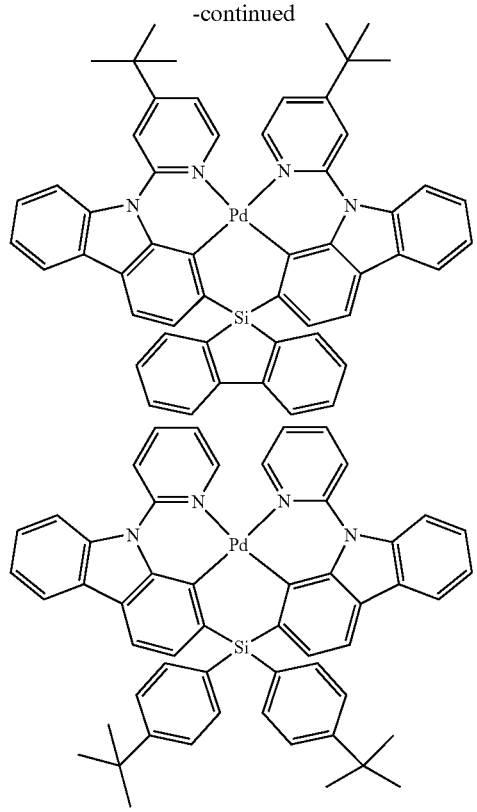
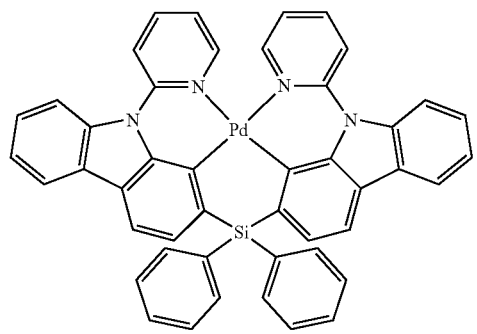
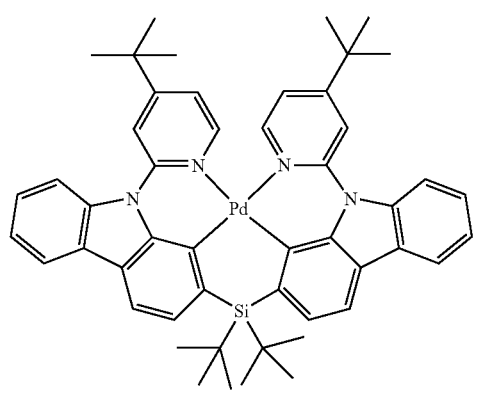
312
-continued
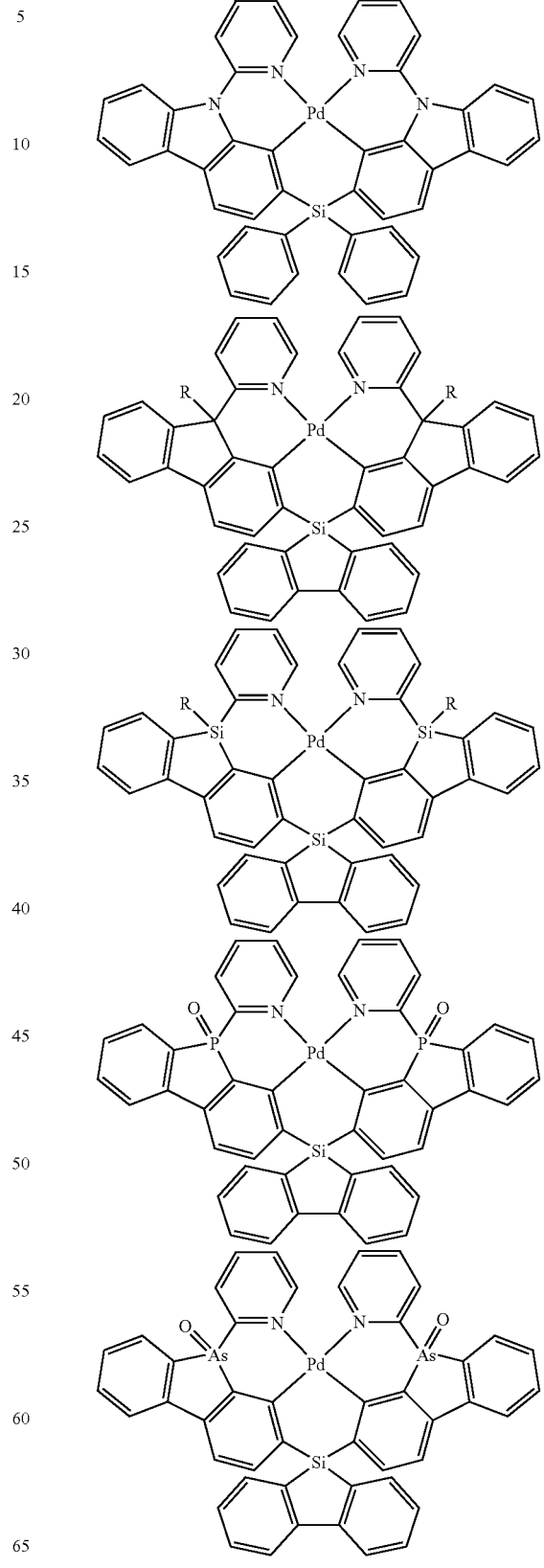

Structure Pd-16
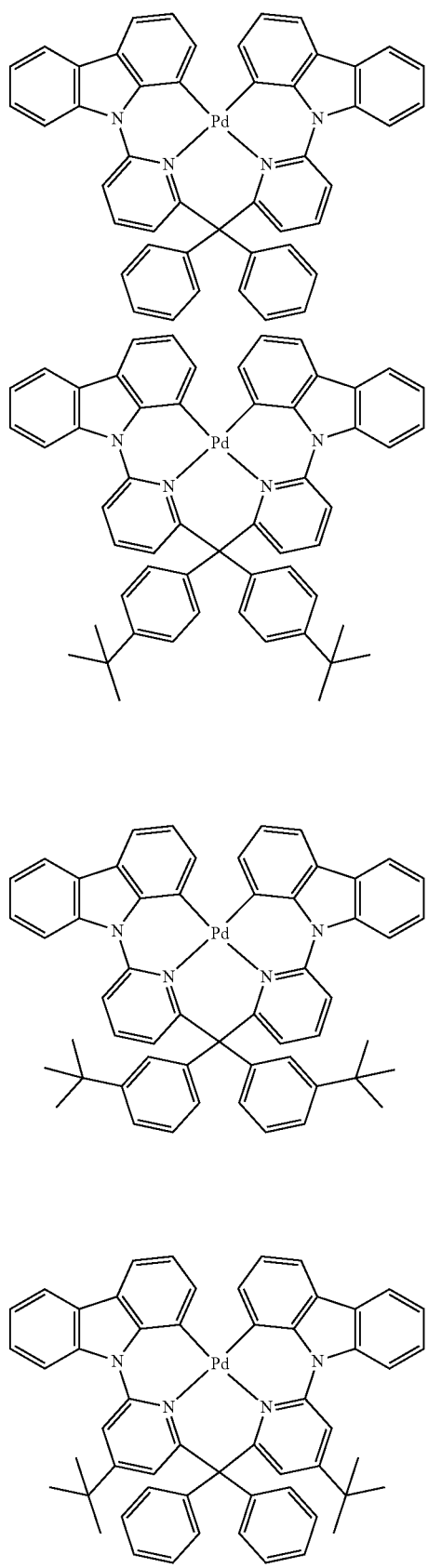
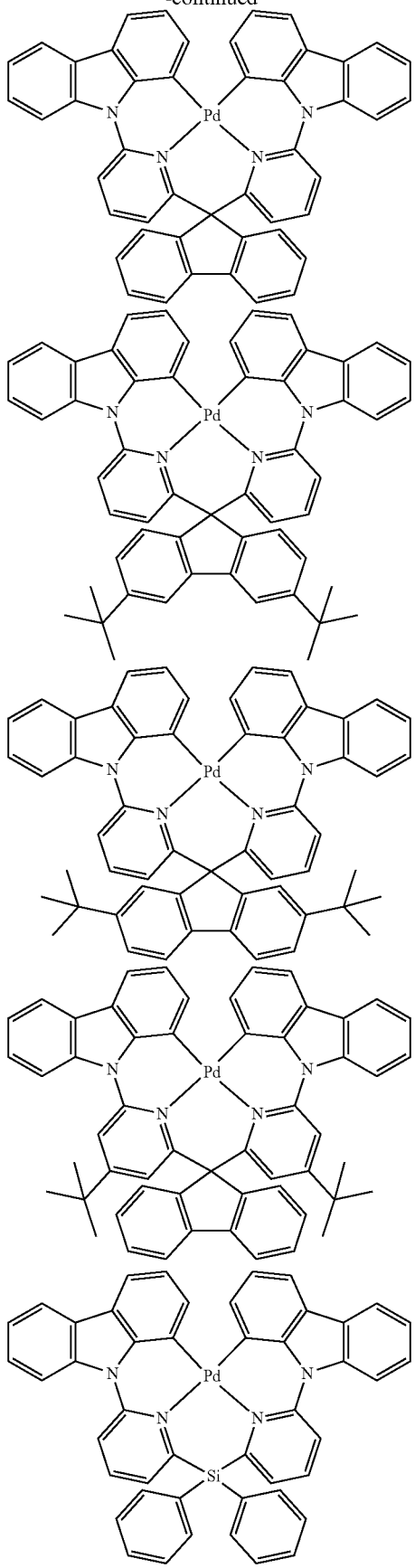

315
-continued
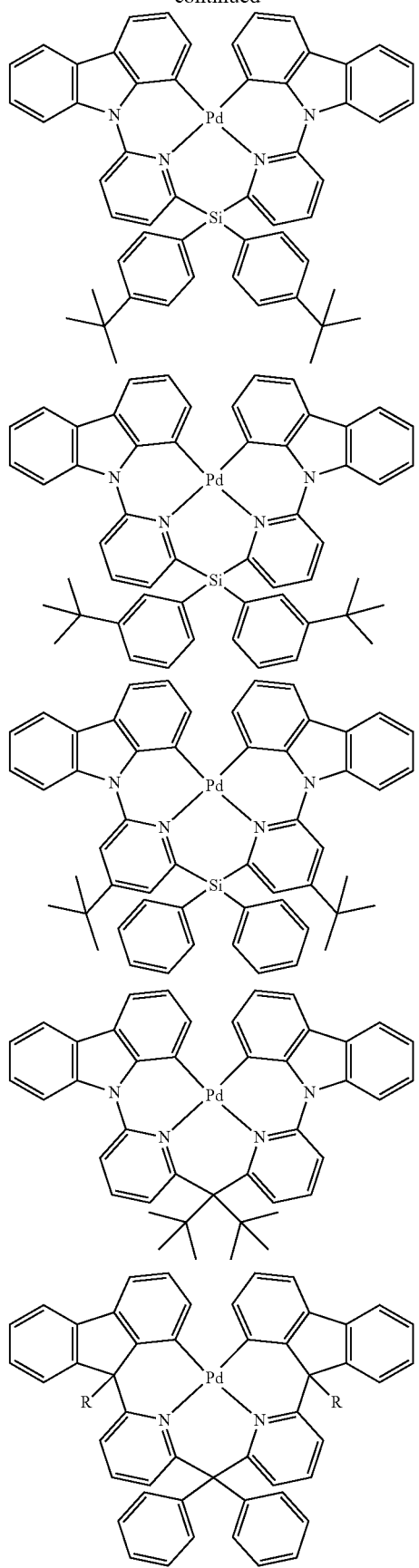
316
-continued
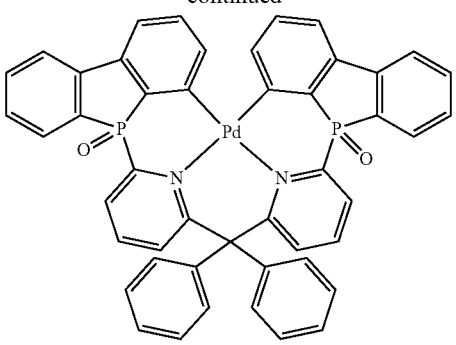
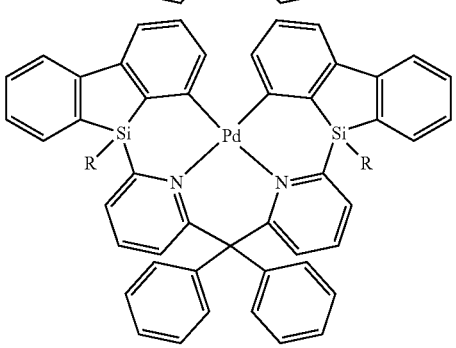
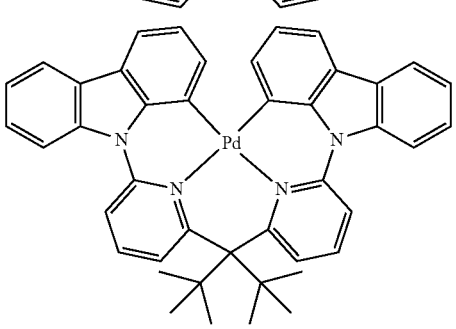
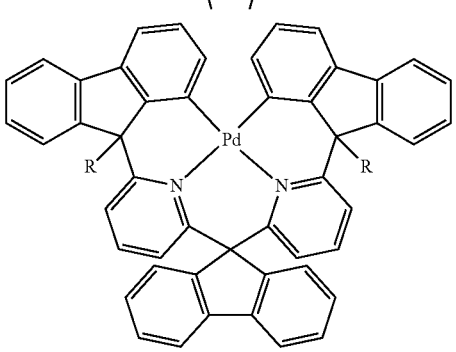
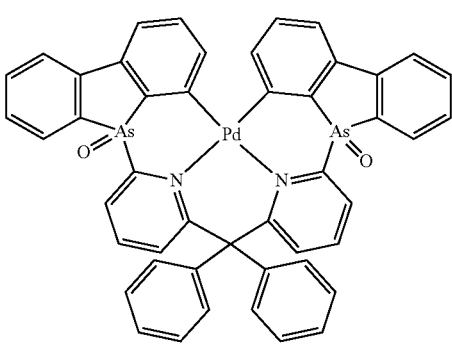

317
-continued
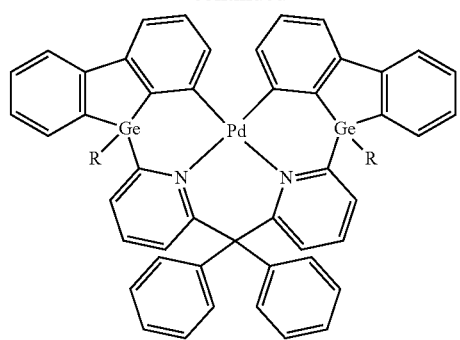
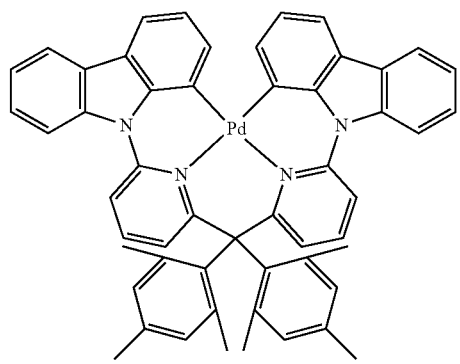
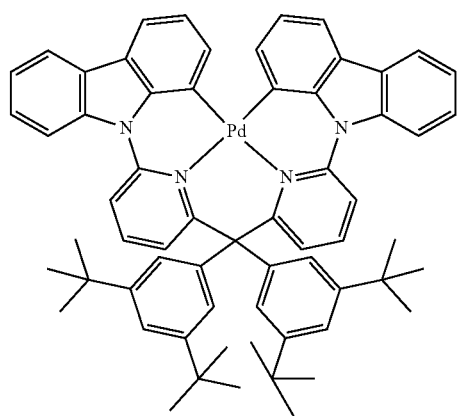
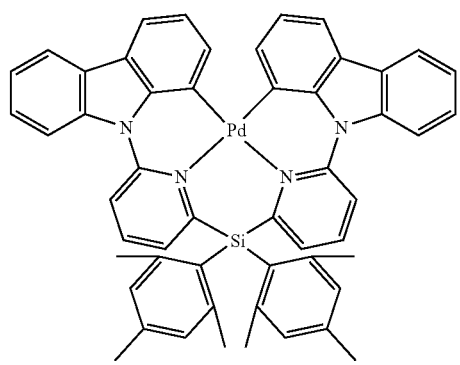
318
-continued
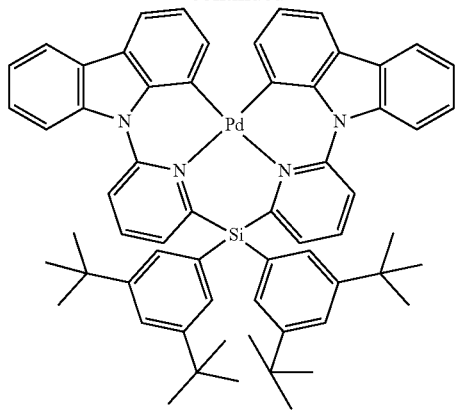
Structure Pd-17
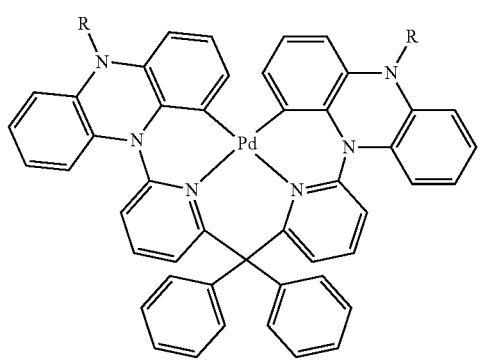
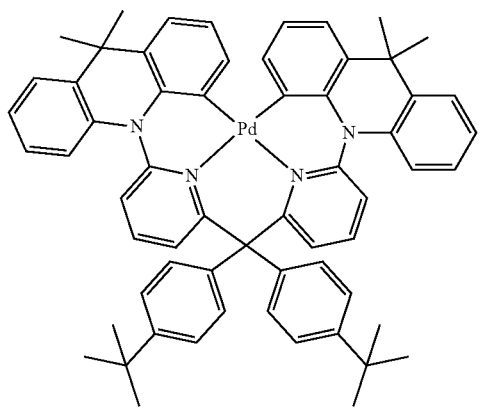
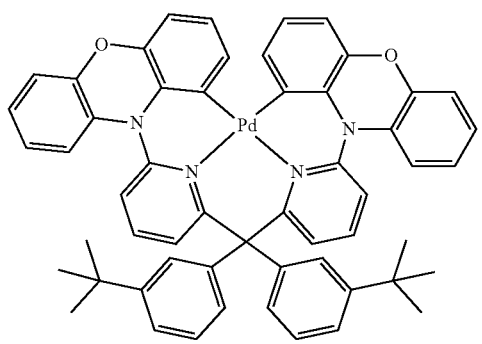

319
-continued
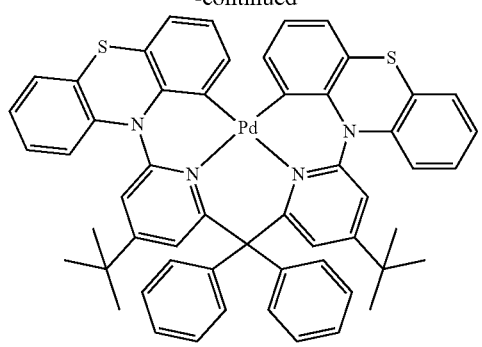
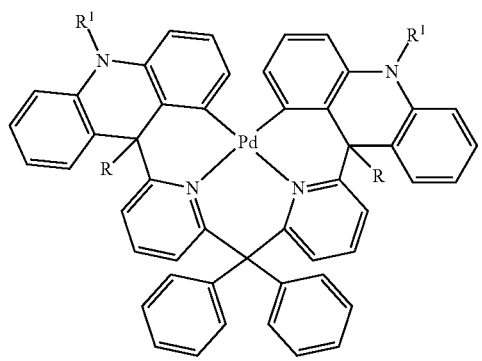
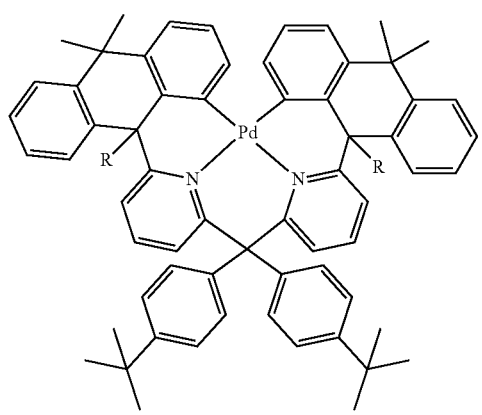
320
-continued
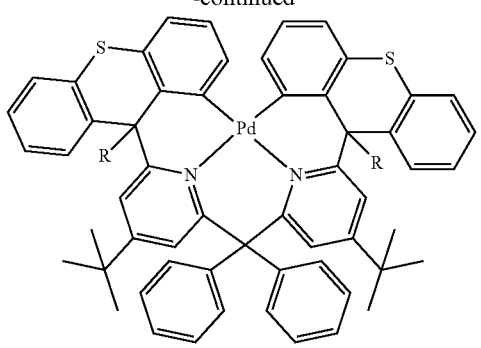
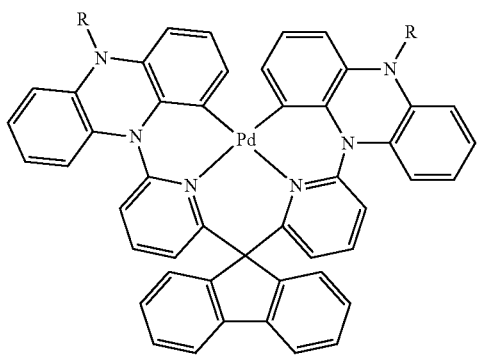
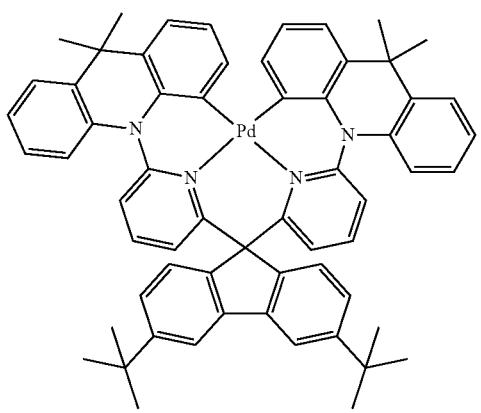
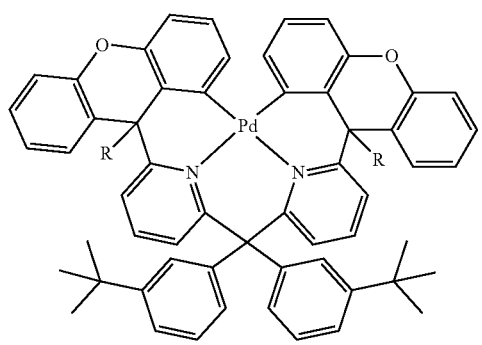

321
-continued
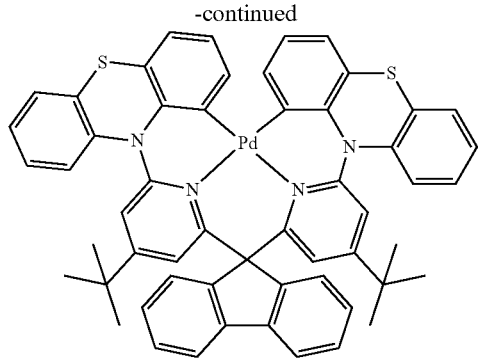
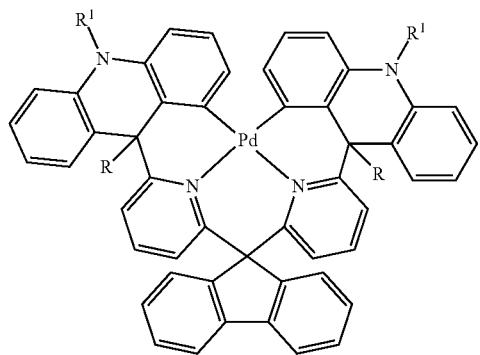
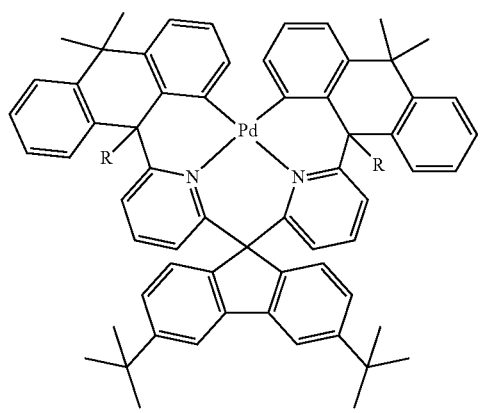
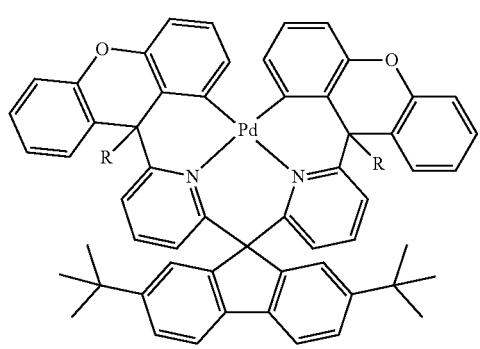
322
-continued
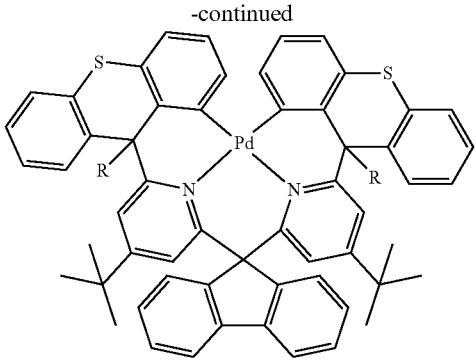
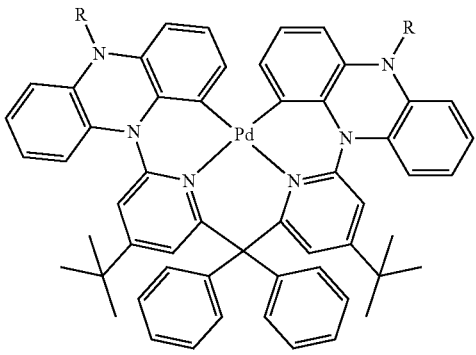
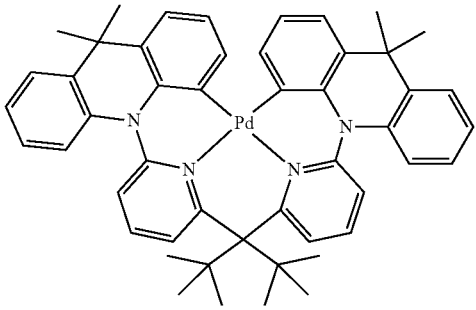
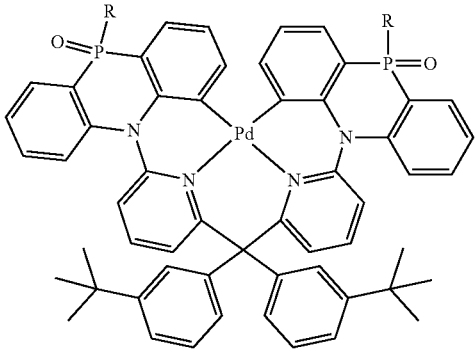
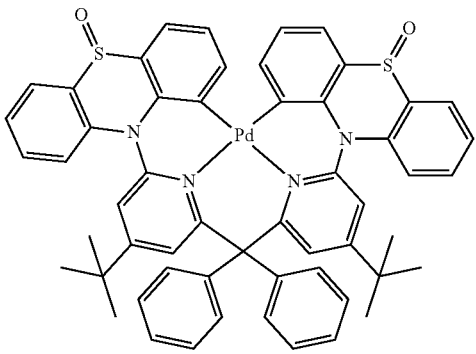

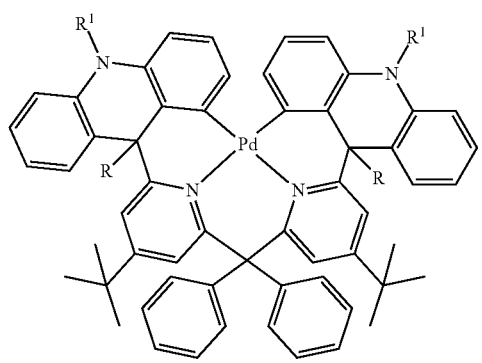
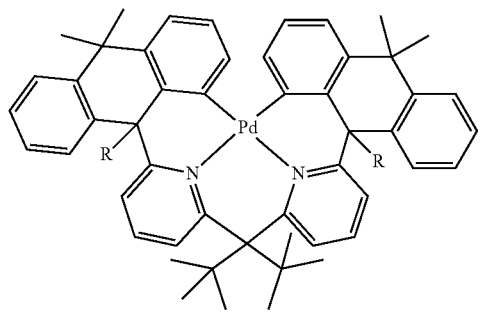
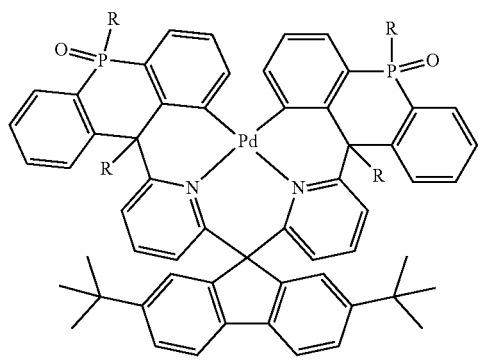
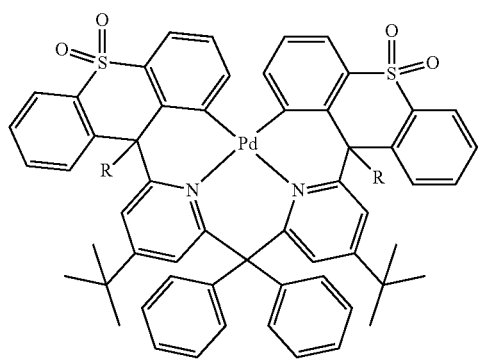
Structure Pd-18
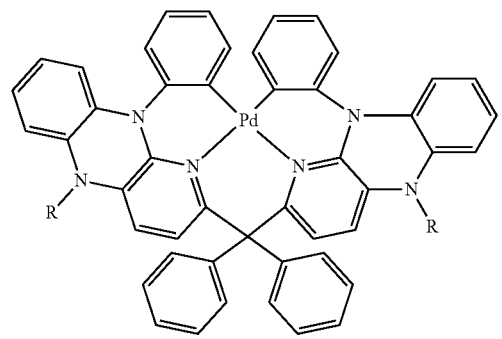
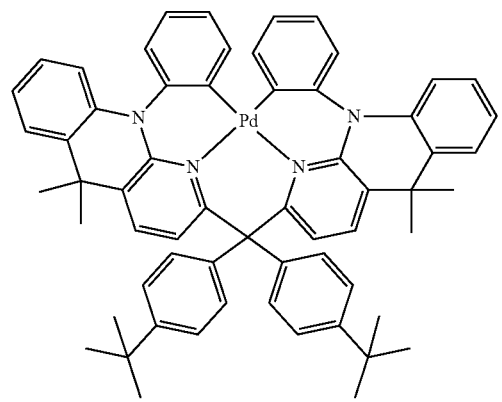
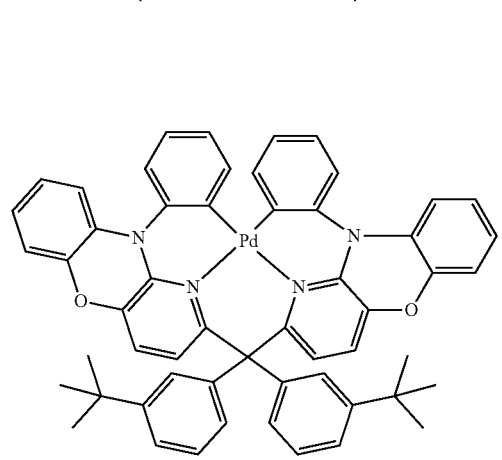
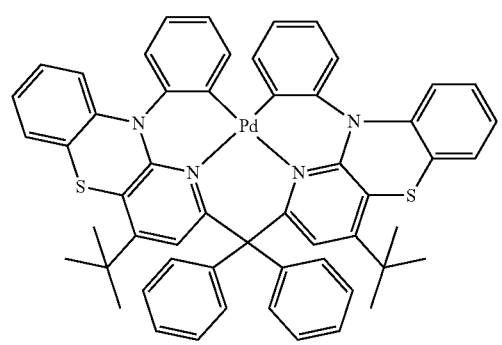

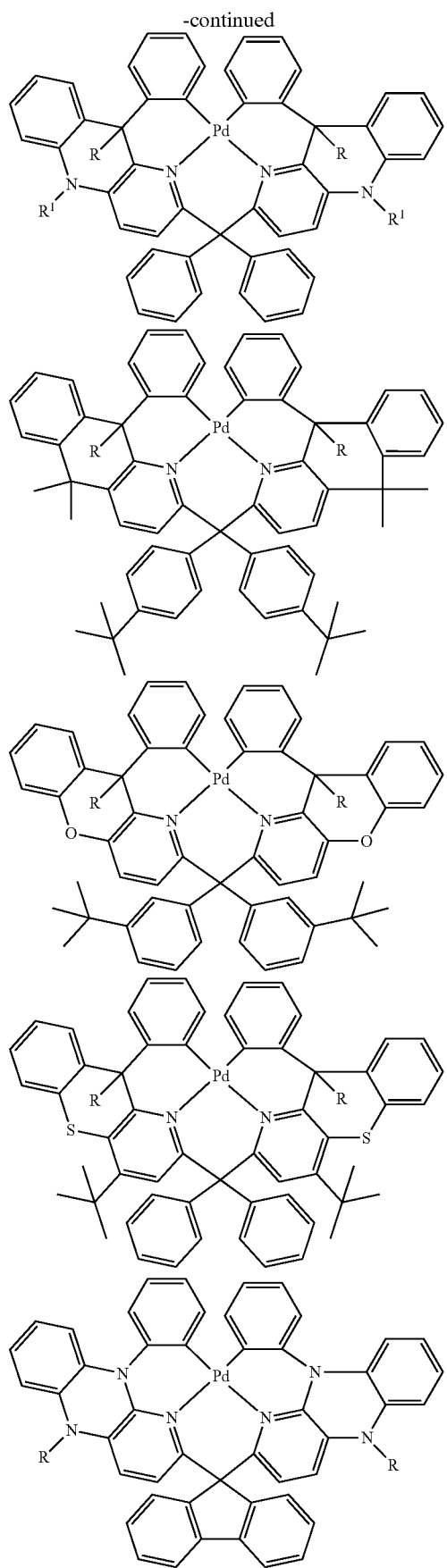
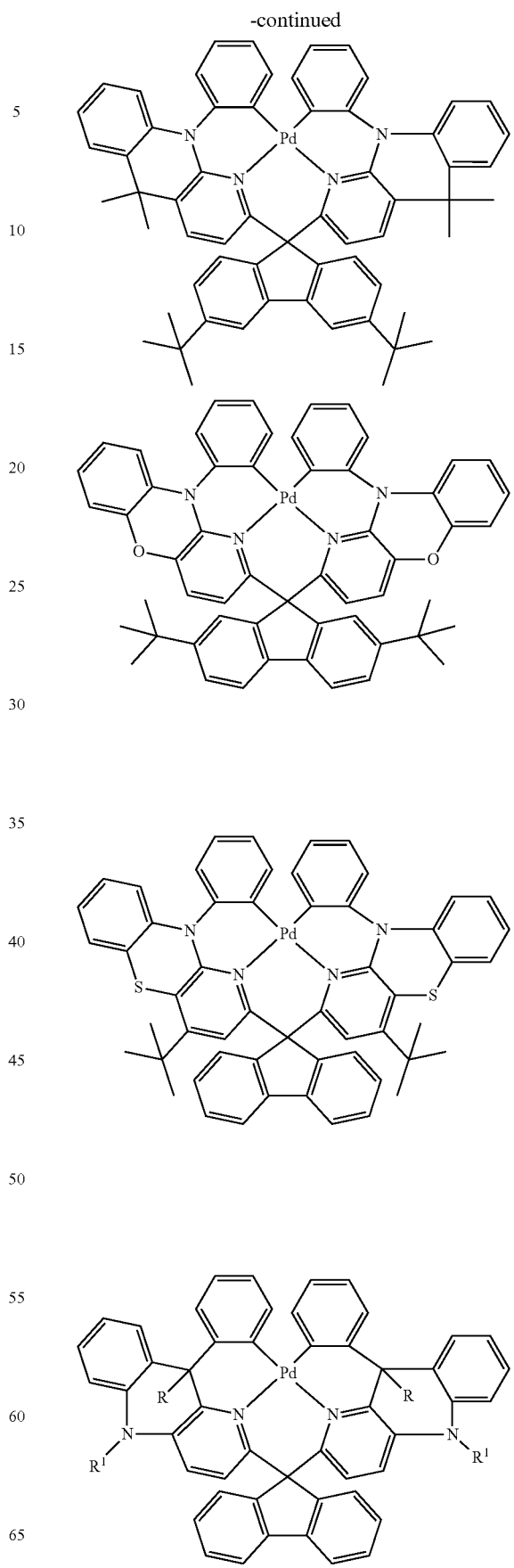

327
-continued
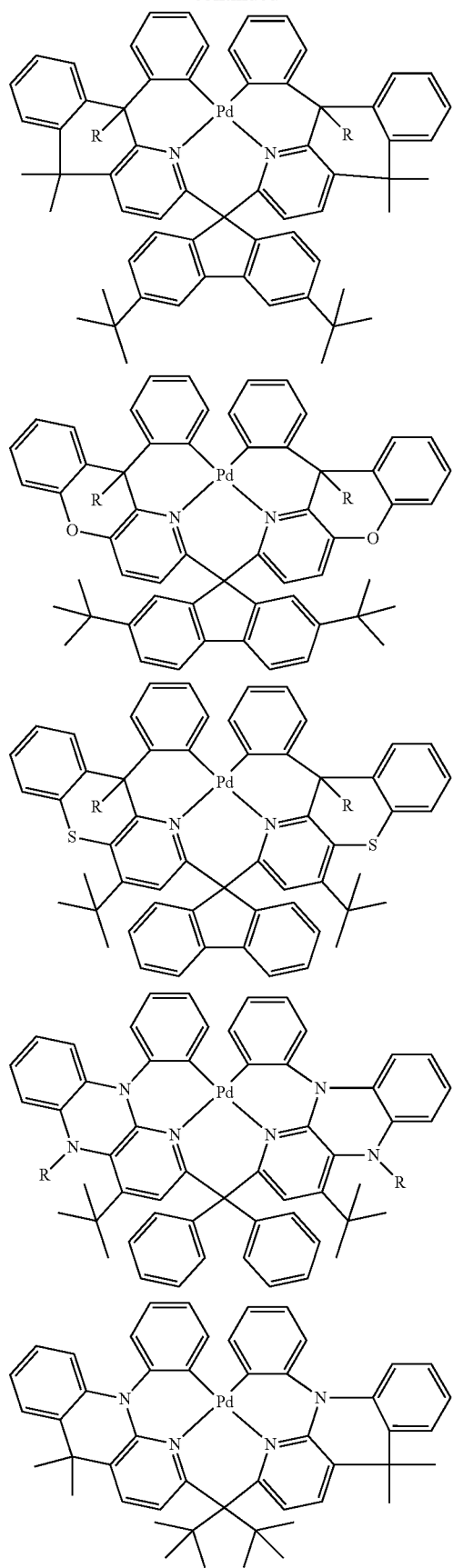
328
-continued
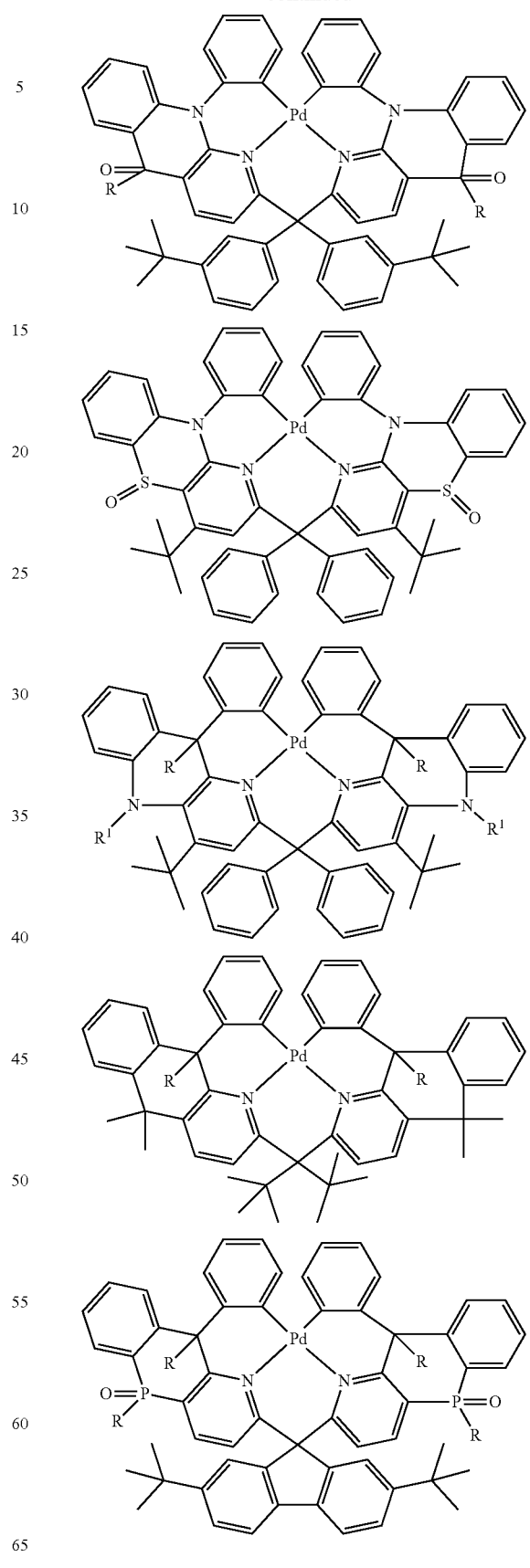

329
-continued
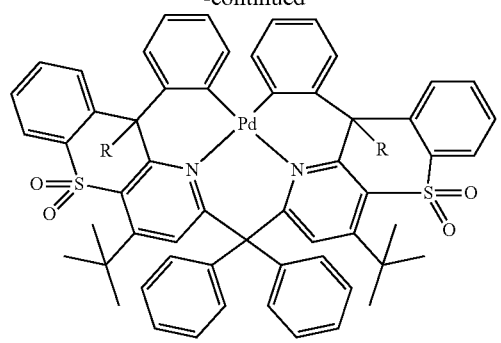
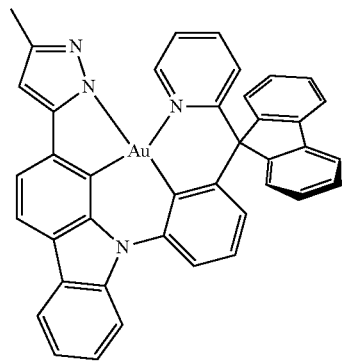
Structure Au-1
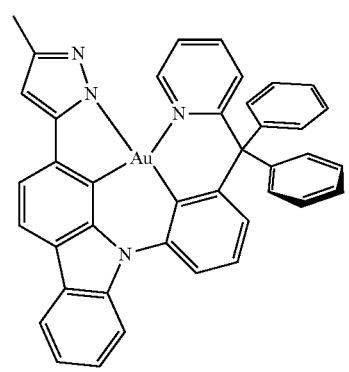
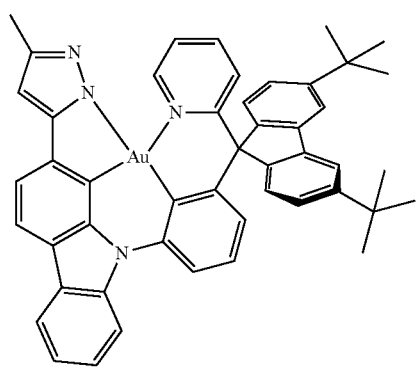
330
-continued
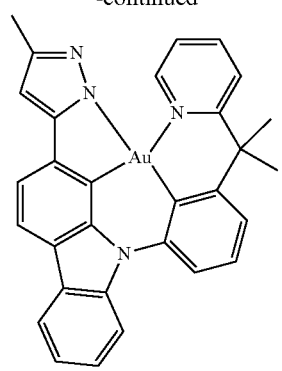
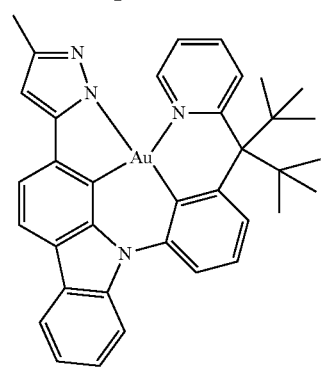
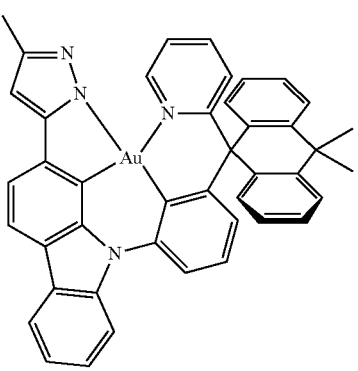
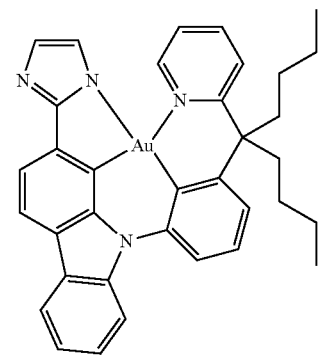

331
-continued
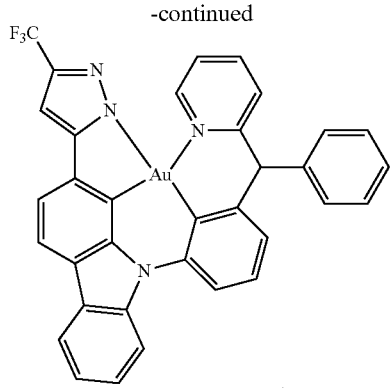
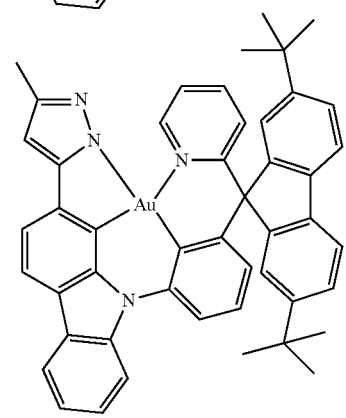
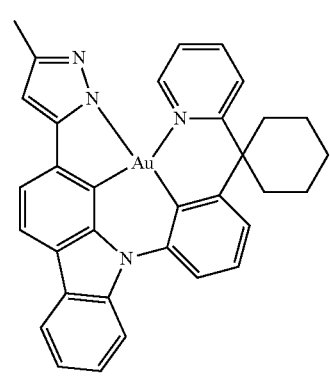
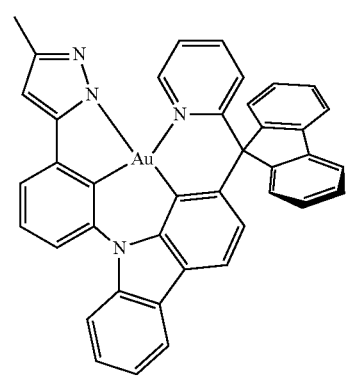
332
-continued
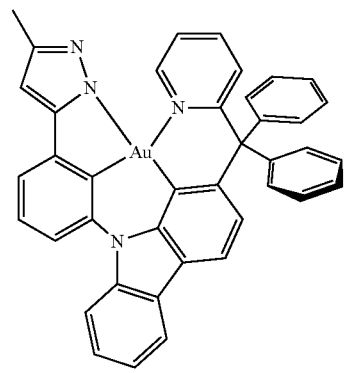
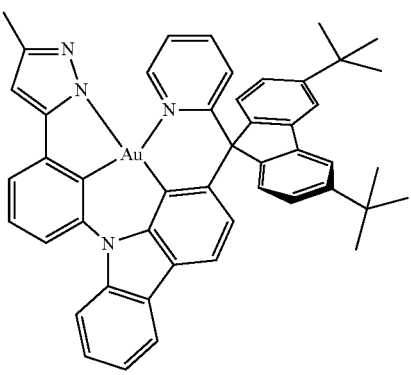
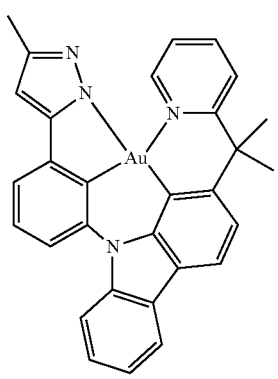
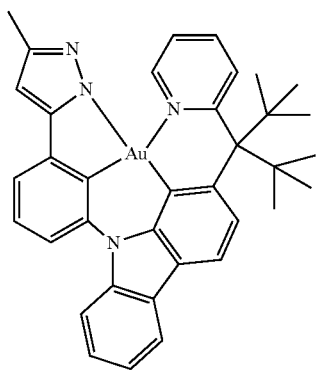

333
-continued
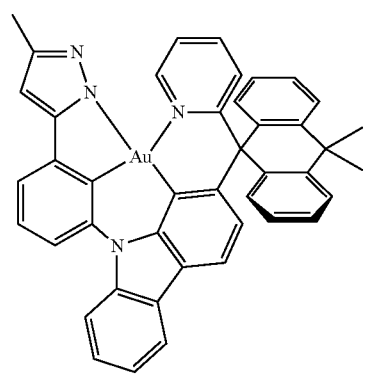
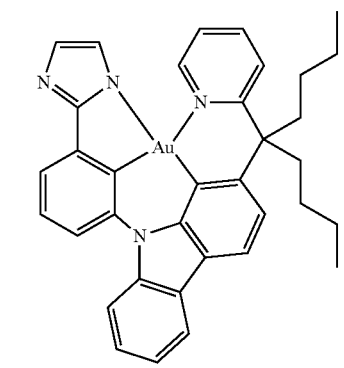
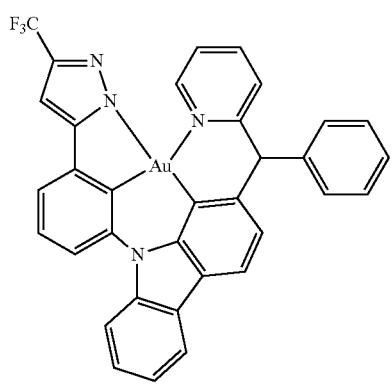
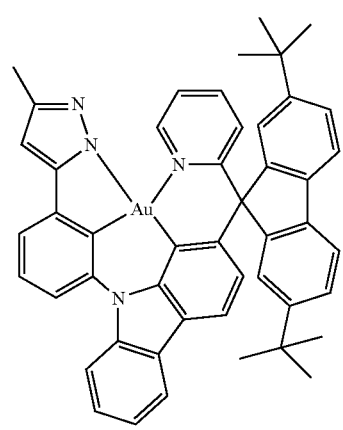
334
-continued
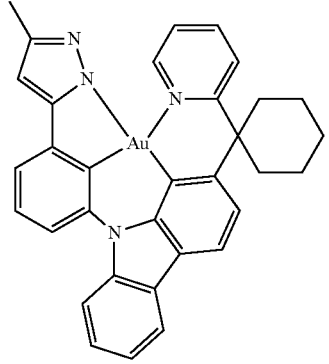
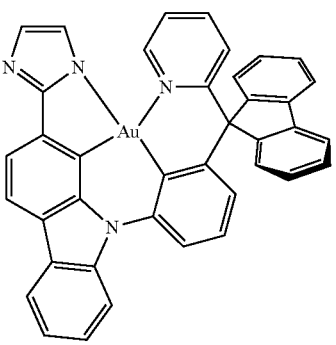
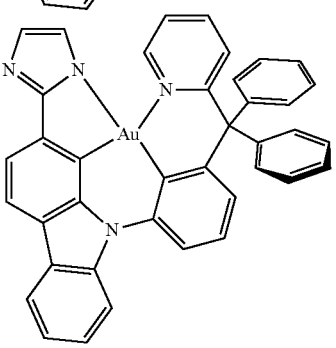
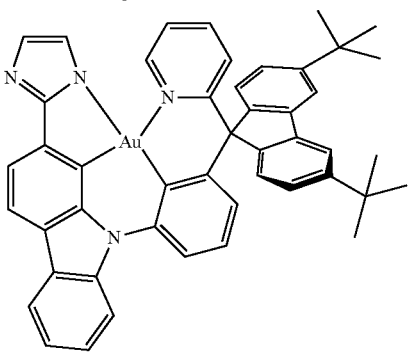
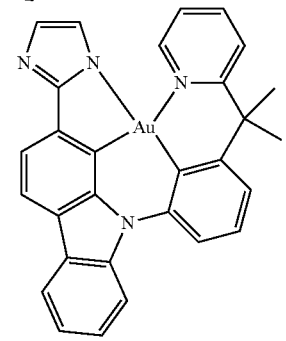

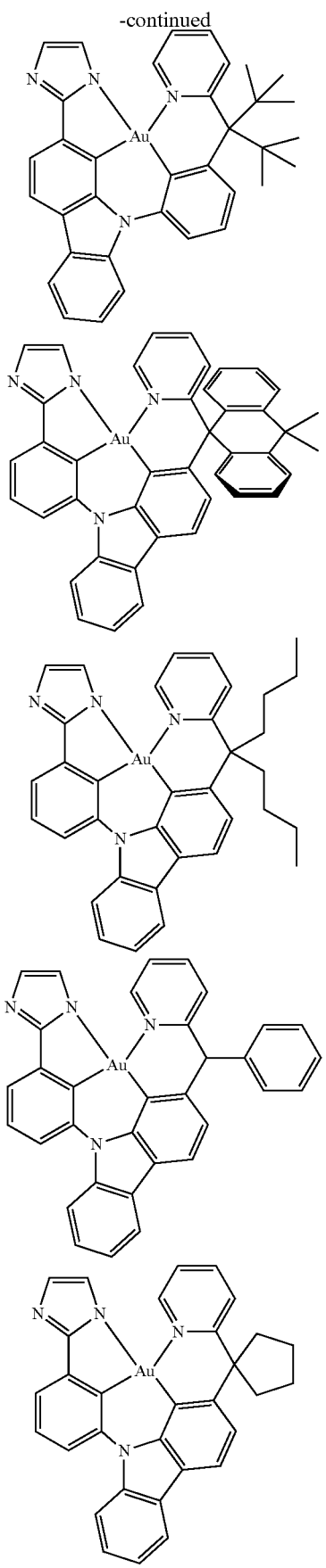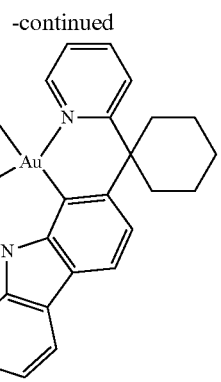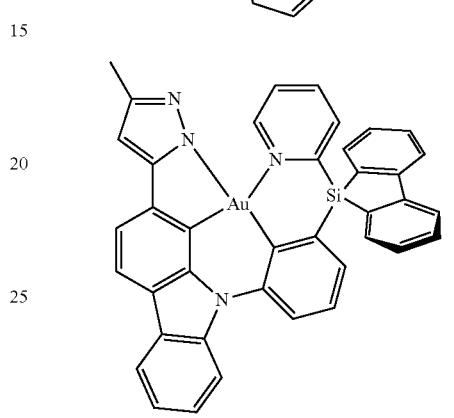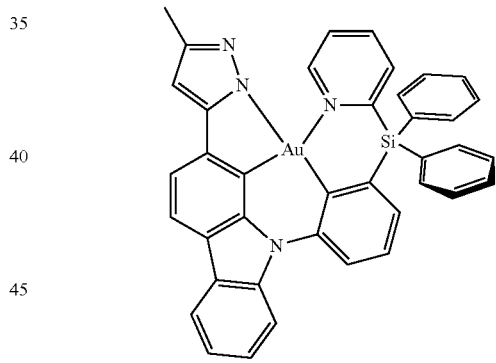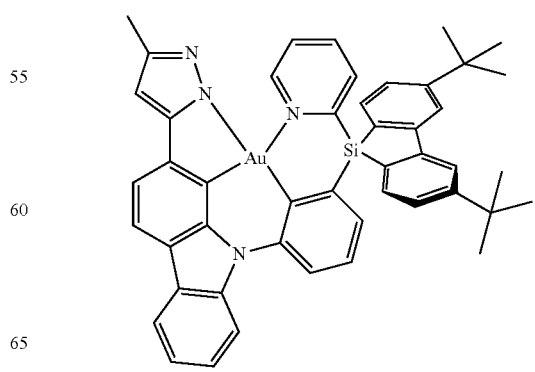
Structure Au-2

337
-continued
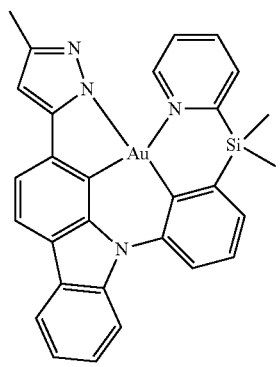
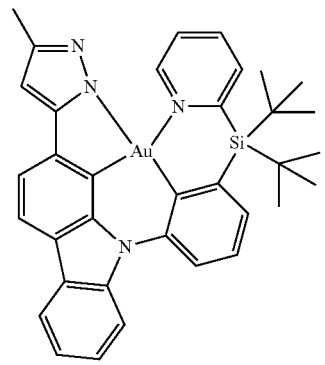
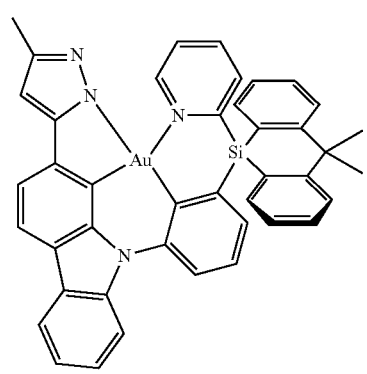
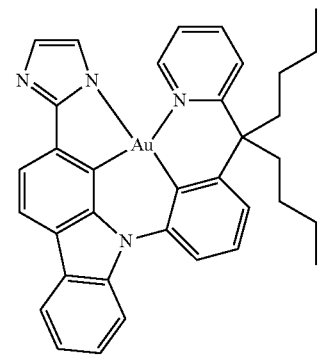
338
-continued
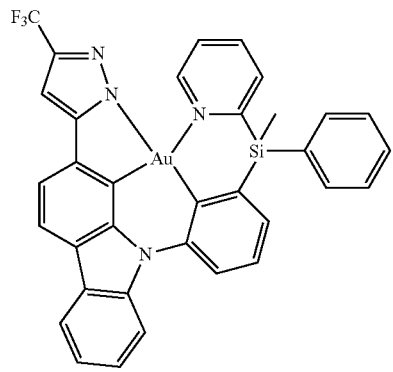
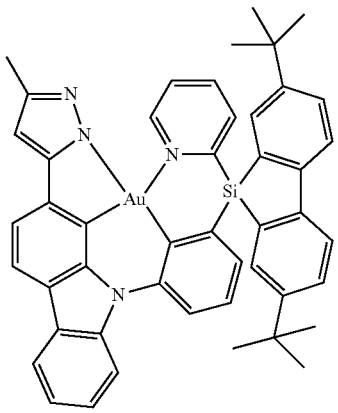
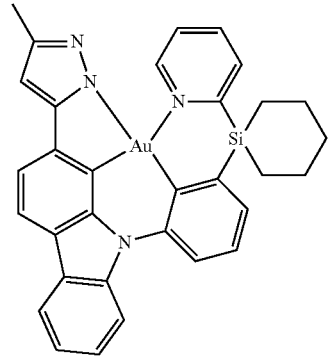
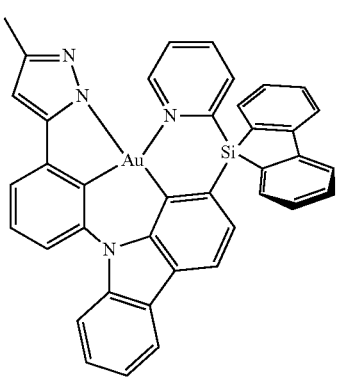

339
-continued
340
-continued
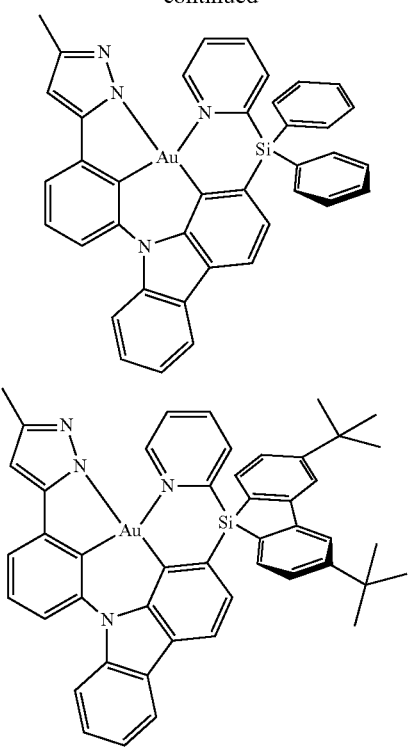
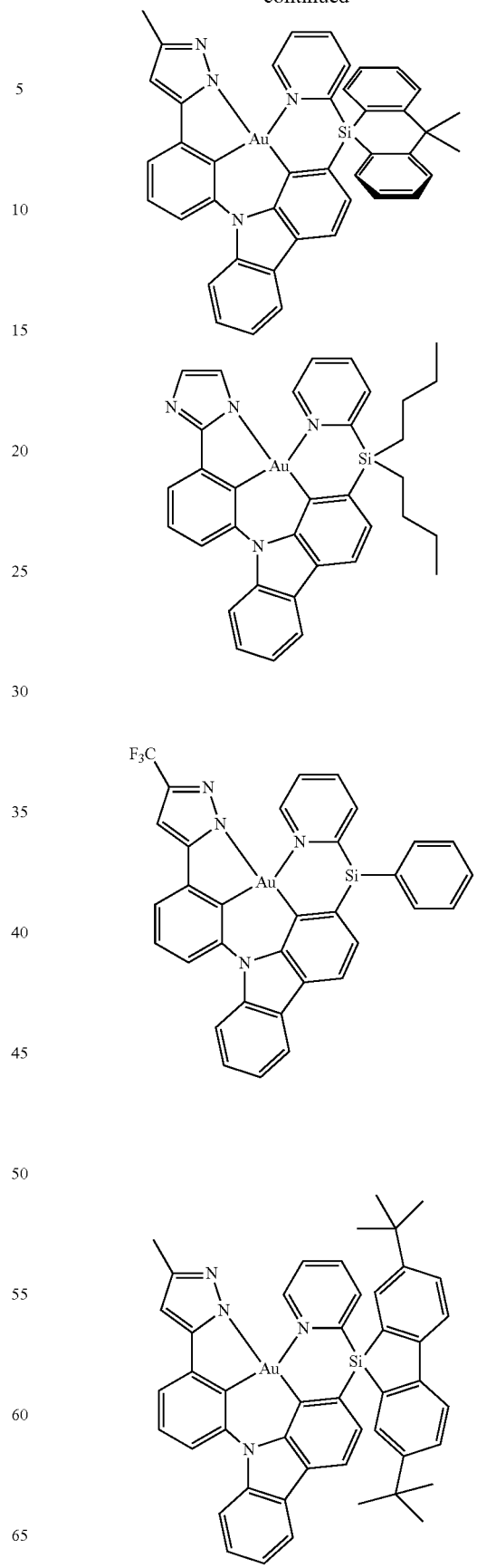

341
-continued
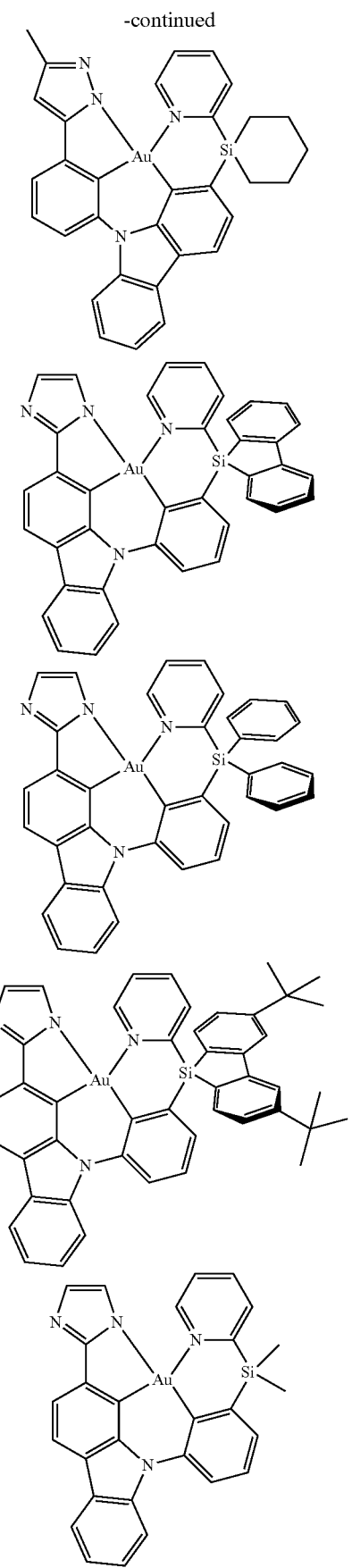
342
-continued
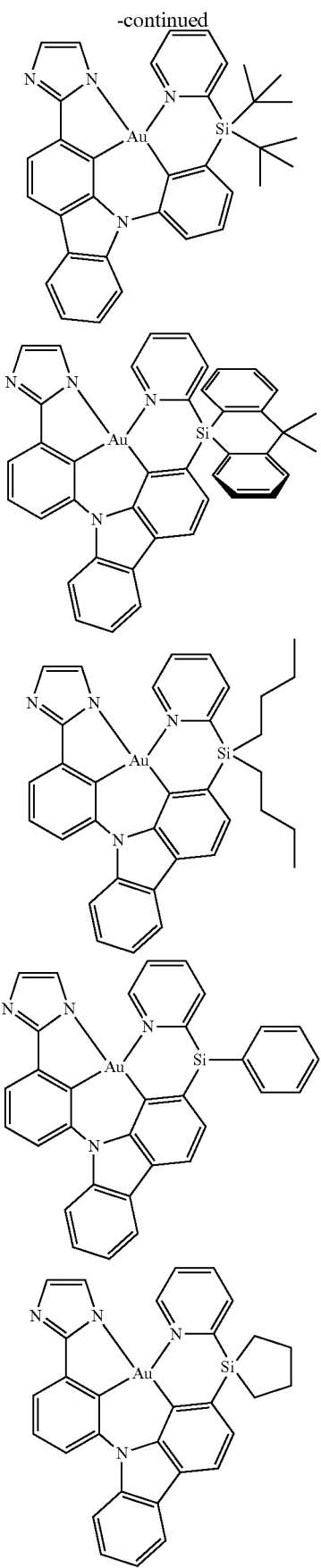

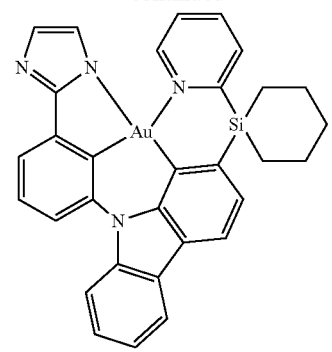
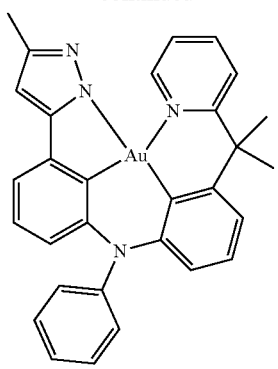
Structure Au-3
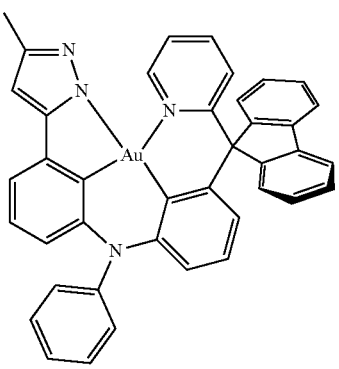
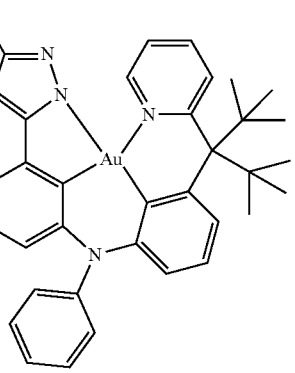
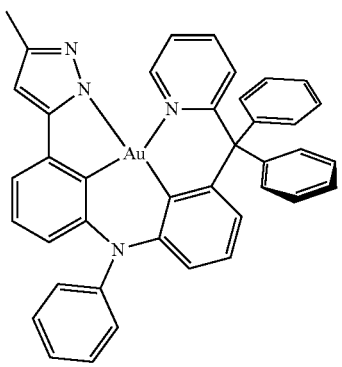
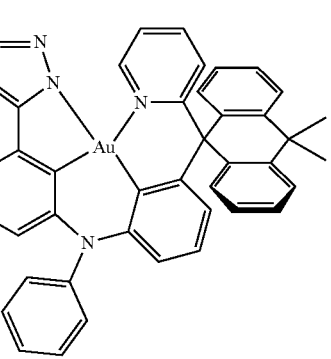
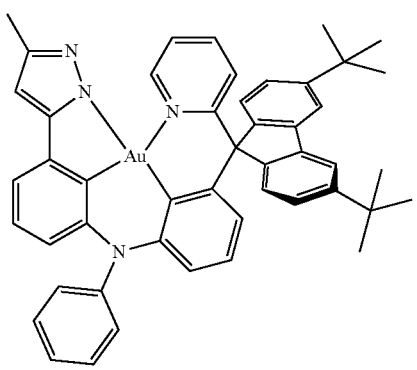
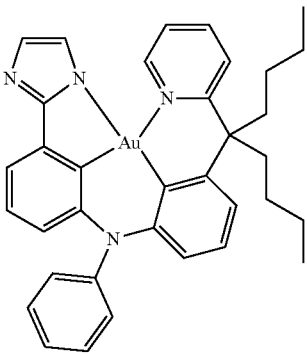

345
-continued
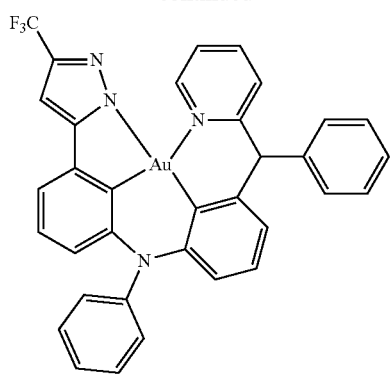
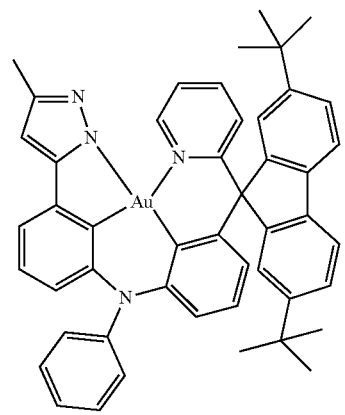
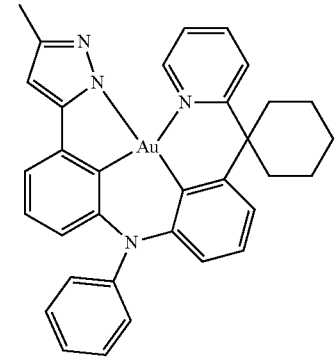
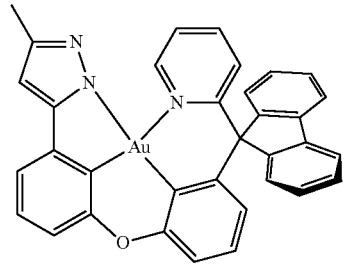
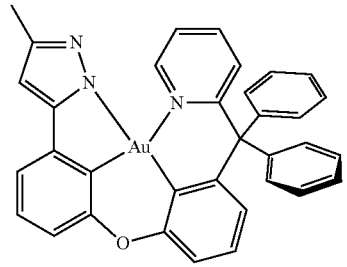
346
-continued
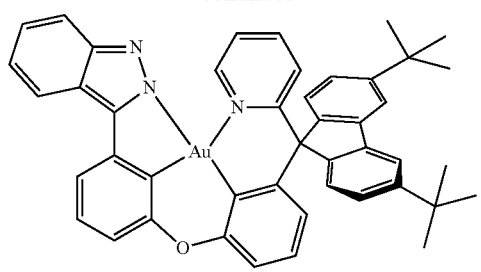
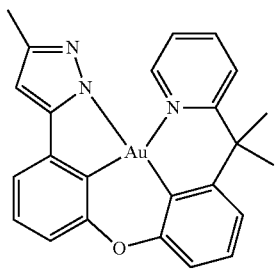
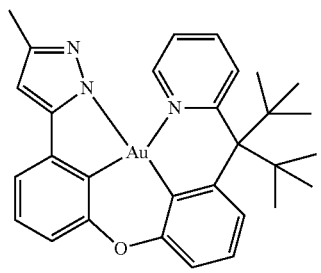
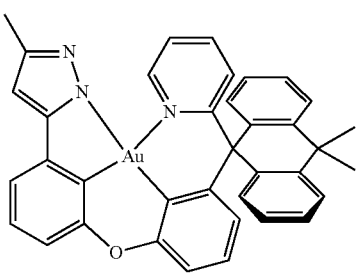
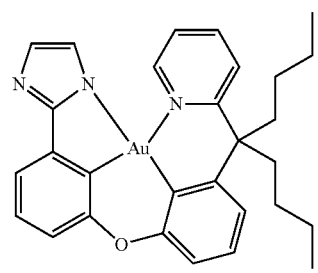
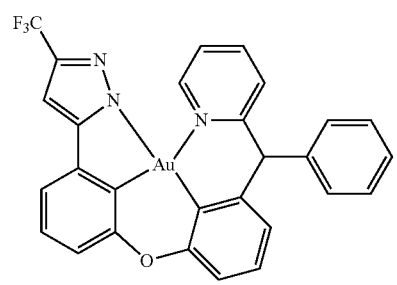

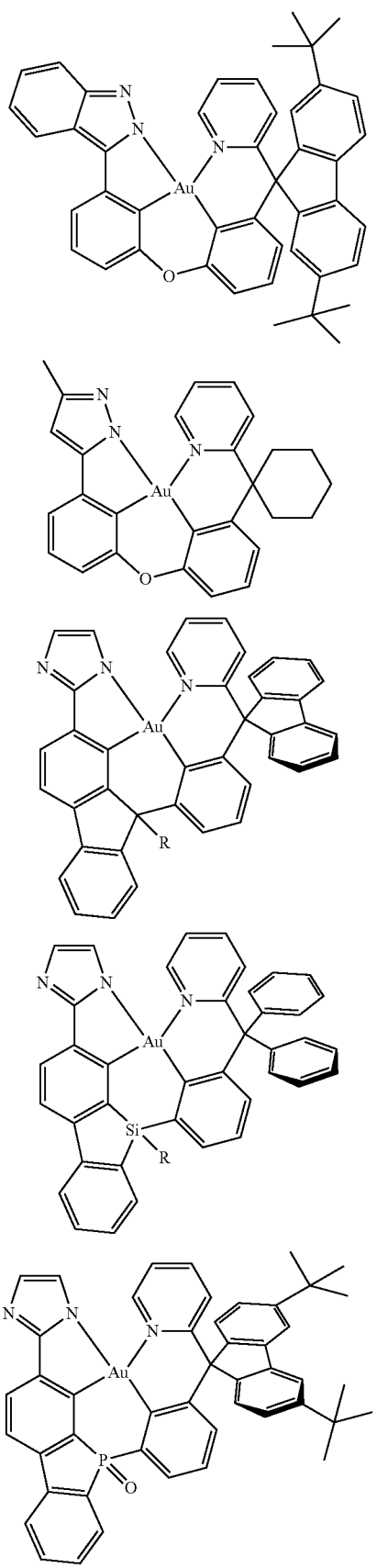
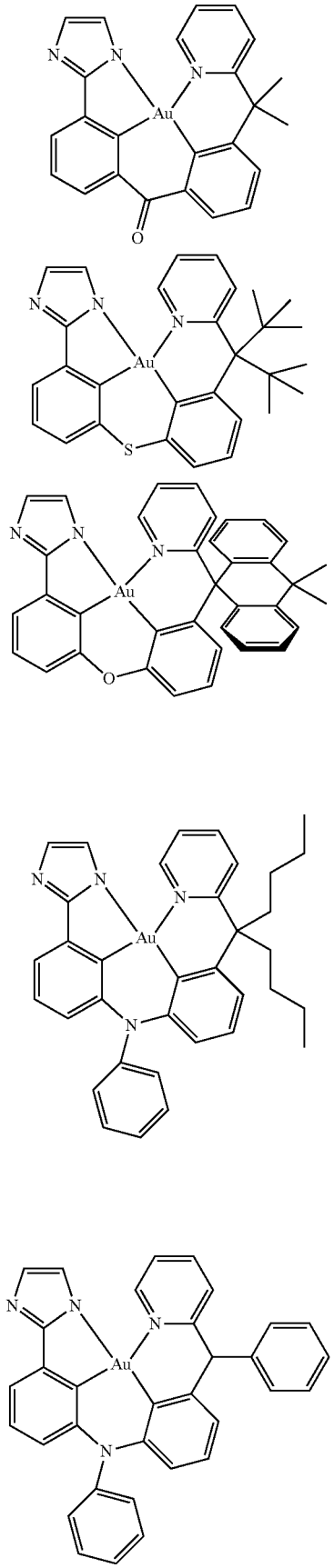

349
-continued
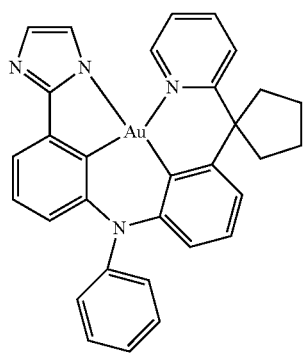
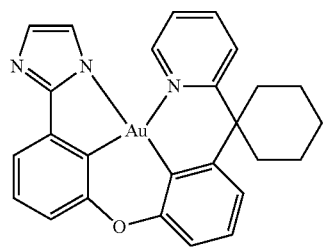
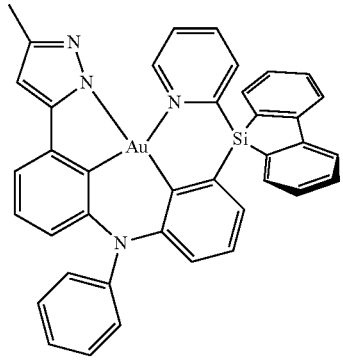
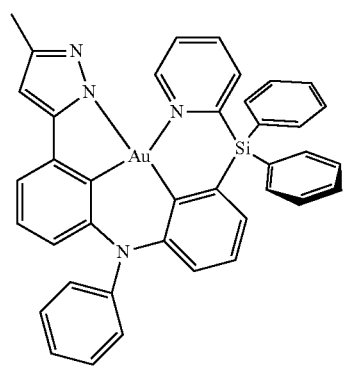
350
-continued
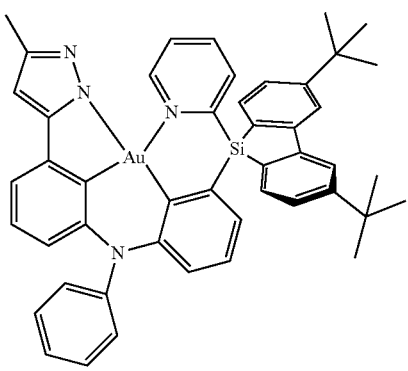
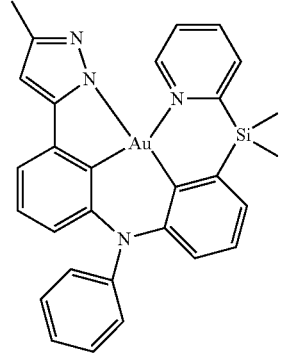
Structure Au-4
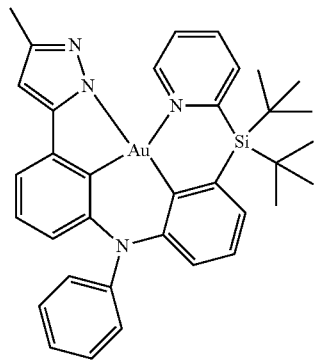
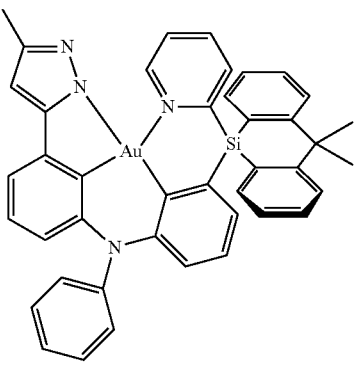

351 -continued
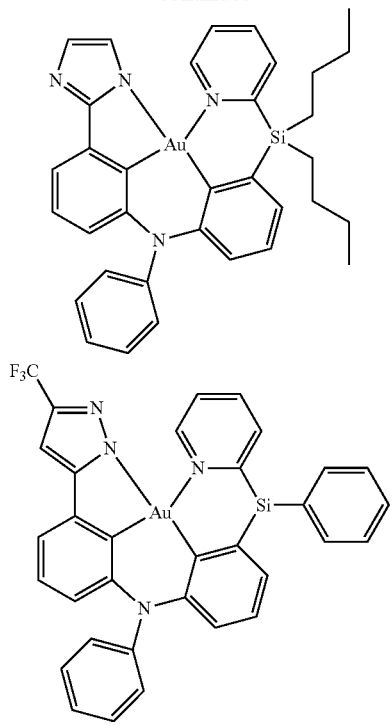
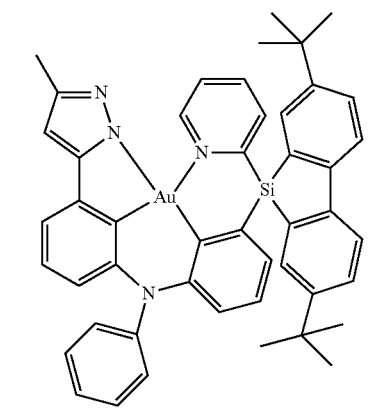
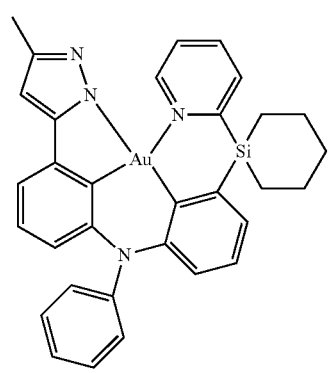
352 -continued
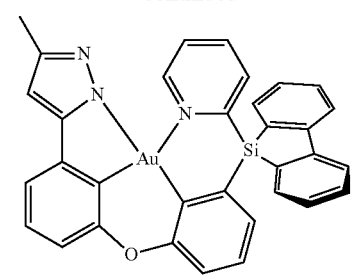
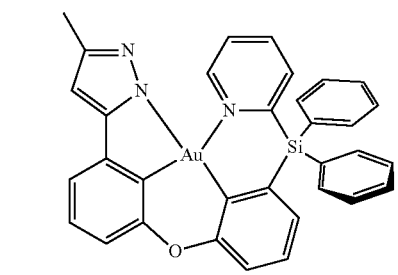
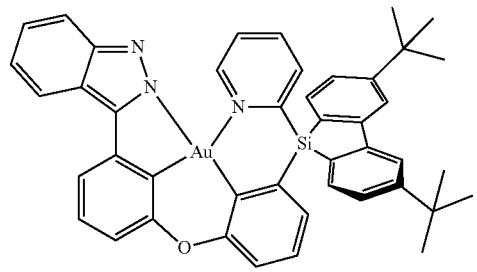
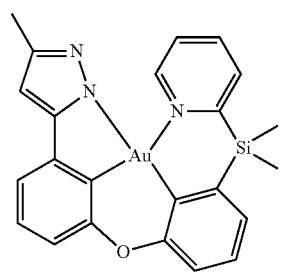
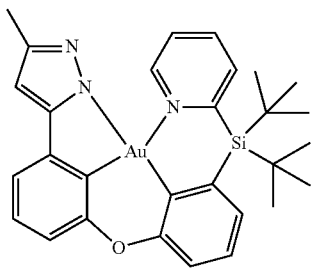
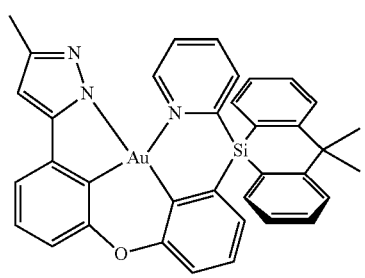

| 353 -continued | 354 -continued |
|---|---|
| 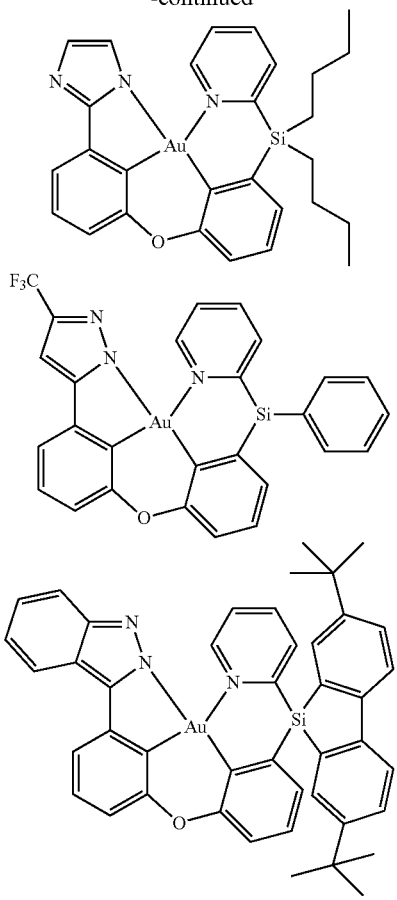 | 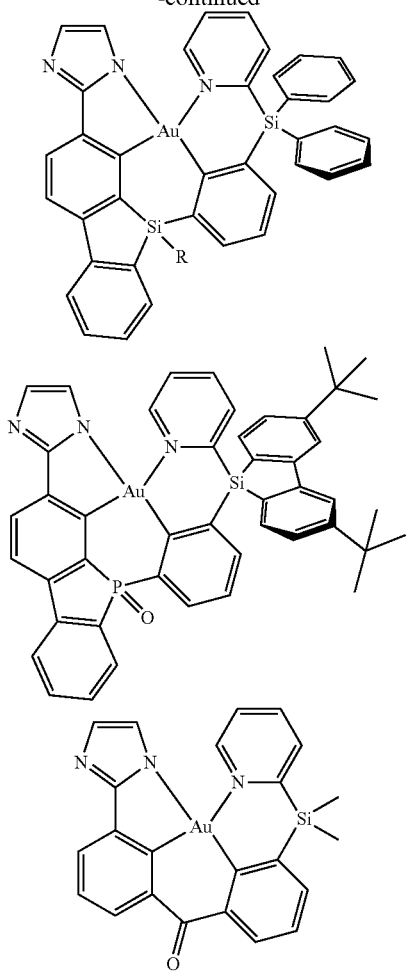 |
| 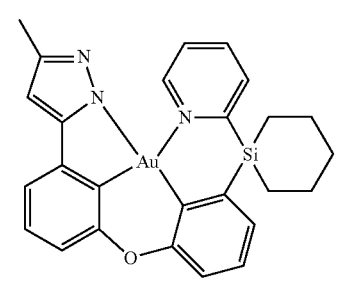 | 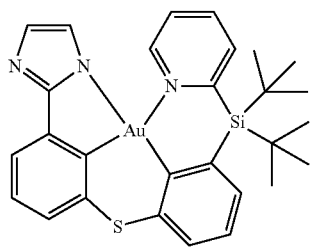 |
| 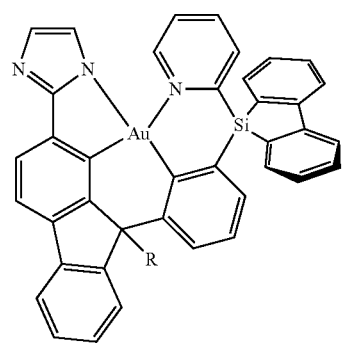 | 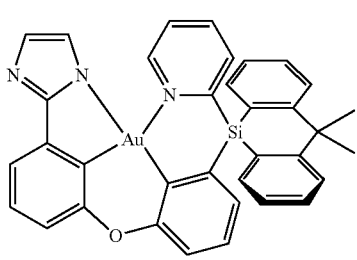 |

355
-continued
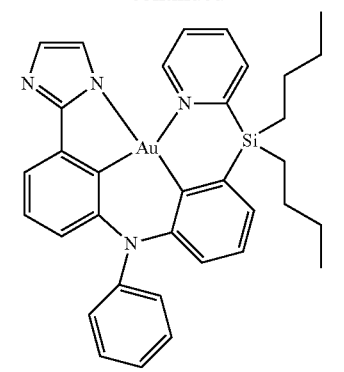
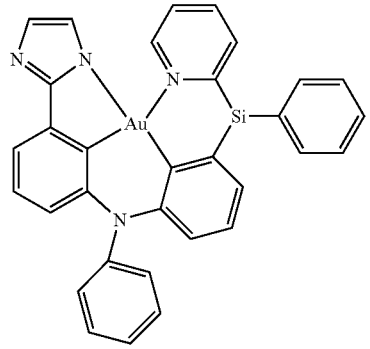
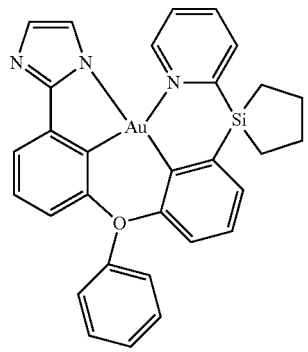
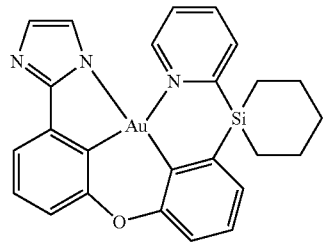
Structure Au-5
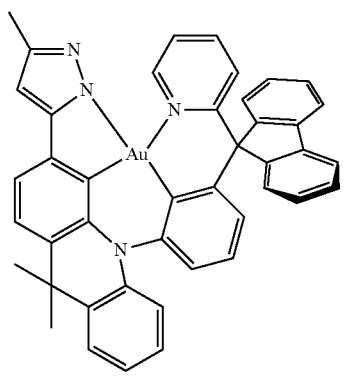
356
-continued
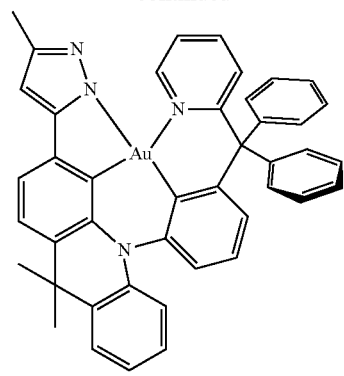
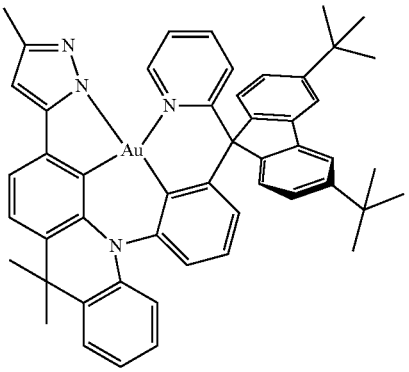
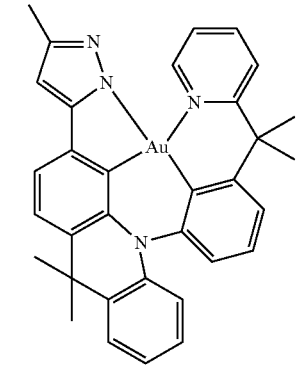
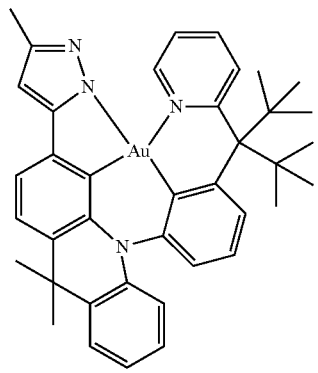

357
-continued
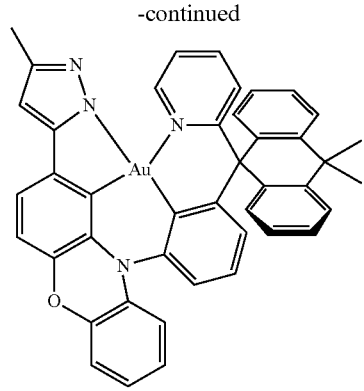
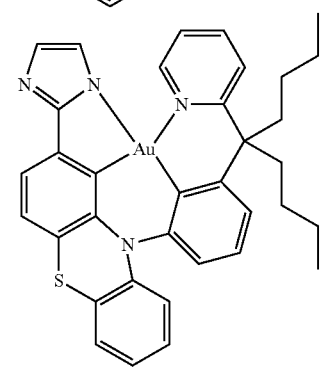
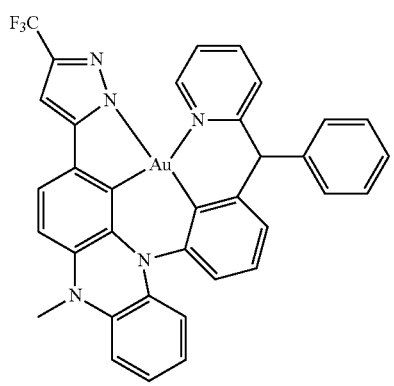
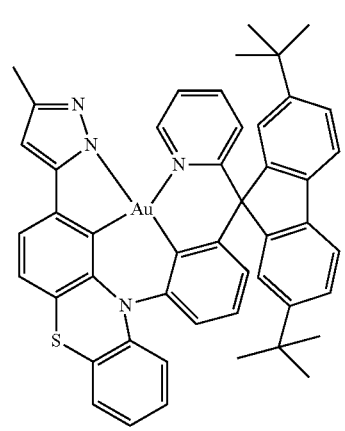
358
-continued
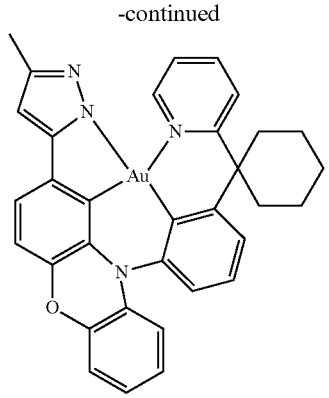
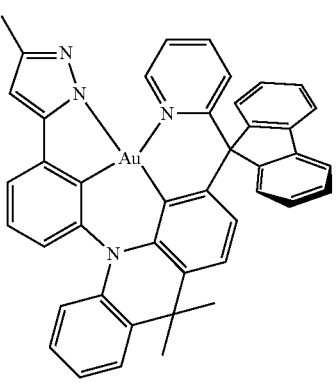
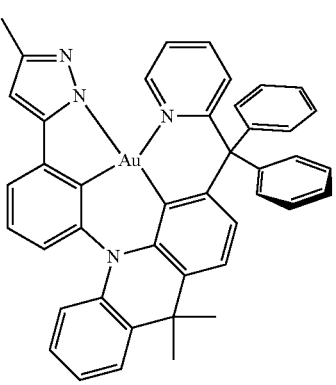
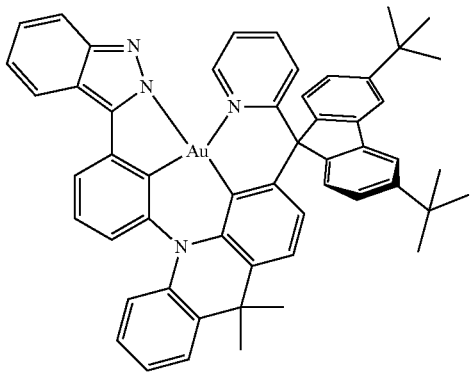

359
-continued
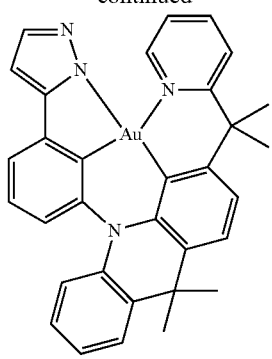
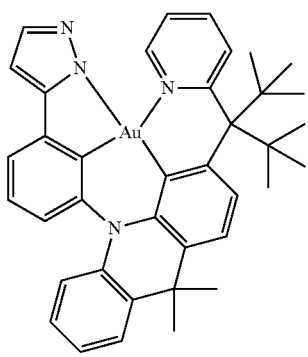
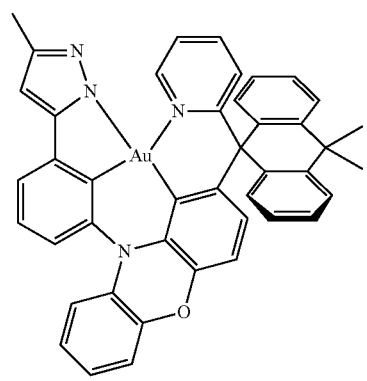
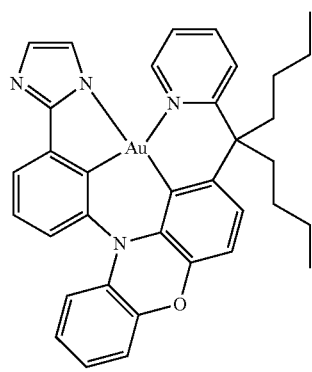
360
-continued
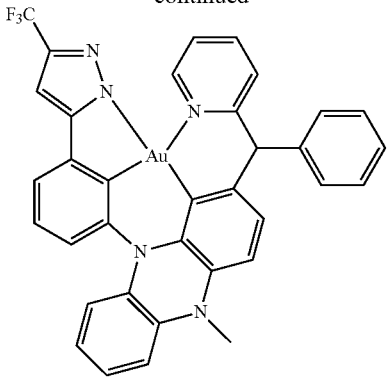
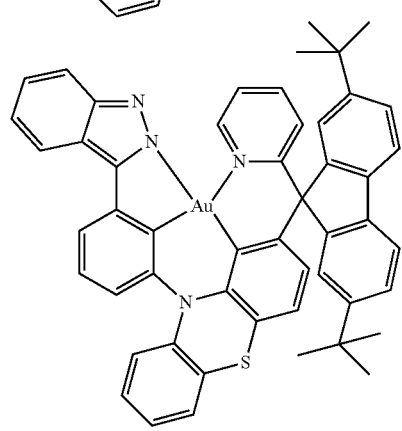
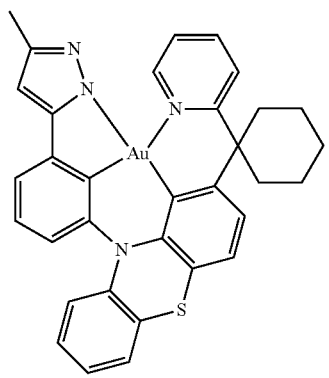
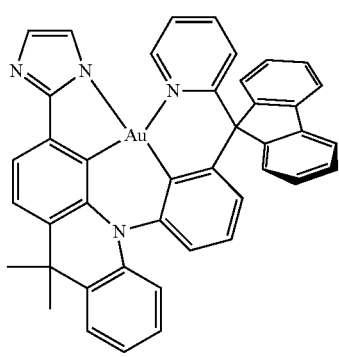

361
-continued
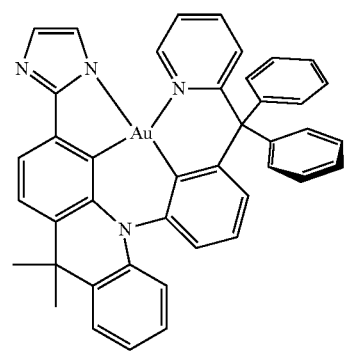
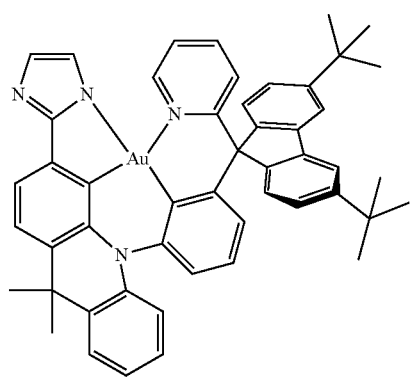
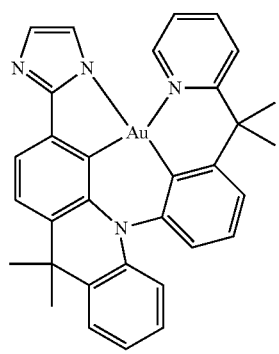
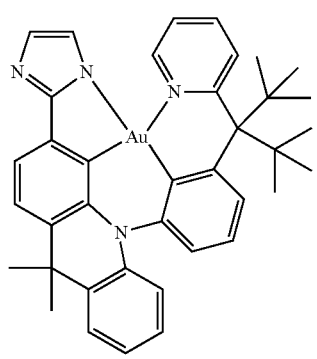
362
-continued
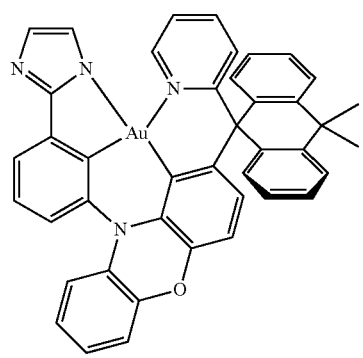
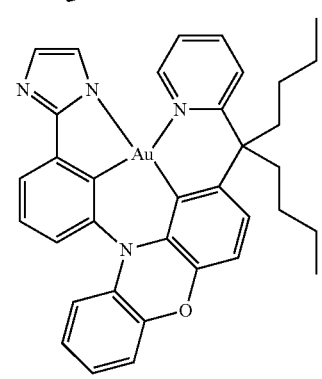
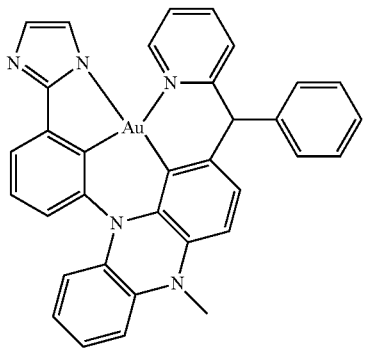
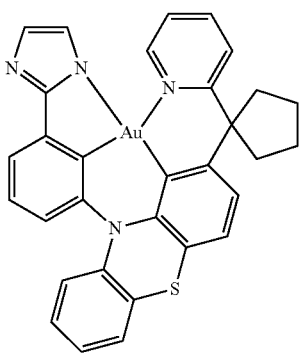

363
-continued
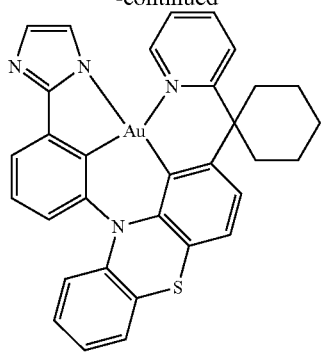
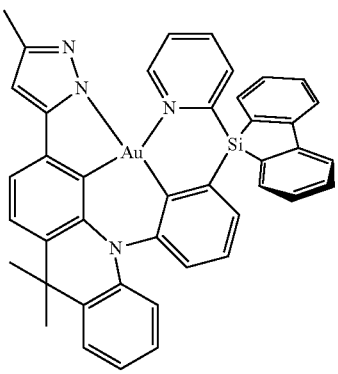
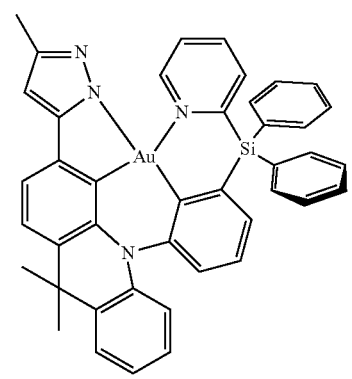
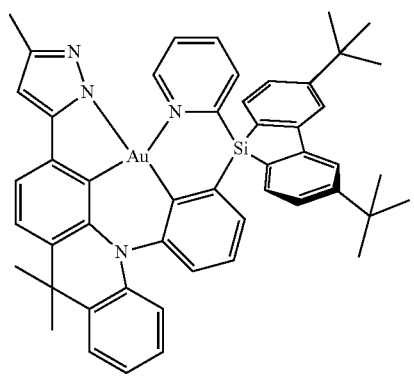
364
-continued
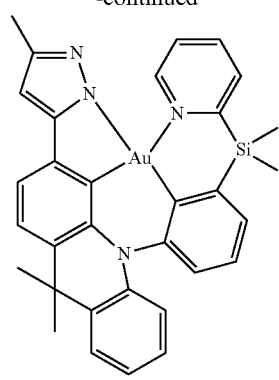
Structure Au-6
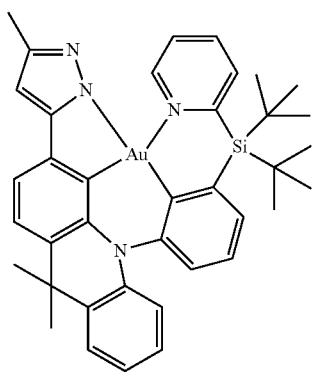
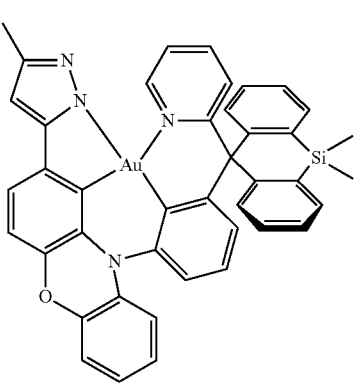
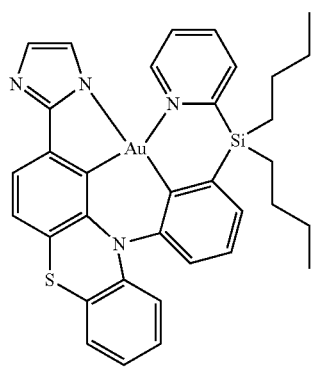

365
-continued
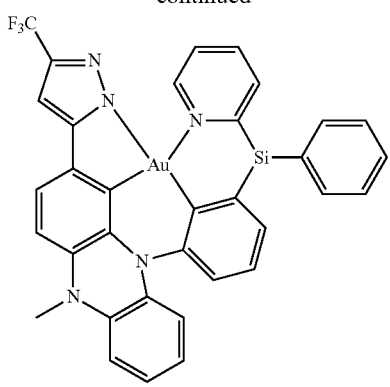
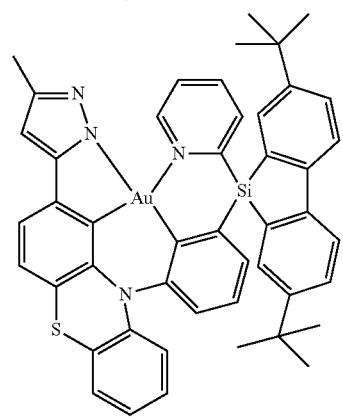
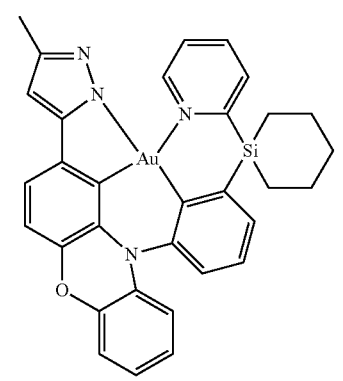
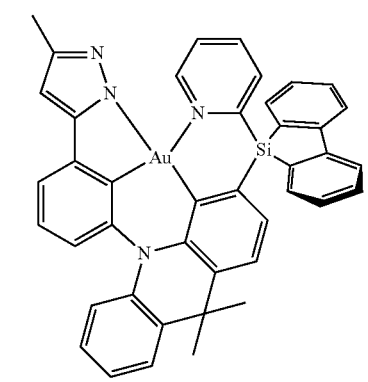
366
-continued
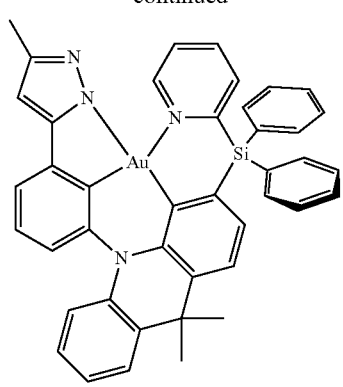
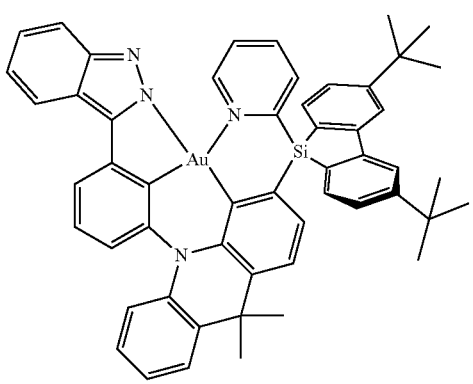
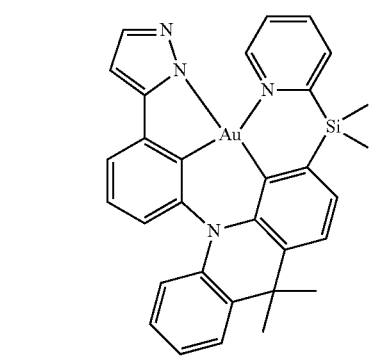
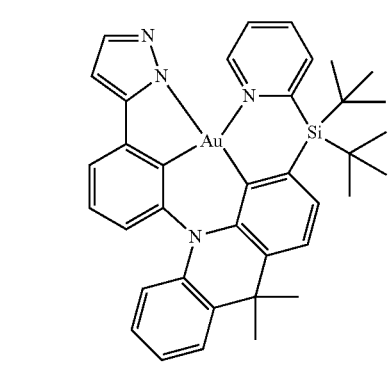

367
-continued
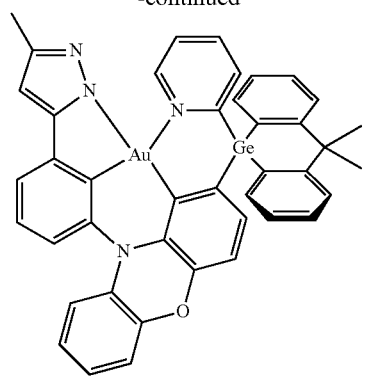
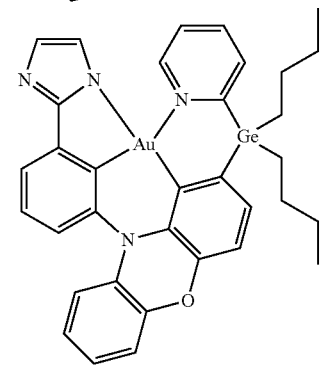
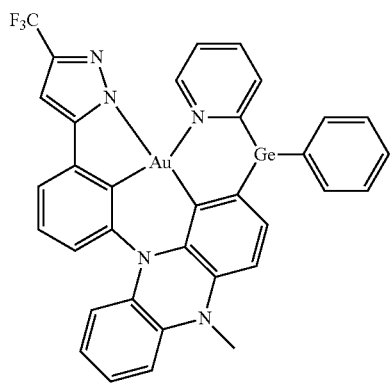
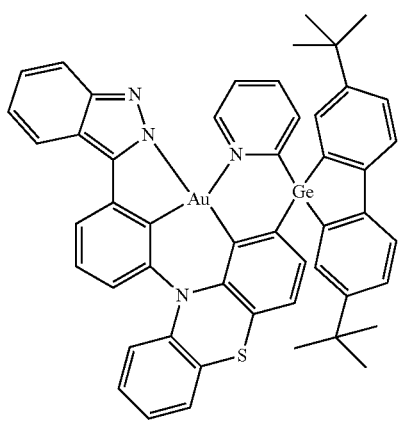
368
-continued
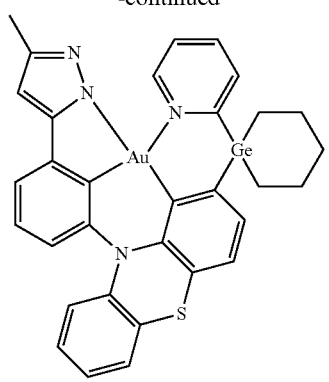
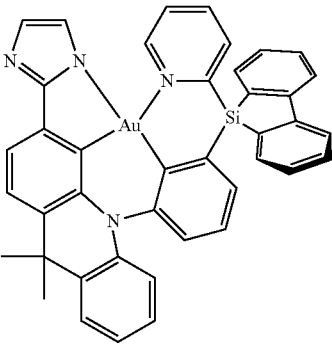
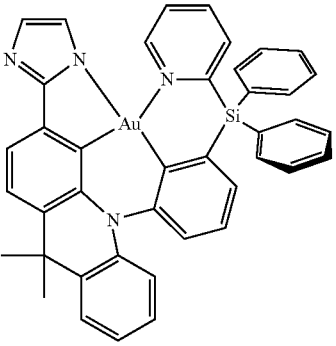
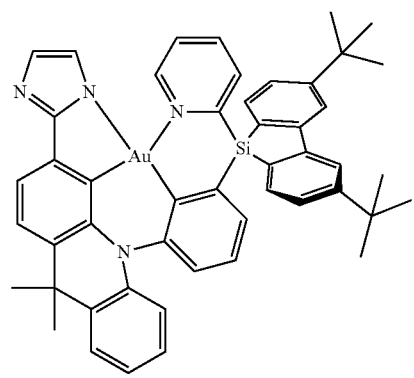

369
-continued
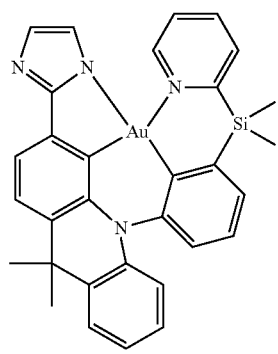
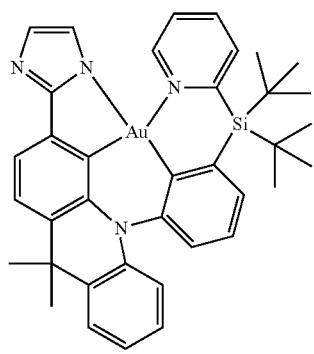
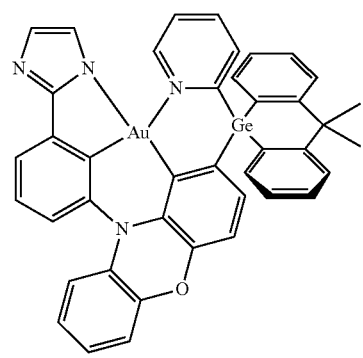
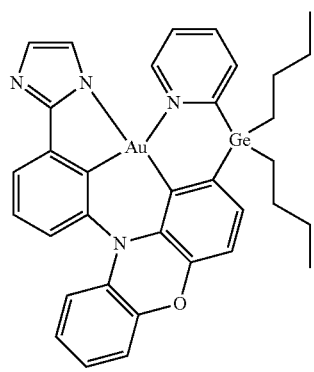
370
-continued
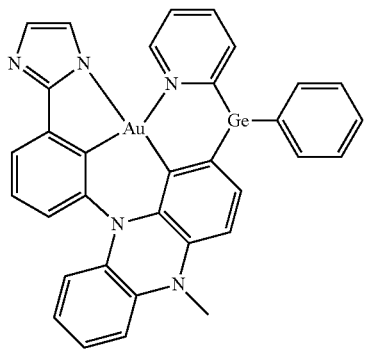
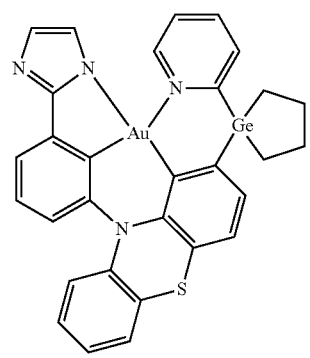
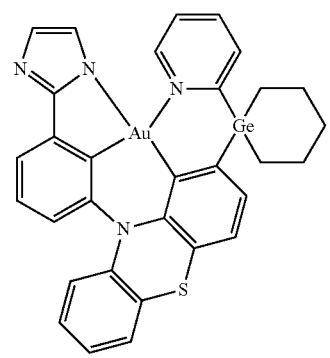
Structure Au-7
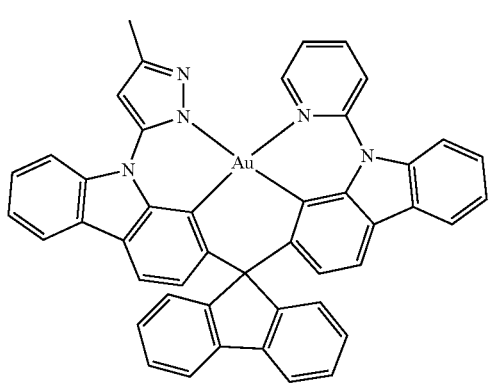

371
-continued
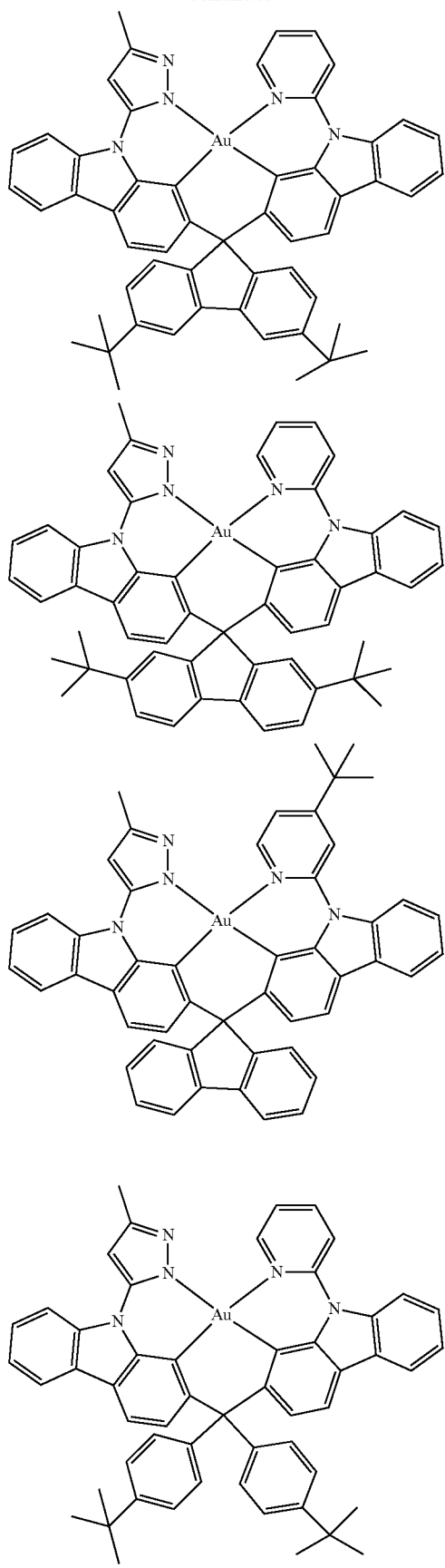
372
-continued
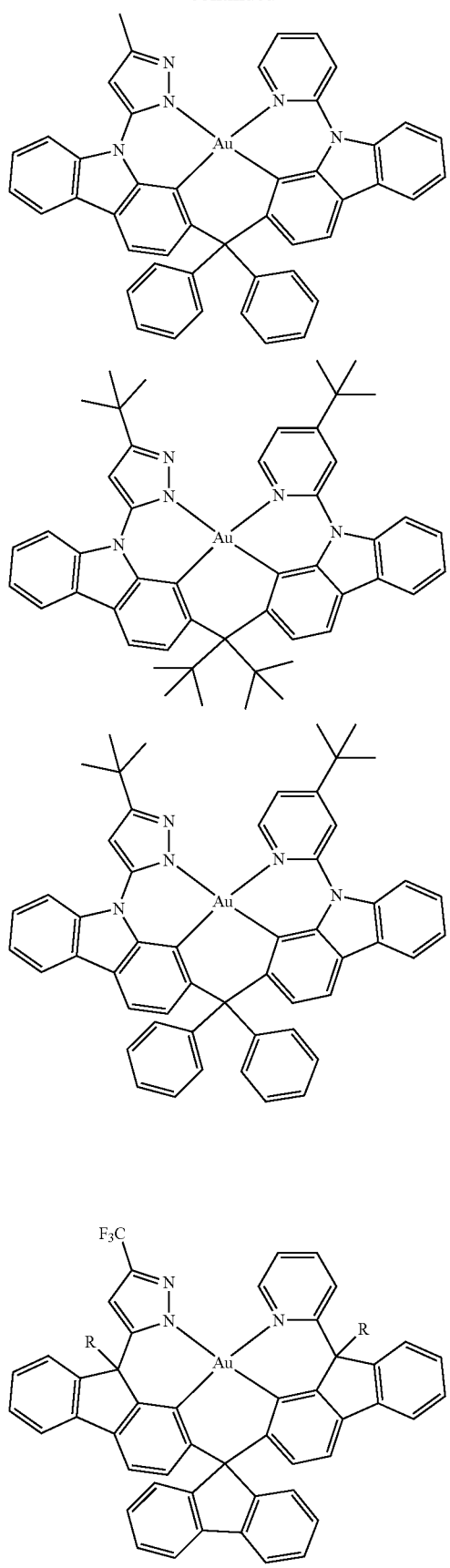

373
-continued
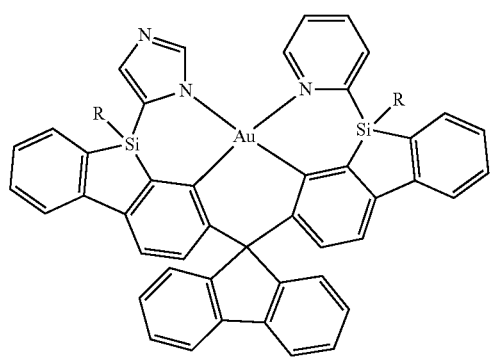
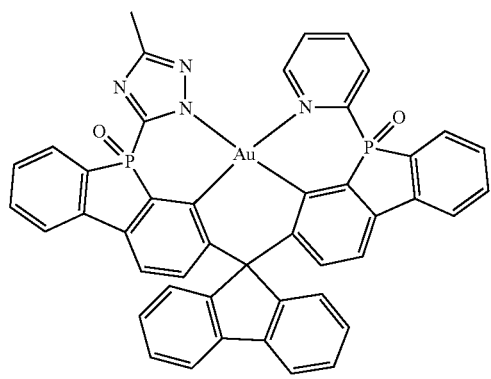
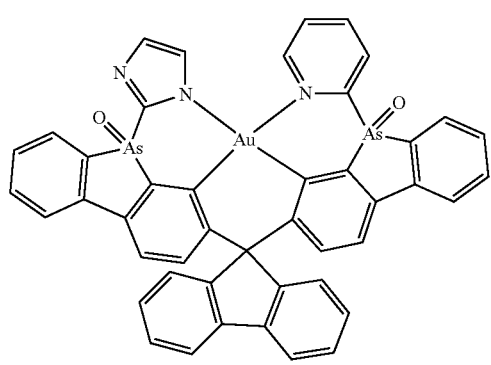
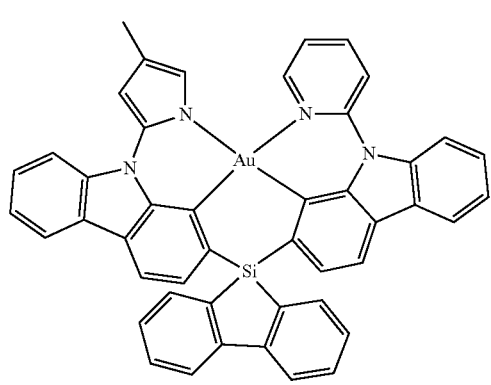
374
-continued
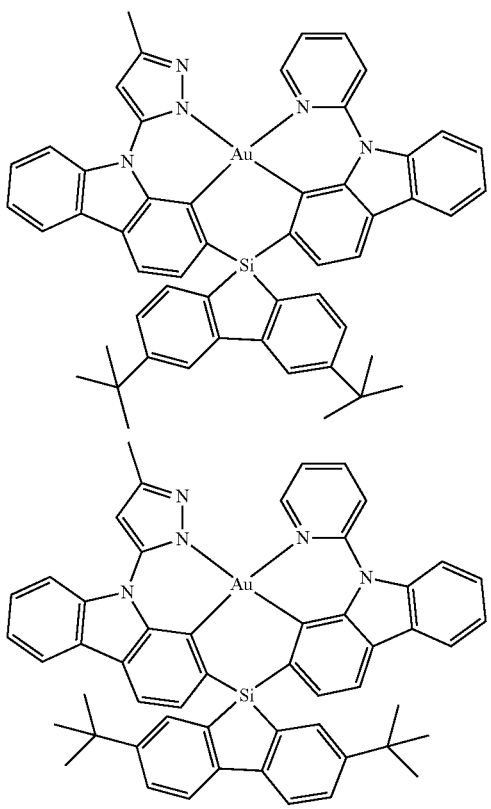
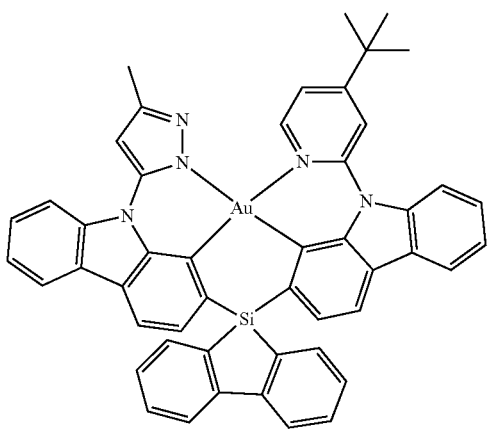
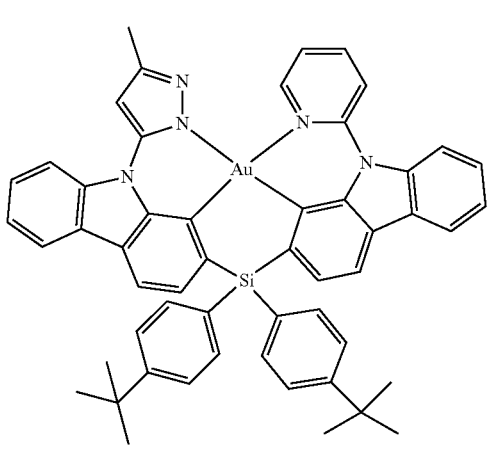

375
-continued
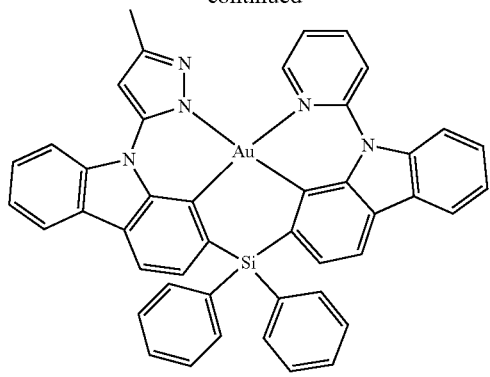
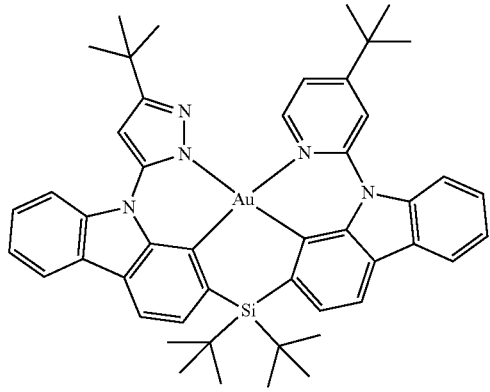
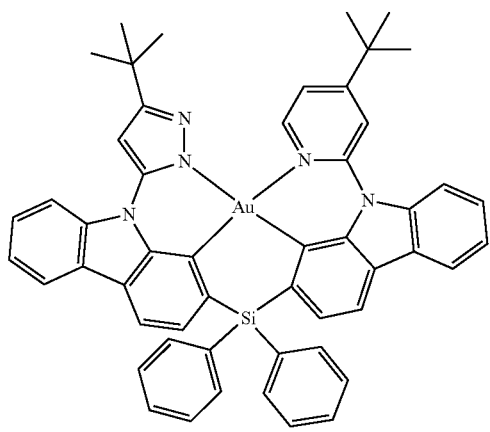
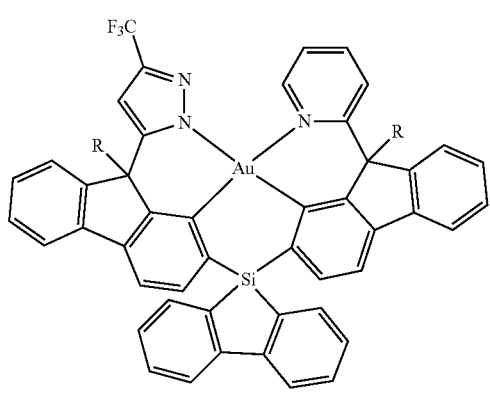
376
-continued
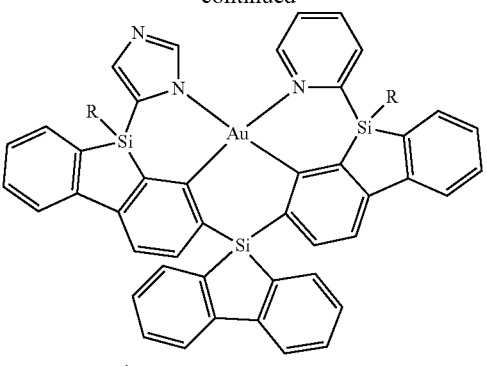
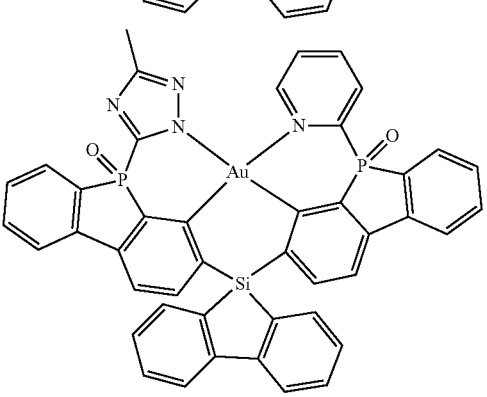
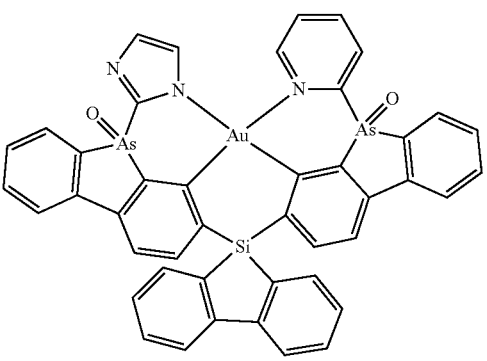
Structure Au-8
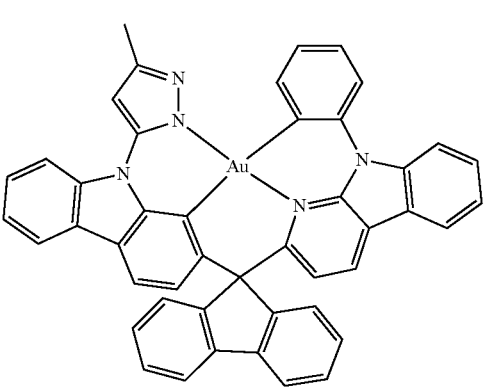

377
-continued
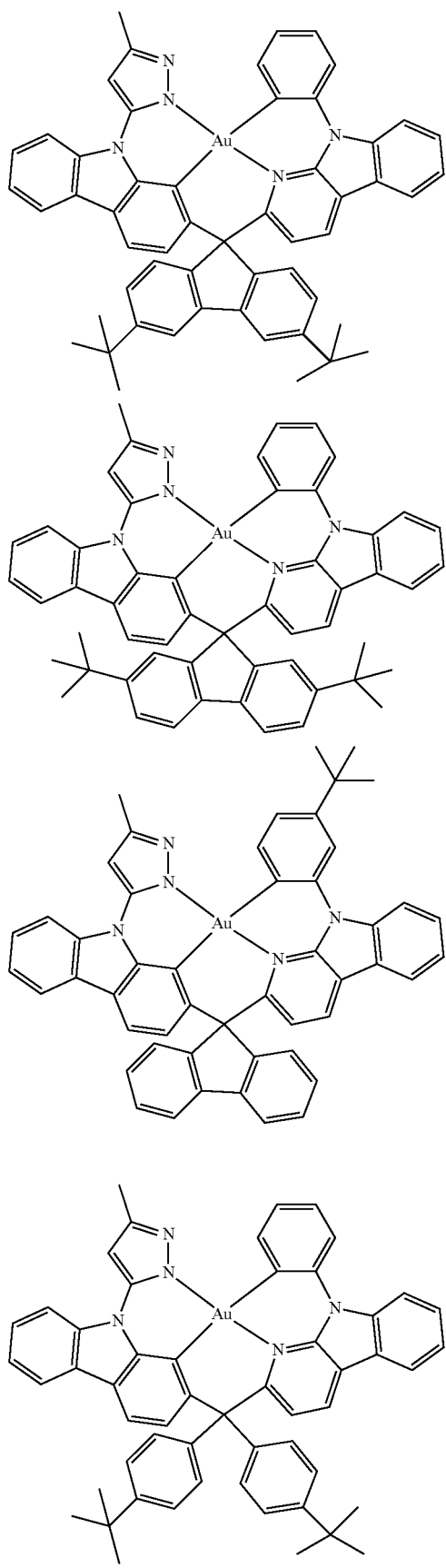
378
-continued
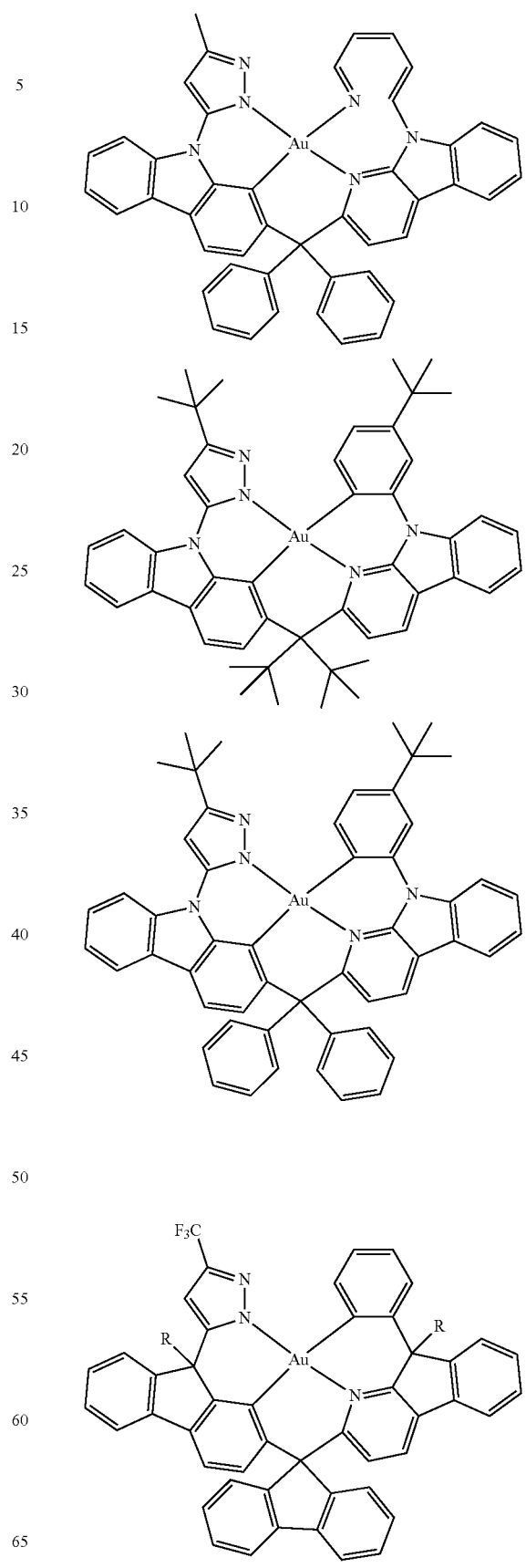

-continued
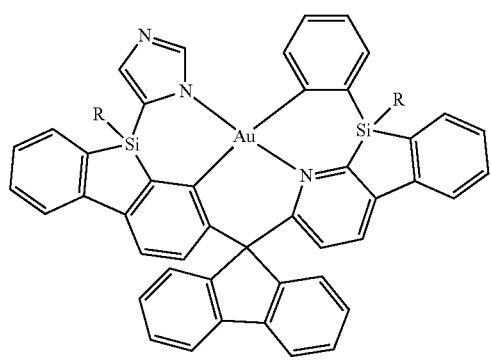
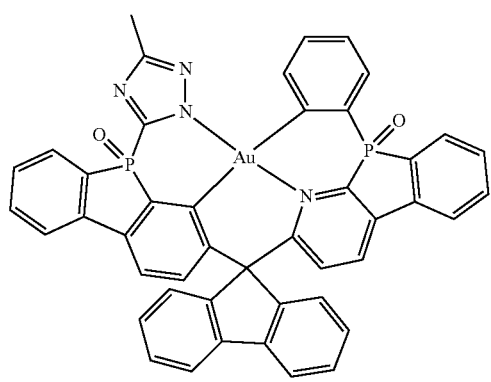
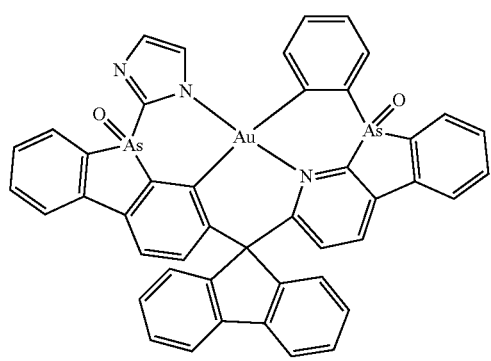
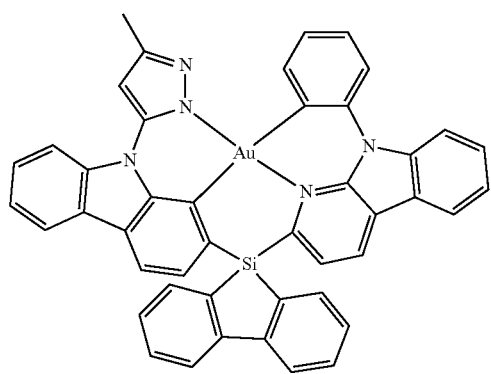
-continued
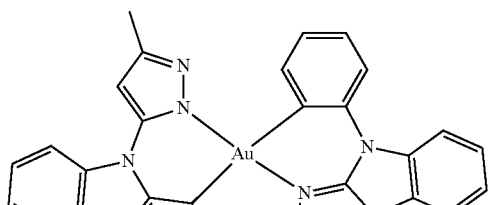
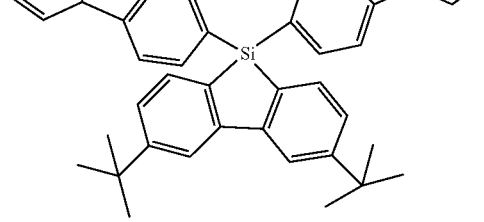
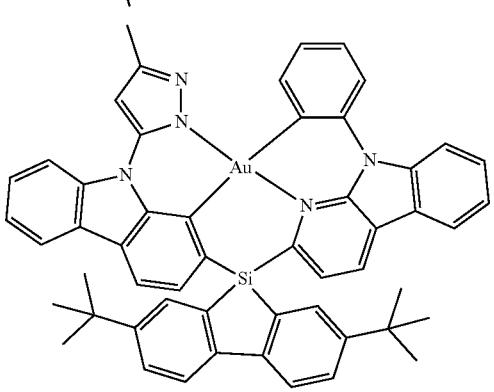
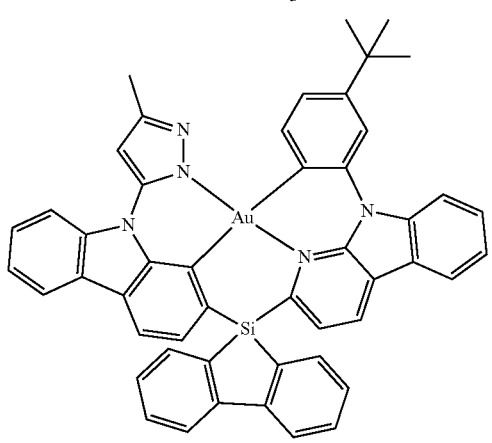
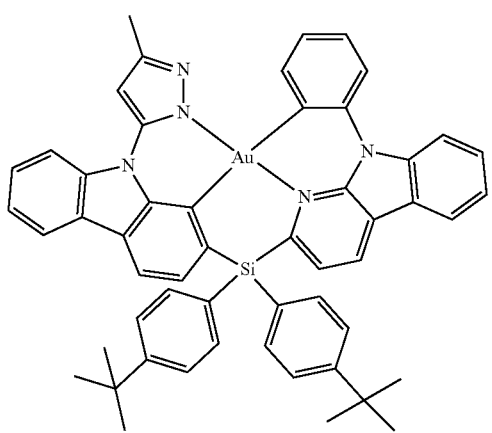

381
-continued
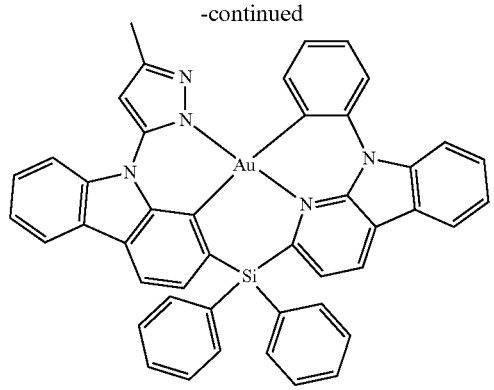
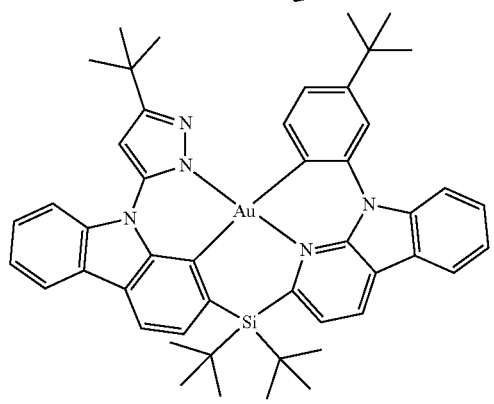
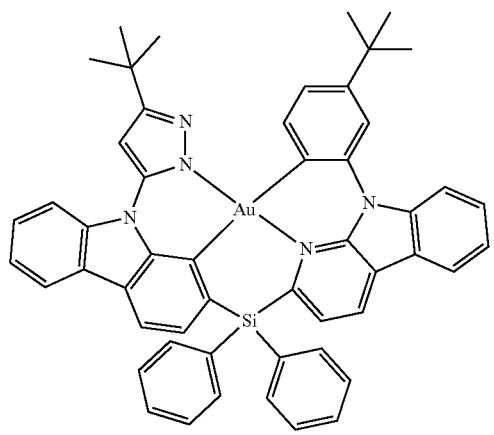
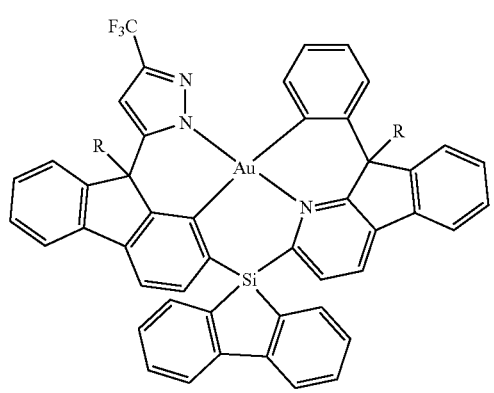
382
-continued
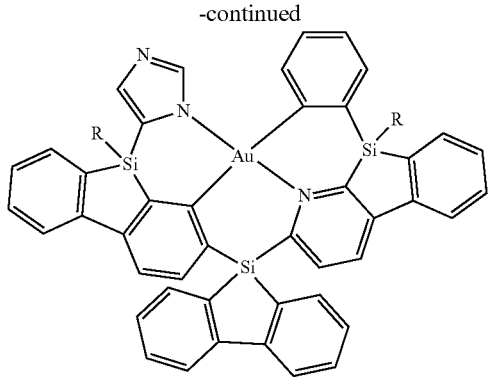
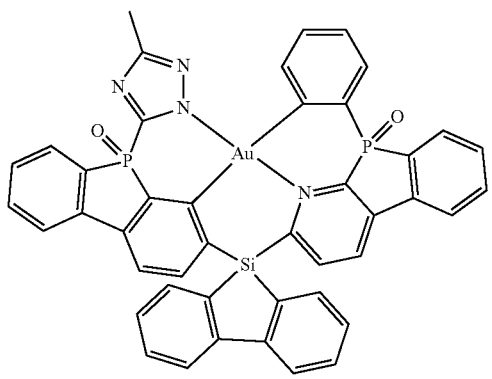
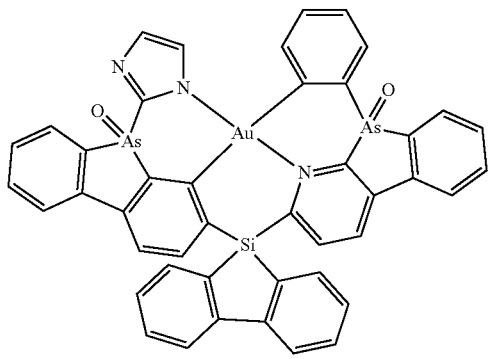
Structure Au-9
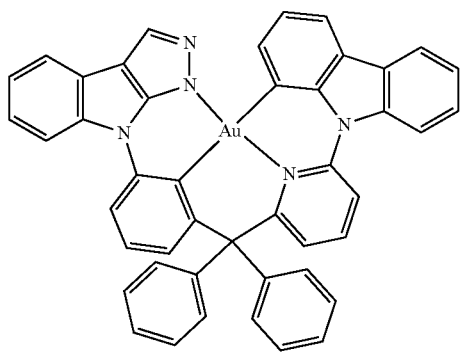

383
-continued
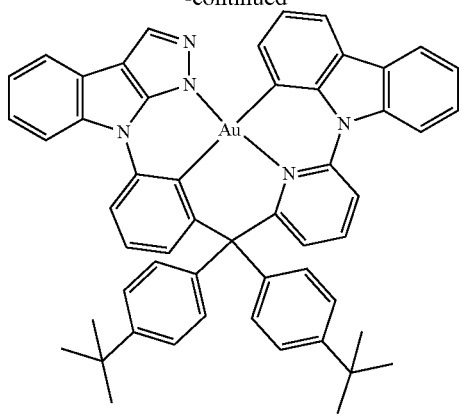
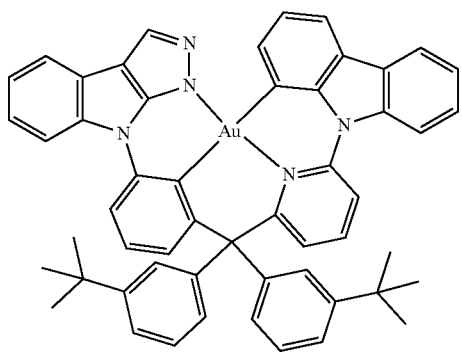
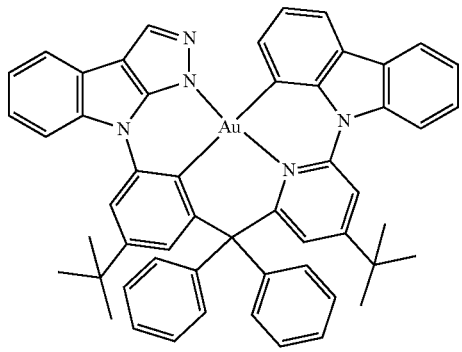
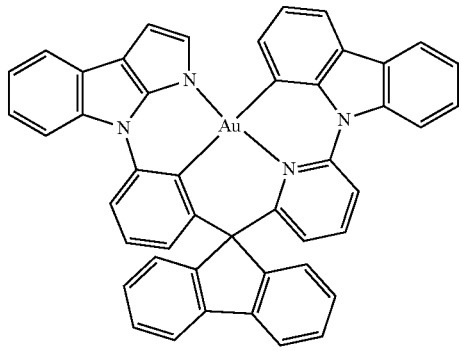
384
-continued
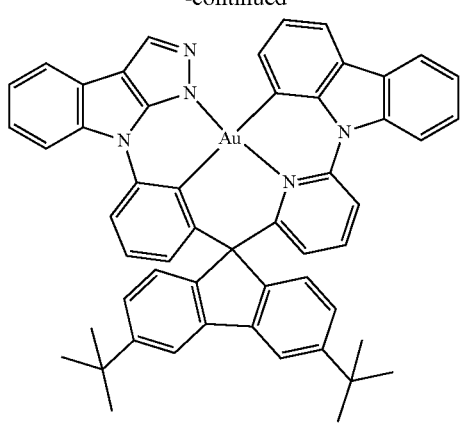
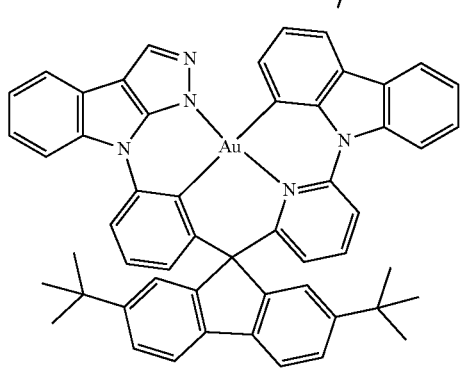
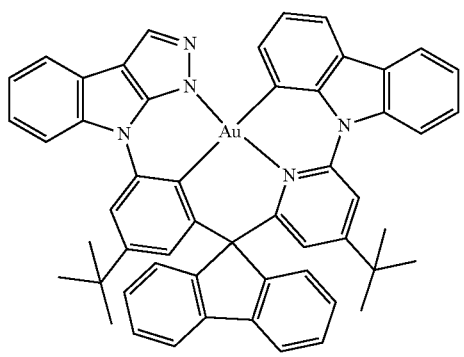
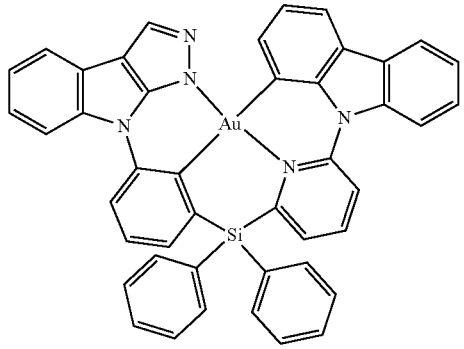

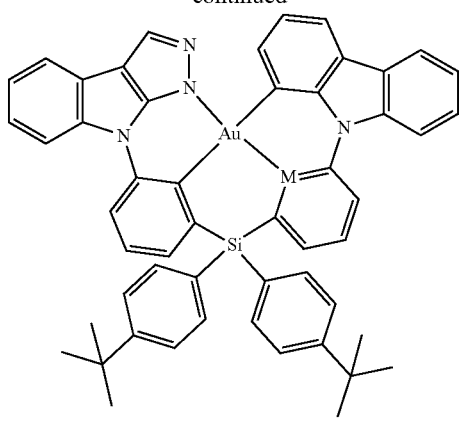
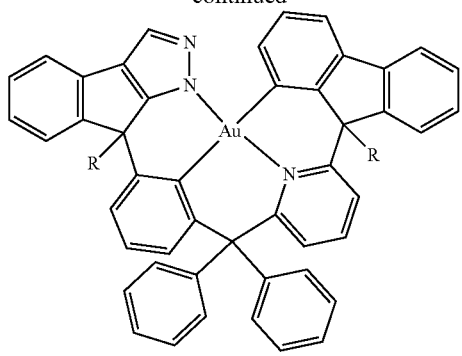
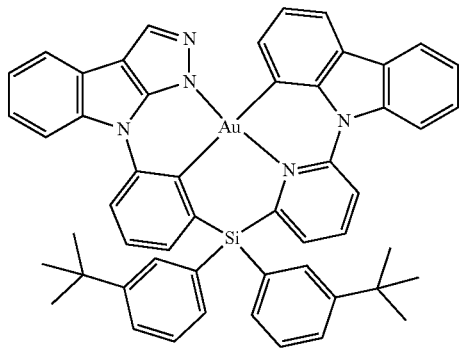
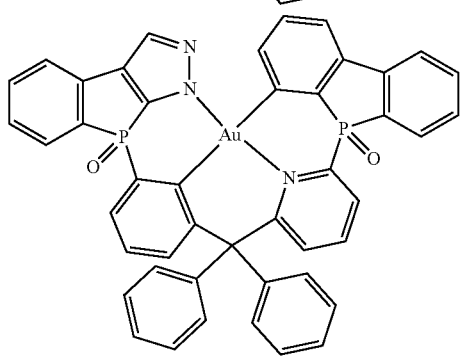
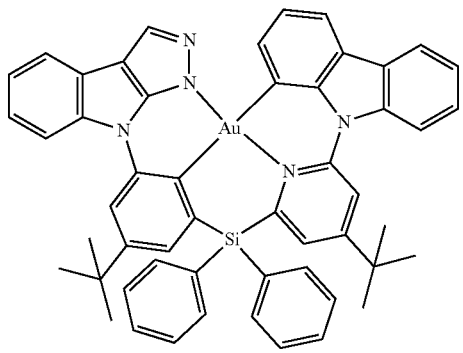
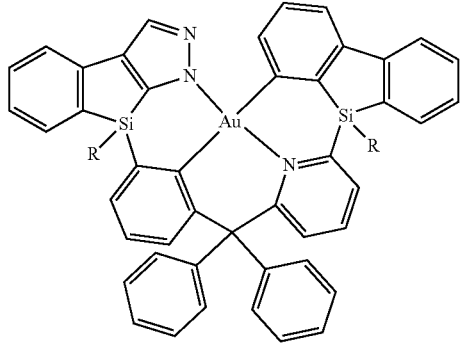
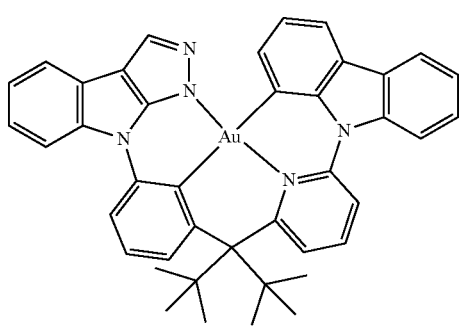
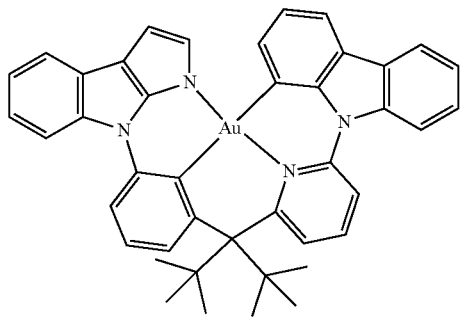
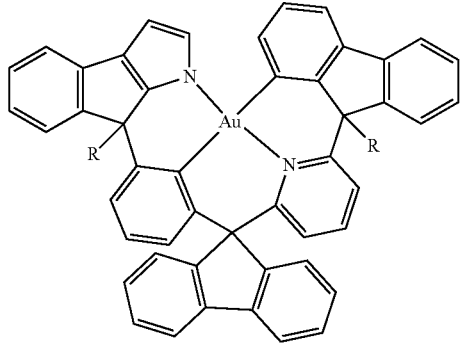

387
-continued
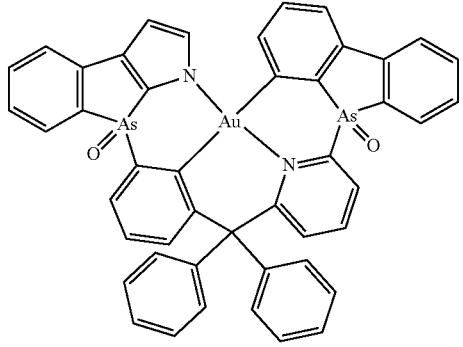
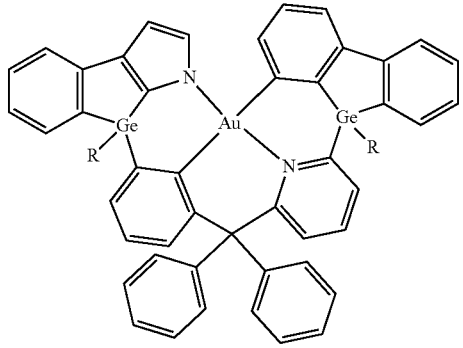
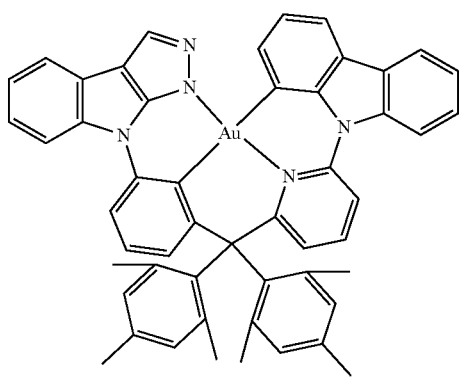
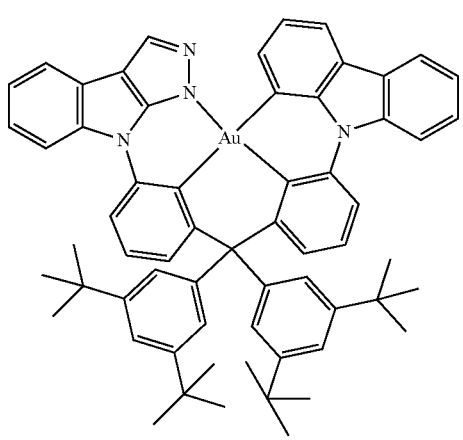
388
-continued
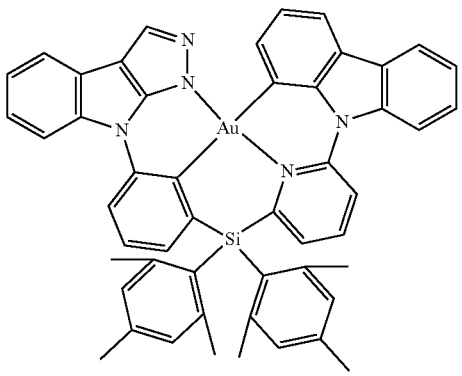
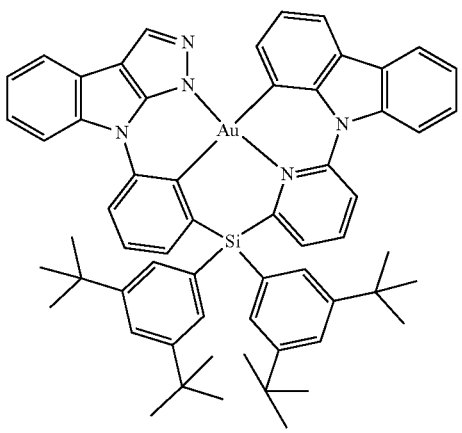
Structure Au-10
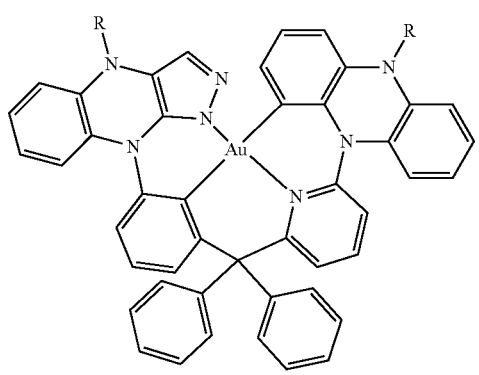
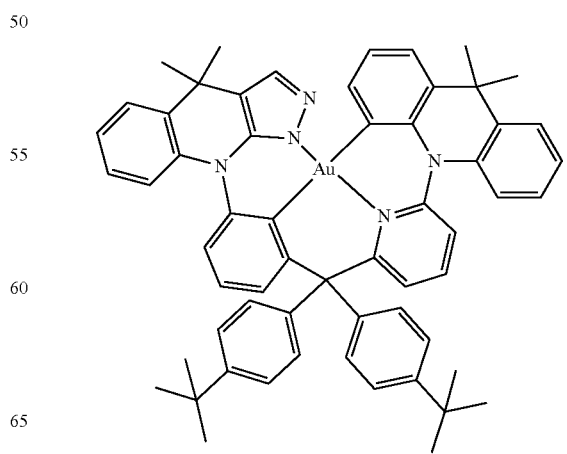

389
-continued
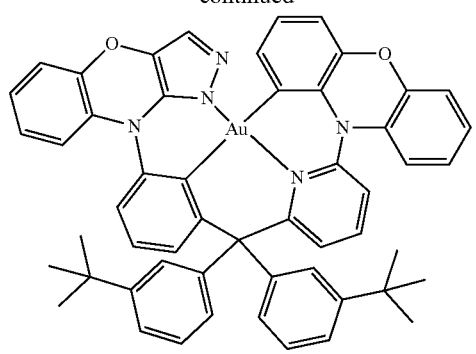
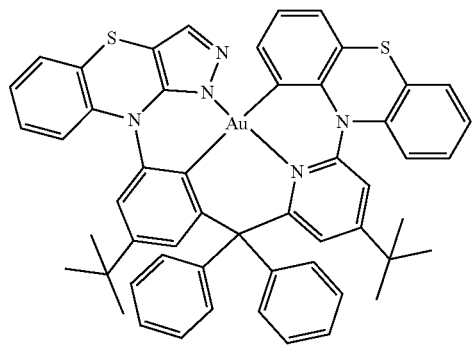
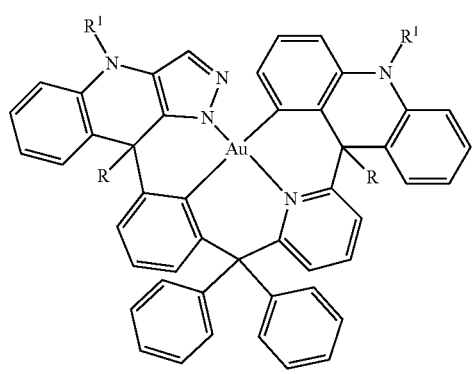
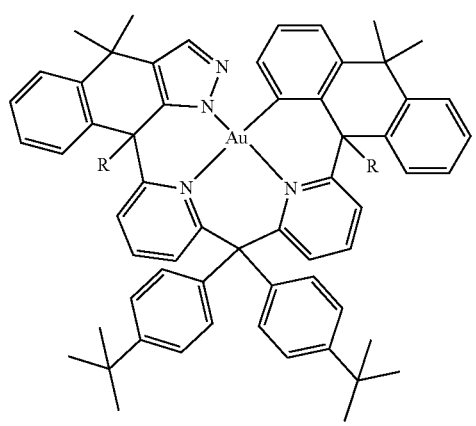
390
-continued
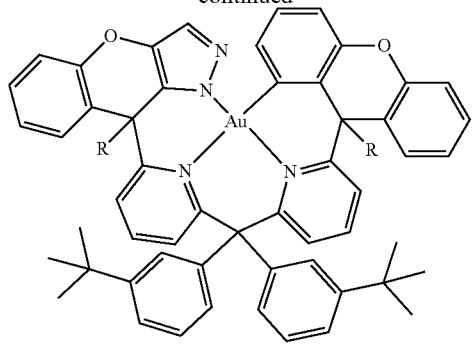
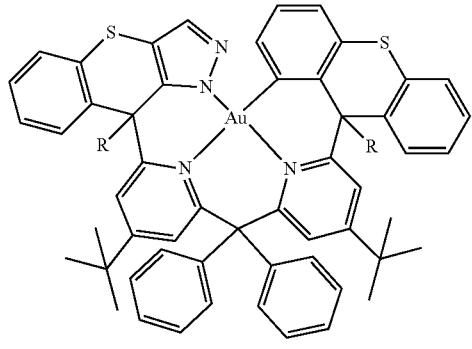
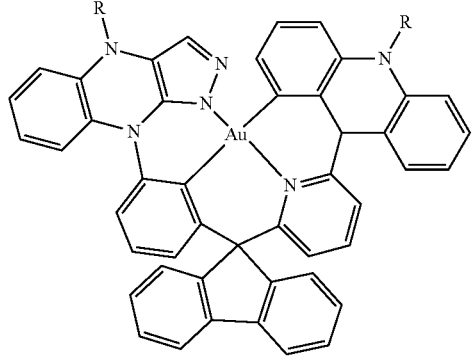
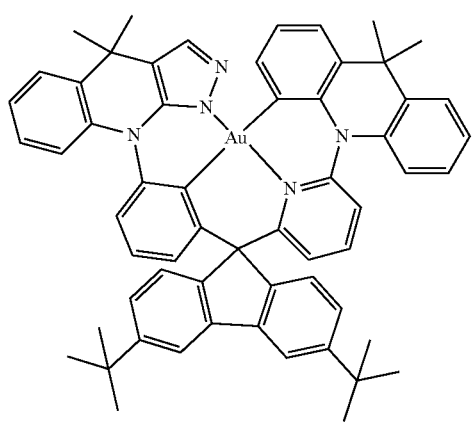

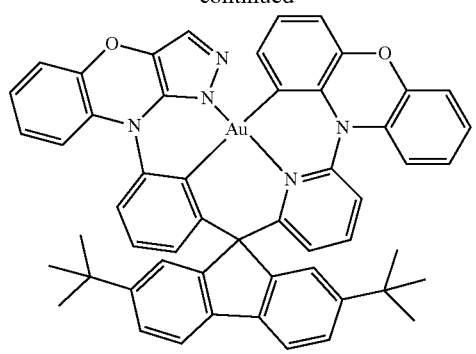
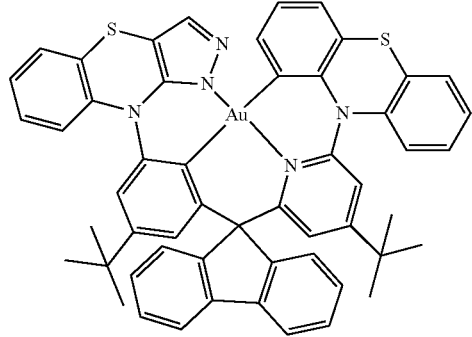
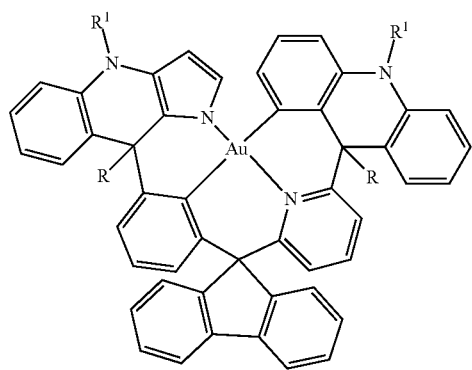
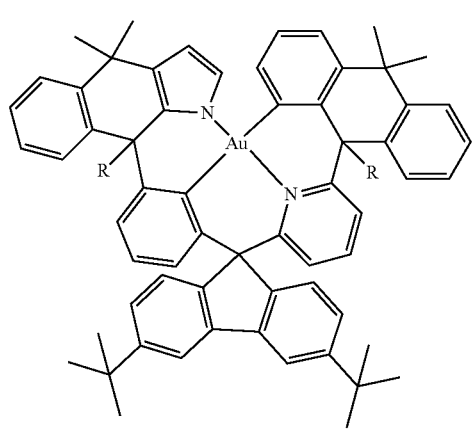
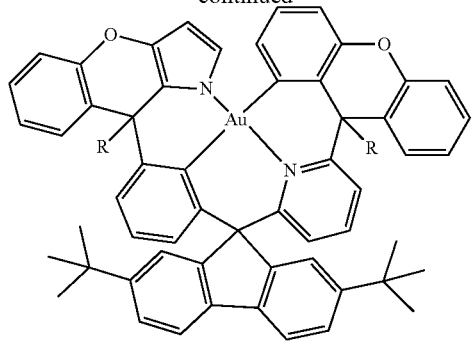
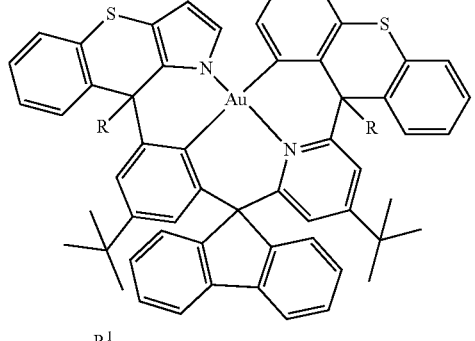
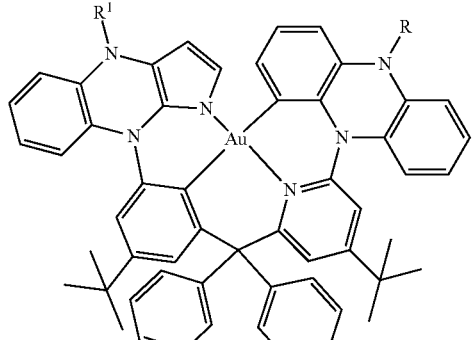
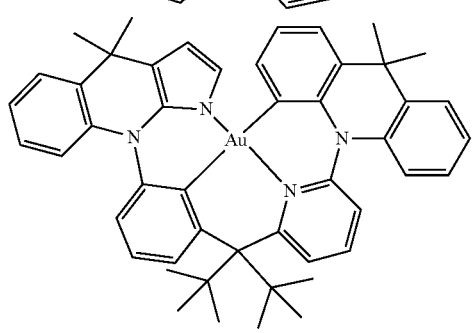
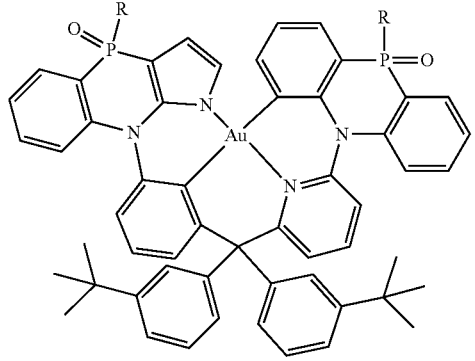

393
-continued

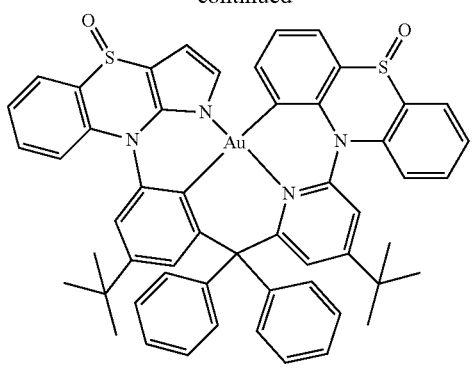

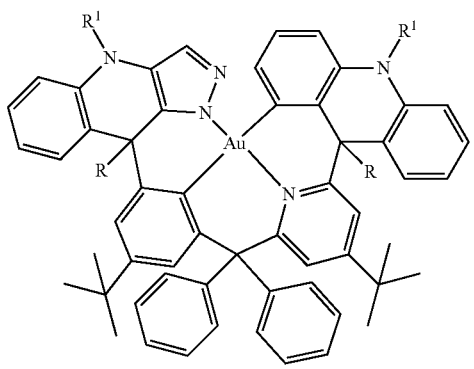

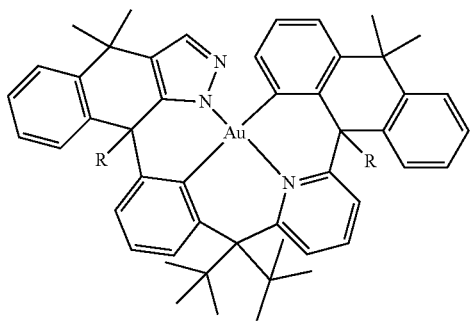

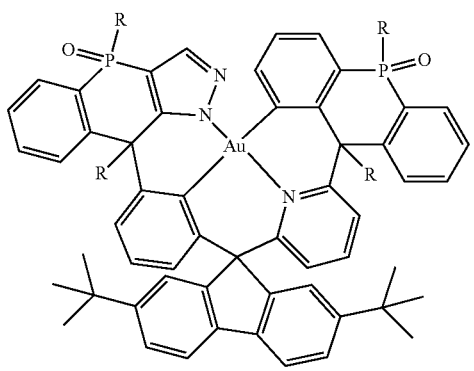

394
-continued

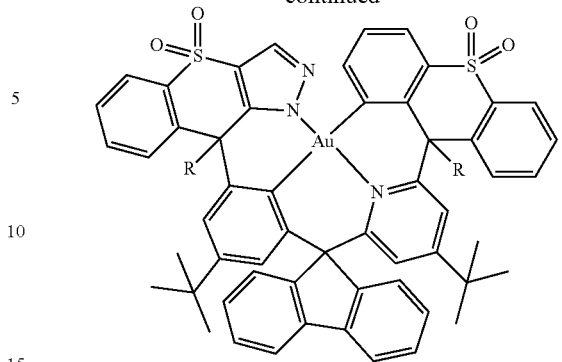

In the compounds shown in Structures Pt-1 through Structures Pt-15, Structures Pd-1 through Structures Pd-15, and Structures Au-1 through Structures Au-7, each of R, $R^1$, $R^2$, $R^3$, and $R^4$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof. In another aspect, each of R, $R^1$, $R^2$, $R^3$, and $R^4$ is independently hydrogen, halogen, hydroxyl, thiol, nitro, cyano; or substituted or unsubstituted: aryl, cycloalkyl, cycloalkenyl, heterocyclyl, heteroaryl, alkyl, alkenyl, alkynyl, or amino. In another aspect, each of R, $R^1$, $R^2$, $R^3$, and $R^4$ is independently hydrogen or substituted or unsubstituted: aryl, cycloalkyl, cycloalkenyl, heterocyclyl, heteroaryl, alkyl, alkenyl, or alkynyl.

2. Devices

Also disclosed herein are devices including one or more of the compounds disclosed herein.

The compounds disclosed herein are suited for use in a wide variety of devices, including, for example, optical and electro-optical devices, including, for example, photo-absorbing devices such as solar- and photo-sensitive devices, organic light emitting diodes (OLEDs), photo-emitting devices, or devices capable of both photo-absorption and emission and as markers for bio-applications.

Compounds described herein can be used in a light emitting device such as an OLED. FIG. 1 depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 1 may include indium tin oxide (ITO), poly(3,4-ethylenedioxythiophene) (PEDOT), polystyrene sulfonate (PSS), N,N'-di-1-naphthyl-N,N-diphenyl-1,1'-biphenyl-4,4'diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds, the host material, or both. Both the hole-transporting material in the HTL layer 106 and the electron-transporting material(s) in the ETL layer 110 may include any suitable hole-transporter known in the art.

Compounds described herein may exhibit phosphorescence. Phosphorescent OLEDs (i.e., OLEDs with phosphorescent emitters) typically have higher device efficiencies than other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to be limiting in scope. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation of the compounds described herein are recited in the examples. These methods are provided to illustrate various methods of preparation, but are not intended to limit any of the methods recited herein. Accordingly, one of skill in the art in possession of this disclosure could readily modify a recited method or utilize a different method to prepare one or more of the compounds described herein. The following aspects are only exemplary and are not intended to be limiting in scope. Temperatures, catalysts, concentrations, reactant compositions, and other process conditions can vary, and one of skill in the art, in possession of this disclosure, could readily select appropriate reactants and conditions for a desired complex.

$^1$H spectra were recorded at 400 MHz, $^{13}$C NMR spectra were recorded at 100 MHz on Varian Liquid-State NMR instruments in CDCl$_3$ or DMSO-d$_6$ solutions and chemical shifts were referenced to residual protiated solvent. If CDCl$_3$ was used as solvent, $^1$H NMR spectra were recorded with tetramethylsilane (δ=0.00 ppm) as internal reference; $^{13}$C NMR spectra were recorded with CDCl$_3$ (δ=77.00 ppm) as internal reference. If DMSO-d$_6$ was used as solvent, $^1$H NMR spectra were recorded with residual H$_2$O (δ=3.33 ppm) as internal reference; $^{13}$C NMR spectra were recorded with DMSO-d$_6$ (δ=39.52 ppm) as internal reference. The following abbreviations (or combinations thereof) were used to explain $^1$H NMR multiplicities: s=singlet, d=doublet, t=triplet, q=quartet, p=quintet, m=multiplet, br=broad.

General Synthetic Routes

A synthetic route for L$^1$-L$^2$ fragments disclosed herein includes:

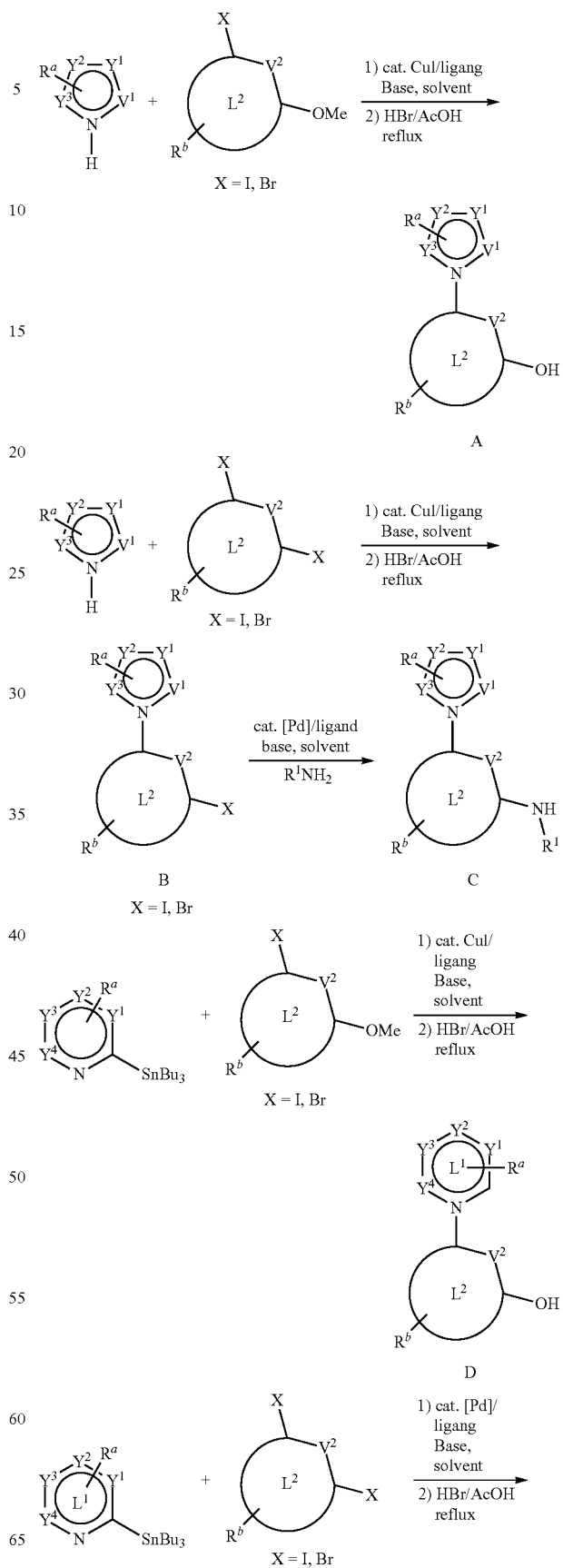

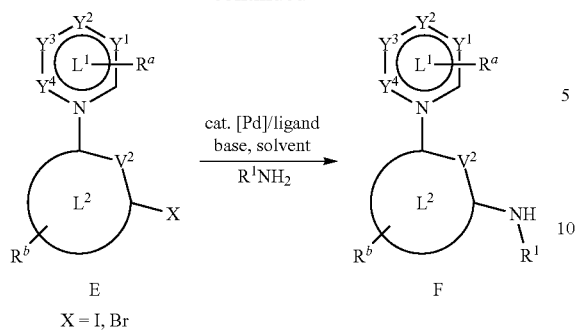
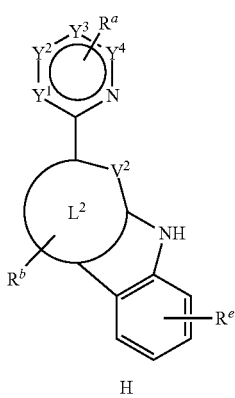
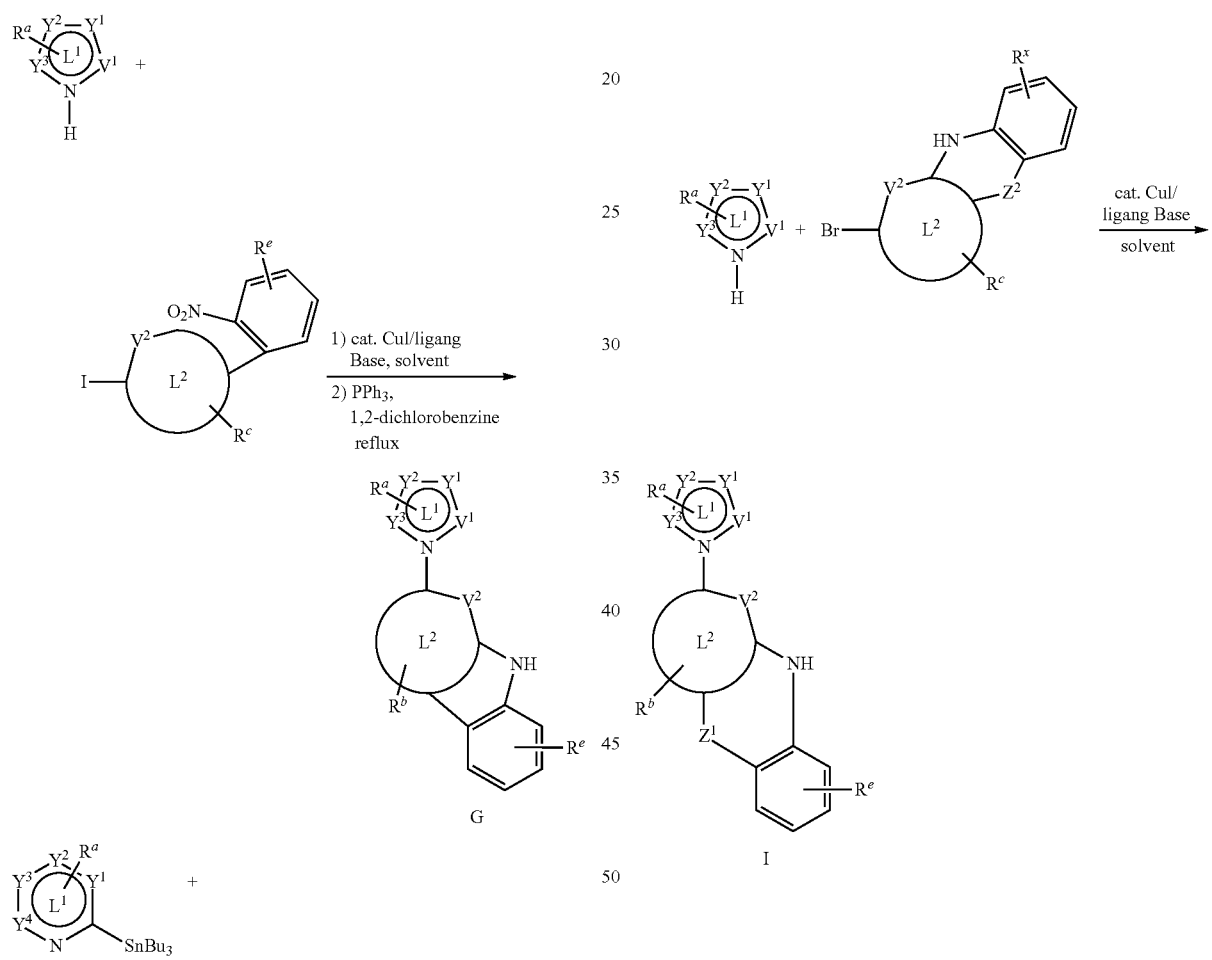
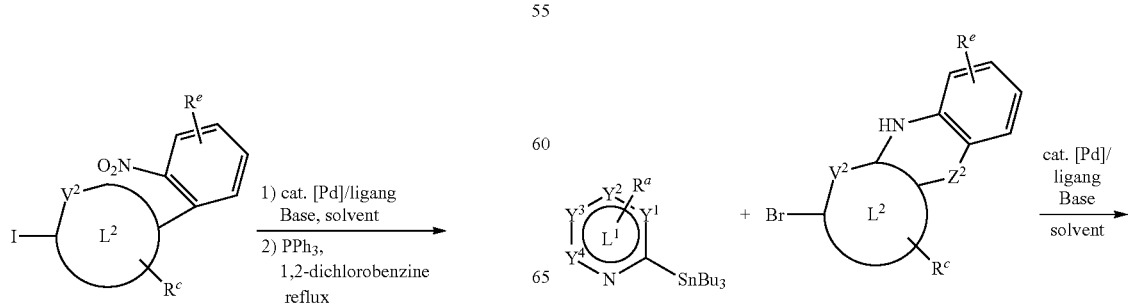

-continued
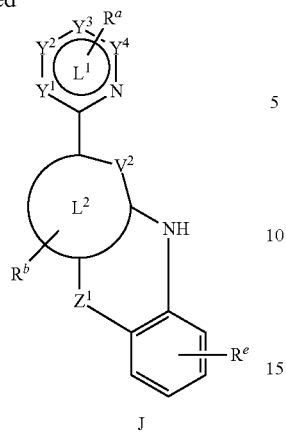
wherein each of $Y^1$, $Y^2$, $Y^3$, and $Y^4$ is independently C, N, O, or S.
A general synthesis route for the $L^3$-$L^4$ fragments disclosed herein includes:
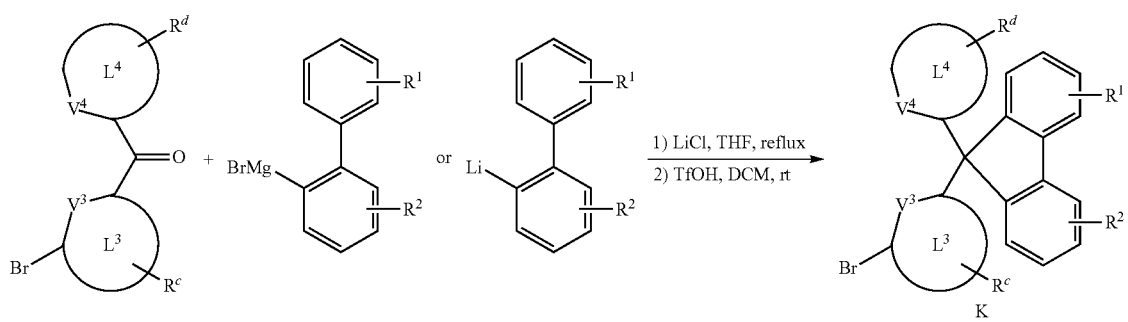
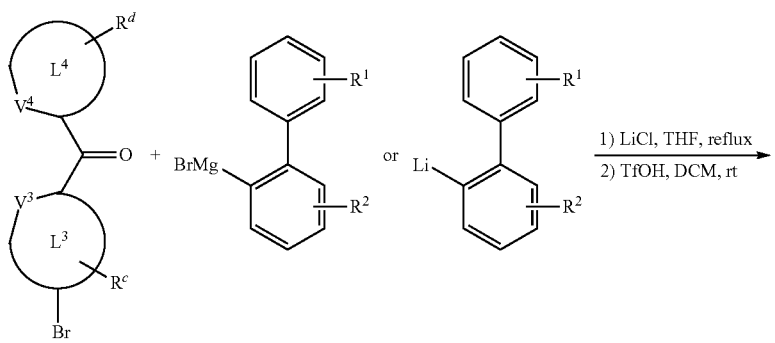

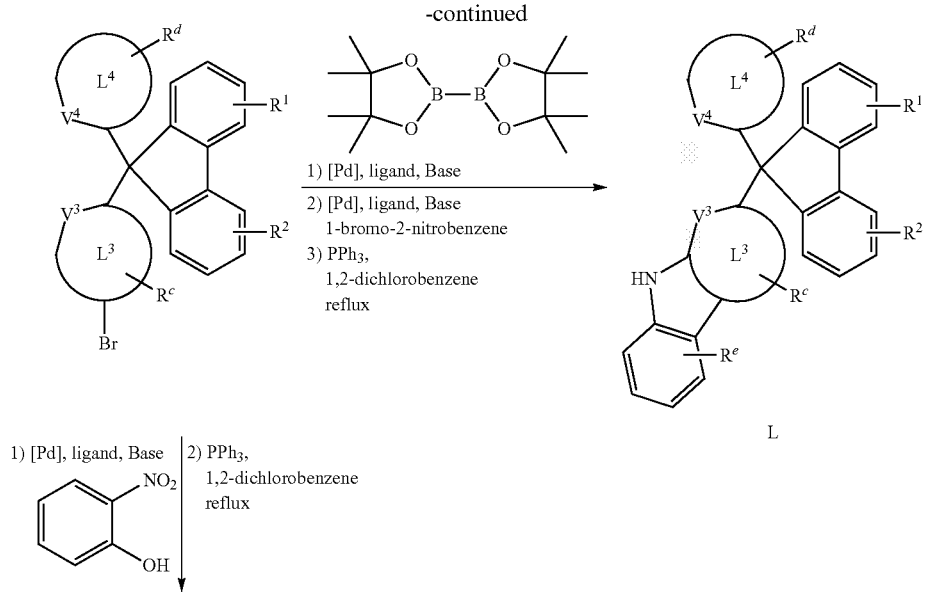
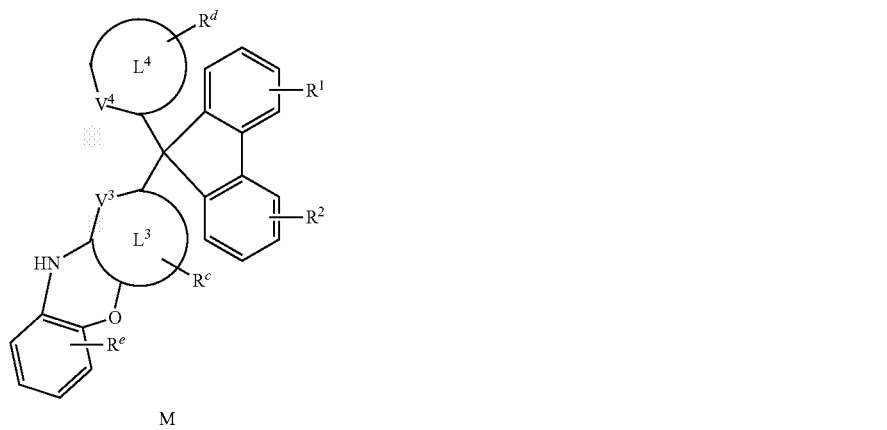
A general synthesis route for the ligands herein includes:
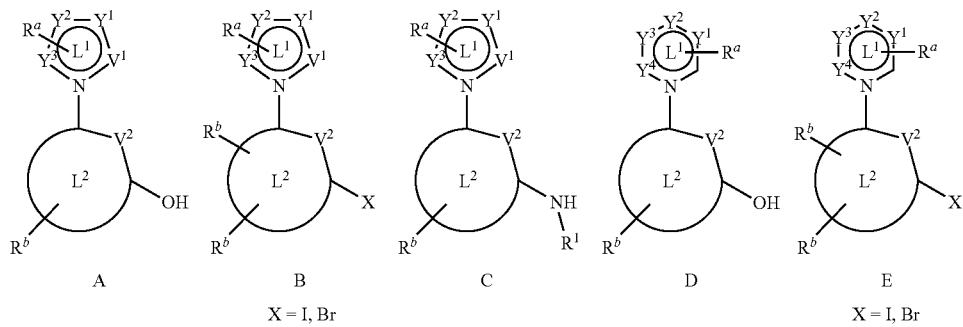

-continued
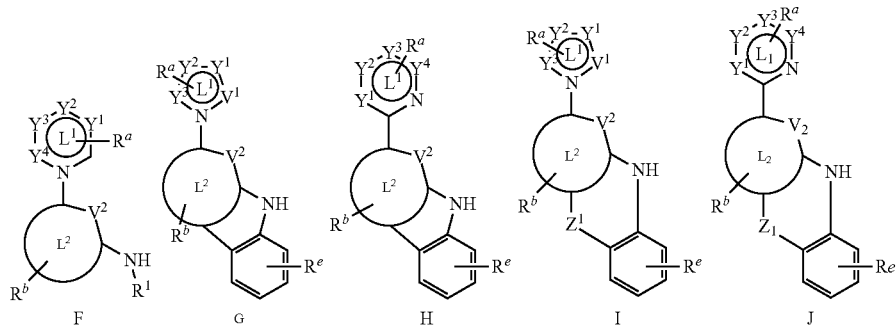
F  G  H  I  J
+
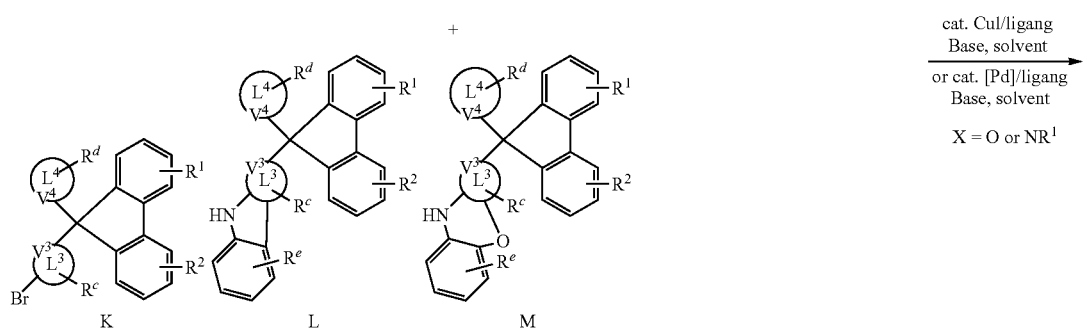
K  L  M
cat. CuI/ligang
Base, solvent
or cat. [Pd]/ligang
Base, solvent
X = O or NR¹
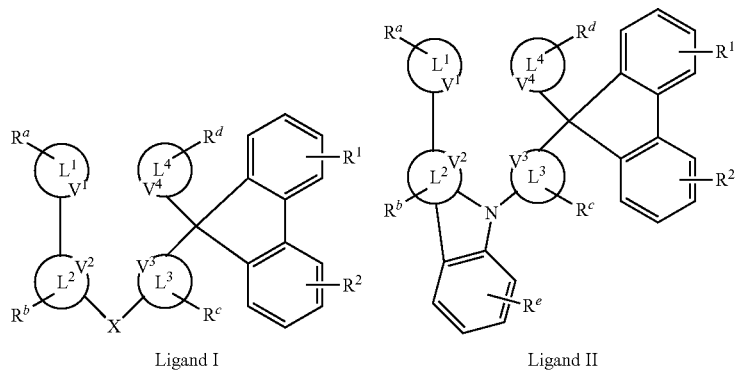
Ligand I          Ligand II
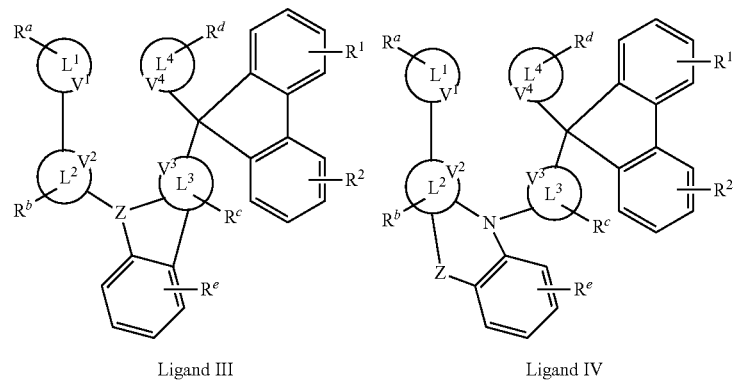
Ligand III        Ligand IV

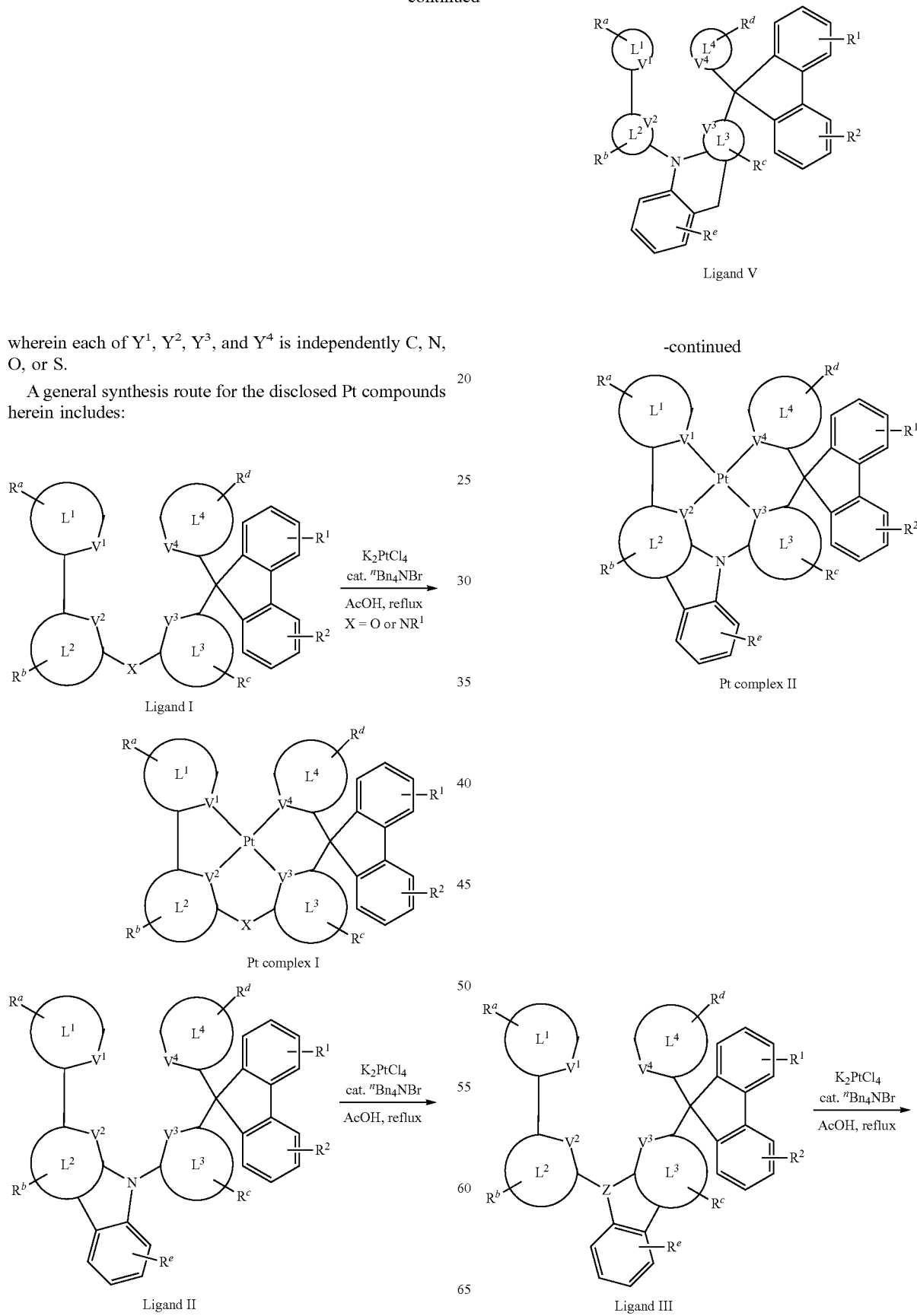
wherein each of $Y^1$, $Y^2$, $Y^3$, and $Y^4$ is independently C, N, O, or S.
A general synthesis route for the disclosed Pt compounds herein includes:

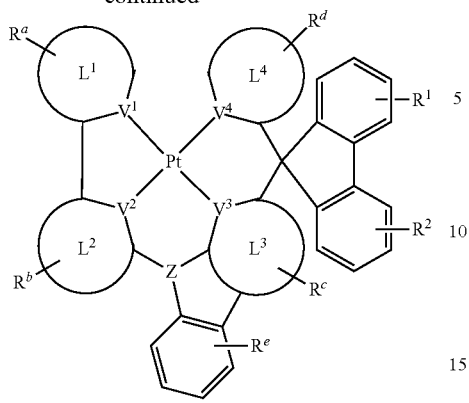
Pt complex III
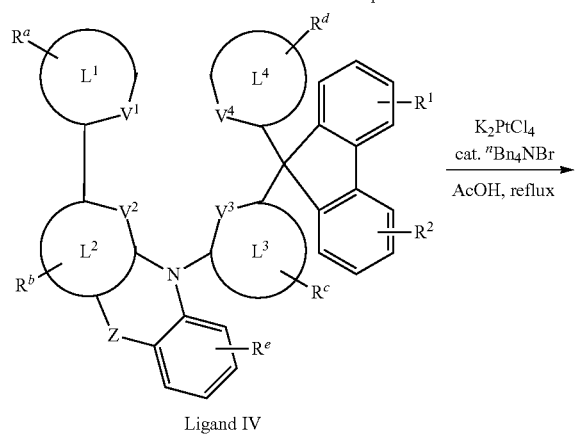
Ligand IV
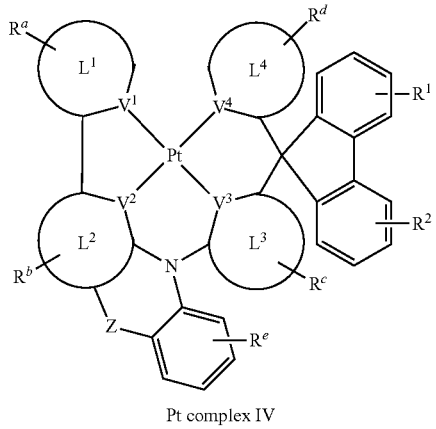
Pt complex IV
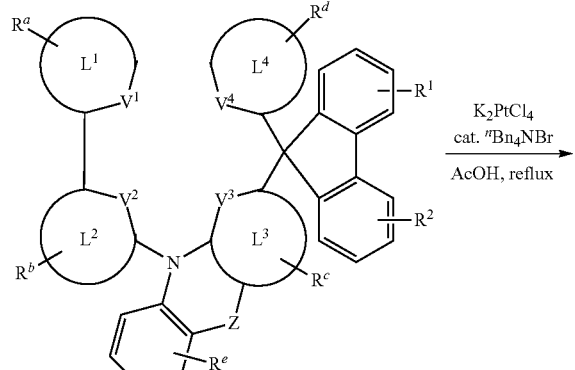
Ligand V
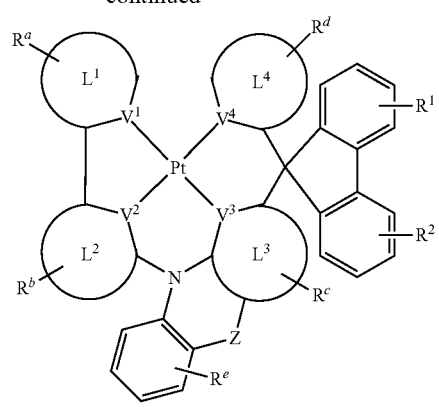
Pt complex V
A general synthesis route for the disclosed Pd compounds herein includes:
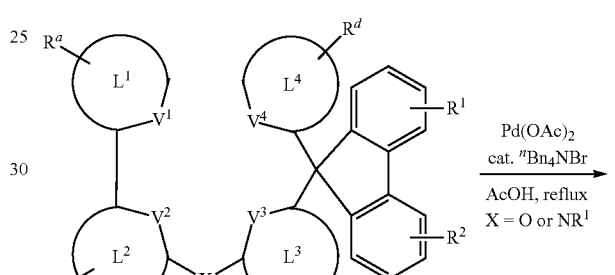
Ligand I
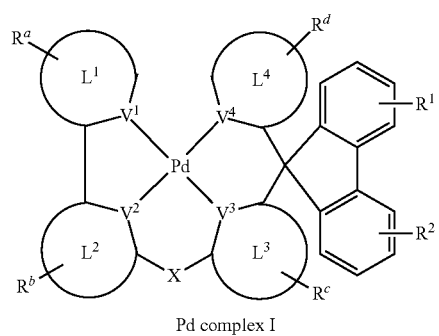
Pd complex I
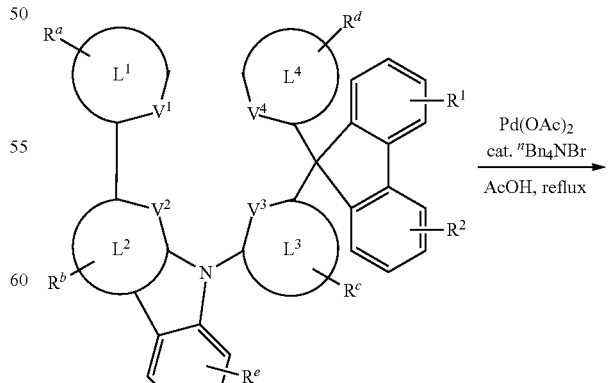
Ligand II

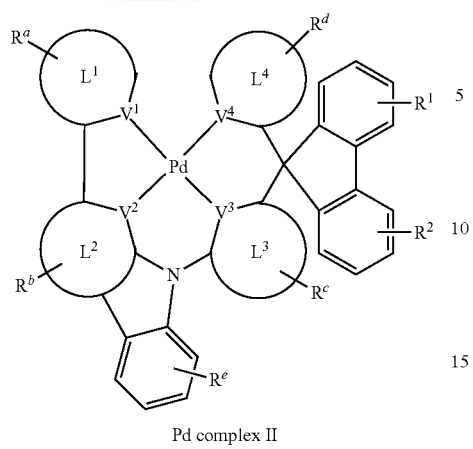
Pd complex II
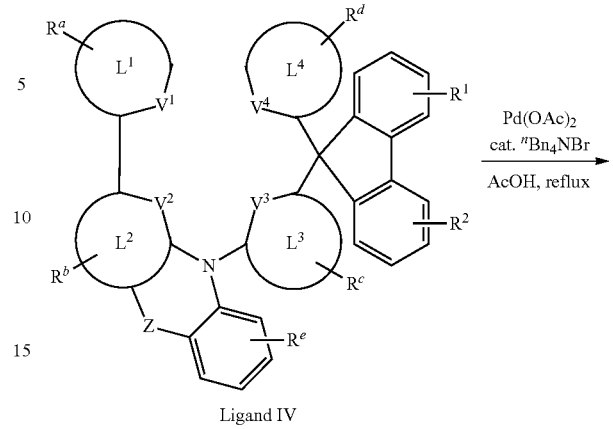
Ligand IV
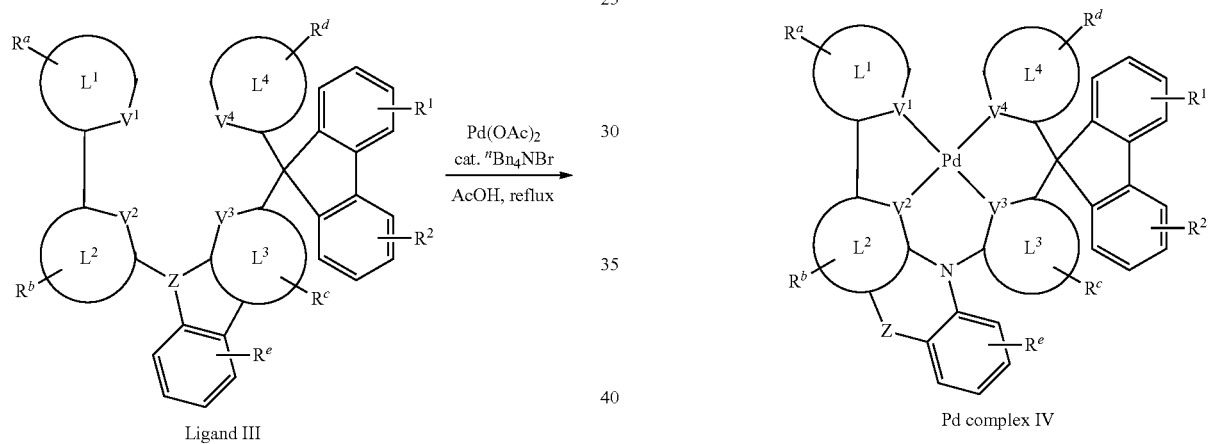
Ligand III
Pd complex IV
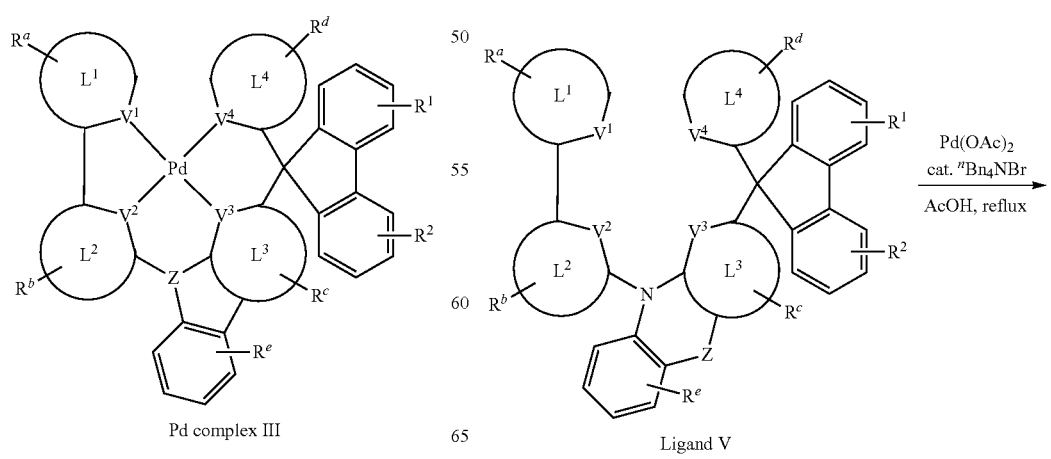
Pd complex III
Ligand V

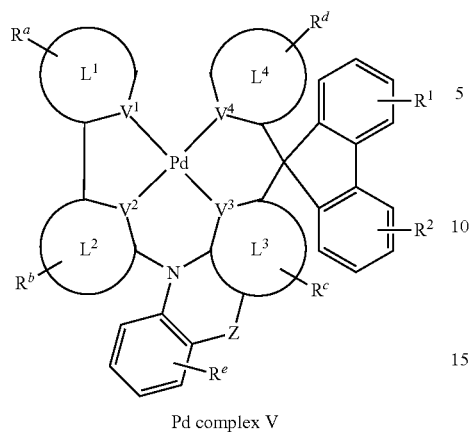
Pd complex V
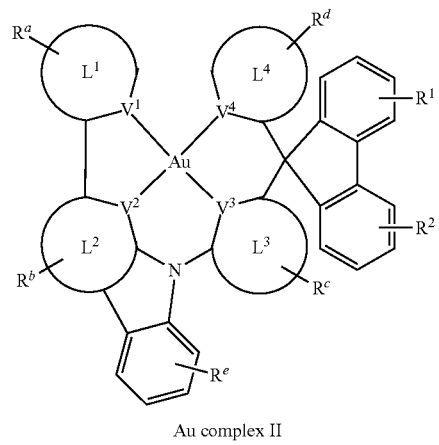
Au complex II
A general synthesis route for the disclosed Au compounds herein includes:
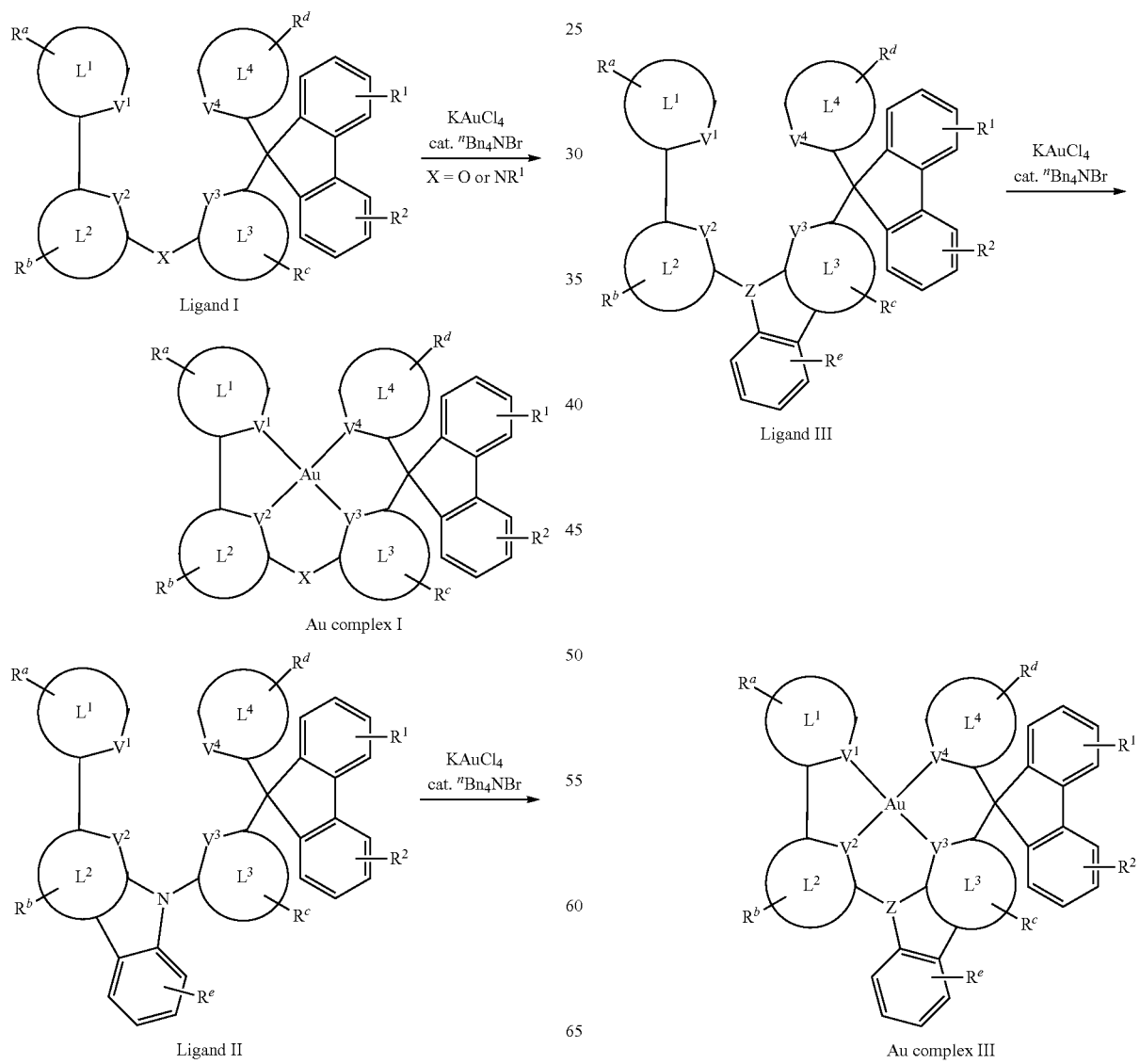

413
-continued
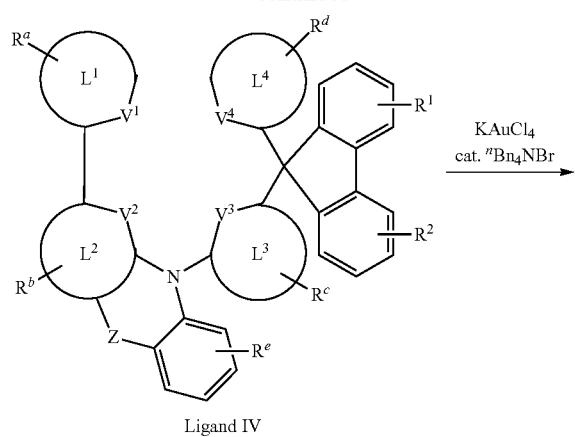
Ligand IV
KAuCl₄
cat. ⁿBn₄NBr
→
414
-continued
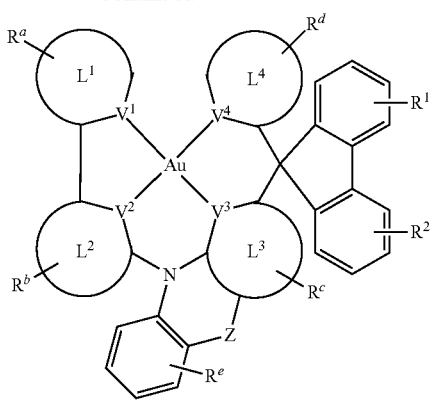
Au complex V
1. Example 1
Platinum complex PtN1C was prepared according to the following scheme:
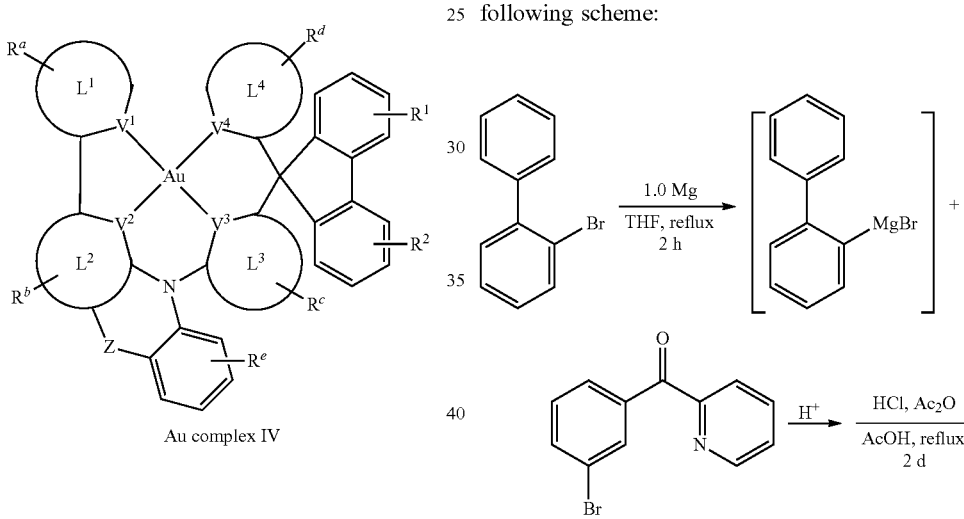
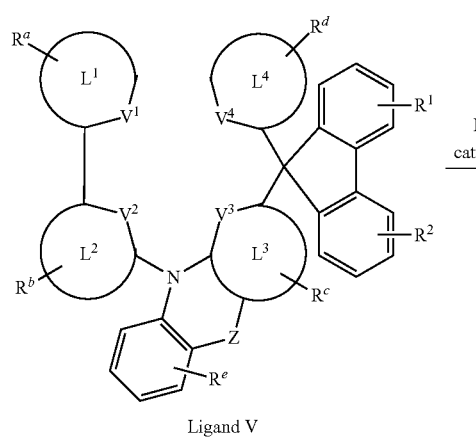
Ligand V
KAuCl₄
cat. ⁿBn₄NBr
→
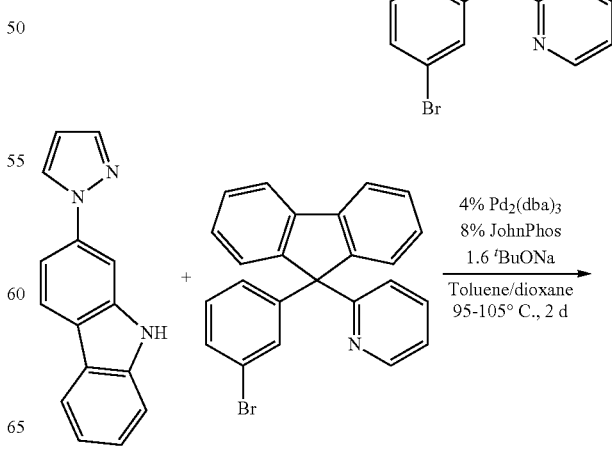
4% Pd₂(dba)₃
8% JohnPhos
1.6 ᵗBuONa
Toluene/dioxane
95-105° C., 2 d
→

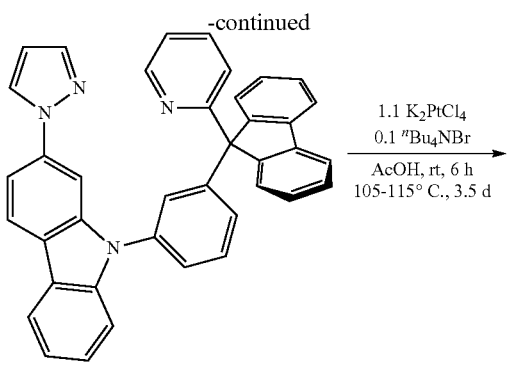

Ligand N1C

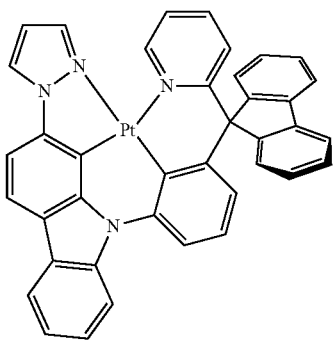

PtN1C

Synthesis of 2-(9-(3-bromophenyl)-9H-fluoren-9-yl)pyridine

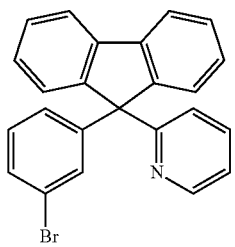 [SMILES: Brc1cccc(C2(c3ccccn3)c3ccccc3-c3ccccc32)c1]

2-(9-(3-bromophenyl)-9H-fluoren-9-yl)pyridine

2-Bromobiphenyl (1.38 mL, 8 mmol, 1.2 eq) was added to a mixture of Mg (192 mg, 8 mmol, 1.2 eq) in dry THF (20 mL) under an atmosphere of nitrogen. Then the mixture refluxed for about 2 hours until the Mg disappeared, and cooled down to ambient temperature. Then (3-bromophenyl)(pyridin-2-yl)methanone (1.75 g, 6.67 mmol, 1.0 eq) was added, and the mixture refluxed for 2 days then cooled down to ambient temperature and quenched by NH$_4$Cl solution. The organic layer was separated and the aqueous layer was extracted by ethyl acetate. The combient organic layer was dried over sodium sulphate and filtered, and the filtrate was concentrated under reduced pressure to get the residue which was used directly for the next step. Ac$_2$O (1 mL) and concentrated HCl (1 mL) were added to a solution of the residue in AcOH (25 mL), and the mixture refluxed for 2 days. After removing the solvent, the residue was diluted with ethyl acetate and washed with Na$_2$CO$_3$ solution. The organic layer was separated and dried over sodium sulfate, and filtered and washed with ethyl acetate. The filtrate was concentrated and the residue was purified through column chromatography on silica gel using hexane and ethyl acetate (10:1-5:1) as eluent to obtain 1.85 g of the desired product in 70% yield. $^1$H NMR (CDCl$_3$, 400 MHz): δ 6.97 (dd, J=6.0, 1.6 Hz, 1H), 7.00 (d, J=8.0 Hz, 1H), 7.07 (t, J=8.0 Hz, 1H), 7.12-7.17 (m, 2H), 7.28-7.32 (m, 3H), 7.40 (td, J=7.6, 1.2 Hz, 2H), 7.46 (td, J=8.0, 2.0 Hz, 1H), 7.56 (d, J=7.6 Hz, 2H), 7.78 (d, J=7.6 Hz, 2H), 8.66-8.68 (m, 1H).

Synthesis of 2-(1H-pyrazol-1-yl)-9-(3-(9-(pyridin-2-yl)-9H-fluoren-9-yl)phenyl)-9H-carbazole Ligand N1C

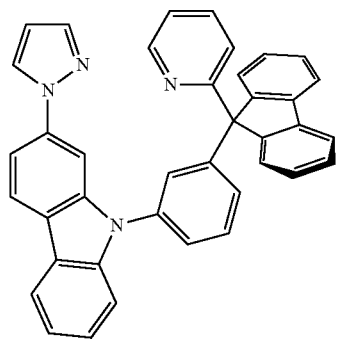

Ligand N1C 2-(9-(3-bromophenyl)-9H-fluoren-9-yl)pyridine (478 mg, 1.2 mmol, 1.2 eq), 2-(1H-pyrazol-1-yl)-9H-carbazole (233 mg, 1.0 mmol, 1.0 eq), Pd$_2$(dba)$_3$ (37 mg, 0.04 mmol, 0.04 eq), JohnPhos (24 mg, 0.08 mmol, 0.08 eq) and $^t$BuONa (154 mg, 1.6 mmol, 1.6 eq) were added to a dry pressure tube equipped with a magnetic stir bar. The tube was evacuated and backfilled with nitrogen, this evacuation and backfill procedure was repeated twice. Then solvent toluene (4 mL) and dioxane (4 mL) were added under nitrogen. The mixture was stirred at 95-105° C. in an oil bath for 2 days and cooled to ambient temperature. The solvent was evaporated under reduced pressure and the residue was purified through column chromatography on silica gel using hexane and ethyl acetate (10:1-5:1-3:1) as eluent to obtain the desired product Ligand N1C as 520 mg of a grey solid in 94% yield.

Synthesis of platinum(II) complex PtN1C

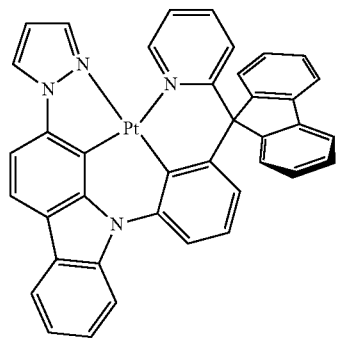

Figure 2:
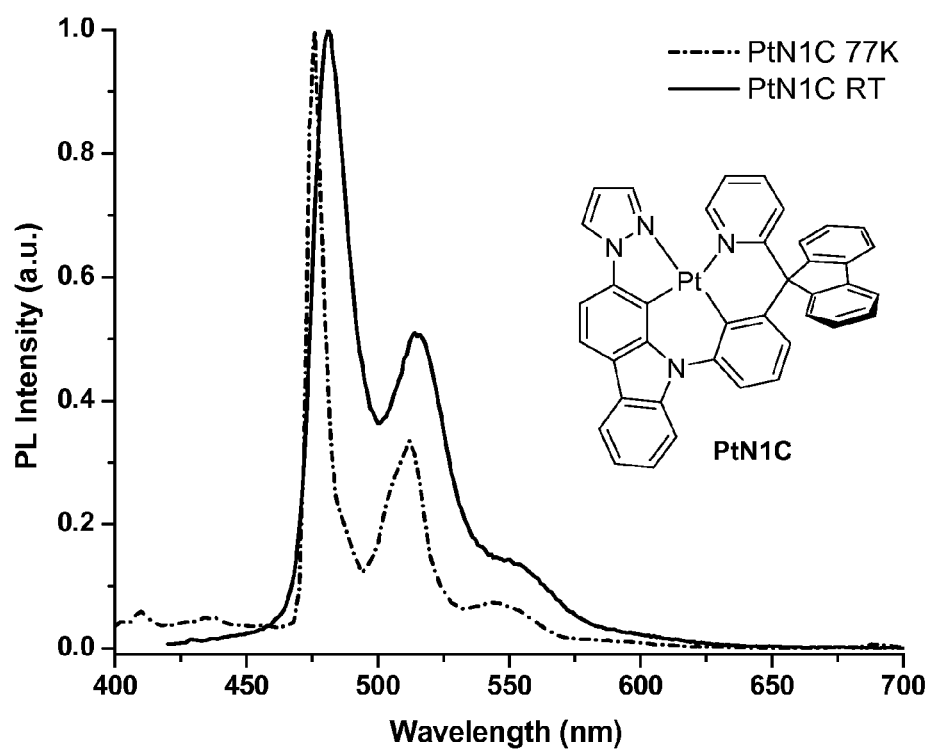
FIG. 2 shows emission spectra of PtN1C in $CH_2Cl_2$ at room temperature and in 2-methyltetrahydrofuran at 77K.

PtN1C 2-(1H-pyrazol-1-yl)-9-(3-(9-(pyridin-2-yl)-9H-fluoren-9-yl)phenyl)-9H-carbazole Ligand N1C (510 mg, 0.92 mmol, 1.0 eq), $K_2PtCl_4$ (427 mg, 1.02 mmol, 1.1 eq) and $^nBu_4NBr$ (30 mg, 0.092 mmol, 0.1 eq) were added to a three-neck flask equipped with a magnetic stir bar and a condenser. Then the flask was evacuated and backfilled with nitrogen, and this evacuation and back-fill procedure was repeated twice. Then solvent acetic acid (55 mL) was added under nitrogen atmosphere. The mixture was bubbled with nitrogen for 30 minutes, stirred at room temperature for 6 hours, followed at 105-115° C. in an oil bath for another 3.5 days, and cooled down to ambient temperature. Water (110 mL) was added slowly. After stirring at room temperature for 10 minutes, the precipitate was filtered off and washed with water three times. Then the solid was dried in air under reduced pressure. The collected solid was purified through column chromatography on silica gel using dichloromethane/hexane (1:1) first, then dichloromethane as eluent to obtain the desired product PtN1C as a yellow solid in low yield. $^1$H NMR (CDCl$_3$, 400 MHz): δ 6.46 (dd, J=8.0, 0.8 Hz, 1H), 6.61 (t, J=2.0 Hz, 1H), 6.81 (t, J=8.0 Hz, 1H), 6.96 (d, J=8.8 Hz, 1H), 7.20-7.29 (m, 3H), 7.34-7.46 (m, 6H), 7.55-7.59 (m, 1H), 7.82 (d, J=7.6 Hz, 2H), 7.83 (d, J=8.0 Hz, 1H), 8.00 (dd, J=8.0, 1.2 Hz, 1H), 8.08 (d, J=8.4 Hz, 1H), 8.11 (d, J=8.8 Hz, 1H), 8.19 (d, J=2.4 Hz, 1H), 8.58 (br, 2H), 9.14 (dd, J=6.4, 1.6 Hz, 1H). MS (MALDI) for $C_{39}H_{24}N_4Pt$ [M]$^+$: calcd 743.16. found 743.47. Emission spectra of PtN1C at room temperature in $CH_2Cl_2$ and at 77K in 2-methyltetrahydrofuran are shown in FIG. 2.

Further modifications and alternative embodiments of various aspects will be apparent to those skilled in the art in view of this description. Accordingly, this description is to be construed as illustrative only. It is to be understood that the forms shown and described herein are to be taken as examples of embodiments. Elements and materials may be substituted for those illustrated and described herein, parts and processes may be reversed, and certain features may be utilized independently, all as would be apparent to one skilled in the art after having the benefit of this description. Changes may be made in the elements described herein without departing from the spirit and scope as described in the following claims.

What is claimed is:

1. A compound of Formula VI:

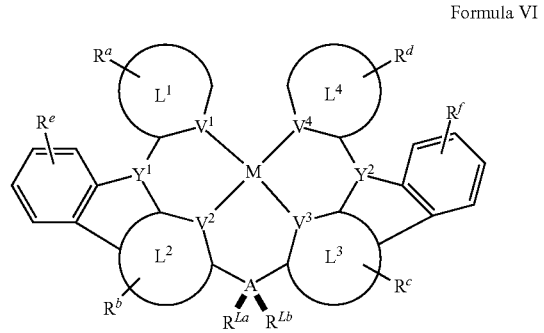

Formula VI wherein:
M is Pt, Pd, or Au,
A is C, Si, or Ge,
each of $L^1$ and $L^4$ is a substituted or unsubstituted pyridyl group, each of $L^2$ and $L^3$ is a substituted or unsubstituted phenyl group, each of $V^1$ and $V^4$ is coordinated with M and is independently N or C, each of $V^2$ and $V^3$ is coordinated with M and is C, each of $Y^1$ and $Y^2$ is independently CH, CR, SiH, SiR, N, P, P=O, As, or As=O, $R^{La}$ and $R^{Lb}$ are covalently bonded to form a fused ring, wherein the fused ring formed by $R^{La}$ and $R^{Lb}$ is substituted by one or more of halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, each of $R^a$, $R^b$, $R^c$, $R^d$, $R^e$, and $R^f$ is independently present or absent, and if present each of $R^b$, $R^c$, $R^e$ and $R^f$ independently represents mono-, di-, or tri-substitutions, each of $R^a$ and $R^d$ independently represents mono-, di-, tri-, or tetra-substitutions, and each of $R^a$, $R^b$, $R^c$, $R^d$, $R^e$ and $R^f$ is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and R is independently R is hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

2. The compound of claim 1, wherein the compound has a neutral charge.

3. The compound of claim 1, wherein

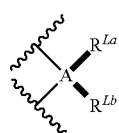

is one of the following structures:
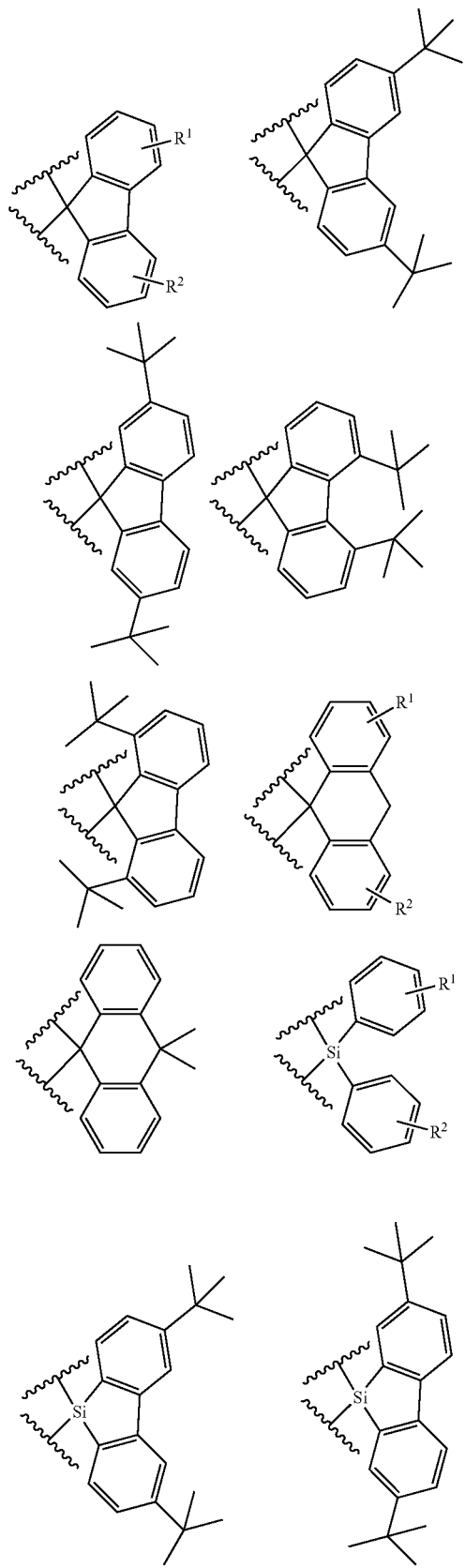
-continued
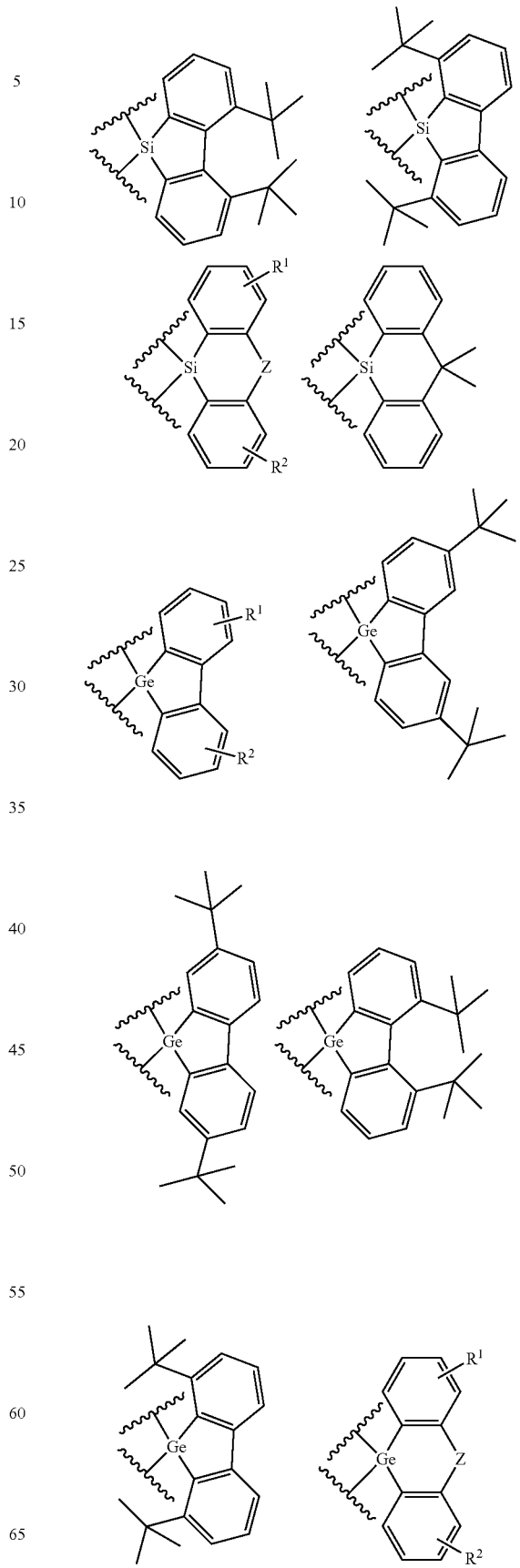

-continued

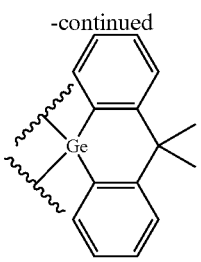

wherein:
each R¹ and R² present, valency permitting, is independently halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, Z is $CH_2$, $CR^xR^y$ $C=O$, $SiR^xR^y$, $GeH_2$, $GeR^xR^y$, NH, $NR^z$, PH, $PR^z$, $R^zP=O$, $AsR^z$, $R^zAs=O$, O, S, $S=O$, $SO_2$, Se, $Se=O$, $SeO_2$, BH, $BR^z$, $R^zBi=O$, BiH, or $BiR^z$, and each of $R^x$, $R^y$, and $R^z$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

4. The compound of claim 1, wherein each of

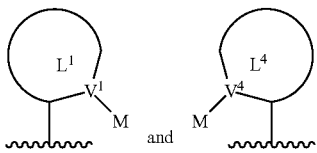

is independently one of the following structures:

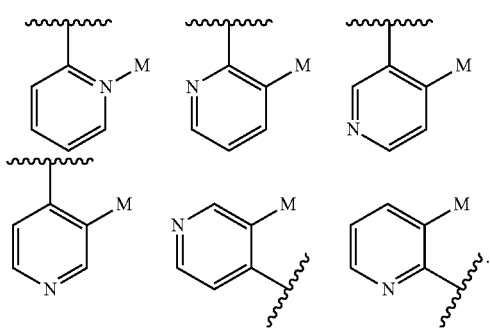

5. An emitter comprising the compound of claim 1, wherein the emitter is a delayed fluorescent and phosphorescent emitter.

6. An emitter comprising the compound of claim 1, wherein the emitter is a phosphorescent emitter.

7. An emitter comprising the compound of claim 1, wherein the emitter is a delayed fluorescent emitter.

8. A device comprising the compound of claim 1.

9. The device of claim 8, wherein the compound is selected to have 100% internal quantum efficiency in the device settings.

10. The device of claim 8, wherein the device is an organic light emitting diode.

11. The compound of claim 1, wherein:
A is C or Si.

12. The compound of claim 1, wherein $Y^1$ and $Y^2$ are N.

13. The compound of claim 1, wherein A is C.

14. A compound selected from one of the following structures:

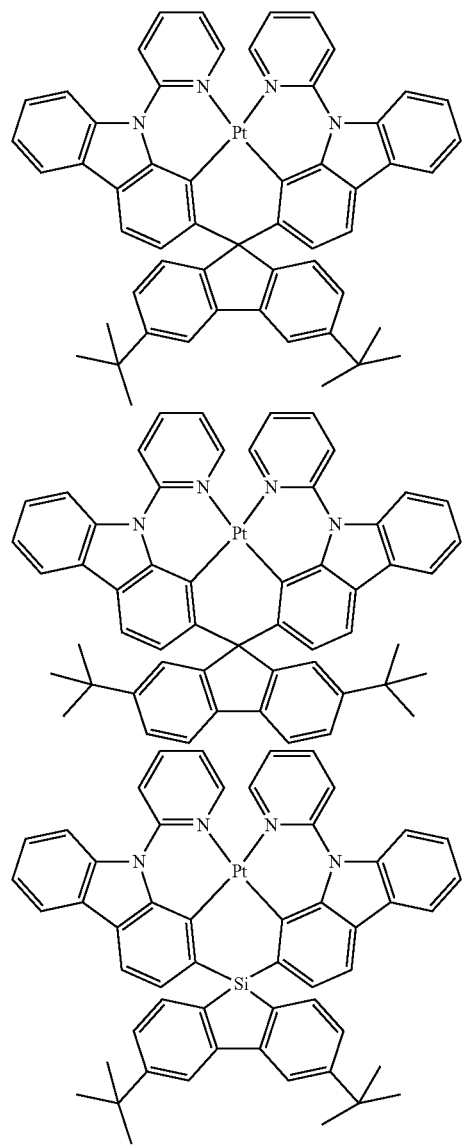

423
-continued
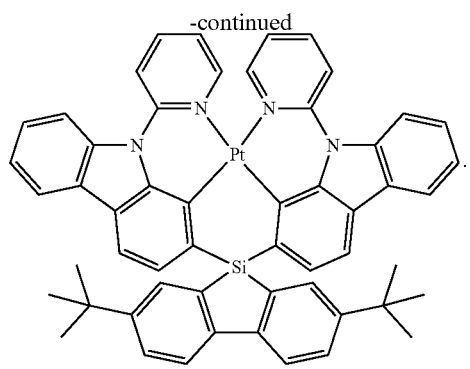
15. A compound selected from one of the following structures:
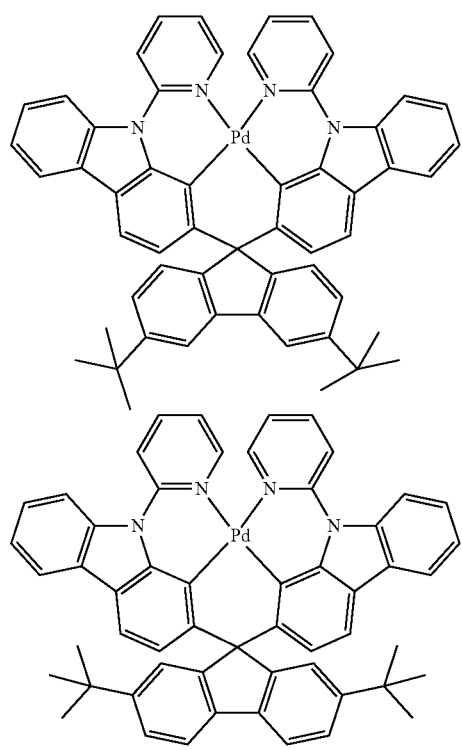
424
-continued
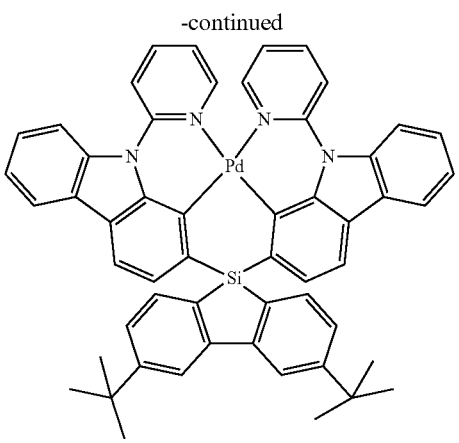
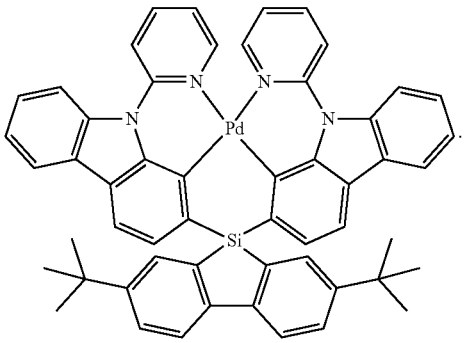
* * * * *